US012116625B2

(12) United States Patent
Kishi et al.

(10) Patent No.: US 12,116,625 B2
(45) Date of Patent: Oct. 15, 2024

(54) BARCODE DIFFUSION-BASED SPATIAL OMICS

(71) Applicant: Digital Biology Inc., Watertown, MA (US)

(72) Inventors: Jocelyn Kishi, Watertown, MA (US); Emma West, Boston, MA (US); Sylvain Lapan, Brookline, MA (US)

(73) Assignee: DIGITAL BIOLOGY, INC., Watertown, MA (US)

( * ) Notice: Subject to any disclaimer, the term of this patent is extended or adjusted under 35 U.S.C. 154(b) by 0 days.

(21) Appl. No.: 18/603,613

(22) Filed: Mar. 13, 2024

(65) Prior Publication Data

US 2024/0287588 A1    Aug. 29, 2024

Related U.S. Application Data

(63) Continuation of application No. PCT/US2023/070424, filed on Jul. 18, 2023.

(60) Provisional application No. 63/509,190, filed on Jun. 20, 2023, provisional application No. 63/390,498, filed on Jul. 19, 2022.

(51) Int. Cl.
*C12N 15/10*   (2006.01)
*C12Q 1/6841*  (2018.01)

(52) U.S. Cl.
CPC ....... *C12Q 1/6841* (2013.01); *C12N 15/1065* (2013.01)

(58) Field of Classification Search
CPC .......................... C12Q 1/6841; C12N 15/1065
See application file for complete search history.

(56) References Cited

U.S. PATENT DOCUMENTS

| | | |
|---|---|---|
| 7,941,279 B2 | 5/2011 | Hwang |
| 8,241,854 B2 | 8/2012 | Yin |
| 8,318,921 B2 | 11/2012 | Pierce |
| 8,415,102 B2 | 4/2013 | Geiss |
| 8,497,364 B2 | 7/2013 | Pierce |
| 8,519,115 B2 | 8/2013 | Webster |
| 8,877,438 B2 | 11/2014 | Yin |
| 8,962,241 B2 | 2/2015 | Yin |
| 8,986,926 B2 | 3/2015 | Ferree |
| 9,217,151 B2 | 12/2015 | Yin |
| 9,284,602 B2 | 3/2016 | Zhang |
| 9,371,563 B2 | 6/2016 | Geiss |
| 9,714,446 B2 | 7/2017 | Webster |
| 9,834,439 B2 | 12/2017 | Yin |
| 10,006,917 B2 | 6/2018 | Dai |
| 10,041,108 B2 | 8/2018 | Barish |
| 10,227,639 B2 | 3/2019 | Levner |
| 10,240,146 B2 | 3/2019 | Zhuang |
| 10,246,700 B2 | 4/2019 | Dunaway |
| 10,472,669 B2 | 11/2019 | Chee |
| 10,501,777 B2 | 12/2019 | Beechem |
| 10,640,816 B2 | 5/2020 | Beechem |
| 10,961,566 B2 | 3/2021 | Chee |
| 10,983,113 B2 | 4/2021 | Chee |
| 10,996,219 B2 | 5/2021 | Chee |
| 11,001,878 B1 | 5/2021 | Chee |
| 11,008,607 B2 | 5/2021 | Chee |
| 11,021,737 B2 | 6/2021 | Church |
| 11,098,303 B2 | 8/2021 | Zhuang |
| 11,193,163 B2 | 12/2021 | Daugharthy |
| 11,293,051 B2 | 4/2022 | Church |
| 11,293,052 B2 | 4/2022 | Church |
| 11,293,054 B2 | 4/2022 | Levner |
| 11,293,917 B2 | 4/2022 | Chee |
| 11,542,554 B2 | 1/2023 | Daugharthy |
| 2010/0021901 A1 | 1/2010 | Yin |
| 2010/0021904 A1 | 1/2010 | Pierce |
| 2015/0176071 A1* | 6/2015 | Fisher ............... C12Q 1/6869 506/2 |
| 2017/0267997 A1 | 9/2017 | Nicol |
| 2019/0360044 A1 | 11/2019 | Chen |
| 2020/0291389 A1 | 9/2020 | Seelig |
| 2021/0040551 A1 | 2/2021 | Mikkelsen |
| 2021/0095331 A1 | 4/2021 | Fan |
| 2021/0310052 A1 | 10/2021 | Daugharthy |

(Continued)

FOREIGN PATENT DOCUMENTS

| | | |
|---|---|---|
| EP | 2794928 B1 | 2/2019 |
| EP | 3425063 B1 | 6/2023 |

(Continued)

OTHER PUBLICATIONS

Castellanos-Rueda, Rocío, et al. "speedingCARs: accelerating the engineering of CAR T cells by signaling domain shuffling and single-cell sequencing." Nature Communications 13.1 (2022): 6555.

Chong, Zheng-Shan, et al. "Pooled extracellular receptor-ligand interaction screening using CRISPR activation." Genome biology 19 (2018): 1-16.

Goodman DB, Azimi CS, Kearns K, Talbot A, Garakani K, Garcia J, Patel N, Hwang B, Lee D, Park E, Vykunta VS, Shy BR, Ye CJ, Eyquem J, Marson A, Bluestone JA, Roybal KT. Pooled screening of CAR T cells identifies diverse immune signaling domains for next-generation immunotherapies. Sci Transl Med. Nov. 9, 2022; 14(670):eabm1463.

(Continued)

*Primary Examiner* — Sahana S Kaup
(74) *Attorney, Agent, or Firm* — Greenberg Traurig, LLP

(57) ABSTRACT

Provided herein are compositions, kits, and methods for collection, integration and analysis of various facets of information from tissues at the cellular or subcellular level. Information includes spatial mapping from nucleic acid barcodes to reconstruct location of nodes of nucleic acid barcode generation in a sample. In some workflows, light-based technologies are incorporated for an additional layer of selective spatial tagging of regions. In further steps, such tags are optionally analyzed by high throughput imaging or Next Generation Sequencing.

40 Claims, 111 Drawing Sheets

(56) References Cited

U.S. PATENT DOCUMENTS

| | | |
|---|---|---|
| 2022/0002790 A1 | 1/2022 | Kishi |
| 2022/0056498 A1 | 2/2022 | Kishi |
| 2022/0180975 A1 | 6/2022 | Regev |

FOREIGN PATENT DOCUMENTS

| | | | |
|---|---|---|---|
| WO | WO-2012106385 A2 * | 8/2012 | ........... C12Q 1/6804 |
| WO | WO 2014/012010 | 1/2014 | |
| WO | WO 2017/143006 | 2/2017 | |
| WO | WO 2018/175296 | 3/2018 | |
| WO | 2020115511 A2 | 6/2020 | |
| WO | WO 20/21119402 | 6/2021 | |

OTHER PUBLICATIONS

Kang, Emily, et al. "A functional mammalian display screen identifies rare antibodies that stimulate NK cell-mediated cytotoxicity." Proceedings of the National Academy of Sciences 118.31 (2021): e2104099118.

Rios, Xavier, et al. "Refining chimeric antigen receptors via barcoded protein domain combination pooled screening." Molecular Therapy 31.11 (2023): 3210-3224.

Valldorf, Bernhard, Hinz, Steffen C., Russo, Giulio, Pekar, Lukas, Mohr, Laura, Klemm, Janina, Doerner, Achim, Krah, Simon, Hust, Michael and Zielonka, Stefan. "Antibody display technologies: selecting the cream of the crop" Biological Chemistry, vol. 403, No. 5-6, 2022, pp. 455-477.

Askary, A., et al., "In situ readout of DNA barcodes and single base edits facilitated by in vitro transcription" Nat Biotechnol. Jan. 2020 ; 38(1): 66-75. doi:10.1038/s41587-019-0299-4.

Bystrykh, L.V., "Generalized DNA Barcode Design Based on Hamming Codes" PLoS One. 2012;7(5): e36852. doi: 10.1371/journal.pone.0036852.

Conrad, T. et al., "Maximizing transcription of nucleic acids with efficient T7 promoters" Commun Biol 3, 439 (2020). https://doi.org/10.1038/s42003-020-01167-x.

Gibson, D.G., et al., "Enzymatic assembly of DNA molecules up to several hundred kilobases" Nat Methods. May 2009;6(5):343-5. doi: 10.1038/nmeth. 1318.

Gopalkrishnan, Nikhil, Punthambaker, Sukanya, Schaus, Thomas, Church, George, Yin, Peng, "A DNA nanoscope that identifies and precisely localizes over a hundred unique molecular features with nanometer accuracy" bioRxiv 2020.08.27.27, 12 pages; doi: https://doi.org/10.1101/2020.08.27.271072.

International Search Report issued Jan. 31, 2024 in PCT/US2023/070424.

International Search Report issued in PCT/US2023/064873 on Sep. 12, 2023.

Kershaw, C.J., et al., "Splint ligation of RNA with T4 DNA ligase" Methods Mol Biol. 2012;941:257-69. doi: 10.1007/978-1-62703-113-4_19.

Kishi, J., "Programmable autonomous synthesis of single-stranded DNA" Nat Chem. Feb. 2018;10(2):155-164. doi: 10.1038/nchem. 2872.

Kishi, J., et al., Supplementary information—"Light-Seq: light-directed in situ barcoding of biomolecules in fixed cells and tissues for spatially indexed sequencing" Nat Methods. Nov. 2022;19(11):1393-1402. doi: 10.1038/s41592-022-01604-1.

Kishi, J., et al., "Light-Seq: light-directed in situ barcoding of biomolecules in fixed cells and tissues for spatially indexed sequencing" Nat Methods. Nov. 2022;19(11):1393-1402. doi: 10.1038/s41592-022-01604-1.

Li, N., et al., "Tn5 Transposase Applied in Genomics Research" Int J Mol Sci. Nov. 6, 2020;21(21):8329. doi: 10.3390/ijms21218329.

Liu, N., et al., "Super-resolution labelling with Action-Paint" Nat Chem. Nov. 2019;11(11):1001-1008. doi: 10.1038/s41557-019-0325-7.

Liu, N., et al., "Super-resolution labelling with Action-Paint" Supplementary Information, Nat Chem. Nov. 2019;11(11), 43 pages, doi: 10.1038/s41557-019-0325-7.

Liu, Y., et al., "High-plex protein and whole transcriptome co-mapping at cellular resolution with spatial Cite-seq" Nat Biotechnol. Feb. 23, 2023. doi: 10.1038/s41587-023-01676-0.

Liu, Yang, et al. "High-spatial-resolution multi-omics sequencing via deterministic barcoding in tissue." Cell 183.6 (2020): 1665-1681.

Moore M.J., & Sharp, P.A., "Site-specific modification of pre-mRNA: the 2'-hydroxyl groups at the splice sites" Science. May 15, 1992;256(5059):992-7. doi: 10.1126/science.1589782.

Piepenburg, O., et al. "DNA detection using recombination proteins" PLoS Biol. Jul. 2006;4(7):e204. doi: 10.1371/journal.pbio.0040204.

Rodriques, S.G., et al., "Slide-seq: A scalable technology for measuring genome-wide expression at high spatial resolution" Science. Mar. 29, 2019;363(6434):1463-1467. doi: 10.1126/science.aaw1219.

Rubanov, M., et al., "Sequential Activation of Spatially Localized Oligonucleotides" ACS Materials Letters 2022 4 (9), 1807-1814 DOI: 10.1021/acsmaterialslett.2c00286.

Schaus, T.E.,"A DNA nanoscope via auto-cycling proximity recording" Nat Commun. Sep. 25, 2017;8(1):696. doi: 10.1038/s41467-017-00542-3.

Sountoulidis, A., et al., "SCRINSHOT enables spatial mapping of cell states in tissue sections with single-cell resolution" PLoS Biol. Nov. 20, 2020;18(11):e3000675. doi: 10.1371/journal.pbio.3000675.

Stickels, R.R., et al., "Highly sensitive spatial transcriptomics at near-cellular resolution with Slide-seqV2" Nat Biotechnol. Mar. 2021;39(3):313-319. doi: 10.1038/s41587-020-0739-1.

Vandereyken, K., Sifrim, A., Thienpont, B. et al. Methods and applications for single-cell and spatial multi-omics. Nat Rev Genet 24, 494-515 (2023). https://doi.org/10.1038/s41576-023-00580-2.

Vincent, M., et al., "Helicase-dependent isothermal DNA amplification" EMBO Rep. Aug. 2004;5(8):795-800. doi: 10.1038/sj.embor.7400200.

Wang, L., et al., "3' Branch ligation: a novel method to ligate non-complementary DNA to recessed or internal 3'OH ends in DNA or RNA" DNA Res. Feb. 1, 2019;26(1):45-53. doi: 10.1093/dnares/dsy037.

Wei, H., et al., "Production of dumbbell probe through hairpin cleavage-ligation and increasing RCA sensitivity and specificity by circle to circle amplification" Sci Rep 6, 29229 (2016). https://doi.org/10.1038/srep29229.

Weinstein, J.A., "DNA Microscopy: Optics-free Spatio-genetic Imaging by a Stand-Alone Chemical Reaction" Cell. Jun. 27, 2019;178(1):229-241.e16. doi: 10.1016/j.cell.2019.05.019.

Xu, M., et al., "DNA Origami Nanostructures with Scaffolds Obtained from Rolling Circle Amplification" ACS Materials Letters 2020 2 (10), 1322-1327, DOI: 10.1021/acsmaterialslett.9b00484.

* cited by examiner

Pairwise

Multiple concatenations

BARCODE DIFFUSION-BASED SPATIAL OMICS

CROSS REFERENCE

This application is a continuation of International Application No. PCT/US2023/070424, filed Jul. 18, 2023, which claims the benefit of U.S. Provisional Application No. 63/390,498, filed Jul. 19, 2022, and U.S. provisional Application No. 63/509,190, filed Jun. 20, 2023, the entire contents of which are incorporated herein by reference.

BACKGROUND

Understanding how molecules are arranged within cells, and how cells are arranged within tissues, is critical to interpreting, predicting, and engineering biological states. Advancements in microscopy have enabled high-resolution reconstructions of subcellular structures (e.g., electron microscopy), but the composition of biomolecules within such structures remains difficult to capture. Several methods are capable of recording pair-wise molecular proximity (FRET, APR, DNA nanoscope, DNA microscopy), but these are generally limited to specific biomolecules (e.g., two proteins detected with antibodies) and are not generalizable for measurements of arbitrary biomolecular distributions. Thus, there is a need for a method to measure spatial locations and conformations of biomolecules from the angstrom scale to supercellular interactions at millimeter scale.

BRIEF SUMMARY

Provided herein are methods of biological information generation, the methods comprising providing node factories on a biological sample at node locations, wherein the node factories comprise one or more node nucleic acids, and wherein each node nucleic acid comprises: a node barcode region, one or more flanking node barcode hybridization regions, and optionally, a node primer region; amplifying the one or more node nucleic acids to generate concatemers of node nucleic acids, wherein the concatemers diffuse away from the node locations over time, cleaving the concatemers into a plurality of node nucleic acids, attaching two or more node nucleic acids generated by the node factories to generate multinode nucleic acids; and analyzing for a frequency of association of the two or more node nucleic acids, where the frequency of association provides information for spatial mapping of the biological sample.

Provided herein are methods of biological information generation, the methods comprising: depositing template nucleic acids on a biological sample at node locations, wherein the template nucleic acids comprise: a node barcode region; and one or more flanking node barcode hybridization regions; amplifying the template nucleic acids to generate node nucleic acids, wherein the node nucleic acids diffuse away from the node locations over time; depositing factory target nucleic acids onto the biological sample, wherein the factory target nucleic acids comprise: a target binding region; and one or more flanking target binding hybridization regions; and attaching at least one of the node nucleic acids to at least one of the factory target nucleic acids to form a concatemer, wherein a combination of the node nucleic acids and the factory target nucleic acids provides biological information for spatial mapping of the biological sample.

Provided herein are methods of information storage, the methods comprising: receiving digital information; converting the digital information to nucleic acid information in the form of a plurality of nucleic acid barcodes; depositing template nucleic acids on a surface at node locations, wherein the template nucleic acids comprise: a node barcode region, each corresponding to one of the plurality of barcodes; and one or more flanking node barcode hybridization regions; amplifying the template nucleic acids to generate node nucleic acids; depositing factory target nucleic acids onto the surface, wherein the factory target nucleic acid comprises: a target binding region; one or more flanking target binding hybridization regions; optionally, a target primer region; and attaching at least one of the node nucleic acids to at least one of the factory target nucleic acids to form a concatemer, wherein the combination of node nucleic acids and factory target nucleic acids provides storage information.

Provided herein are methods of information storage, the methods comprising: receiving digital information; converting the digital information to nucleic acid information in the form of a plurality of nucleic acid barcodes; depositing a first oligonucleotide onto a surface, wherein the first oligonucleotide comprises: optionally, a surface binding region; a first barcode region corresponding to a barcode of the plurality of barcodes; and one or more flanking first oligonucleotide hybridization regions, wherein the surface binding region and the one or more flanking hybridization regions optionally comprise a photoreactive nucleobase; optionally selectively radiating the surface to form covalently linked oligonucleotides; depositing a second oligonucleotide on the surface, wherein the second oligonucleotide comprises: a second barcode region corresponding to a barcode of the plurality of barcodes; and one or more flanking second oligonucleotide hybridization regions, wherein the one or more flanking second oligonucleotide hybridization regions comprise a photoreactive nucleobase, and wherein at least one of the one or more flanking first oligonucleotide hybridization regions is complementary to at least one of the one or more flanking second oligonucleotide hybridization regions; and selectively radiating the surface to covalently link the second oligonucleotide to the first oligonucleotide; and optionally repeating the second depositing and radiating steps one or more times, thereby generating a concatemer.

Provided herein are methods of biological information generation comprising depositing node factories comprising a matrix on a biological sample at node locations, wherein each node factory comprises a plurality of node nucleic acids, and wherein each node nucleic acid comprises: a node barcode region; one or more flanking node barcode hybridization regions; optionally, a node primer region, a target binding region, a target barcode region; one or more flanking target binding hybridization regions; and optionally, a target primer region, releasing at least one of the node nucleic acids from the node factory, wherein the releasing provides biological information for spatial mapping of the biological sample.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24A illustrates polymerization extending both strands to generate a double stranded nucleic acid comprising regions from both strands.

FIG. 24B illustrates polymerization wherein the node barcode strand comprises a non-hybridized domain 3' of a hybridization sequence, extending the target nucleic acid to generate a single-stranded nucleic acid comprising regions from both strands.

FIG. 24C illustrates polymerization wherein the target nucleic acid strand comprises a non-hybridized domain 3' of a hybridization sequence, extending the node barcode strand to generate a single-stranded nucleic acid comprising regions from both strands.

FIG. 24D illustrates polymerization extending both strands to generate a double stranded nucleic acid comprising regions from both strands.

FIG. 24E illustrates polymerization wherein the node barcode strand comprises a non-hybridized domain 3' of the hybridization sequence, extending the target nucleic acid to generate a single-stranded nucleic acid comprising regions from both strands.

FIG. 24F illustrates polymerization wherein the target nucleic acid strand comprises a non-hybridized domain 3' of the hybridization sequence, extending the node barcode strand to generate a single-stranded nucleic acid comprising regions from both strands.

FIG. 25A illustrates polymerization extending both strands to generate a double stranded nucleic acid comprising regions from both strands.

FIG. 25B illustrates polymerization wherein the node barcode strand comprises a non-hybridized domain 3' of a hybridization sequence, extending the target nucleic acid to generate a single-stranded nucleic acid comprising regions from both strands.

FIG. 25C illustrates polymerization wherein the target nucleic acid strand comprises a non-hybridized domain 3' of a hybridization sequence, extending the node barcode strand to generate a single-stranded nucleic acid comprising regions from both strands.

FIG. 25D illustrates polymerization extending both strands to generate a double stranded nucleic acid comprising regions from both strands.

FIG. 25E illustrates polymerization wherein the node barcode strand comprises a non-hybridized domain 3' of a hybridization sequence, extending the target nucleic acid to generate a single-stranded nucleic acid comprising regions from both strands.

FIG. 25F illustrates polymerization wherein the target nucleic acid strand comprises a non-hybridized domain 3' of a hybridization sequence, extending the node barcode strand to generate a single-stranded nucleic acid comprising regions from both strands.

FIG. 26A illustrates polymerization extending both strands to generate a double stranded nucleic acid comprising regions from both strands.

FIG. 26B illustrates polymerization extending the target nucleic acid to generate a single-stranded nucleic acid comprising regions from both strands.

FIG. 26C illustrates polymerization extending the node barcode strand to generate a single-stranded nucleic acid comprising regions from both strands.

FIG. 26D illustrates polymerization extending both strands to generate a double stranded nucleic acid comprising regions from both strands.

FIG. 26E illustrates polymerization wherein the node barcode strand comprises a non-hybridized domain 3' of a hybridization sequence, extending the target nucleic acid to generate a single-stranded nucleic acid comprising regions from both strands.

FIG. 26F illustrates polymerization wherein the target nucleic acid strand comprises a non-hybridized domain 3' of a hybridization sequence, extending the node barcode strand to generate a single-stranded nucleic acid comprising regions from both strands.

FIG. 26G illustrates polymerization extending both strands to generate a double stranded nucleic acid comprising regions from both strands.

FIG. 26H illustrates polymerization wherein the node barcode strand comprises a non-hybridized domain 3' of the hybridization sequence, extending the target nucleic acid to generate a single-stranded nucleic acid comprising regions from both strands.

FIG. 26I illustrates polymerization extending the node barcode strand to generate a single-stranded nucleic acid comprising regions from both strands.

FIG. 27A illustrates an exemplary hybridization schema.

FIG. 27B illustrates an exemplary hybridization schema, wherein the node barcode strand further comprises a non-hybridized domain 3' of the hybridization domain.

FIG. 27C illustrates an exemplary hybridization schema, wherein the cDNA/ISH probe strand further comprises a non-hybridized region 3' of the hybridization domain.

FIG. 27D illustrates an exemplary hybridization schema, wherein the hybridization domain comprises the first PCR primer and node barcode domains, and wherein the node barcode strand further comprises a non-hybridized region 3' of the hybridization domain.

FIG. 27E illustrates an exemplary hybridization schema, wherein the node barcode strand further comprises a unique modifier.

FIG. 27F illustrates an exemplary hybridization schema, wherein the node barcode strand further comprises a unique modifier, and wherein the node barcode strand further comprises a non-hybridized domain 3' of the hybridization domain.

FIG. 27G illustrates an exemplary hybridization schema, wherein the node barcode strand further comprises a unique modifier, and wherein the cDNA/ISH probe strand further comprises a non-hybridized domain 3' of the hybridization domain.

FIG. 37B padlock probe was used to generate the images in FIG. 37E. FIG. 37C padlock probe was used to generate the images in FIG. 37F.

FIG. 43Q is an image of an agarose gel run with samples from one step and sequential release of generated nucleic acids compared to a mock template of the expected size.

FIG. 43R is a barplot showing mapped genes using samples receiving externally generated target nucleic acid, samples without reverse transcriptase, or samples from in situ generated target nucleic acid.

Figure 43A:
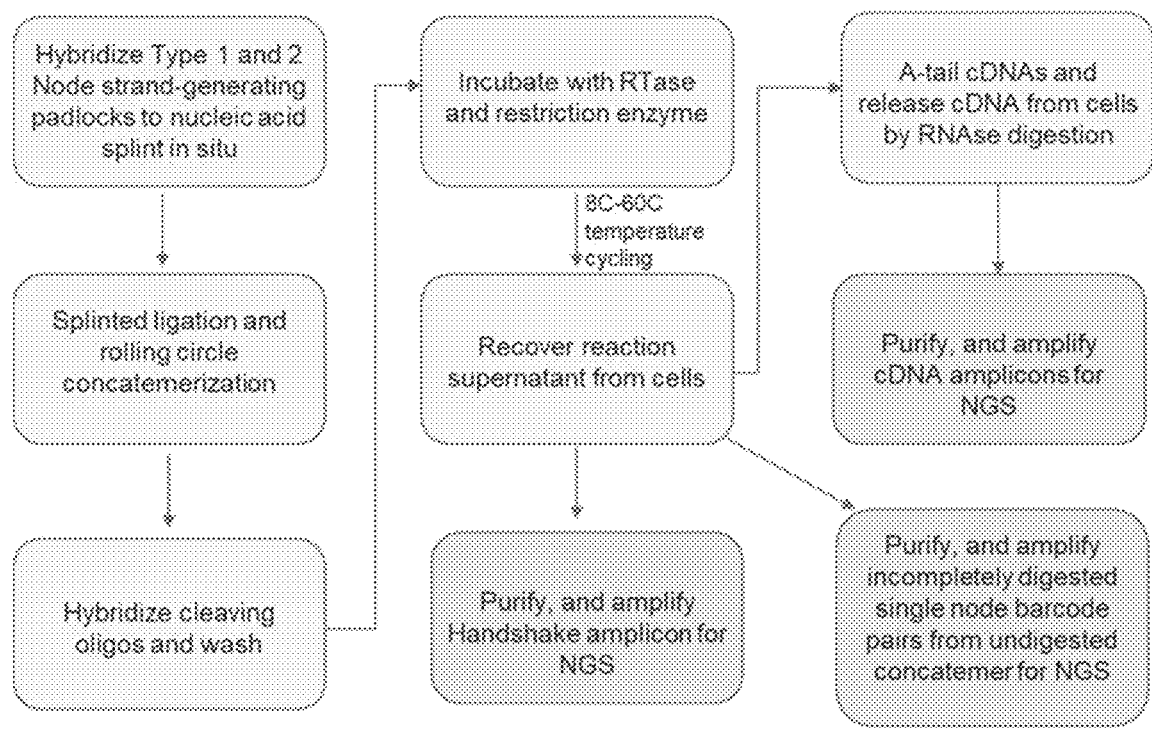
FIG. 43A illustrates the workflow used to release two types of strands from a single node source for both priming reverse transcription of cellular mRNAs and conjugating to one other node nucleic acids.
Figure 43B:
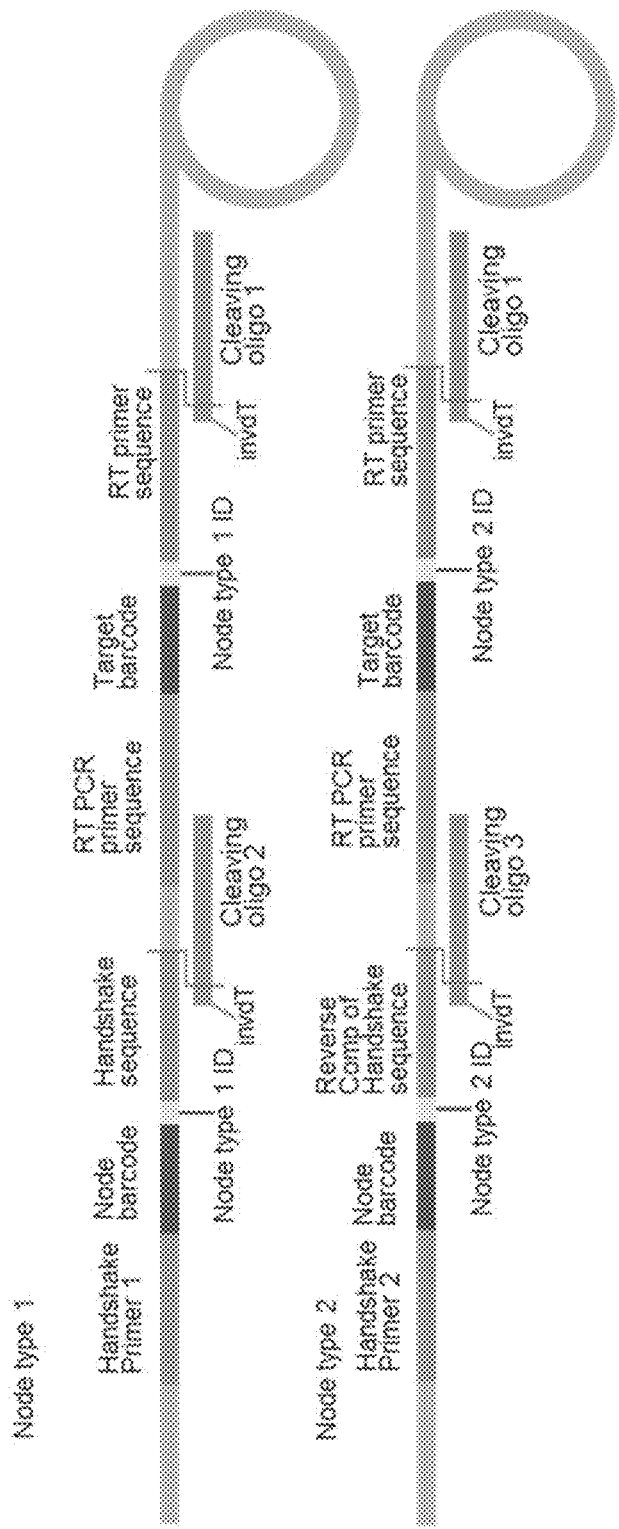
FIG. 43B is a schematic of concatemers capable of generating target nucleic acids that conjugate to cDNAs and also generate node nucleic acids used in node-node handshakes.
Figure 43C:
FIG. 43C is a schematic of the nucleic acids generated from two different RCA factories, including two types of node nucleic acids and two types of target nucleic acids.
Figure 43D:
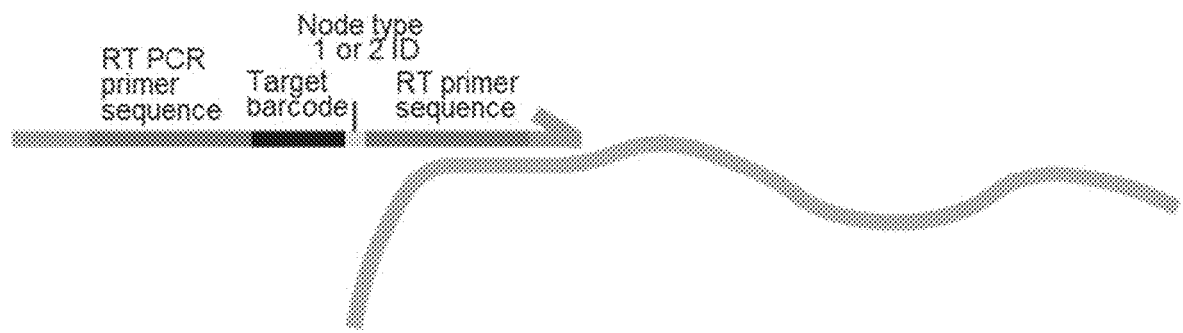
FIGS. 43D-43F are schematics illustrating the 'one step' release of target nucleic acids hybridizing to a target mRNA (FIG. 43D), association of reverse transcriptase (FIG. 43E), and generation of a factory target nucleic acid—cDNA concatemer (FIG. 43F).
Figure 43E:
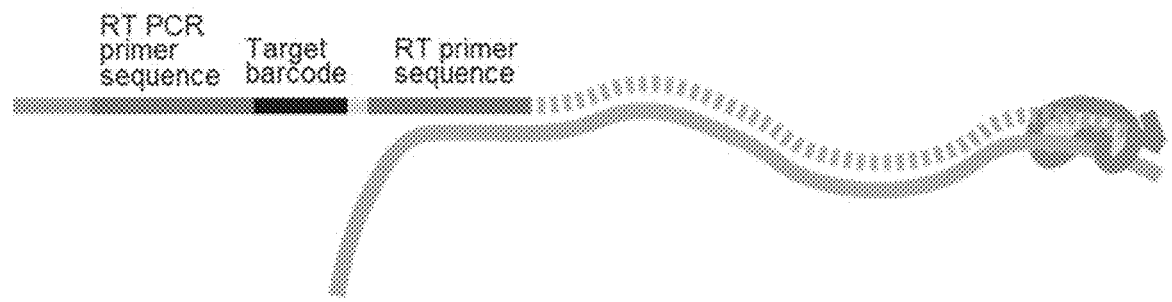
Figure 43F:
Figure 43G:
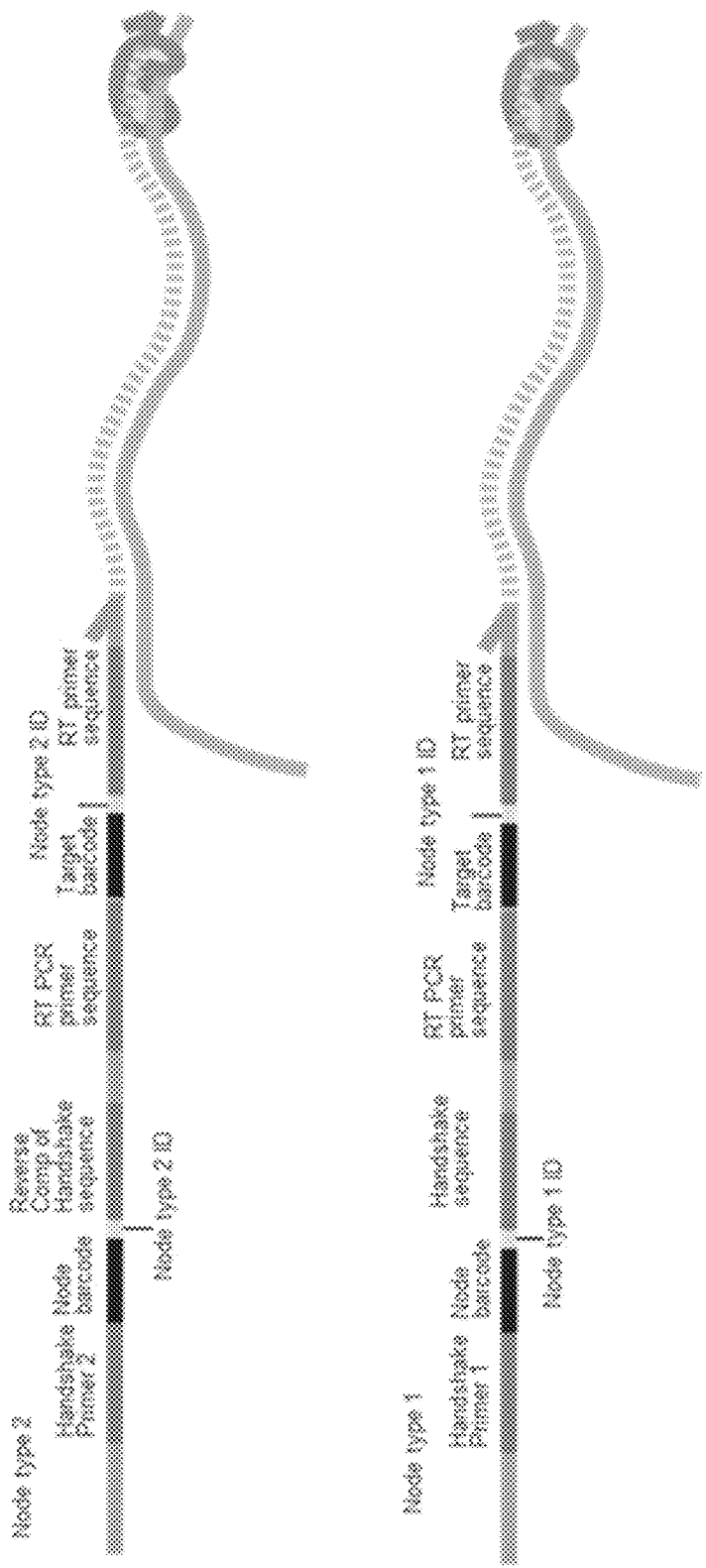
FIGS. 43G AND 43H are schematics illustrating the sequential release of two types of combined node and nucleic acids to hybridize by the RT primer sequence on the target nucleic acid (FIG. 43G) and hybridization of cleaving oligos to the cleavage site between the node nucleic acid and target nucleic acid (FIG. 43H).
Figure 43H:
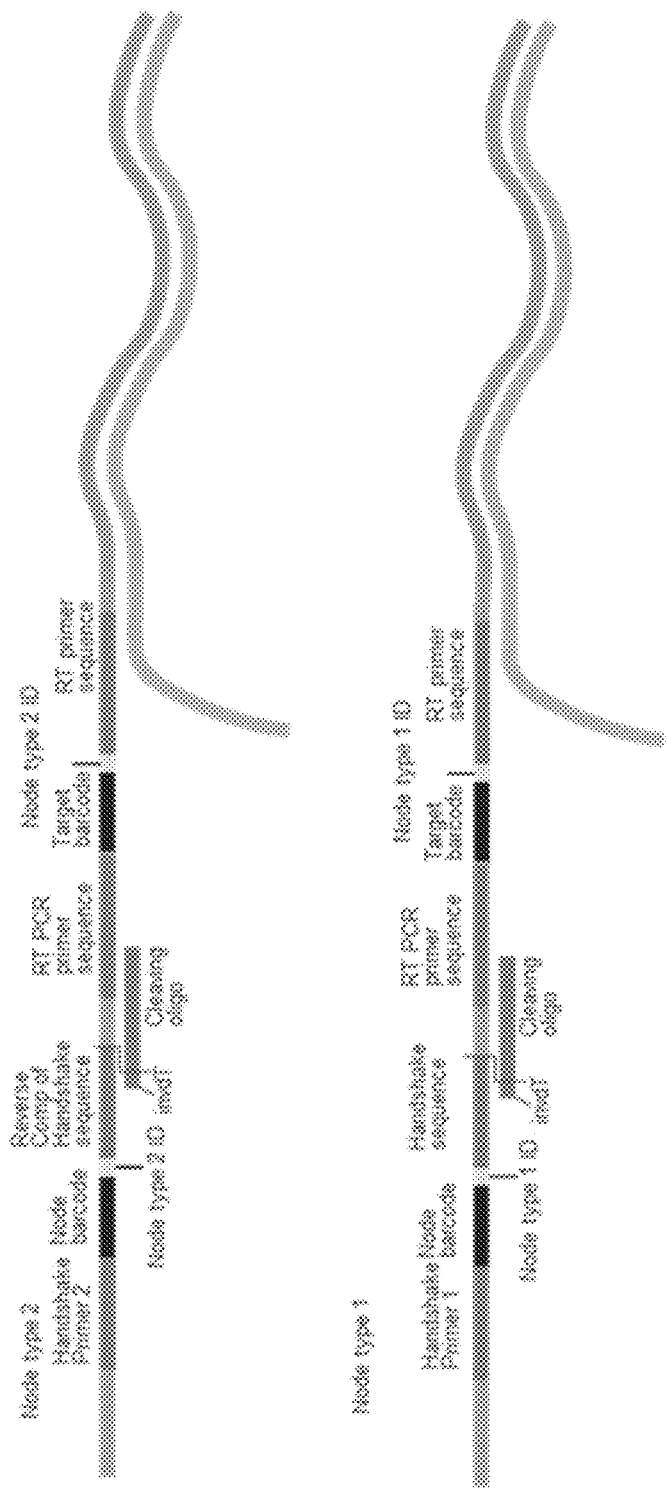
Figure 43I:
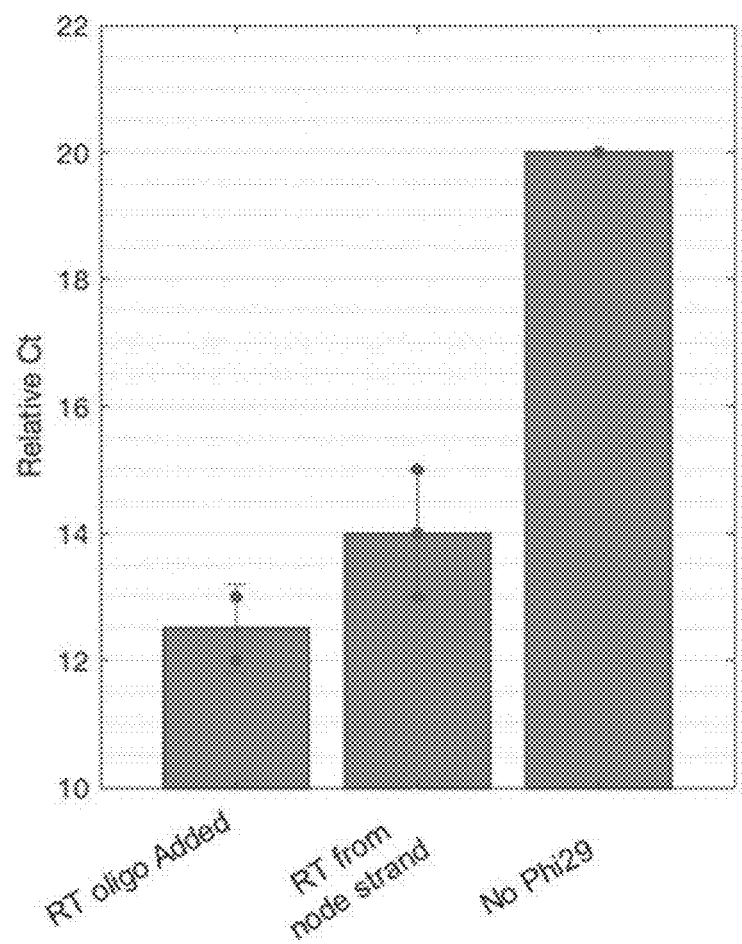
FIG. 43I is a bar chart of quantifying relative qPCR Ct from input cDNA in samples receiving externally generated target nucleic acid, target nucleic acid generated by RCA, and samples with no Phi29.
Figure 43J:
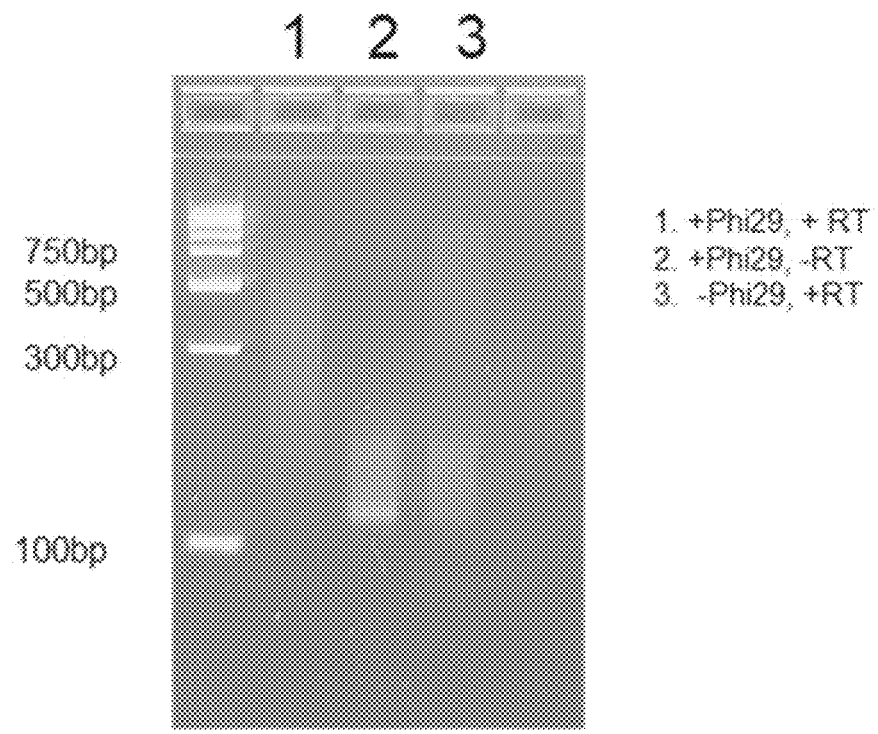
FIG. 43J is an image of an agarose gel showing the size range of the amplified cDNA; lane 1 is a sample contacted with Phi29 and reverse transcriptase, lane 2 is a sample contacted with Phi29 but no reverse transcriptase, and lane 3 is a sample not contacted with Phi29 but with reverse transcriptase.
Figure 43K:
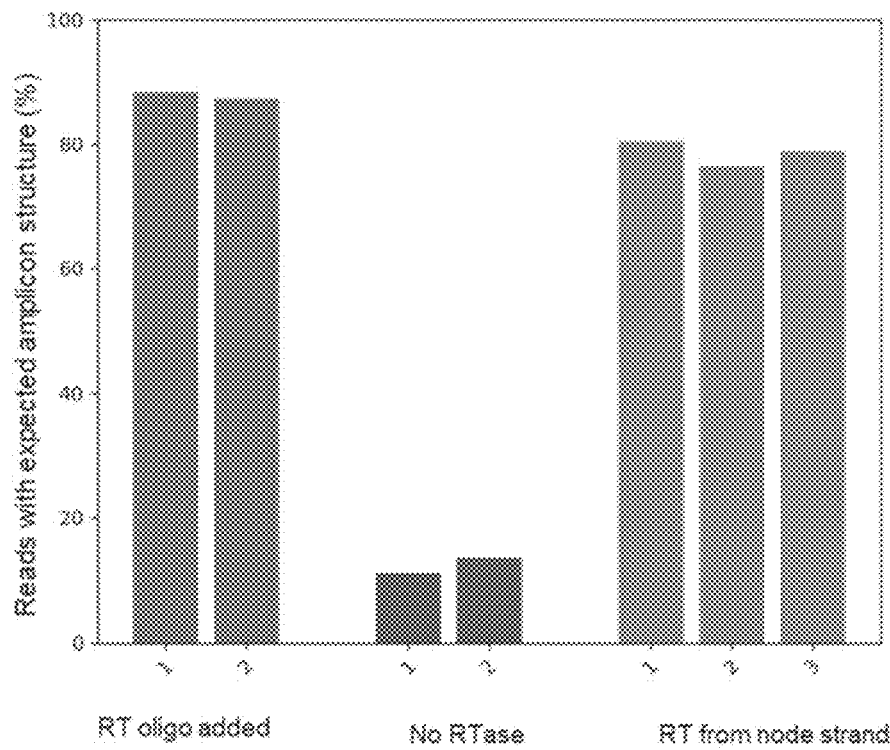
FIG. 43K is a barplot showing the percent of node strand-barcoded cDNAs that conform to the expected amplicon structure based on NGS reads in samples receiving externally generated target nucleic acids, samples receiving no reverse transcriptase, and sample with generated target nucleic acid directing reverse transcription.
Figure 43L:
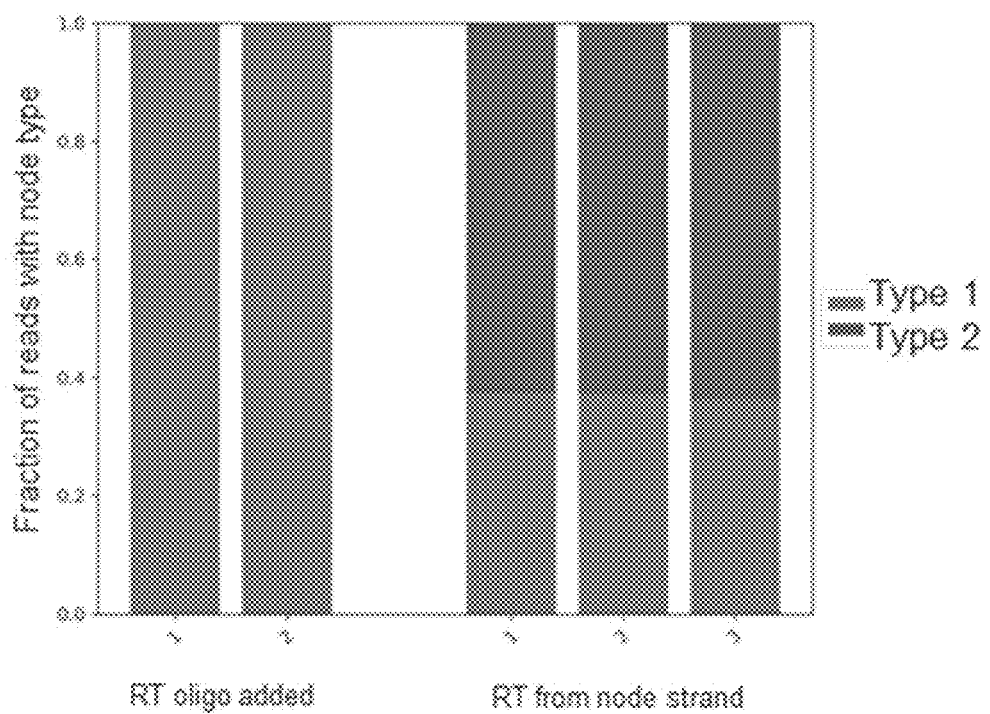
FIG. 43L is a barplot illustrating the fraction of reads attributed to type 1 and type 2 templates in samples receiving externally generated node nucleic acids or samples receiving type 1 and type 2 in situ generated target nucleic acids.
Figure 43M:
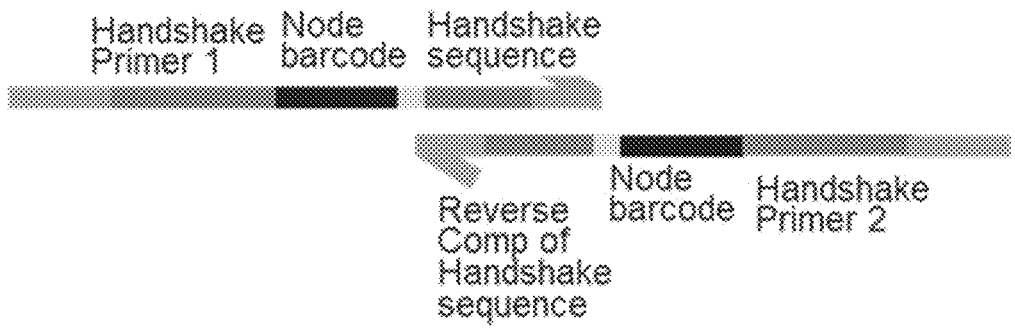
FIGS. 43M-43O are schematics showing progression of hybridization of handshake sequences from two node nucleic acids and extension of both nucleic acids to generate a double stranded node handshake.
Figure 43N:
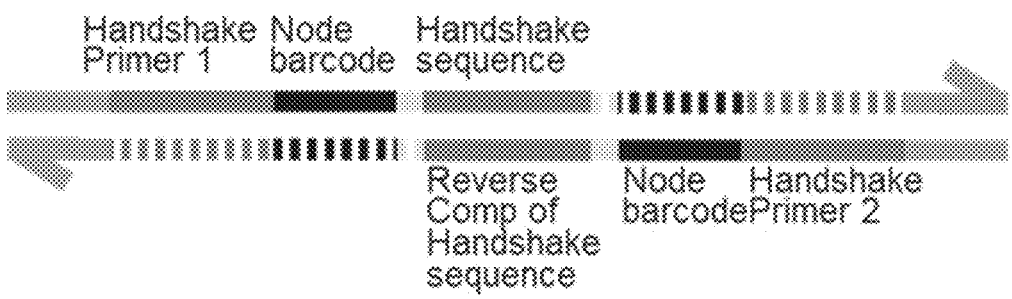
Figure 43O:
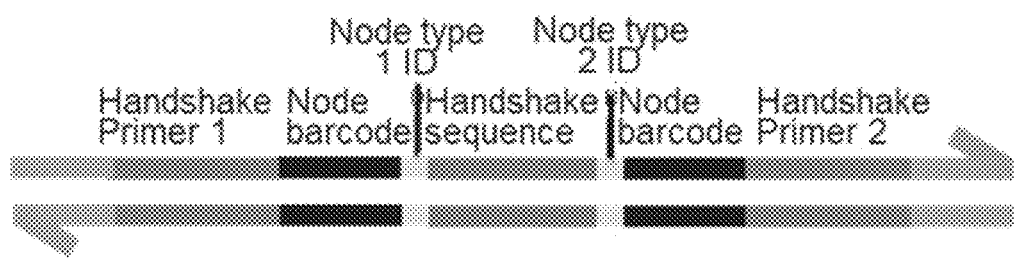
Figure 43P:
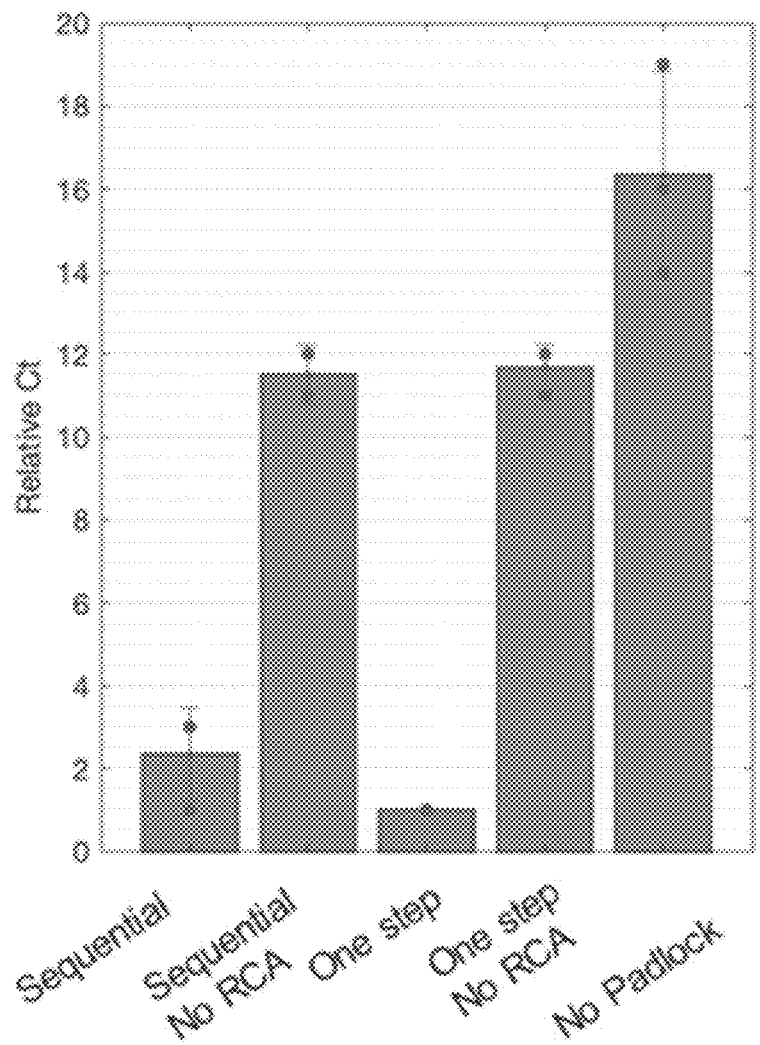
FIG. 43P is a bar plot showing relative Ct values from different transcription and release conditions wherein generation with sequential barcode release and one step release displayed high input cDNA count, reflected in low relative Ct, and samples with no RCA or no padlock displayed low cDNA count, reflected in high relative Ct.
Figure 43Q:
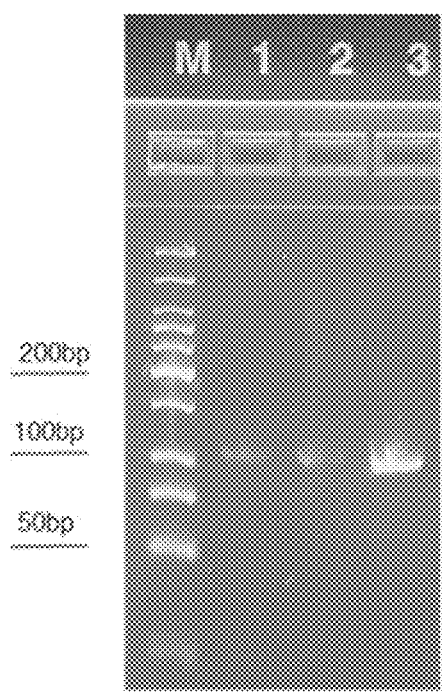
Figure 43R:
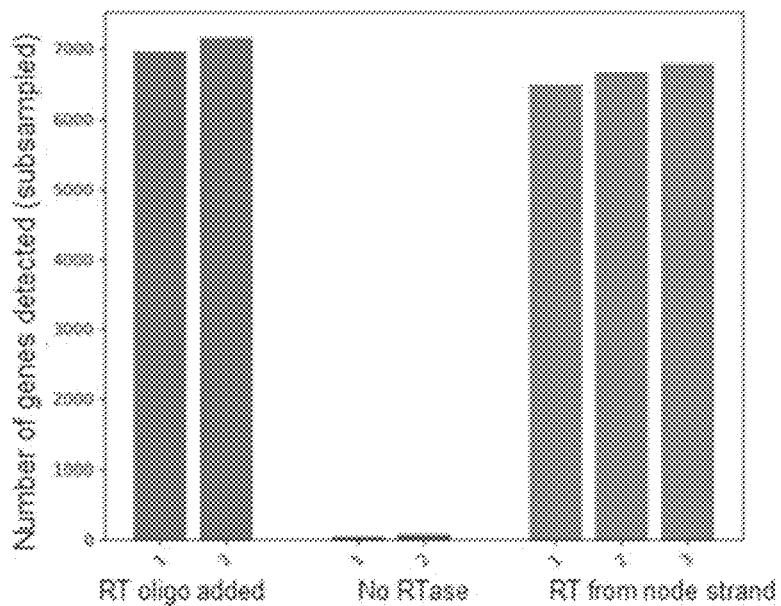
Figure 43S:
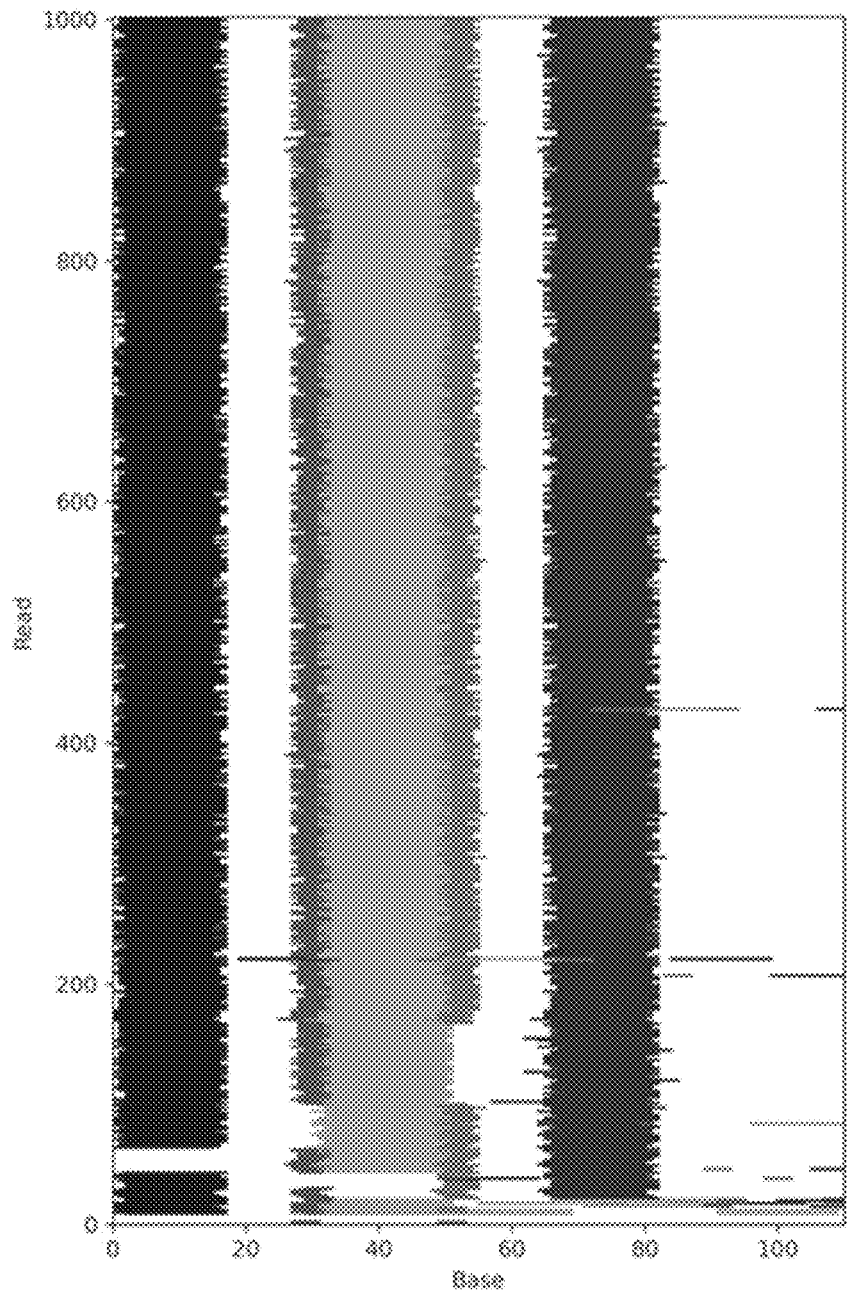

FIG. 43S is a compilation of alignments of generated node nucleic acids, showing consistent alignment of 1) Handshake PCR primer 1, 2) Handshake PCR primer 2, 3) Handshake sequence, 4) Node 1 ID+the first 10 bases of the Handshake sequence, and 5) the last 10 bases of the Handshake sequence+Node 2 ID across 1000 reads.

Figure 44A:
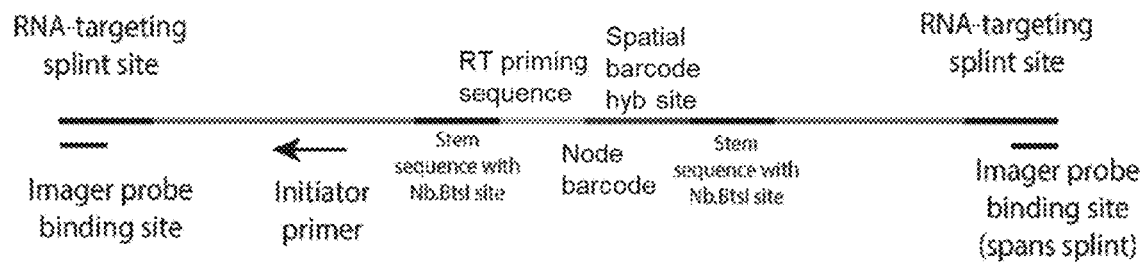

FIG. 44A is a schematic showing the structure of a padlock probe sequence used in RCA to generate a concatemer with nicking sites on secondary hairpin structures.

Figure 44B:
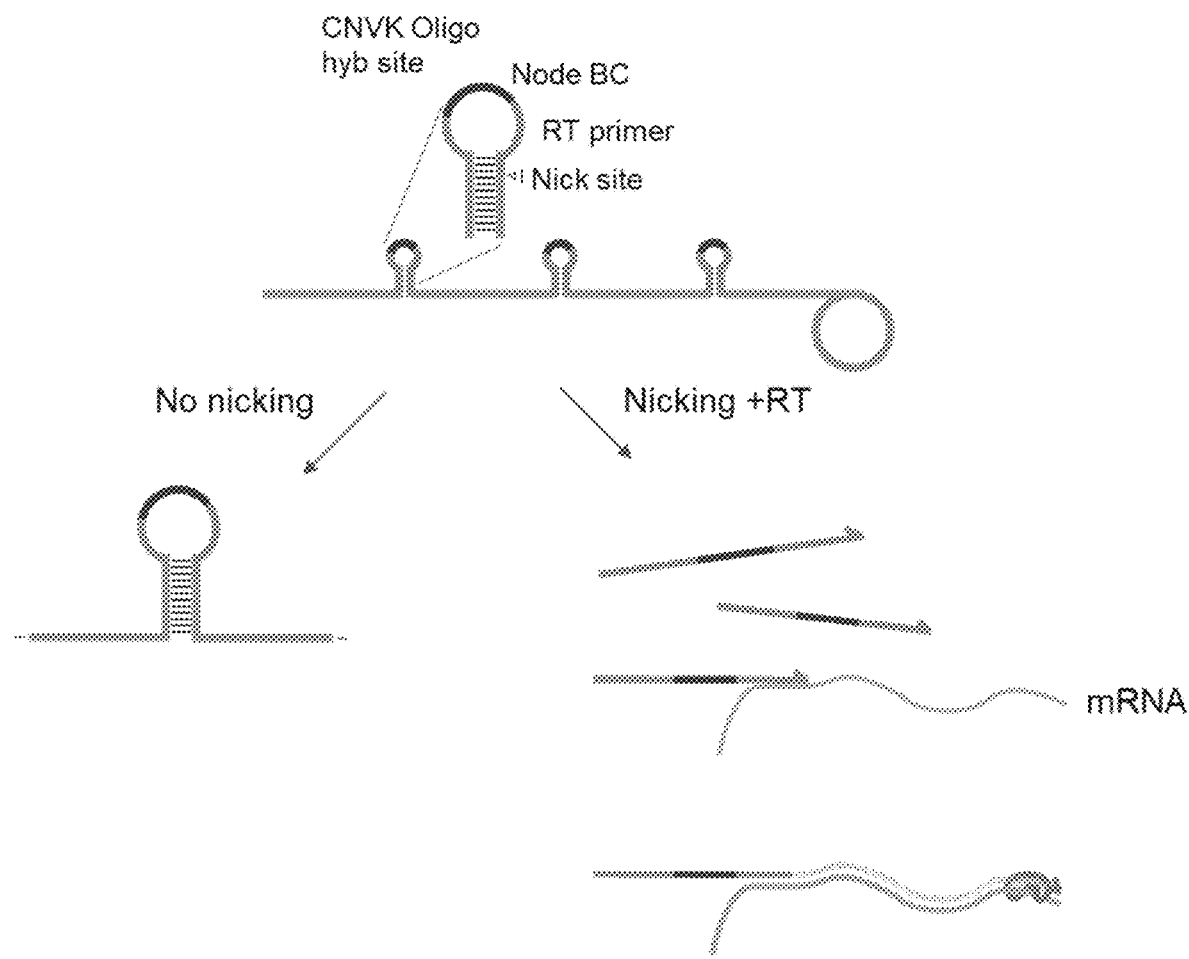

FIG. 44B illustrates a target hybridization method, including cleavage of the target nucleic acids by nicking at the double-stranded hairpin region, hybridization to mRNA, and reverse transcription of the mRNA.

Figure 44C:
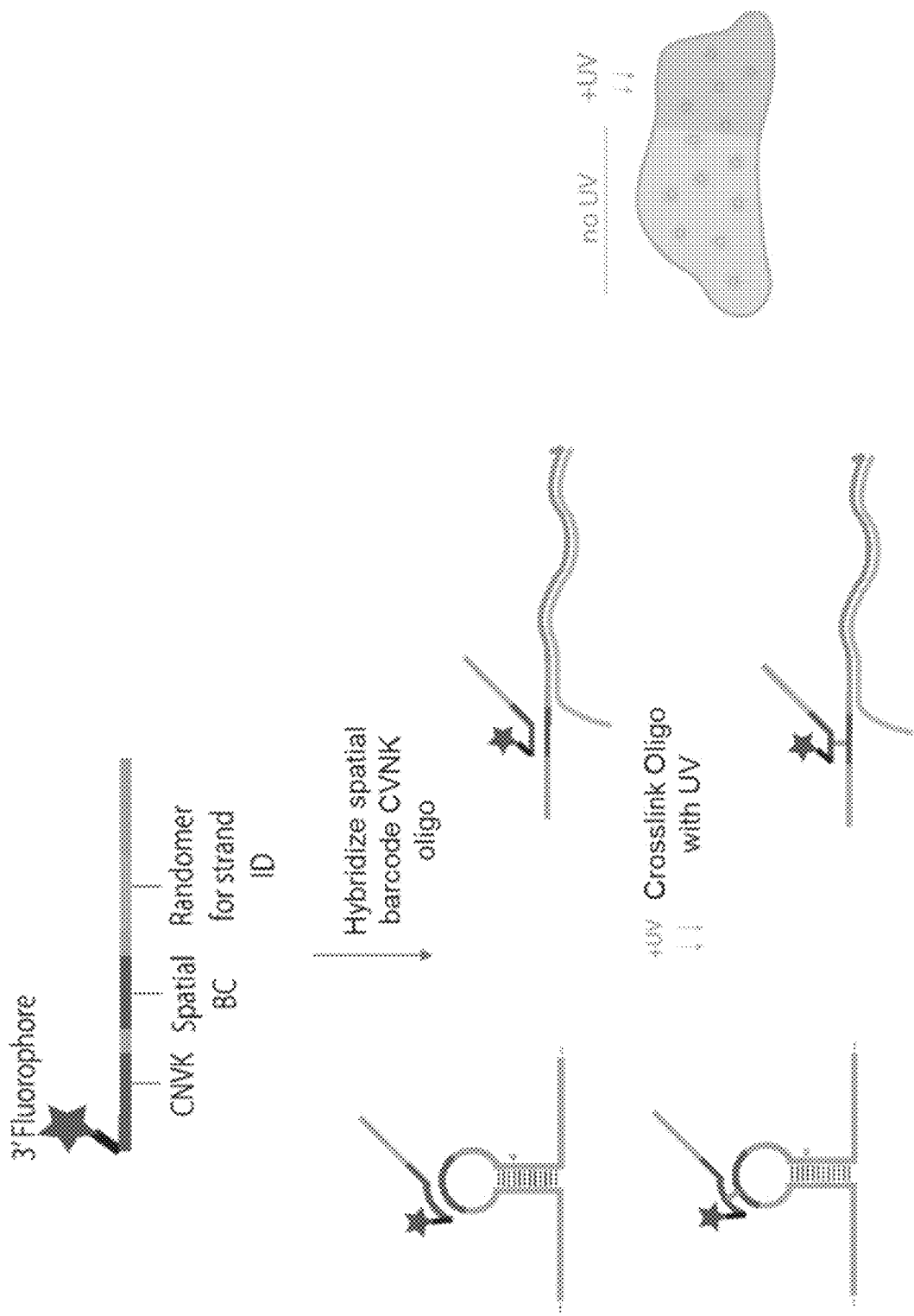

FIG. 44C illustrates CNVK barcode sequence crosslinking a target nucleic acid both in the concatemer form, in this case with a hairpin secondary structure, and to the target nucleic acid hybridized to an mRNA.

Figure 44D:
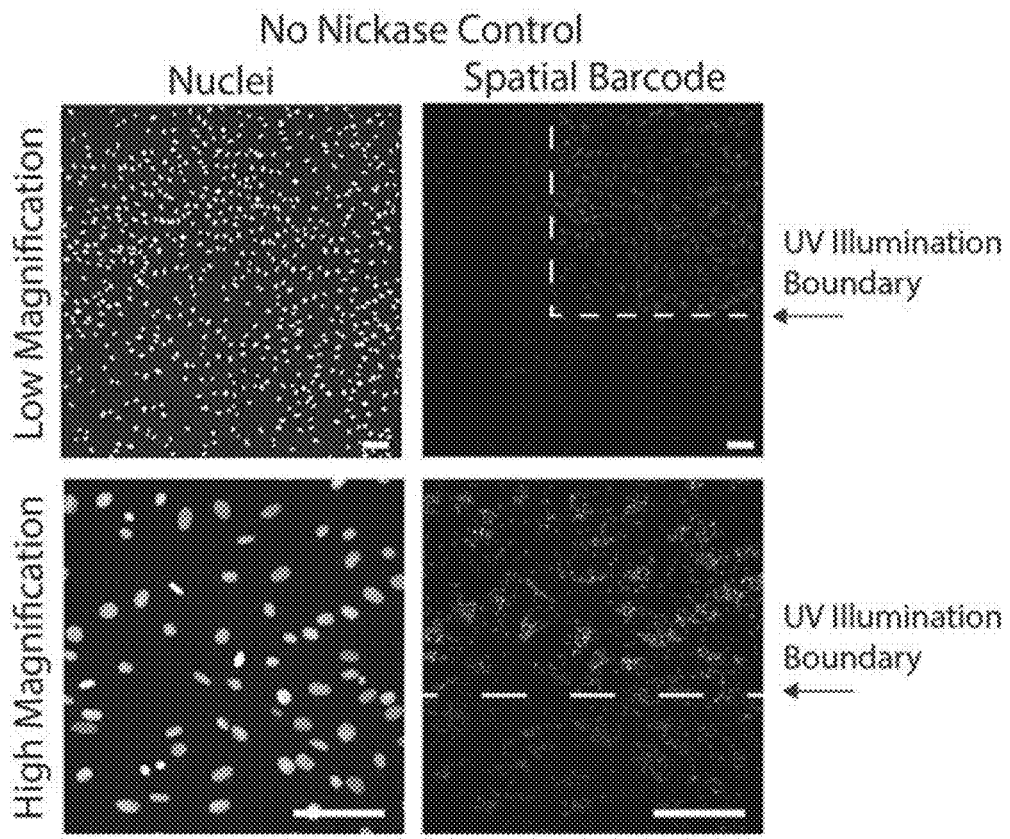
Figure 44E:
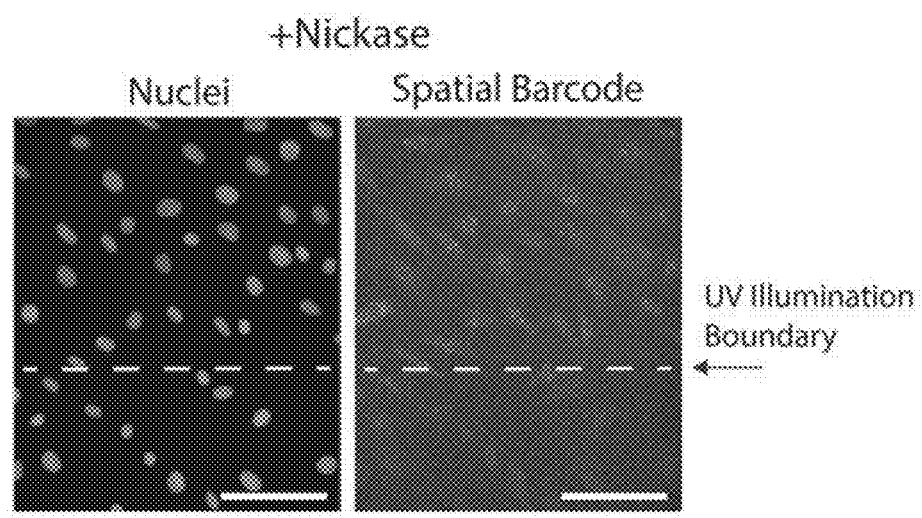

FIGS. 44D-44E are images of cells treated with nuclear stain and spatial barcodes with an attached fluorophore, indicating cross-linking to both cut and uncut concatemers.

Figure 45A:
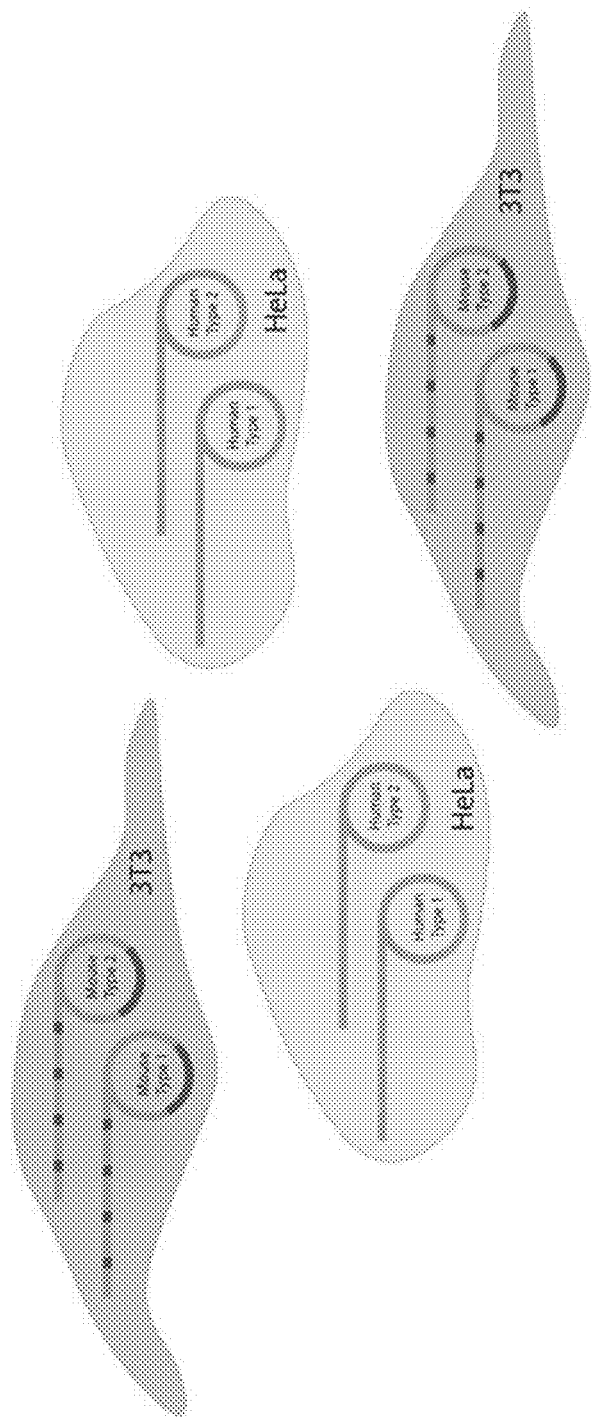

FIG. 45A is a schematic demonstrating use of different padlock probes to target different cells in a mixed culture.

Figure 45B:
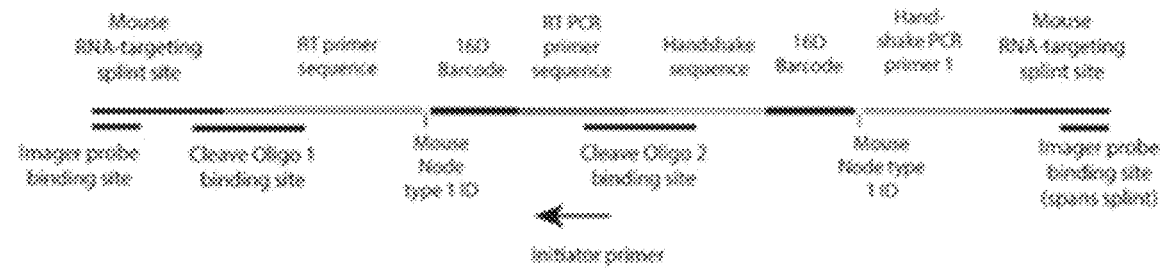
Figure 45B:
Figure 45B:
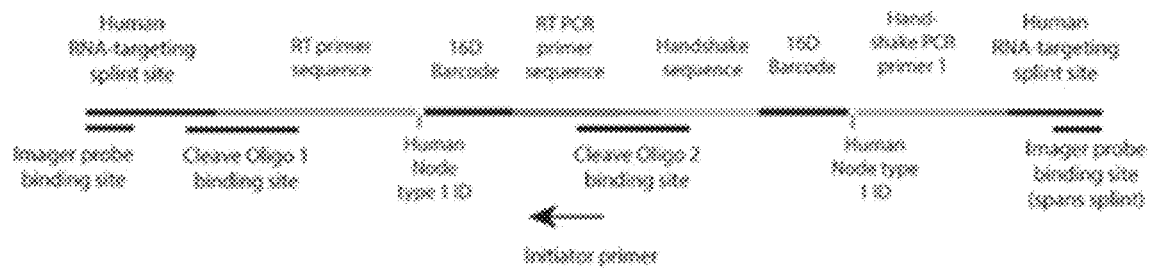
Figure 45B:
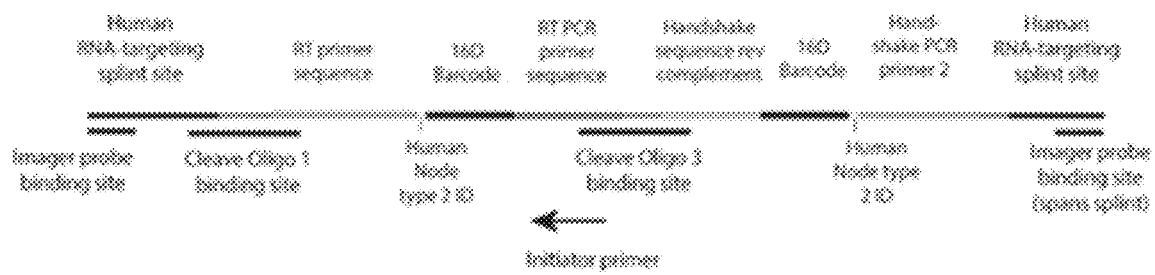

FIG. 45B is a schematic of the four padlock probe structures used to generate two types of mouse-targeting and two types of human-targeting nucleic acids.

Figure 45C:
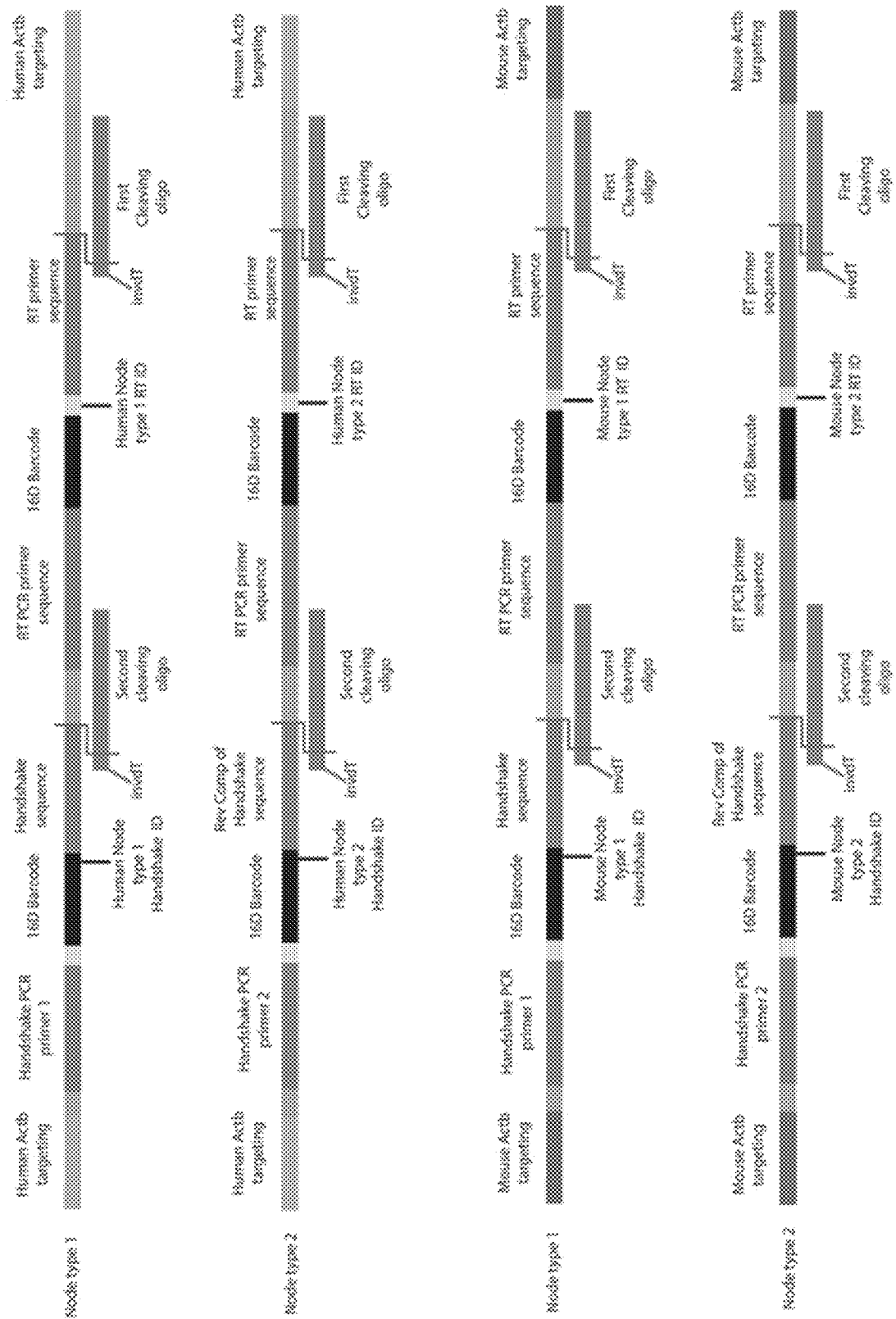

FIG. 45C is a schematic of a single repeat from a generated concatemer with associated cleaving oligonucleotides at restriction sites from padlock probes described in FIG. 45B.

Figure 45D:
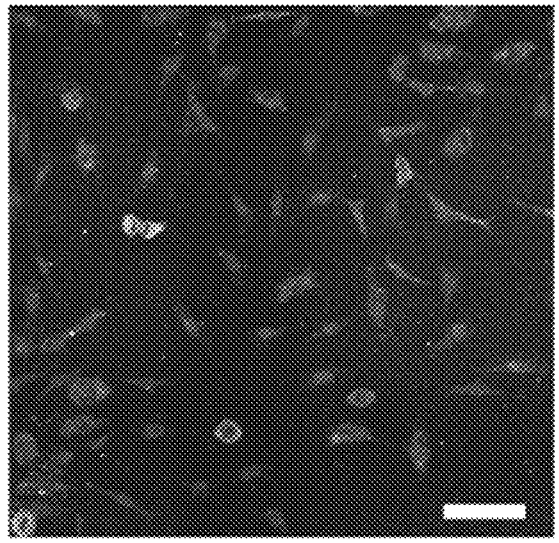
Figure 45E:
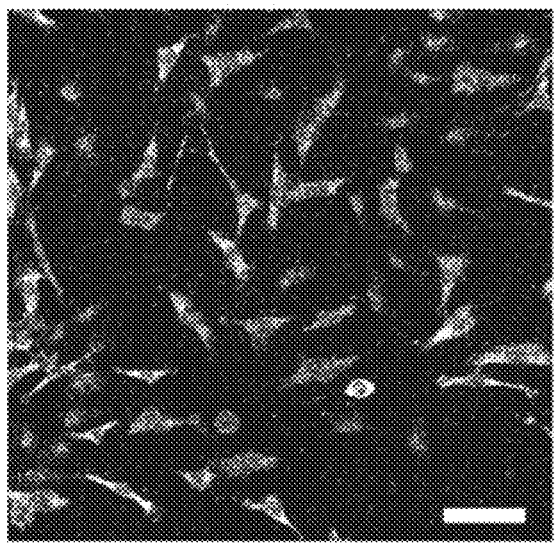

FIGS. 45D and 45E are images of a HeLa and 3T3 co-culture; FIG. 45D is an image of FAM stained HeLa cells, FIG. 45E is an image of cy3 stained 3T3.

Figure 45F:

FIG. 45F is a schematic of the combined RT and handshake nucleic acids, indicating the two primer regions.

Figure 45G:
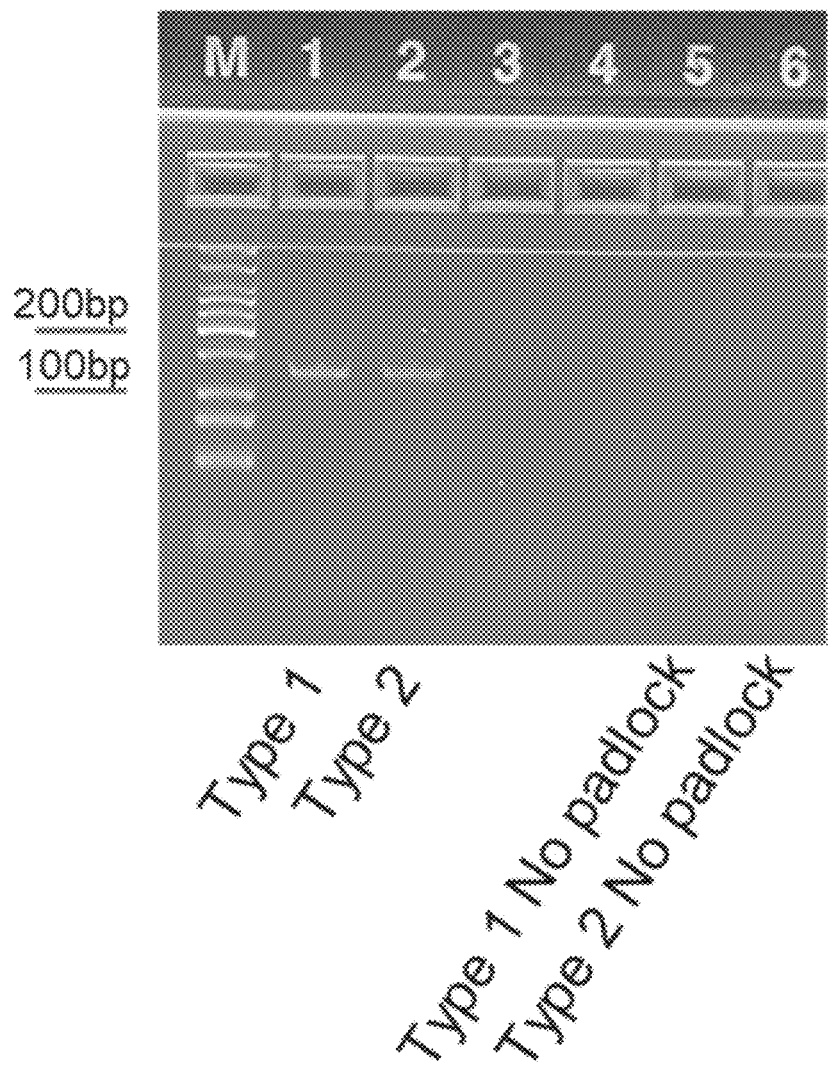

FIG. 45G is an image of an agarose gel, showing similar sized replication products generated by each primer region referenced in FIG. 45F.

Figure 45H:
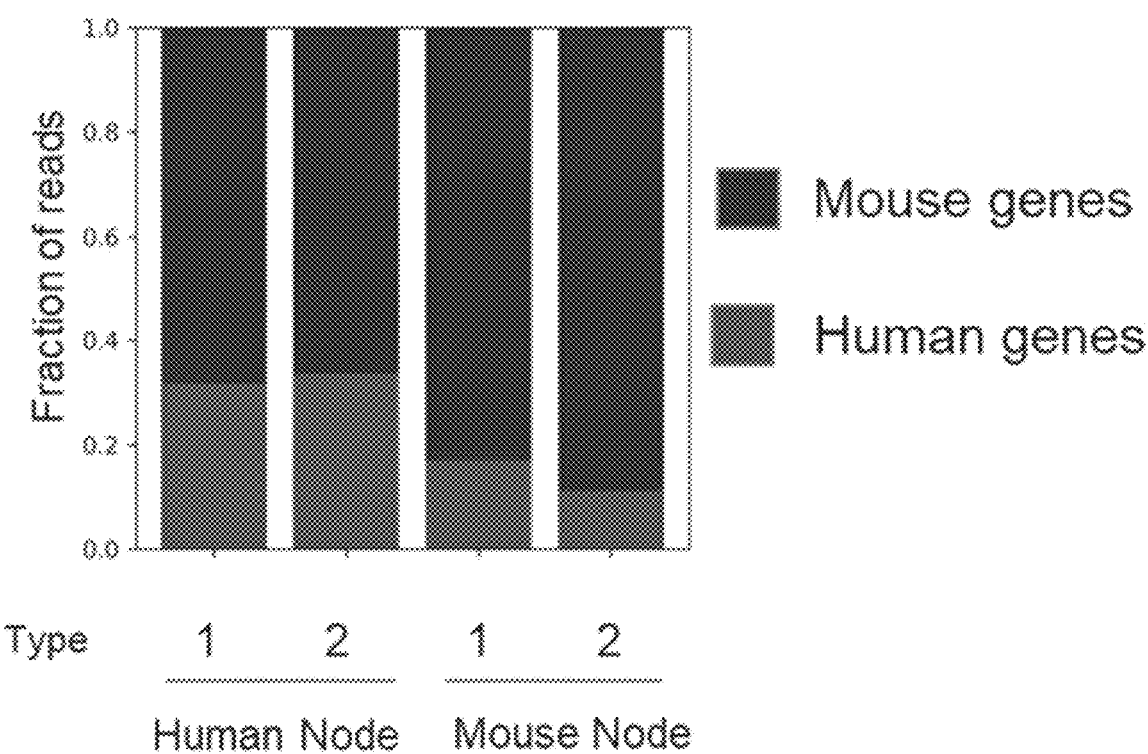

FIG. 45H is a barplot presenting the fraction of cDNA reads that map to human or mouse using human-targeting and mouse-targeting padlock probes.

Figure 45I:
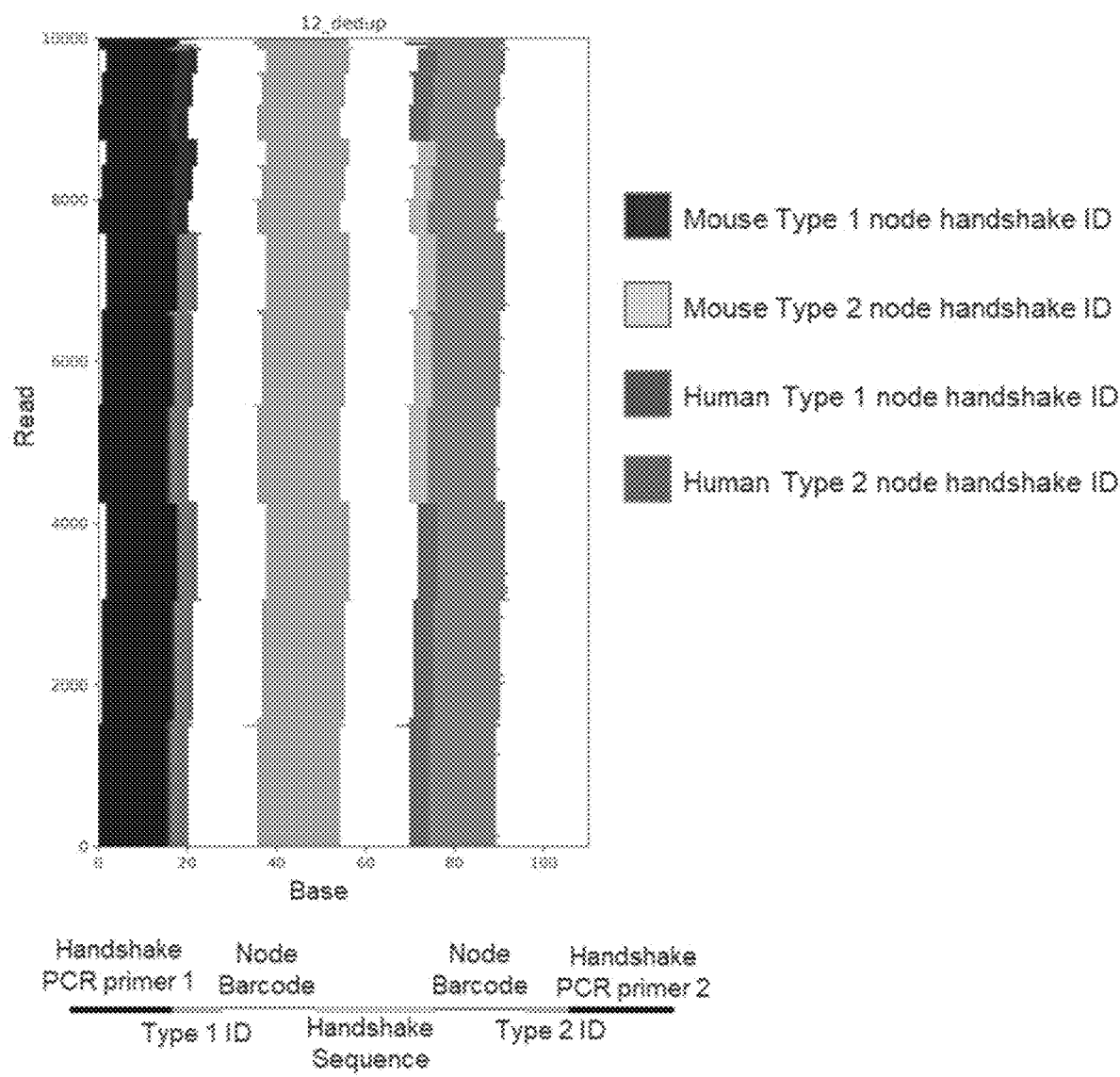

FIG. 45I is a compilation of approximately 10,000 reads of sequences of associations between handshake sequences generated by mouse and human-directed padlock probes.

Figure 46A:
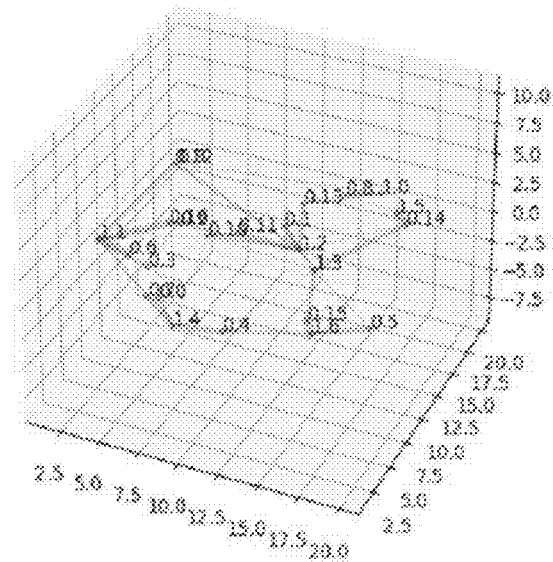
Figure 46B:
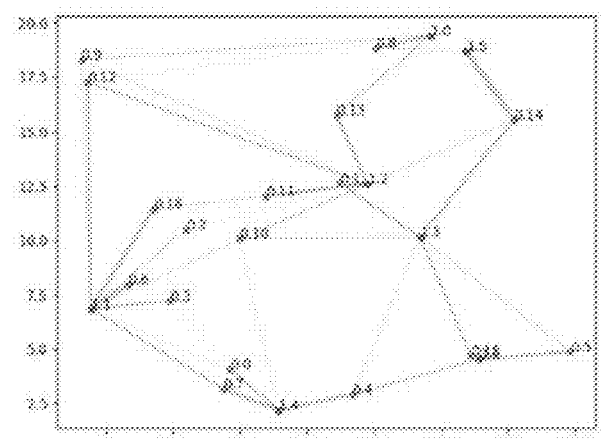
Figure 46C:
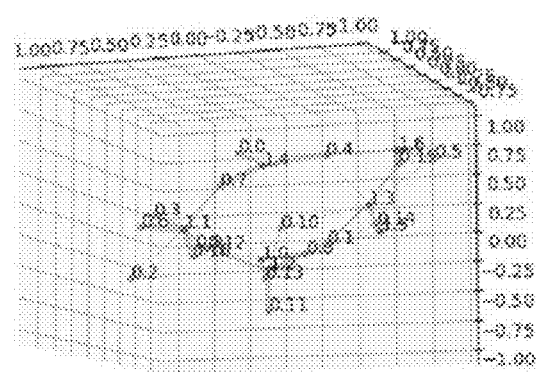
Figure 46D:
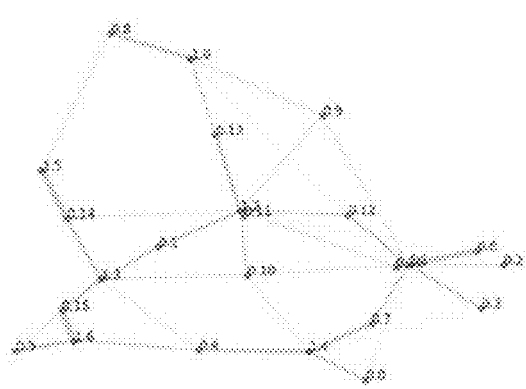
Figure 46E:
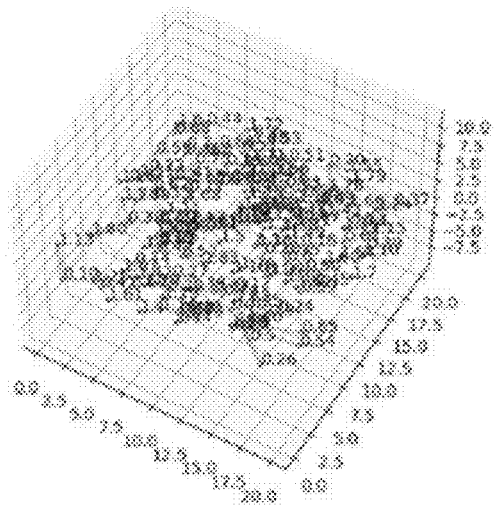
Figure 46F:
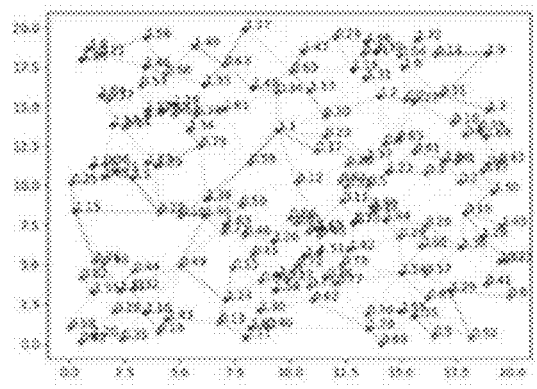
Figure 46G:
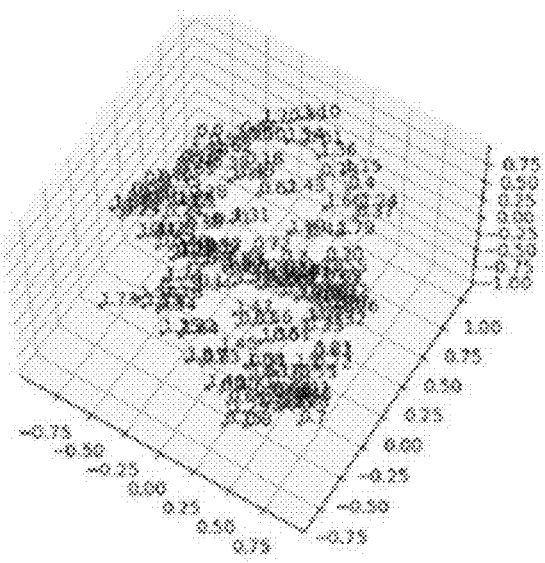
Figure 46H:
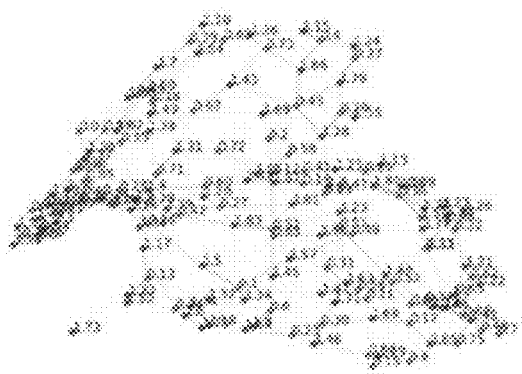
Figure 46I:
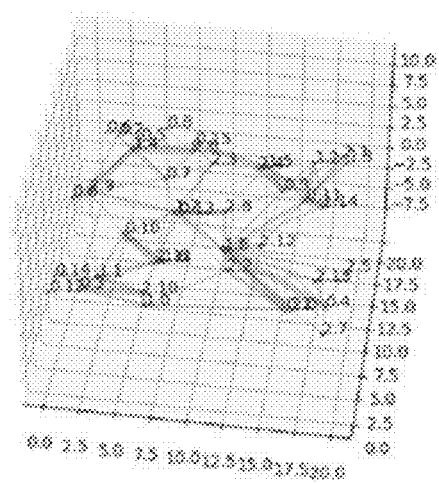
Figure 46J:
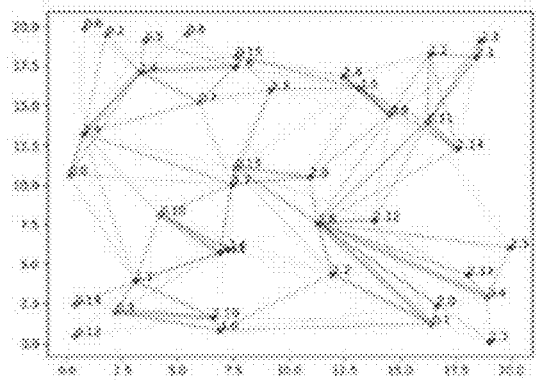
Figure 46K:
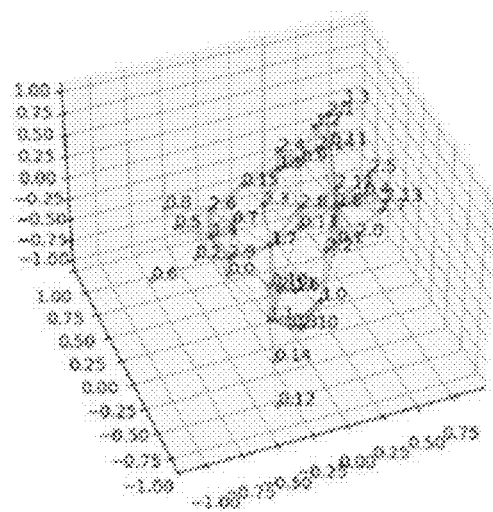
Figure 46L:
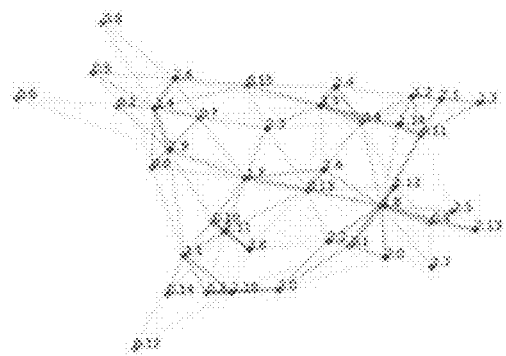
Figure 46M:
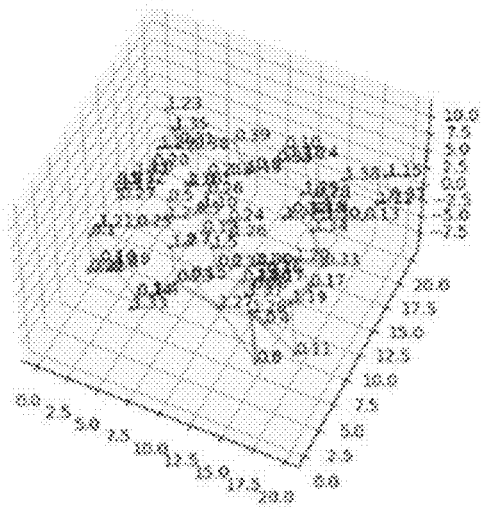
Figure 46N:
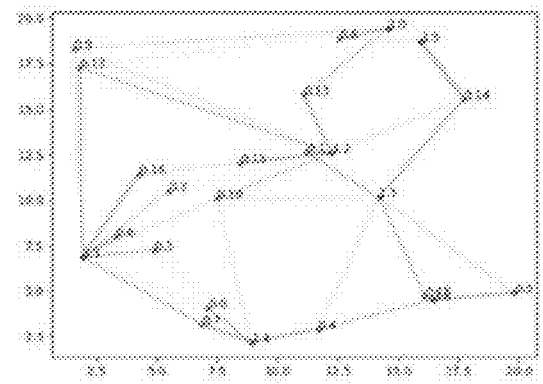
Figure 46O:
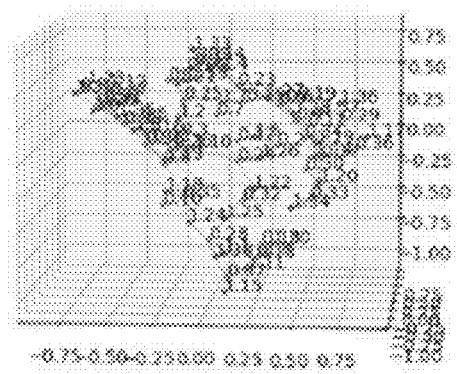
Figure 46P:
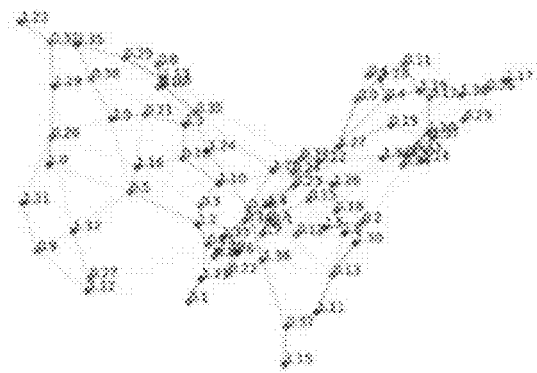
Figure 46Q:
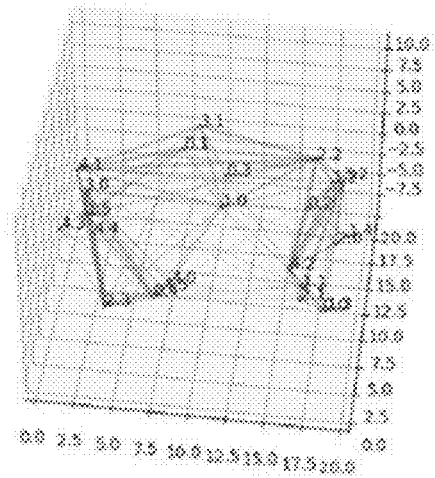
Figure 46R:
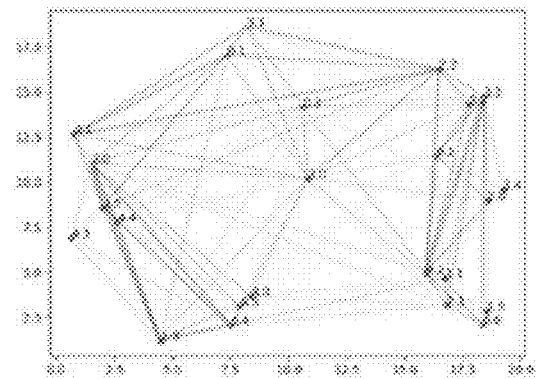
Figure 46S:
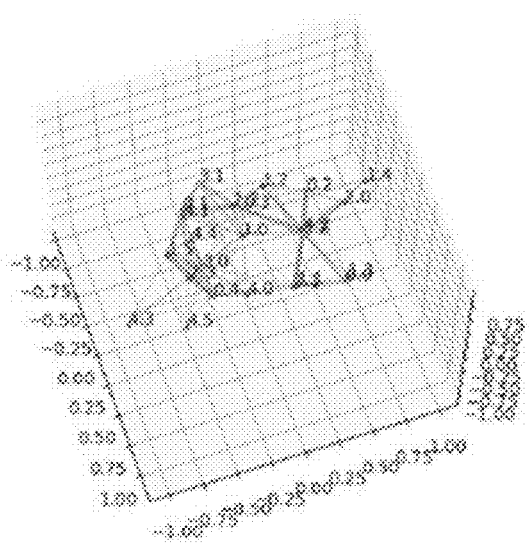
Figure 46T:
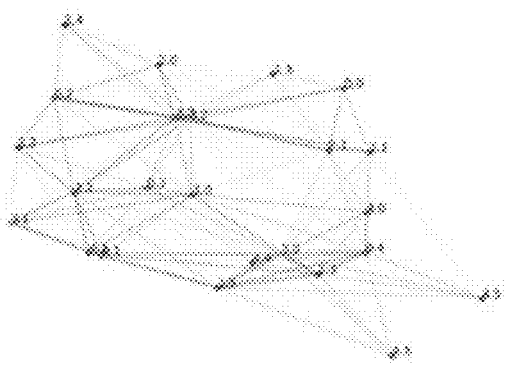

FIGS. 46A-46T are plots of node reconstructions based on simulated barcoding simulations.

DETAILED DESCRIPTION

Provided herein are compositions, devices, methods, and systems for use in proximity coding in a sample. Such processes may incorporate deposition of nucleic acids at node locations. Unique barcodes are generated at the node locations in a sample. Barcodes can diffuse out therefrom, generating clouds of different barcodes. These barcodes can interact with nearby biomolecules to form identifiable sequences that reveal information about the local biomolecular environment of a node. In embodiments wherein barcode clouds overlap, barcodes in the overlapping portions optionally concatenate into unique and identifiable sequences. Analysis of the concatenated barcodes allows for mapping of a particular sequence between individual node locations. Spatial analysis using methods described herein can provide resolution not limited by light diffraction or sample dimension. Spatial analysis is optionally combined with visual selection methods that can directly link multi-dimensional and high-resolution cellular phenotypes (including morphology, protein markers, spatial organization) to transcriptomic, genomic, or proteomic profiles for diverse sample types. Processes described herein are applicable to analysis of cellular states in tissue, in synthetic tissue, in isolated or cultured cells, or in solution. Further described herein are applications of such compositions, systems, and methods for information data storage purposes.

Diffusion Labelling

Figure 1A:
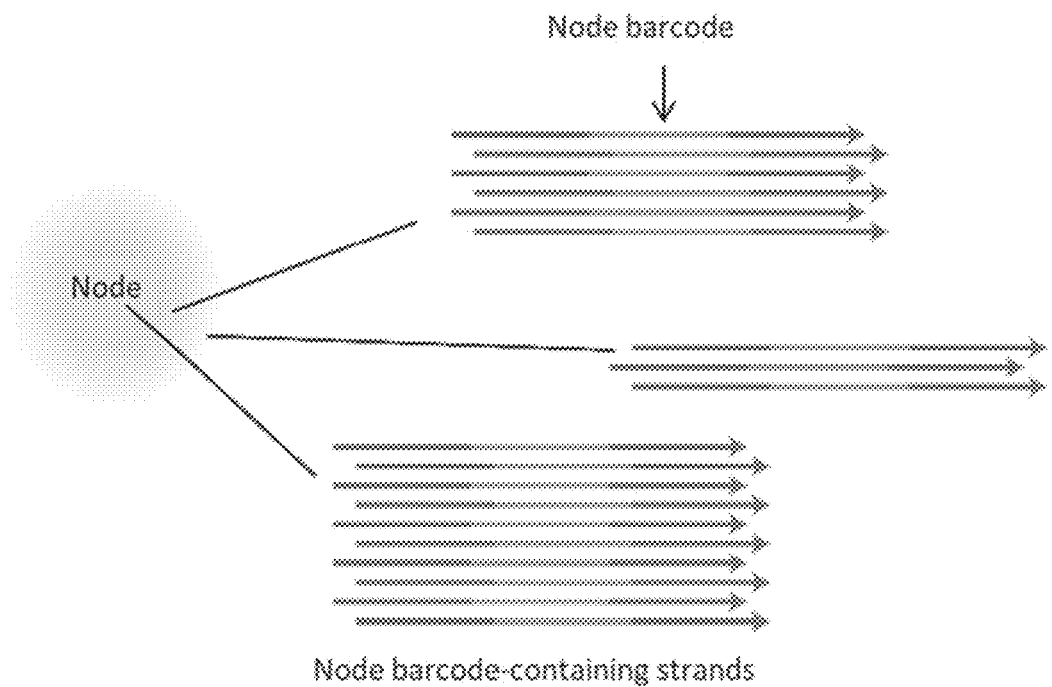
FIG. 1A illustrates a concentration gradient in a diffusion cloud of barcode strands generated from a node.
Figure 1B:
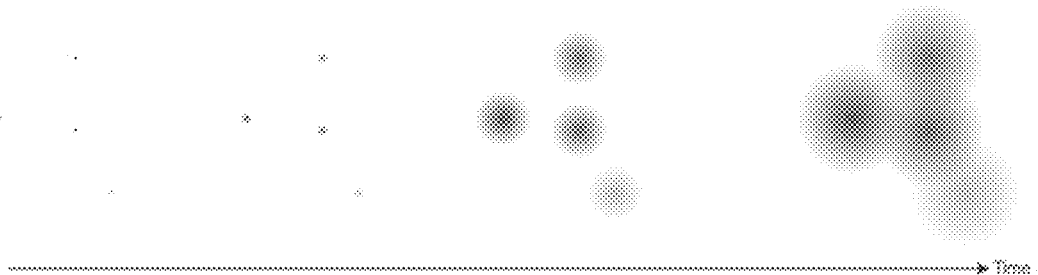
FIG. 1B illustrates expansion of diffusion clouds over time from four separate node locations of barcode generation.
Figure 1C:
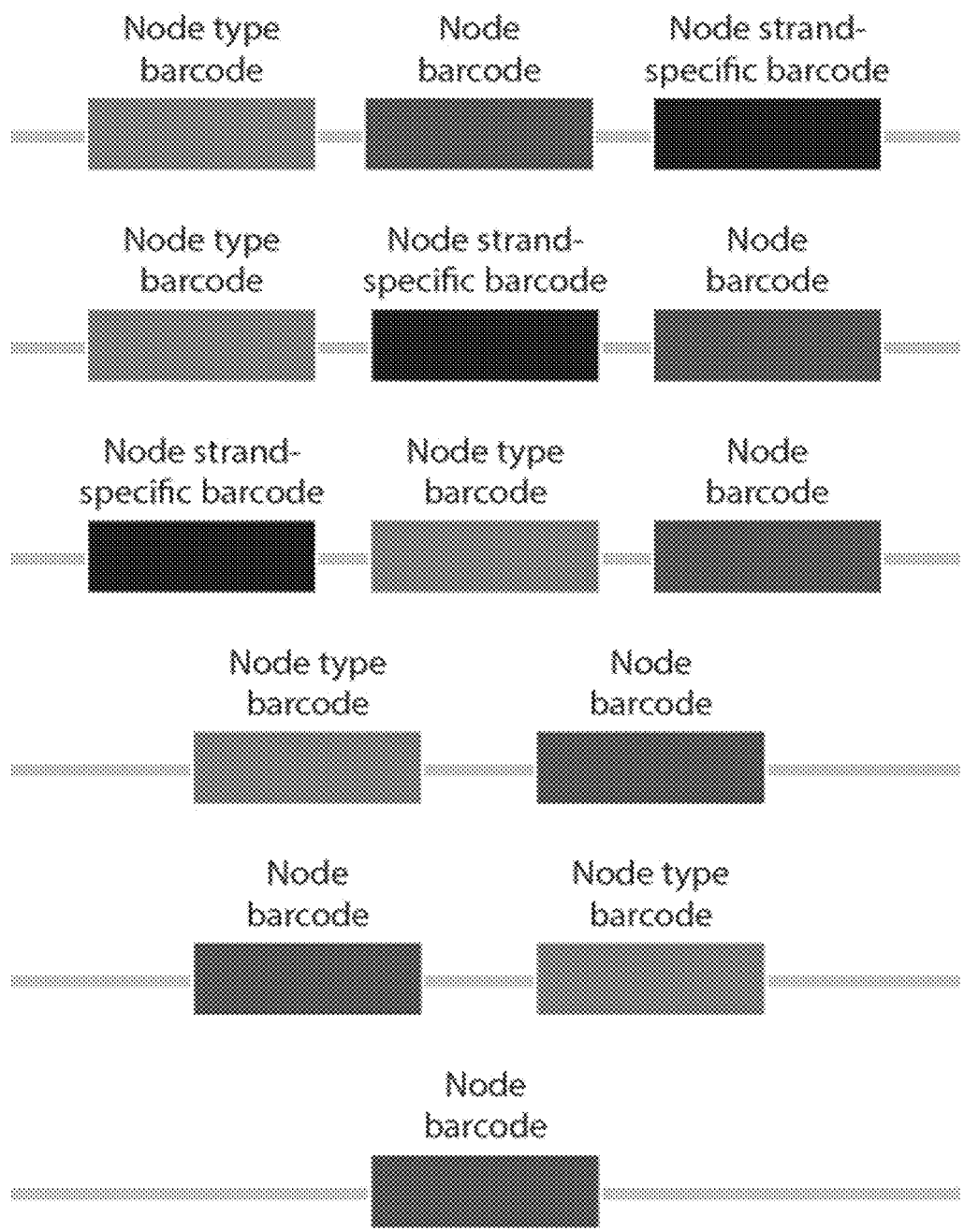
FIG. 1C illustrates possible combinations of barcodes to identify strands generated from node factories, comprising node type barcodes, node barcodes, and unique identifiers.

Provided herein are methods for generation of nucleic acid strands from a template strand, which subsequently diffuse out from a point source, referred herein as a node location. A strand, as used herein, comprises a nucleic acid, or a chain of nucleotides. Interaction between nucleic acids generated from different node locations or with target molecules can provide additional information on the relative proximity of tagged agents. In some embodiments, a node nucleic acid comprises a node barcode. In further embodiments, the node barcode provides information specific to the node location, thereby allowing a downstream means for node location identification. Mechanisms of generation described herein can produce multiple copies of nucleic acid strands comprising a unique barcode. Generated strands can diffuse away from the generation site, creating a diffusion area, or cloud. In some embodiments, the diffusion cloud comprises a concentration gradient around each node. In some embodiments, the concentration of generated node barcode strands decreases as a factor of distance from the generation site. As depicted in FIG. 1A, a node acts as a factory for generation of node barcode strands. In some embodiments, the node factories comprise copies of the node nucleic acids. The copies of node nucleic acids are released from the node factories to diffuse away from the node location. In some embodiments, the node factories comprise a template nucleic acid, comprising a sequence complementary to the node nucleic acid. Copies of the node nucleic acid are generated from the node factory, according to methods described herein, and diffuse away from the node location. As the strands diffuse out from the node, a cloud comprising a concentration gradient is generated. The concentration of node barcode strands at a point in the center of the diffusion cloud will be much higher than the concentration at a point farther out from the center. The lowest concentration of node barcode strands is found on the edge of the cloud. FIG. 1B shows a timeline of diffusion for four node locations. Node barcode strands are generated, either for a set time period or continuously. Over time, the generated strands diffuse away from the node locations, generating diffusion clouds. In some embodiments, diffusion clouds of generated strands are distinct and do not overlap. In some embodiments, diffusion clouds expand to overlap with adjacent diffusion clouds. In some embodiments, node barcode strands are single-stranded. In some embodiments, node barcode strands are double stranded. In some embodiments, node nucleic acids comprise RNA. In some embodiments, node nucleic acids comprise DNA. In some embodiments, each type of node is identifiable by a node type barcode encoded in the template strand. In some embodiment, a node type barcode is consistent across a type of node. In some embodiments, each node is identifiable by a node barcode encoded in the template strand. In some embodiment, a node barcode is specific to an individual node. In some embodiments, each strand produced by a node is identifiable by a unique modifier. In some embodiments, a unique modifier is specific to each nucleic acid strand. Exemplary combinations of identifying sequences are shown in FIG. 1C. Intervening spaces between identifying sequences can comprise nothing, a linker, a primer, a flanking L or R sequence, or a promoter.

Figure 2:
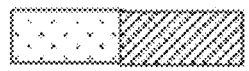
FIG. 2 illustrates exemplary pairwise or multiple concatemers generated from overlapping diffusion clouds.
Figure 2:
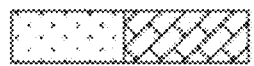
Figure 2:
Figure 2:
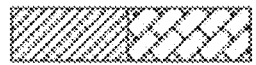
Figure 2:
Figure 2:
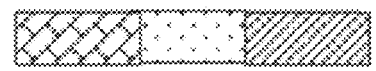
Figure 2:
Figure 3:
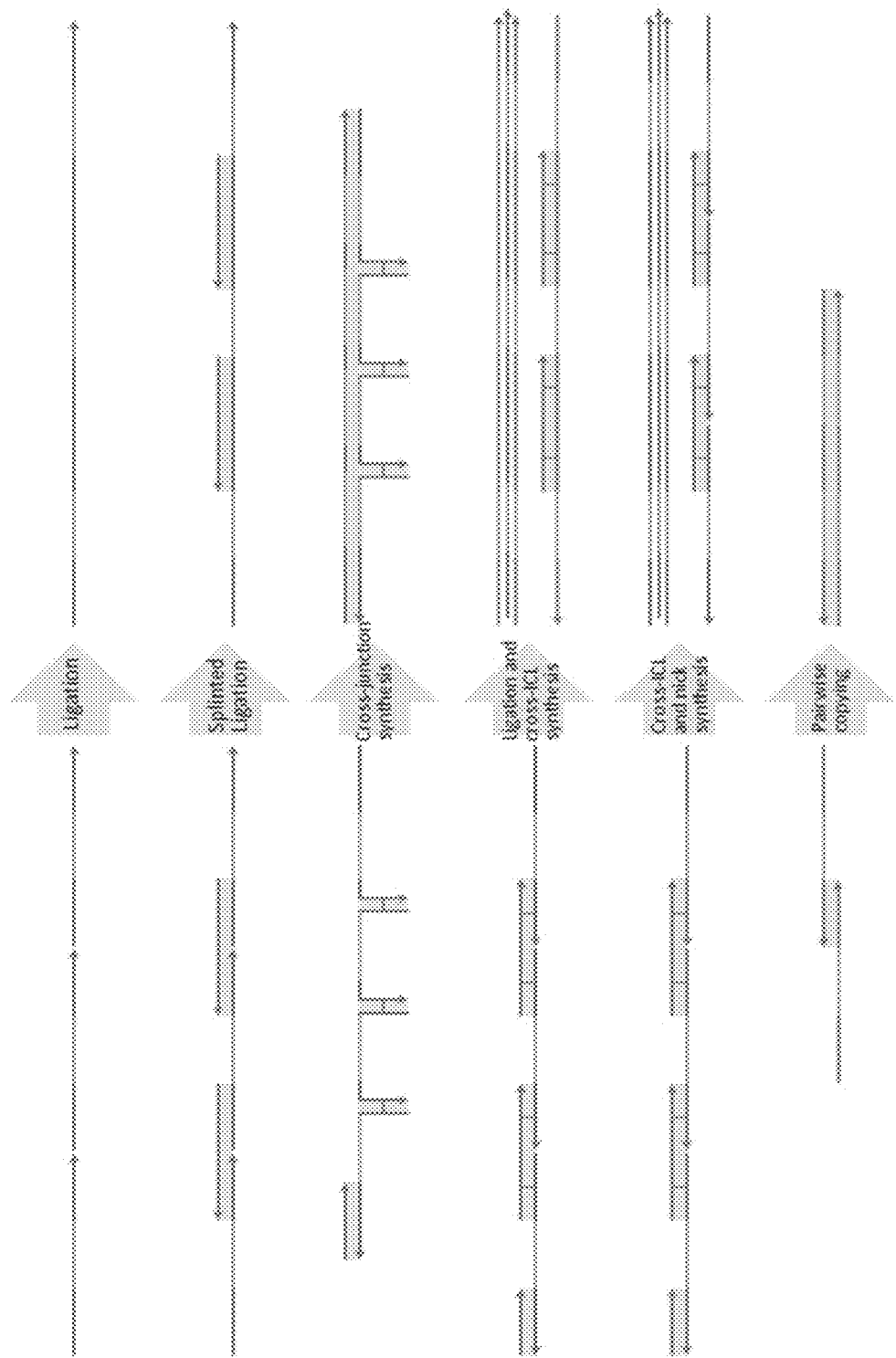
FIG. 3 illustrates representative modes of concatemerization, including ligation, splinted ligation, cross-junction synthesis, ligation and cross-interstrand crosslink (ICL) synthesis, cross-ICL and nick synthesis, and pairwise copying.
Figure 4:
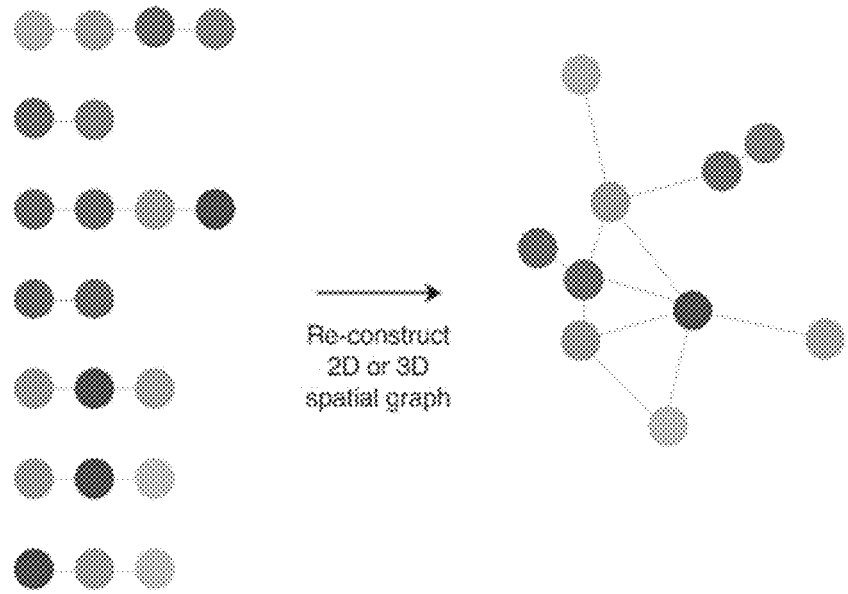
FIG. 4 illustrates reconstruction of the 2D or 3D spatial arrangement of node locations calculated from the concatemerization of node barcodes in overlapping diffusion clouds.

In some embodiments, diffused node barcode strands in the overlapping diffusion clouds are combined by concatenation. As shown in FIG. 2, concatemers can comprise two or more different node barcode strands. Concatenation can be pairwise, or can comprise multiple concatenations. Concatemers of node barcode strands, as shown in FIG. 3, can form by ligation, splinted ligation, cross-junction synthesis, ligation and cross-interstrand crosslink (ICL) synthesis, cross ICL and nick synthesis, pairwise copying, or any combination thereof. In some embodiments, concatenation of barcodes is sequential to node barcode generation. In some embodiments, concatenation of barcodes is simultaneous to node barcode generation. Exemplary reconstruction of relative node locations based on a frequency of node barcodes is shown in FIG. 4. Spatial orientation of node locations is determined through mapping of sequenced concatemers. In some embodiments, a concatemer comprises 2, 3, 4, 5, 6, 7, 8, 9, 10, 20, 30, 40, 50, 60, 70, 80, 90, 100 or more different node barcodes. In some embodiments, the spatial orientation is one dimensional, two dimensional, or three dimensional.

In some embodiments, node barcode strands contain canonical DNA bases, RNA bases, or any combination thereof. Bases may be edited or modified in situ after production, using enzymatic editing or any other means.

Bases may further incorporate modified nucleotides, e.g. dUTP, fluorophore-labeled dNTPs, fluorophore-labeled NTPs, 2'-O-Me NTPs, non-canonical bases, or otherwise modified dNTPs or NTPs).

In some embodiments, the node barcodes comprise a series of random bases (e.g., NNNNN, NNNNNNNNNN, NNNNNNNNNNNNNNN, DDDDDD, DDDDDDDD, HHHHH, HHHHHHHHH, wherein "N" represents bases A, C, G, or T/U; "D" represents bases A, G, or T/U; and "H" represents bases A, C, or T/U) or any combination of random and non-random bases. Node barcodes may be between 1 and 50 nt in length or longer. There may be multiple node barcodes on each node barcode strand. In some embodiments, the node barcode is from about 1 to about 10 nucleotides, from about 10 to about 20 nucleotides, from about 20 to about 30 nucleotides, from about 30 to about 40 nucleotides, from about 40 to about 50 nucleotides, or more than 50 nucleotides. In some embodiments, the node barcodes is about 3 to about 30 nucleotides. In some embodiments, the node barcode comprises a three-letter code.

Node barcode strands comprise a node barcode region. In some embodiments, the node barcode strand further comprises one or more flanking regions, herein designated "L" and "R" regions. In some embodiments, flanking regions comprise PCR primers, strand barcodes, affinity sequences, hybridization sequences complementary to downstream components, or other sequences to enable immobilization. In some embodiments, the affinity sequences comprise additional barcodes, aptamers, DNAzymes, RNAzymes, ISH probes, primers, or any combination thereof. In some embodiments, flanking regions comprise binding sites for fluorophore-labeled oligos.

Flanking regions can be from 1 to about 500 nucleotides. In some embodiments, flanking regions are about 1 to about 50 nucleotides, about 50 to 100 nucleotides, about 100 to about 150 nucleotides, about 150 to about 200 nucleotides, about 200 to about 250 nucleotides, about 250 to about 300 nucleotides, about 300 to about 350 nucleotides, about 350 to about 400 nucleotides, about 400 to about 450 nucleotides, about 450 to about 500 nucleotides. In some embodiments, flanking regions are about 10 to about 40 nucleotides.

In some embodiments, node barcode strands further comprise a unique modifier. A unique modifier comprises universal bases or other base modifications to create heterogeneity in the node barcode strands. A unique modifier can comprise universal bases or other base modifications to create heterogeneity in the node barcode sequences. In some embodiments, each node barcode strand comprises a unique modifier to allow more quantitative measurements. In some embodiments, node barcodes or unique modifiers further comprise targetable sequences for base editing. In some embodiments, node nucleic acids strands are edited using CRISPR techniques. In some embodiments, targetable sequences are modulated over time.

The total length of a node barcode strand can affect characteristics including quality, diffusion rate, diffusion restriction and sequencing efficiency. In some embodiments, the full node barcode strand is about 150 to about 200 nucleotides. In some embodiments, the full node barcode strand is, about 20 to about 50, about 50 to about 100, about 100 to about 150, about 150 to about 200, about 200 to about 250, about 250 to about 300, about 300 to about 350, about 350 to about 400, about 400 to about 450, about 450 to about 500, about 500 to about 550, about 550 to about 600, about 600 to about 700, about 700 to about 800, about 800 to about 900, about 900 to about 1000, about 100 to about 1500, or about 1500 to about 2000 nucleotides in length.

In some embodiments, node nucleic acid strands comprise bases on the 5' or 3' end beyond the complementary template sequence. Additional bases can be added through reaction heterogeneity, enzyme activity, or other means. In some embodiments, T7 RNA polymerase includes from 1 to 3 bases (G) from the end of the promoter sequence on the 5' end of the transcribed RNA strand.

Node Immobilization and Barcode Assembly

Provided herein are methods comprising node immobilization and barcode assembly. In some embodiments, node locations are spatially limited in a sample in order to provide location data. In some embodiments, node locations are transiently fixed in a sample. In some embodiments, node locations are permanently fixed in a sample. In some embodiments, node locations are diffusing in a sample. In some embodiments, node locations are incorporated in an expression system. In some embodiments, the expression system is comprised in a genome. In some embodiments, the genome is a viral genome. In some embodiments, a polymerase is part of the node barcode strand generation mechanism. In some embodiments, the polymerase is a DNA polymerase, an RNA polymerase, an engineered polymerase, a mix of polymerases, or any combination thereof. Polymerases may have strand displacing or no strand displacing activity. Polymerases may have exonuclease or no exonuclease activity. The polymerase may be tethered, hybridized, crosslinked, or photo-crosslinked to a substrate or sample, to or near a promoter or the template strand to localize synthesis to that area. In some embodiments, the template strand or a strand complementary to a domain on the template strand contains additional sequence domains to enable tethering in a sequence-specific manner. In some embodiments, template strands, complementary sequences, promoter, or primer sequences are immobilized in vitro on beads, on surfaces, on slides, into LNP's, AAV's, lentiviruses, other viruses, exosomes, or in situ to a sample. Immobilization can be via attachment, conjugation, or hybridization to targets or substrates or by direct incorporation into the sequences of targets, for example by transposon. The immobilization may be achieved through affinity reactions including hybridization, binding, crosslinking, photo-crosslinking, or any combination thereof. Immobilization methods may be specific to particular subcellular, cellular, cell-type specific, or supercellular structures, such as membranes, mitochondria, proteins, nucleic acids, lipids, protein-protein complexes, protein-RNA complexes, or any combination thereof. In some embodiments, template strands are randomly dispersed throughout a substrate by random binding, non-specific binding, conjugation to a surface, incorporation into a hydrogel, or any other means or combination thereof. In some embodiments, template strands bind multiple targets. In some embodiments, the multiple targets are a general class of molecule, such as, for example, a protein, lipid, or carbohydrate. In some embodiments, the multiple targets are a specific class of molecules, such as, for example, kinases, antibodies, or phospholipids. In some embodiments, the target or multiple targets further bind another set of multiple targets. For example, template strands can be bound to kinases, which in turn bind to ADP or ATP and a substrate. As such, the multiple kinases can bind multiple substrates. In another example, template strands bind ATP, which will bind to multiple kinases. In some embodiments, template strands are focused within a specific area through depositing reagents on a specific region, spatially confined crosslinking, photo-crosslinking, or any other means or combination thereof. Template strands may be cross-linked or photo-crosslinked in place, with optional wash or additional sample preparation steps after attachment or immobilization. Cross-linked template strands may only be photo-crosslinked to specific spatial regions using focused light on particular regions of interest (ROI). In order to accommodate attachment chemistry, one or more template strands may contain extra sequences on the 5' or 3' end, complementary to an immobilized strand. In some embodiments, PCR primer domains are included in the 5' or 3' domains of a template strand and/or primer strand. One or more strands may contain phosphorothioate, 2'O Methyl, inverted dT, or other modifications to protect them from exonuclease activity.

In some embodiments, assembly of the node complex is based on hybridization (e.g. DNA-DNA, DNA-RNA, RNA-RNA, or any variation or combination thereof), immobilization (as described above), or via assembly/strand concatenation methods including ligation, splinted ligation, cross-junction synthesis, ligation and cross-intercrosslink (ICL) synthesis, cross-ICL and nick synthesis, Primer Exchange Reactin (PER), asymmetric PCR, Gibson assembly, transposase-based concatenation (e.g., Tn5 transposition for RNA-DNA hybrids), or any variation or combination thereof.

In some embodiments, a node of nucleic acid generation is attached to a target molecule. A target may be DNA molecules, RNA molecules, proteins, lipids, antibodies, or other molecules that have been conjugated to, hybridized to, crosslinked to, photo-crosslinked to, or directly attached on the same or a different sequence backbone to a nucleic acid strand that has or can be made to have a single-stranded overhang on its 3' or 5' end.

Diffusion from anode can be modulated by adjusting the sample environment, nucleic acid strand length, any other factor affecting diffusion, or any combination thereof. Diffusion in a solution is controlled through modulation of parameters affecting the rate that molecules can move through a solution. Parameters affecting diffusion comprise viscosity, time, temperature, crowding agents, pH, electric field, physical features, or any combination thereof. In some embodiments, diffusion of nucleic acids are modulated by addition of molecular crowding agents. Crowding agents can comprise dextran sulfate, glycerol, polymers, crystals. In some embodiments, diffusion of nucleic acids are enhanced by heating the tissue samples or population of cells provided herein. In some embodiments, diffusion is enhanced by heating to more than 30° C., more than 35° C., more than 40° C., more than 45° C., more than 50° C. In some embodiments, diffusion is enhanced by heating to about 30° C., about 35° C., about 37° C., about 40° C., about 45° C., about 50° C.

In some embodiments, the sample environment is varied in viscosity, crowding agents, fixation, polymerization of reagents in solution, concentration of reagents within solution, attachment of molecules to scaffolds endogenous to the sample, attachment of molecules to externally introduced scaffolds, or any other method to affect diffusion, immobilization, or mobility within the sample. In some embodiments, a node is embedded in a substrate or medium. Viscosity of a sample can be modulated, for example with a hydrogel or any excipient that increases the poise measure of the environment. In some embodiments, the sample medium has a viscosity greater than 1 centipoise (cP). In some embodiments, the sample medium has a viscosity of from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP. Crowding agents comprise, in some embodiments, dextran sulfate, glycerol, polymers, crystals, or any combination thereof. Sample fixation can be done by heating, microwaving, cryopreservation, or chemical means. Chemical fixation comprises crosslinking fixatives, such as aldehydes, including formaldehyde or glutaraldehyde; precipitating fixatives, such as alcohols, including ethanol, methanol, or acetone; oxidizing agents, such as osmium tetroxide, potassium dichromate, chromic acid, and potassium permanganate; mercurials, such as B-5 and Zenker's fixative; picrates; or hepes-glutamic acid buffer-mediated organic solvent protection effect (HOPE) fixative. In some embodiments, the sample is crystallized, for example by silver fixation. In some embodiments, a node is attached to a sample substrate using any of the methods described herein.

In some embodiments, diffusion is modified by modulating features including reaction time, temperature, chemistry, electromagnetic forces, or adapting physical features. Physical features can include subcellular, cellular, or supercellular structures, or incorporating physical features to block, inhibit, or bind node barcode strands. In some embodiments, samples are protected from physical disturbance during barcode node generation. In some embodiments, barcode generation is performed on an isolation platform, to minimize vibration or disturbance. In some embodiments, nucleases such RNase, DNase, exonucleases, or endonucleases, are used to limit the distance that node nucleic acids diffuse. In some embodiments, node nucleic acids are tethered to a long scaffold, which restricts the distance that they can diffuse. In some embodiments, the concatemer can be tethered to a Rolling Circle Amplification complex as it is being elongated. In some embodiments, a concatemer growing out from a point source can be used to produce extendable ends that can flexibly bind to biomolecules in their vicinity without freely diffusing as individual strands in solution. In some embodiments, diffusion is initiated by a modulating feature. In some embodiments, diffusion is initiated before, during, or after addition of node nucleic acids. In some embodiments, diffusion in stopped by a modulating feature. In some embodiments, diffusion is stopped before, during, or after addition of node nucleic acids.

In some embodiments, targets may diffuse toward nodes. In some embodiments, a sample comprises fixed nodes and diffusing targets. In some embodiments, a sample comprises a mixed population of nodes, wherein a subpopulation of nodes generate diffusion products and another subpopulation of nodes generate fixed nucleic acids.

In some embodiments, node nucleic acid strands comprise one or more photolabile protecting groups. Such provision for light activation, or "photocaging", provides for controlled initiation of node nucleic acid production. Synthesis can be time-delimited. In some embodiments, photocaging allows for spatial control of node nucleic acid strand generation. In some embodiments, photocaging is controlled with targeted light microscopy. Without limitation, photolabile protecting groups include (2-nitropheynyl)ethyl groups, 2-nitrobenzyl-based groups, carbonyl-based groups, benzyl-based groups, coumarin-based groups, borondipyrromethene (BODIPY)-based groups, cyanine-based groups, ortho-nitrobenzyl (NB)-based groups, or any variation or combination thereof.

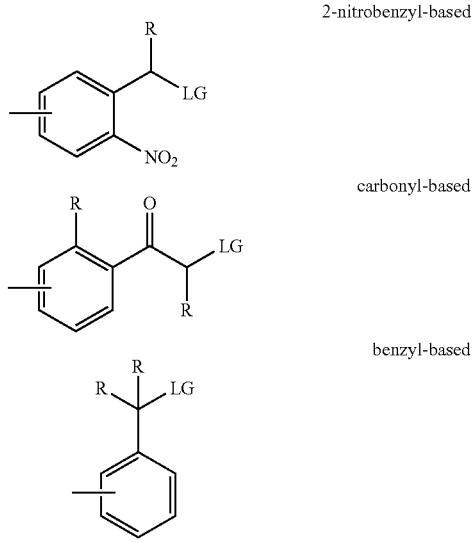

Figure 5A:
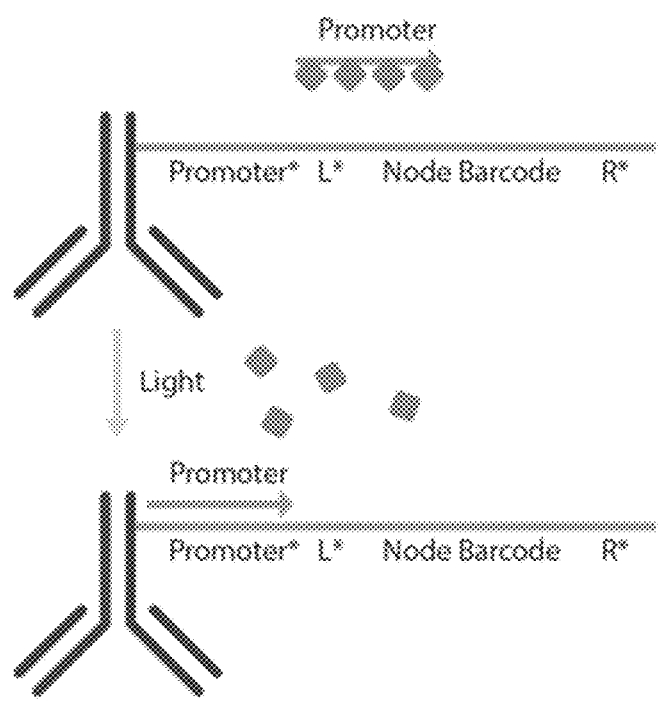
FIG. 5A illustrates activation of node barcode generation with a promoter protected with photo-caging groups.

In some embodiments, a promoter sequence comprises photocaging protecting groups. With light activation, the promoter binds the template strand, allowing replication to proceed. FIG. 5A shows an exemplary embodiment wherein a template node barcode strand is fixed to a sample via a conjugated binding moiety. A promoter protected with photolabile protecting groups is added to the sample. Concurrently or subsequent to addition of the promoter, the sample is exposed to light, releasing the photolabile protecting groups, allowing hybridization of the promoter to the complementary sequence to initial replication.

In some embodiments, sequences comprise a photo-crosslinker, providing for light-controlled synthesis. In some embodiments, activation of a photo-crosslinking agent induces or increases synthesis. In some embodiments, activation of a photo-crosslinking agent reduces or stops synthesis. Exemplary photo-crosslinking agents include, aryl azides, azido-methyl-coumarins, benzophenones, anthraquinones, certain diazo compounds, diazirines, psoralen derivatives, or any combination thereof. In some embodiments, the photo-crosslinking agent is 3-cyanovinylcarbazole nucleoside (CNVK).

Figure 5B:
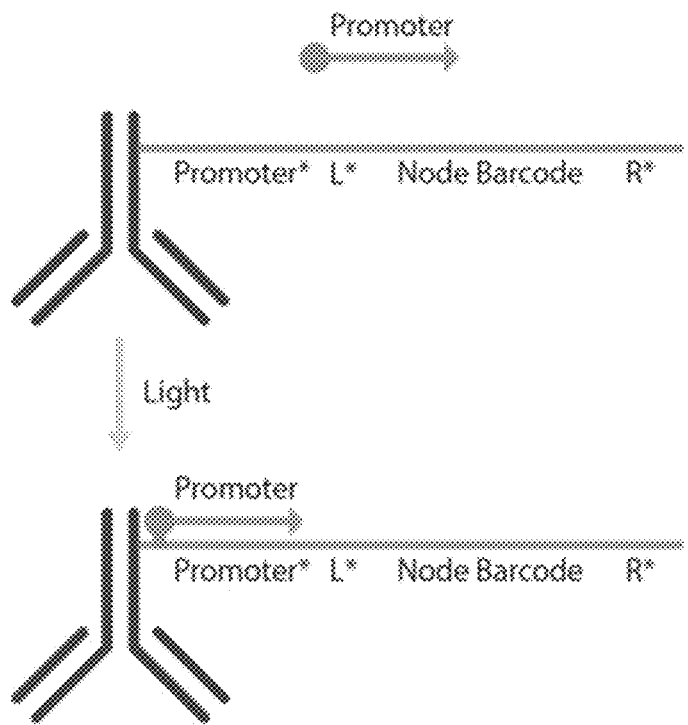
FIG. 5B illustrates activation of node barcode generation using a photo-crosslinked promoter.

In some embodiments, a promoter comprises a photo-crosslinking agent. FIG. 5B shows an exemplary embodiment wherein a promoter sequence comprises a CNVK group. Concurrently or subsequent to addition of the promoter, the sample is exposed to light, cross-linking the promoter to the complementary region of the template strand.

In some embodiments, generation of node nucleic acid strands is modulated over time using one or more methods, alone or in any combination, of time tracking or gating of node nucleic acid strand production. NTPs and/or dNTPs that degrade can be used in lieu of or in combination with standard NTPs/dNTPs. Incorporation of hot start NTPs and/or dNTPs allows for modulation or monitoring through temperature control. Addition of base editing enzymes or mutagens provides for mutation of node barcodes and unique modifiers over time.

In some embodiments, sample or substrate temperature is modulated during production of the node barcode strands. The temperature may be held constant, or it may be cycled, e.g., between 12° C. and 42° C., between 4° C. and 95° C., or any temperature in between. Temperature modulation may be by any means, such as PCR machines, flat top incubators, water baths, Piezo devices, heating chambers around a microscope, flowing of heated buffer across the sample or substrate, or any other means or combination thereof.

Node Barcode Strand Composition

In addition to node barcode regions, node barcode strands can comprise further domains, modifications, or other additions. Such elements can direct strand generation, provide for immobilization of template nucleic acid strands or provide for spatial identification thereof. In some embodiments, node locations in a sample may comprise one or more nucleic acid strands. Node locations may be immobilized on a substrate, in a substrate, or in a sample. In some embodiments, a node location comprises a template nucleic acid strand on which a polymerase can generate copies of node barcode strands. In some embodiments, the generated node barcode strands diffuse away from the node location.

Figure 6:
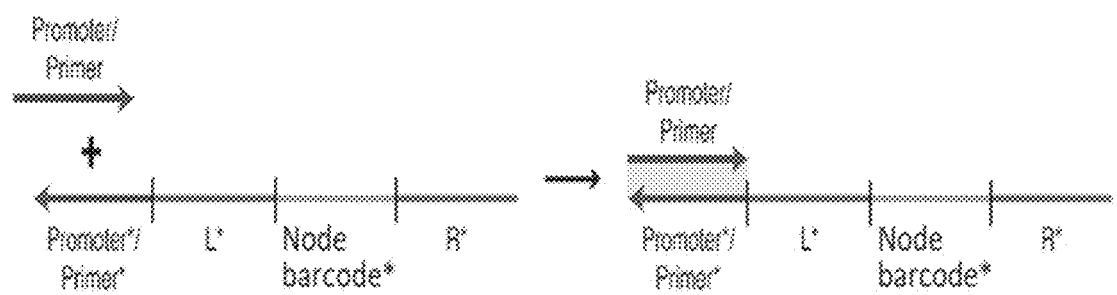
FIG. 6 illustrates binding of a promoter or primer to a template node barcode strand.

As shown in FIG. 6, the template nucleic acid strand encodes a promoter/primer hybridization region ("Promoter*/Primer*"), left and right flanking regions ("L*" and "R*"), and a node barcode region (Node barcode*). In some embodiments, a primer hybridizes to the hybridization region on the template strand and a polymerase drives extension of the node barcode strand. In some embodiments, synthesis may be enabled by a promoter region and transcription. In some embodiments, synthesis may depend on another enzyme to start de novo synthesis on the template strand.

One or more of the template strands in the node complex may comprise additional domains or modifications. In some embodiments, additional domains or modifications may facilitate immobilization in or on a substrate or in a sample. In some embodiments, additional domains or modification are used for spatial identification. In some embodiments, template strands further comprise biotin, antibodies, fluorophores, dyes, aptamers, probes, barcodes, or any combination thereof. In some embodiments, additions or modifications are intercalated into the template strand.

Figure 7:
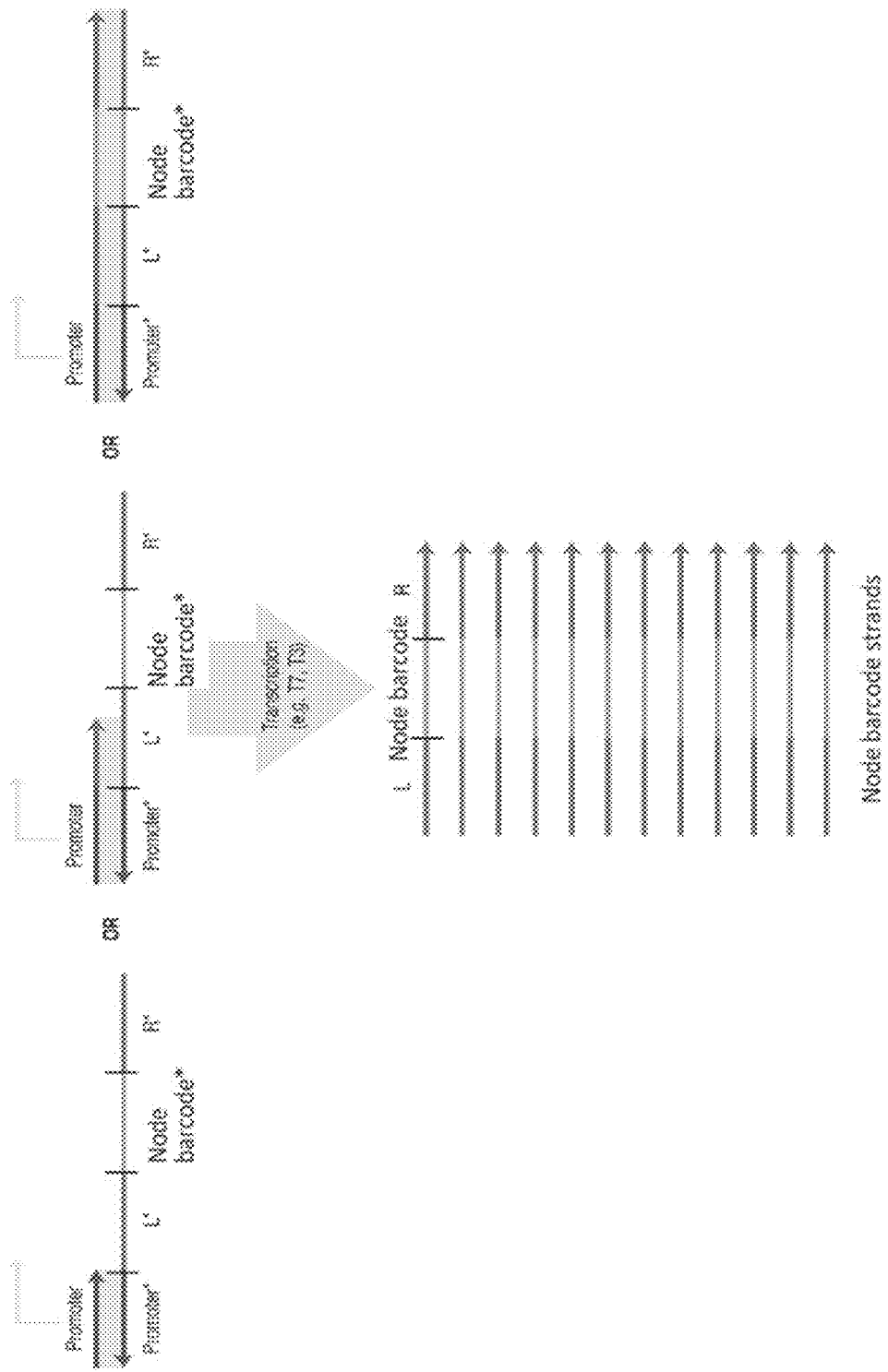
FIG. 7 illustrates amplification of a template node barcode strand comprising a promoter region.
Figure 8:
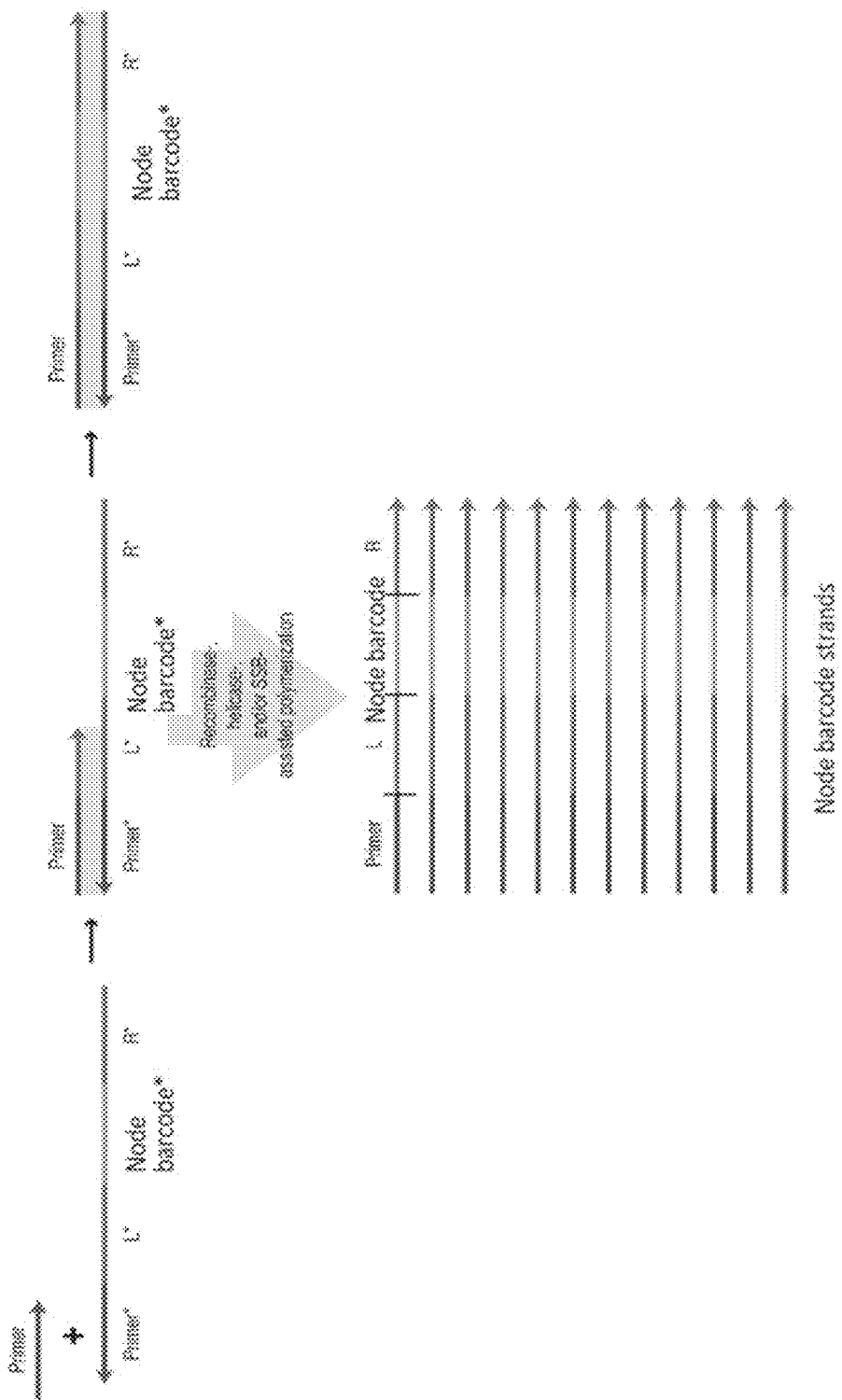
FIG. 8 illustrates amplification of a node barcode strand comprising a primer.

In some embodiments, node barcode strands are produced from a template strand comprising a promoter site ("Promoter*" on template strands in FIG. 7). A promoter is a specific regulatory DNA sequence found upstream to the transcription initiation site. Promoters control gene transcription by providing binding sites for RNA polymerase and other transcription factors. As shown in FIG. 7, in some embodiments, the promoter region is upstream of any functional regions of the node barcode template. In some embodiments, the promoter region comprises one or more functional regions of the node barcode template, or up to the entire length of the node barcode template. In some embodiments, the template strand forms a secondary structure. In some embodiments, the secondary structure is a hairpin. Transcription of the template strand is effected with a polymerase. In some embodiments, the polymerase is a DNA polymerase. In some embodiments, the DNA polymerase comprises Phi29, Pol I, Pol II, Pol III, Pol IV, Pol V, T4, Phusion®, Taq ligase, Klenow fragment, Bsm, Bst, reverse transcriptase, or any combination thereof. In some embodiments, the polymerase is an RNA polymerase. In some embodiments, the RNA polymerase comprises T7, T3, SP6, or any combination thereof. In some embodiments, a polymerase comprises exonuclease activity, degrading an encountered downstream strand via 5' to 3' exonuclease activity. In some embodiments, a node barcode sequence is flanked by additional sequences (e.g., L and R domains) that accommodate the downstream chemistry for target proximity and node barcode proximity recording.

Figure 9:
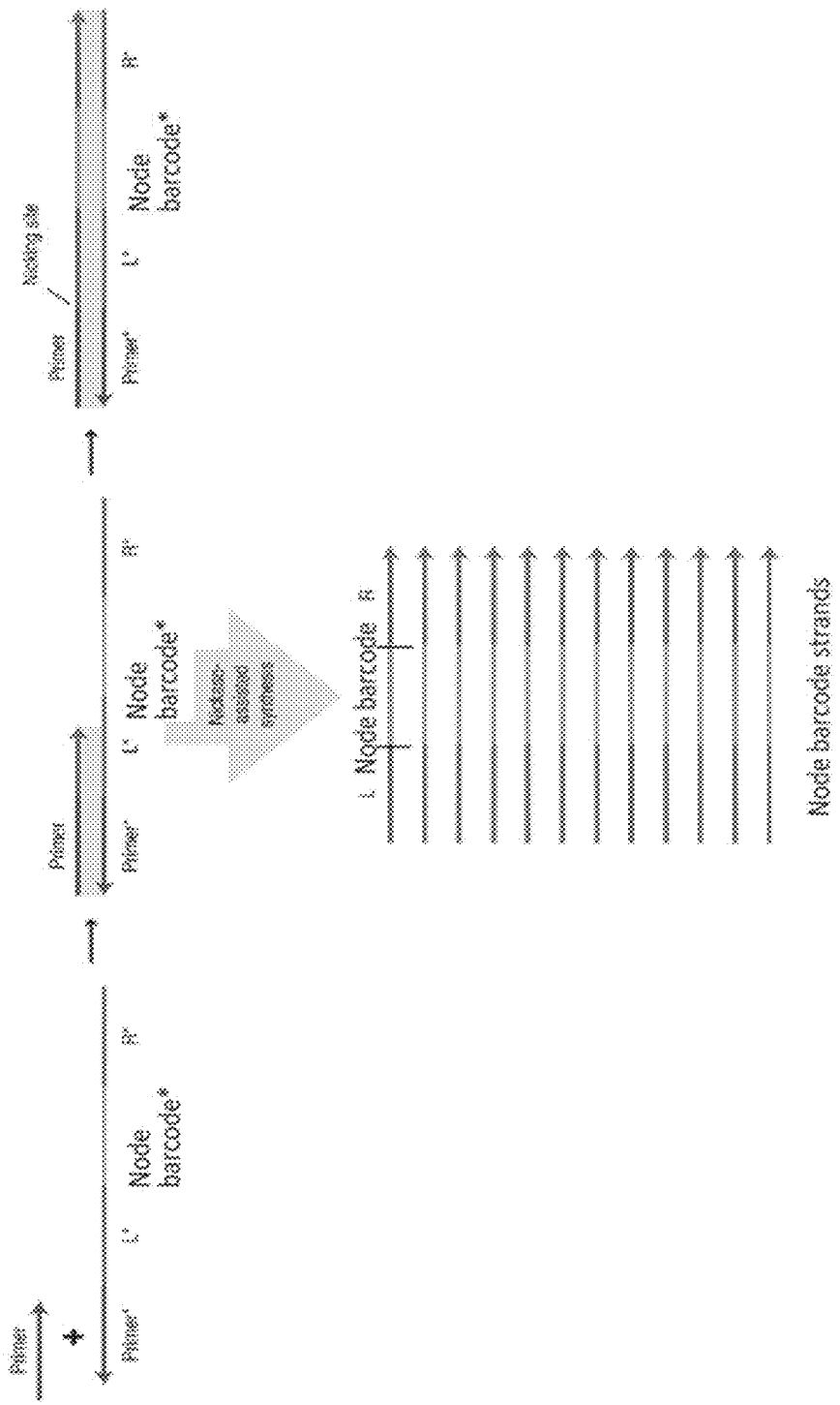
FIG. 9 illustrates amplification of a node barcode strand comprising a primer and a nicking site.

In some embodiments, methods of generation of node barcode strands comprise use of primers that bind to template strands and are extended by a one or more polymerases to create copies of the template strand. In some embodiments, a primer is a short nucleotide sequence for amplification of target DNA. Primers serve as a starting sequence for new strand synthesis. In some embodiments, generation is enabled by additional enzymes such as recombinases, helicases, single-stranded binding proteins, or nickases. FIG. 9 illustrates an exemplary amplification of template node nucleic acids using a primer that hybridizes to a complementary region of the template strand. In some embodiments, the primer region is upstream of any functional regions of the node barcode template. In some embodiments, the primer region comprises one or more functional regions of the node barcode template, or up to the entire length of the node barcode template. The strand is extended with a DNA or RNA polymerase. In some embodiments, the polymerase comprises a recombinase, a helicase, SSB-assisted polymerization, or any variation or combination thereof. FIG. 9 illustrates an exemplary amplification of template node nucleic acids utilizing nickase-assisted synthesis. A primer hybridizes to a complementary region of the template strand. In some embodiments, the primer binds to another region on the template strand and forms a secondary structure. In some embodiments, the secondary structure is a hairpin. During or after strand extension, a nickase introduces a single-stranded cut in the extended strand. In some embodiments, the nickase is a Cas9 or any variation thereof. In some embodiments, the polymerase comprises a recombinase, a helicase, SSB-assisted polymerization, or any variation or combination thereof. In some embodiments, amplification is effected by rolling circle amplification (RCA), strand-displacement amplification (SDA), Nicking Enzyme Amplification Reaction (NEAR), exponential amplification reaction (EXPAR), enzymatic oligonucleotide synthesis via internal inosine modification and exonuclease V, nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), primer exchange reaction (PER), or any variation or combination thereof. In some embodiments, the polymerase comprises a strand-displacing polymerase comprising Phi29, Bst polymerase, or any combination or variation thereof.

Methods of amplification described herein are interchangeable and stackable. In some embodiments, amplification products from a described amplification are used as a template in a subsequent round of amplification by the same or different method. In some embodiments, amplification productions from one method are concurrently amplified by another method. In some embodiments, the same method of amplification is used in multiple rounds.

Rolling Circle Amplification

Rolling circle amplification (RCA) is a method of generating multiple copies of a nucleic acid in a continuous strand from a circular template. RCA amplifies a template nucleic acid into a long and repeated single-stranded oligonucleotide. In general, RCA comprises formation of a circular template nucleic acid. In some embodiments, a template nucleic acid, or padlock probe, is annealed with a ligation template, or nucleic acid splint. In some embodiments, the splint and the template nucleic acid comprise DNA or RNA. The template nucleic acid is circularized using a ligase. In some embodiments, the ligase comprises T4 ligase, CircLigase®, Ampligase®, SplintR® Ligase, or any combination thereof. In some embodiments, a primer sequence, a polymerase, and deoxynucleotide triphosphates (dNTPs) are incubated with the template nucleic acid to generate a concatemer of single stranded DNA comprising repeat copies complementary to the circular template. In some embodiments, the polymerase comprises Phi29, Bst, Vent exo-DNA polymerase, or T7 RNA polymerase.

In some embodiments, the nucleic acid comprising the splint sequence is a region of a nucleic acid in a sample. In some embodiments, the splint sequence is a region of genomic DNA, mRNA, cDNA, or other nucleic acid in a sample. In some embodiments, the splint sequence is on mRNA encoding a gene. In some embodiments, the splint sequence is a regulatory RNA. In some embodiments, the splint sequence is circular RNA (circRNA), ribosomal RNA (rRNA), 16S ribosomal RNA (16S rRNA), transfer RNA (tRNA), small nucleolar RNA (snoRNA), small nuclear RNA (snRNA), a non-coding RNA, long non-coding RNA (lncRNA), or microRNA (miRNA).

Hybridizing to a nucleic acid in a sample allows for node factory deposition at a fixed location. In some embodiments, the padlock probe hybridizes to a splint sequence at a fixed location in a sample. In some embodiments, the splint sequence is located on a surface, in a cell, in a nucleus, or in a tissue. In this context, the splint sequence acts as an anchor or tether for the RCA machinery. In some embodiments, the padlock probe hybridizes to a splint sequence on a nucleic acid encoding a gene in a sample.

In some embodiments, RCA generates at least 10, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000 copies of the template.

In some embodiments, a ligation template or splint is conjugated to a surface, a protein, a small molecule, a nucleic acid, a lipid or any combination thereof. In some embodiments, a surface comprises glass, a bead, a microwell plate, a scaffold, or another substrate. In some embodiments, the protein comprises a receptor, a ligand, an antibody, or any functional fragment thereof.

In some embodiments, a concatemer generated by a node factory provides extendable ends that flexibly bind to biomolecules in their vicinity. The "tethered" generated end of an RCA concatemer diffuses locally in a sample rather than diffusing freely.

RCA templates can further encode for restriction sites, allowing for endonuclease cleavage of generated concatemers. In some embodiments, a restriction site is encoded on the RCA template. In some embodiments, a single-strand-specific nuclease cleaves a nucleic acid at a single-stranded restriction site. In some embodiments, the template encodes a recognition site for a double-stranded nuclease, wherein a nuclease makes a double stranded cut at a recognition site. In some embodiments, oligonucleotides comprising a complementary sequence to the region encoding the recognition sequence are deposited on the concatemer and allowed to hybridize to the nucleic acid. In some embodiments, the endonuclease is then added to the concatemer to make a double-stranded cut at the restriction site. In some embodiments, an endonuclease can be added concurrently with an RCA polymerase. In some embodiments, RCA occurs at the same time as digestion. In some embodiments, the concatemer forms a secondary hairpin structure comprising the region of the recognition sequence, thereby providing a double-stranded region for the endonuclease cleavage. In some embodiments, a double-strand specific endonuclease makes a single-stranded cut in a double stranded sequence. In some embodiments, the concatemer forms a secondary hairpin structure comprising the region of the recognition sequence, thereby providing a double-stranded region for the endonuclease cleavage. In some embodiments, a double-stranded restriction enzyme cuts across a single base pair, generating blunt ends. In some embodiments, a double-stranded restriction makes a staggered cut across different base pairs generating sticky ends. In some embodiments, the cleavage is performed by a DNAzyme, RNAzyme, or CRISPR endonuclease, for cleavage of concatemers.

Figure 10:
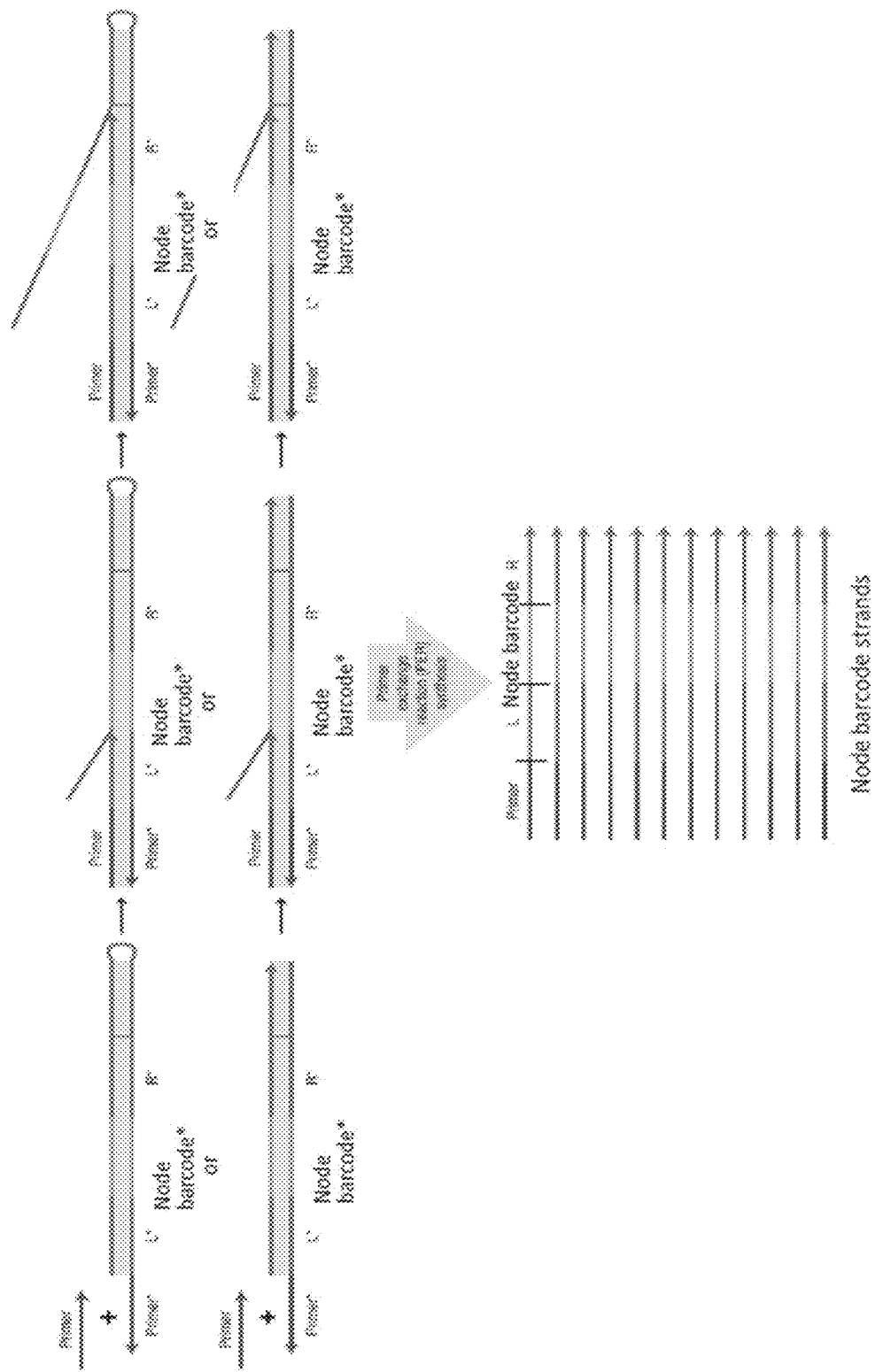
FIG. 10 illustrates amplification of a node barcode strand by Primer Exchange Reaction (PER).

In some embodiments, a Primer Exchange Reaction (PER) is used to generate single-stranded barcode node strands. Hairpin oligonucleotides or double-stranded constructs are used to template stepwise synthesis of single-stranded DNA. As shown in FIG. 10, primers bind to short 3' overhangs on hairpins and get extended by a strand displacing polymerase until a 'stopper' is reached. The stopper is any modification on the template strand that halts progression of the polymerase. Three-way branch migration, mediated by random breathing of DNA strands, results in a newly-synthesized product displaced off of the hairpin or double-stranded construct. The new strand can then dissociate from the template. Multiple hairpins or constructs can be included to template multiple synthesis steps. In some embodiments, a hairpin or double-stranded template comprises a 3' overhang. In some embodiments, single-stranded barcode strands are generated using asymmetric PCR, or any strategy that creates self-replicating nucleic acids. Some methods described herein comprise additional enzymes or the use of PER with strand-displacing polymerases, thereby preclude use of high temperature denaturation steps during synthesis of node barcode strands.

Nucleic acids are generated by methods described herein. In some embodiments, nucleic acids are generated by an isothermal reaction. In some embodiments, addition of nucleotides does not require thermocycling. In some embodiments, synthesis comprises thermal cycling. In some embodiments, synthesis of nucleic acids comprises replication or transcription. In some embodiments, methods of synthesis comprise cross-junction synthesis.

Figure 11:
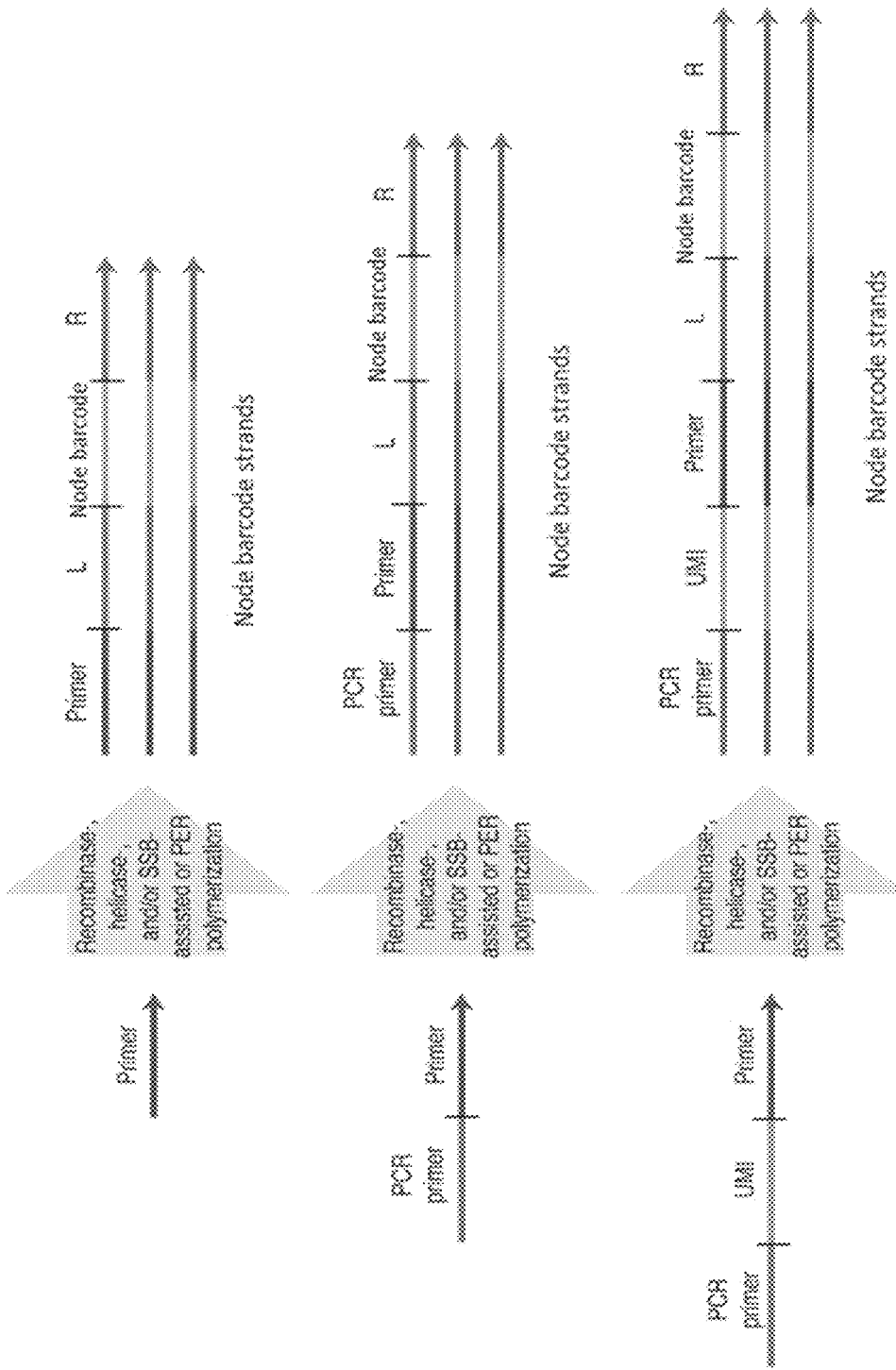
FIG. 11 illustrates amplification of a node barcode strand, wherein the hybridized primer comprises domains upstream of the primer domain, and wherein the upstream domains are included in the resulting transcript.

In some embodiments, amplification of node barcode strands comprising a primer further comprises additional domains. FIG. 11 shows exemplary embodiments wherein a primer additionally comprises a PCR primer, a unique identifier sequence, any other functional or non-functional domains, or any combination thereof. Primers with additional domains can be used to create longer node barcode strands that also contain these domains.

Figure 12:
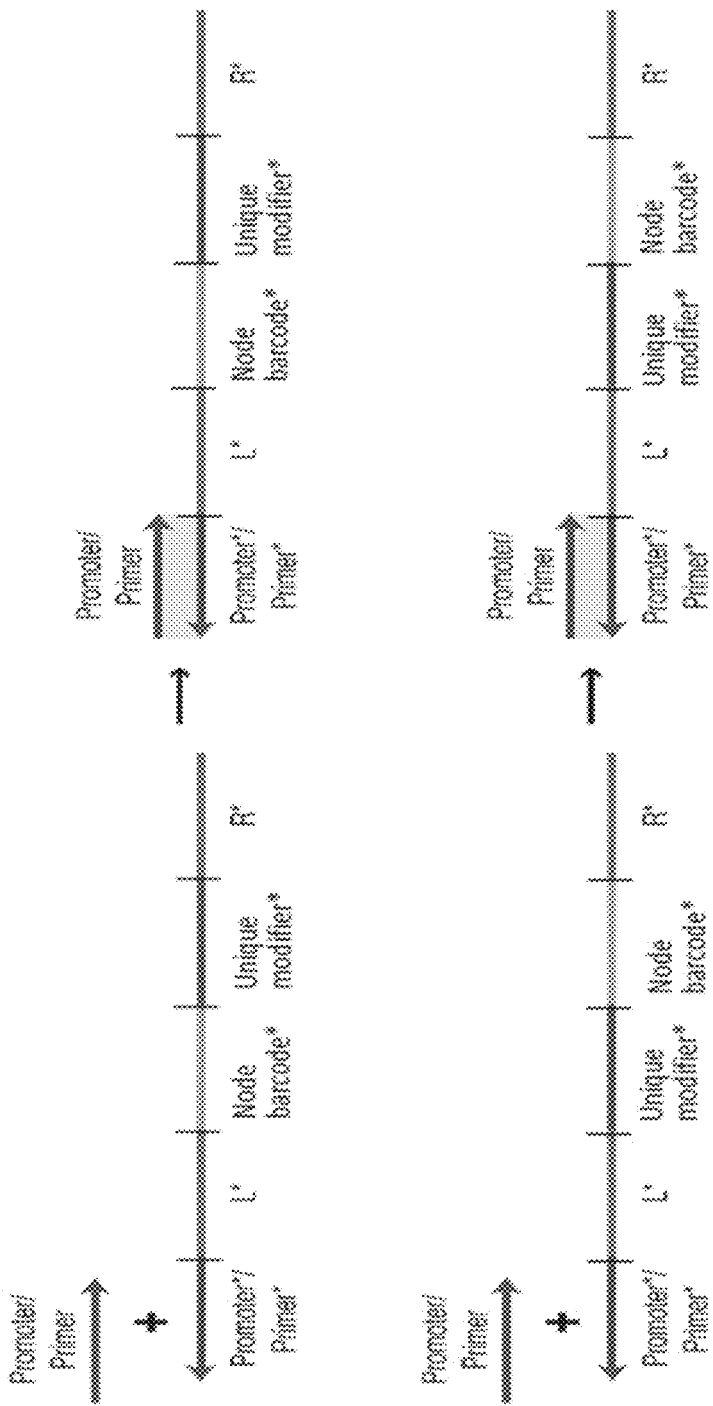
FIG. 12 illustrates node barcode templates comprising a unique modifier domain either 3' or 5' of the node barcode domain.

Template strands may additionally contain one or more unique modifiers. In some embodiments, a unique modifier comprises one or more universal bases, non-canonical bases, or other bases or modifications that a polymerase can pair either random or incorrect bases at to result in a random sequence that is specific or semi-specific to the specific node barcode strand. Unique modifier domains may contain a mix of these and normal nucleotides, and there may be one or more unique modifier domains dispersed throughout the node barcode strand sequence. Thus, while strands produced at each node should have the same node barcode sequence, they may have different unique modifier sequences. FIG. 12 shows exemplary embodiments, wherein the unique modifier region is 3' of the node barcode region or 5' of the node barcode region. In some embodiments, unique modifier information is used downstream, after next generation sequencing, to deduplicate reads and obtain more quantitative information about the number of proximity recording events.

Handshake Sequences

In some embodiments, a flanking region on a node nucleic acid comprises a hybridization domain. In some embodiments, the hybridization domain is reverse complementary to the flanking region of another node nucleic acid. In some embodiments, node nucleic acids further comprise a primer. Hybridized node nucleic acids have primers on both hybridized strands, allowing for extension of both strands, generating a double-stranded nucleic acid. These hybridization domains, or handshake sequences, allow for hybridization of node nucleic acids from different node factories. Hybridization of node nucleic acids from different node factories generates multinode nucleic acids. Sequencing of combined node nucleic acids provides spatial triangulation information, or handshakes, between node locations. The combination of handshake sequences between node nucleic acids provides triangulation information for vertices, or node locations. In some embodiments, target nucleic acids/cDNA complexes and handshake node nucleic acids are amplified by PCR and sequenced. In some embodiments, the original association between the target nucleic acids and node nucleic acids on each concatemer is cataloged by sequencing incompletely digested concatemers, to enable association between barcoded cDNAs and node nucleic acids. An exemplary embodiment of node nucleic acid hybridization is provided in Example 12 and FIGS. 43M-43O.

Order of Operations

Synthesis, diffusion, cleavage, and binding of barcoded nucleic acids are not temporally constrained in the order or even if all steps must be performed. In some embodiments, node factories generate nucleic acids concurrently with diffusion and target binding of generated nucleic acids. In some embodiments, node factories generate nucleic acids concurrently with cleavage, diffusion and target binding of generated nucleic acids. In some embodiments, node factories generate nucleic acids, diffusion occurs subsequent to generations, and target binding occurs subsequent to diffusion. In some embodiments, node factories generate nucleic acids, followed by concurrent cleavage, diffusion, and target binding of generated nucleic acids. In some embodiments, factory generation of nucleic acids, cleavage, diffusion, and target binding occur sequentially. In some embodiments, factory generation is followed by tethered diffusion of the generated concatemer and target binding, after which concatemers are cleaved.

Imaging Nodes or Diffusion Clouds

In some embodiments, nodes, node concatemers, or node nucleic acid diffusion clouds are visualized by incorporating one or more dyes or stains. In some embodiments, the dye or stain comprises fluorophore-labelled NTPs, fluorescent-labelled probes, dyes or stains as described elsewhere herein. In some embodiments, a dye or stain intercalates into nucleic acid. In some embodiments, a modified nucleotide, dye or stain is added during synthesis of the node barcode strands. In some embodiments, the node barcode strand is hybridized to a complementary fluorophore-labelled oligonucleotide. In some embodiments, the modified nucleotide is selected from a fluorophore-labeled, DIG-labeled, or biotin-labeled dNTP/NTP. In some embodiments, the modified nucleotide is selected from an EdU, BrdU, or PdU.

Fixed Nucleic Acids

In some embodiments, displacement of barcoded nucleic acids comprises application of a reagent to release a nucleic acid comprising a barcode from the surface. The reagent to release a nucleic acid comprising a barcode may comprise an RNAse, DNAse, and/or proteinase. In some embodiments, record extraction and sequencing comprises displacement of barcoded nucleic acids. Displacement is optionally achieved with application of an RNA hydrolyzing enzyme. In some embodiments, the RNA hydrolyzing enzyme is RNaseH. Cross-junction synthesis to generate continuous nucleic acids can also effect displacement of the barcoded nucleic acids. Enzymatic displacement and synthesis reactions can be combined or performed sequentially. After sequences have been extracted from the sample, further imaging or other assays (e.g., mass spectrometry, H&E staining) may be performed on the sample. Subsequent Polymerase Chain Reaction (PCR) amplification and optional purification is followed by optional library preparation and next generation sequencing. The resulting sequence analysis is merged with the captured imaging data to provide integrated spatial and sequence-based information output.

Analysis using methods described herein are applicable to an immobilized nucleic acid. In some embodiments, the immobilized nucleic acid is fixed to a substrate. In some embodiments, the fixation is via formalin/formaldehyde treatment. In some embodiments, the fixation is via ethanedial or oxalaldehyde treatment. Analysis using methods described herein are applicable to any fixed nucleic acid. In some embodiments, described methods are used to characterize nucleic acids, proteins, or any combination thereof. In some embodiments, fixed nucleic acids are immobilized through affinity reactions, including hybridization, conjugation, binding, crosslinking, photo-crosslinking, priming and extension, or any combination thereof. In some embodiments, affinity reactions are specific to particular subcellular, cellular, cell-type specific, or supercellular structures such as membranes, mitochondria, genomic DNA, proteins, nucleic acids, lipids, protein-protein complexes, protein-RNA complexes, or any combination thereof. Accordingly, in some embodiments, the fixed nucleic acids bind multiple targets in the sample. In some embodiments, the target or multiple targets further bind another set of multiple targets. In some examples, template strands bind to kinases, which in turn bind to ADP or ATP and a substrate. In such instances, the multiple kinases bind multiple substrates. In another example, template strands bind to ATP, which will bind to multiple kinases. In some embodiments, immobilization is randomly dispersed throughout a substrate through random binding, non-specific binding, or conjugation to a surface, defined or random incorporation into a hydrogel, or focused within a specific area. In some embodiments, focused deposition is through depositing reagents on a specific region, spatially confined crosslinking, or photo-crosslinking as described herein. Fixed nucleic acids can be conjugated to an affinity molecule or immobilized to a scaffold, a substrate, a surface, a bead, or a column. Methods described herein can be used to profile in situ hybridization (ISH) probes, DNA conjugated to antibodies, DNA encoded libraries, cDNA libraries, CRISPR libraries, viral libraries and/or genomes, nucleic acids covalently linked to cleared hydrogels, nucleic acid conjugated proteins, aptamers, guide RNAs, nucleic acids localized on a surface (e.g., glass slide or micro-array), or in situ generated sequences (e.g., by in vitro transcription (IVT)). Methods described herein can be used to profile peptide libraries, protein libraries, nanobody libraries, aptamer libraries, or antibody libraries. In some embodiments, proteins or their variants are attached directly to their respective coding mRNA transcripts, such as through ribosomal stalling during translation. Attached mRNA transcripts can be treated as a nucleic acid "tag" in identifying the associated protein using methods as described herein. In some embodiments, samples are fixed prior to node barcode strand generation and/or subsequent to node barcode strand generation.

In some embodiments, the fixed nucleic acid is conjugated to an affinity molecule. In some embodiments, an affinity molecule comprises a component of a ligand/receptor complex. In some embodiments, an affinity molecule comprises an antibody or component thereof. In some embodiments, the antibody component is an antibody fragment, a nanobody, or other affinity reagent. In some embodiments, an antibody fragment, as described herein, is a $F(ab')_2$ fragment, an Fab' fragment, an Fab fragment, an Fv fragment, an IgG fragment, an Fc fragment, or any combination thereof. In some embodiments, the antibody is an IgA, IgG, or IgM antibody or a functional fragment thereof.

In some embodiments, the fixed nucleic acid is conjugated to a scaffold. In some embodiments, a scaffold is biodegradable. In some embodiments, a scaffold is non-biodegradable. In some embodiments, a scaffold is biocompatible. In some embodiments, a scaffold comprises synthetic materials. In some embodiments, the synthetic materials comprise silicone, polylactic acid (PLA), polyglycolic acid (PGA), polycaprolactone (PCL), poly-lactic-co-glycolic acid (PLGA), or any combination thereof. In some embodiments, the scaffold comprises natural materials. In some embodiments, the natural materials comprise derivatives of the extracellular matrix, collagen, fibrin, polysaccharides including chitosan or glycosaminoglycans (GAGs), or any combination thereof. In some embodiments, glycosaminoglycans (GAGs) comprise hyaluronic acid.

In some embodiments, the fixed nucleic acid is incorporated in a hydrogel. In some embodiments, a hydrogel comprises poly(2-hydroxyethyl methacrylate) (PHEMA), 2-hydroxyethyl methacrylate (HEMA), polyethylene glycol (PEG), methacrylic acid (MAA), PEG-PEGMA, carboxymethyl cellulose (CMC), polyvinylpyrrolidone (PVP), acrylamide/acrylic acid copolymer, linear cationic polyallylammonium chloride, poly(N-isopropyl acrylamide) (PNIPAM), chitosan, acrylate-modified PEG and acrylate-modified hyaluronic acid, heparin, amine end-functionalized 4-arm star-PEG, or any combination thereof.

In some embodiments, the fixed nucleic acid is conjugated to a surface comprising a flexible material. In some embodiments, the flexible material comprises, without limitation, modified nylon, unmodified nylon, nitrocellulose, polypropylene or any combination thereof. In some embodiments, the surface comprises a rigid material. In some embodiments, the rigid material comprises, without limitation, glass, fuse silica, silicon, silicon dioxide, silicon nitride, plastics (for example, polytetrafluoroethylene, polypropylene, polystyrene, polycarbonate, and blends thereof, metals (for example, gold, platinum), or any combination thereof. Surfaces described herein may be fabricated from a material comprising silicon, polystyrene, agarose, dextran, cellulosic polymers, polyacrylamides, polydimethylsiloxane (PDMS), glass, or any combination thereof.

In some embodiments, the fixed nucleic acid is conjugated to a bead. In come embodiments, the bead is a magnetic bead. In some embodiments, the bead is an immunoaffinity bead.

In some embodiments, the fixed nucleic acid comprises a surface binding region. In some embodiments, the surface binding region hybridizes with a complementary sequence on a surface. In some embodiments, a surface binding region comprises an activated molecule that interacts with a molecule or coating on a surface. In some embodiments, the surface binding region comprises a conjugated molecule that interacts with a molecule or coating on a surface.

In some embodiments, multiple copies of the fixed nucleic acid are conjugated to the bead. In some embodiments, the conjugation is a reversible conjugation. In some embodiments, the reversible conjugation is photocleavable, photoactivatable (e.g., azobenzene modification), heat labile, chemically cleavable (e.g., by adjusting the salt concentration or pH), enzymatically cleavable (e.g., by restriction enzymes or endonucleases), or otherwise reversible. In some embodiments, beads comprising conjugated nucleic acids are deposited at node locations on a surface or sample. Conjugated barcodes are released from bead through cleavage. Released barcodes diffuse away from node locations. In some embodiments, the fixed nucleic acids are encapsulated and can be reversibly released. In some embodiments, the encapsulation is in an LNP, bead, AAV, lentivirus, or exosome.

In methods described herein, a sample is in suspension, in solution, or in a hydrogel. In some embodiments, a hydrogel comprises poly(2-hydroxyethyl methacrylate) (PHEMA), 2-hydroxyethyl methacrylate (HEMA), polyethylene glycol (PEG), methacrylic acid (MAA), PEG-PEGMA, carboxymethyl cellulose (CMC), polyvinylpyrrolidone (PVP), acrylamide/acrylic acid copolymer, linear cationic polyallylammonium chloride, poly(N-isopropyl acrylamide) (PNIPAM), chitosan, acrylate-modified PEG and acrylate-modified hyaluronic acid, heparin, amine end-functionalized 4-arm star-PEG, or any combination thereof.

Resolution of detection using barcoding methods described herein is not limited by light diffraction. Such barcoding methods allow for detection samples with very high density as well as very low density of targets. Additionally, barcoding methods described herein can be applied in two dimensions or three dimensions without loss of resolution or significant adaptation of methods.

Application of methods described herein include and are not limited to identification of drug targets, identification of biomarkers, profiling, characterization of cells and disease models, characterization of differentiation status and cell state, tissue mapping, and multi-dimensional analysis.

Sample Preparation

Provided herein are methods for preparing samples for downstream biological analysis steps. In some embodiments, samples as provided herein comprise a population of cells. In some embodiments, samples provided herein comprise a tissue sample. In some embodiments, samples provided herein comprise a laminar cell culture. Non-limiting examples of samples that can be used include: intact tissue, dissected tissue, dissociated cells, an organoid, engineered tissue, cultured cells, sub-cellular compositions, a suspension of cells, organs, organelles, tissue biopsies, frozen tissue, tissue section, tissue block, membrane-bound structures, cell-free systems or lysates, formalin-fixed paraffin-embedded (FFPE) samples, exosomes, nuclei, fixed nuclei, fixed exosomes, protein complexes, RNPs, or any combination thereof. In some embodiments, samples provided herein comprise a population of cultured cells. Cultured cells can include but are not limited to primary cell cultures, dissociated cells, dissected cells, passaged cell lines, and/or transformed cells. In some embodiments, the population of cells provided herein comprise an engineered tissue. In some embodiments, the engineered tissue comprises a population of human in vitro-differentiated cells. In some embodiments, the human in vitro-differentiated cells are derived from human induced pluripotent stem cells (hiPSCs), embryonic stem cells, or adult stem cells. In some embodiments, the human in vitro-differentiated cells are in vitro-differentiated cardiomyocytes, in vitro-differentiated neurons, in vitro-differentiated hepatocytes, in vitro-differentiated endothelial cells, in vitro-differentiated epithelial cells, in vitro-differentiated smooth muscle cells, in vitro-differentiated skeletal muscle cells, or in vitro-differentiated kidney cells. In some embodiments, the population of cells provided herein comprise retinal cells. In some embodiments, the population of cells provided herein are obtained from a subject. In some embodiments, samples are unfixed or fixed. In some embodiments, the subject is a mammal. In some embodiments, the mammal is a primate, a non-human primate, a human, a mouse, a rat, a goat, a rabbit, a dog, a camelid, or a cat.

In some embodiments, the population of cells comprises a homogeneous population of cells (e.g., cells of the same type or of the same species). In some embodiments, the population of cells comprise a heterogenous population of cells (e.g., cells of different types, different species, or any combination thereof). In some embodiments, the population of cells comprises cells from one species. In some embodiments, the population of cells comprises cells from two or more species. In some embodiments, the population of cells comprises one cell type. In some embodiments, the population of cells comprises cells from two or more different cell types. In some embodiments the population of cells comprises cells from at least 2, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 250, at least 500, at least 1000 or more species. In some embodiments the population of cells comprises cells from at least 2, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 250, at least 500, at least 1000 or more different cell types.

In some embodiments, samples used in methods described herein are a tissue sample. In some embodiments, tissue samples provided herein comprise connective tissue, epithelial tissue, muscle tissue, or nervous tissue. In some embodiments, tissue samples provided herein comprise a combination of tissues. An organ comprises tissues of different types and has a specific function. In some embodiments, a combination of tissues is an organ. In some embodiments, a combination of tissues is an organoid. In some embodiments, the tissue sample is obtained from a subject. In some embodiments, tissues samples provided herein are obtained from a brain, an eye, a lung, a liver, a bladder, a kidney, a heart, a stomach, an intestine, a lymph node, a skeletal muscle, a smooth muscle, a pharynx, a larynx, an artery, a liver, a gallbladder, a bone, a spleen, a vein, a pancreas, a reproductive organ, a tumor, an infected tissue, or any combination thereof. In some embodiments, tissue samples provided herein are a whole organ or a biopsy tissue. In some embodiments, the biopsy tissue comprises a tissue that has or is suspected of having abnormal proliferation or growth. In some embodiments, the biopsy tissue comprises cancer cells.

In some embodiments, a population of cells described herein comprises one or more microorganisms. In some embodiments, the population of cells comprises prokaryotic or eukaryotic cells. In some embodiments, a population of cells provided herein comprise bacterial cells, fungal cells, archaeic cells, eukaryotic cells, or any combination thereof. In some embodiments, the population of cells comprises mammalian cells. In some embodiments, the mammalian cells are human, non-human primate, primate, pig, horse, sheep, cat, rat, mouse, dog, llama, rabbit, or goat cells. In some embodiments, the population of cells further comprises a virus. In some embodiments, the virus is a pathogenic virus. In some embodiments, the population of cells comprise a viral vector. In some embodiments, the population of cells have been genetically modified. Non-limiting examples of genetic modifications include base editing, gene silencing (e.g., by CRISPR/Cas9 systems), gene insertions, gene deletions.

In some embodiments, the population of cells are fixed and then frozen. In some embodiments, the population of cells are frozen, then fixed after thawing and/or sectioning. In some embodiments, the fixed population of cells is sectioned and then fixed a second time. In some embodiments, the population of cells is stored at room temperature after fixing. In some embodiments, the population of cells is fixed with organic solvents, such as alcohols and acetones. In some embodiments, the population of cells (e.g., tissue) are embedded in paraffin prior to fixing. In some embodiments, the population of cells are fixed with cross-linking reagents. In some embodiments, the cross-linking reagent comprises formalin, formaldehyde, paraformaldehyde, dithio-bis(succinimidyl propionate) (DSP) or any combination thereof. In some embodiments, a permeabilization step is performed. In some embodiments, no permeabilization is performed. In some embodiments, permeabilization occurs concurrently with fixation. In some embodiments, permeabilization is performed following fixation. In some embodiments, a permeabilization reagent comprises acetone, alcohol, detergent, or any combination thereof.

In some embodiments, a population of cells for analysis as provided herein are live cells. In further embodiments, the live cells are contacted directly with a barcode sequence, or indirectly via a linking molecule. In some embodiments, the linking molecule binds to cell surface receptors. In some embodiments, the linking molecule binds a cell surface molecule. In some embodiments, the cell surface molecule is a protein or nucleic acid. The nucleic acid may be RNA or DNA. The protein may be a cell receptor. In some embodiments, the cell surface molecule is located at cell adhesion points. In some embodiments, barcode sequences are introduced intracellularly into live cells. In some embodiments, barcode sequences are attached to lipid nanoparticles (LNPs) as carriers for delivery into the cell. In some embodiments, AAV's, lentiviruses, exosomes, or other encapsulations are carriers for delivery of barcode sequences into the cell. In some embodiments, cells are transfected or transformed to receive barcode sequences. In some embodiments, cells are mechanically perturbed to enable cellular uptake of barcode sequences.

In some embodiments, a sample described herein comprises a nucleic acid. In some embodiments, a sample comprises nucleic acid bound or tethered directly or indirectly to a surface. In some embodiments, a sample comprises nucleic acid in solution. In some embodiments, a sample comprises nucleic acid in a hydrogel, expanded hydrogel, biological sample embedded in a hydrogel, biological sample embedded in an expanded hydrogel, with or without sample clearing. In some embodiments, a sample comprises nucleic acid in a scaffold. In some embodiments, the nucleic acid is attached directly or indirectly to a synthetic matrix. In some embodiments, the synthetic matrix comprises a bead or semi-solid gel.

In some embodiments, a sample described herein comprises a cell. In some embodiments, the cell is bound to a surface. In some embodiments, the cell is in solution. In some embodiments, the cell is connected to a hydrogel. In some embodiments, the cell is connected to a synthetic scaffold. In some embodiments, the cell is attached directly or indirectly to a synthetic scaffold. In some embodiments, the synthetic scaffold comprises a bead or semi-solid gel. In some embodiments, the synthetic scaffold comprises an extracellular matrix protein. In some embodiments, the extracellular matrix protein comprises collagen or fibronectin.

In some embodiments, samples provided herein are frozen at $-5°$ C.--$-200°$ C. In some embodiments, samples provided herein are frozen at about $-5°$ C., about $-10°$ C., about $-15°$ C., about $-20°$ C., about $-25°$ C., about $-30°$ C., about $-35°$ C., about $-40°$ C., about $-45°$ C., about $-50°$ C., about $-55°$ C., about $-60°$ C., about $-65°$ C., about $-70°$ C., about $-75°$ C., about $-80°$ C., about $-85°$ C., about $-90°$ C., about $-95°$ C., about $-100°$ C., or any combination thereof. In some embodiments, a tissue sample or a population of cells provided herein is flash frozen. In some embodiments, a tissue sample or a population of cells provided herein are frozen by slow, or equilibrium, freezing.

Fixation may impact protein biochemistry in some cases, masking an epitope. In some embodiments, a sample described herein is further treated with an antigen retrieval method. In some embodiments, the antigen retrieval method is protease-induced epitope retrieval (PIER). In some embodiments, the antigen retrieval method is heat-induced epitope retrieval (HIER). In some embodiments, the antigen retrieval method is any other method capable of reversing the masking of an epitope. In some embodiments, the antigen retrieval step is combined with a permeabilization step. In some embodiments, the antigen retrieval step is performed independently.

In some embodiments, samples provided herein are fixed on a microscope slide or coverslip. In some embodiments, the microscope slide is a chamber slide. In some embodiments, the chamber slide comprises one or more chambers. In some embodiments, the slide comprises polystyrene. In some embodiments, the slide comprises glass. In some embodiments, the coverslip comprises glass. In some embodiments, the coverslip comprises a UV transparent material. In some embodiments, the coverslip comprises quartz.

In some embodiments, the slide comprises a coating to promote adherence of a tissue sample or a population of cells provided herein to a surface of the slide. In some embodiments, the coating comprises poly-L-lysine or poly-D-lysine. In some embodiments, the coating comprises a gelatin. In some embodiments, the coating comprises a 3-aminopropyltriethoxysilane (APES). In some embodiments, samples are adhered to the slide using an adhesive tape. In some embodiments, the adhesive tape is polyvinylidene chloride, polyester/silicone, polypropylene film, cellophane, synthetic rubber-resin hot melt, low density polyethylene film, polyester film, or any combination thereof.

In some embodiments, samples are embedded in a hydrogel. In some embodiments, the hydrogel comprises a synthetic gel or polyepoxide. In some embodiments, embedding a sample generates at tissue-hydrogel matrix. In some embodiments, embedding a sample provides for expansion of a tissue sample or a population of cells provided herein. In some embodiments, the hydrogel is a natural hydrogel, a synthetic hydrogel, or a synthetic/natural hybrid hydrogel. In some embodiments, the natural hydrogel is a protein, a polysaccharide, a protein/polysaccharide, DNA, or any combination thereof. In some embodiments, the protein hydrogen comprises collagen, elastin, fibrin, silk, lysozyme, Matrigel® (Corning Inc., Corning, NY), genetically engineered proteins, or any combination thereof. In some embodiments, the polysaccharide comprises hyaluronic acid (HA), alginate, chitosan, dextran, or any combination thereof. In some embodiments, the protein/polysaccharide comprises collagen/HA, laminin/cellulose, fibrin/alginate, gelatin/agarose, chitosan, alginate, dextran, or any combination thereof. In some embodiments, the DNA hydrogel comprises X-DNA, Y-DNA, T-DNA, linear plasmid DNA, or any combination thereof. In some embodiments, the synthetic hydrogel is a nonbiodegradable hydrogel, a biodegradable hydrogel, a bioactive hydrogel, or any combination thereof. In some embodiments, the nonbiodegradable hydrogel comprises poly(2-hydroxyethyl methacrylate) (PHEMA), poly(2-hydroxypropyl methacrylate) (PHPMA), poly(N-isopropylacrylamide (PNIPAm), poloxamer (Pluronic®, ThermoFisher Scientific, Inc., Waltham, MA), poly(ethylene glycol) diacrylate (PEGDA), poly(vinyl alcohol (PVA), or any combination thereof. In some embodiments, the biodegradable hydrogel comprises degradable polyethylene glycol (PEG), polypropylene fumarate-PEG (PPF-PEG), poly(2-hydroxyethyl methacrylate-poly($\epsilon$-caprolactone (PHEMA-PCL), synthetic peptides, or any combination thereof. In some embodiments, the bioactive hydrogel comprises a cell-adhesive hydrogel, an enzyme-sensitive hydrogel, a growth factor-bearing hydrogel, another bioactive hydrogel, or any combination thereof. In some embodiments, the synthetic/natural hybrid hydrogel comprises PEG/dextran, heparin, HA, chondroitin sulfate (CS), one or more proteins, PNIPAm/proteins, chitosan, alginate, synthetic peptides/proteins, polysaccharides, PVA/DNA, Pluronic/dextran, PHPMA/protein, or any combination thereof.

In some embodiments, a sample comprises cells. In some embodiments, a sample comprises cells from a suspension. In some embodiments, a sample comprises a whole organism. In some embodiments, the whole organism is a multicellular organism. In some embodiments, the whole organism is a single cell organism. Example multicellular organisms include, without limitation, roundworm (*Caenorhabditis elegans*), zebrafish (*Danio rerio*), and a *Drosophila*. Example single cell organisms include, without limitation, bacteria and yeast. In some embodiments, a sample comprises tissue. In some embodiments, the sectioned tissue is sliced. In some embodiments, the slices are up to about 5 μm, about 10 μm, about 15 μm, about 20 μm, about 25 μm, about 30 μm, about 35 μm, about 40 μm, about 45 μm, about 50 μm, or more in thickness.

In some embodiments, samples described herein are imaged using a microscope. In some embodiments, a microscope used in methods described herein includes a compound microscope, a fluorescent microscope, a confocal microscope, a light sheet microscope, a Raman microscope, or a digital microscope.

Barcoding Workflow

Figure 13A:
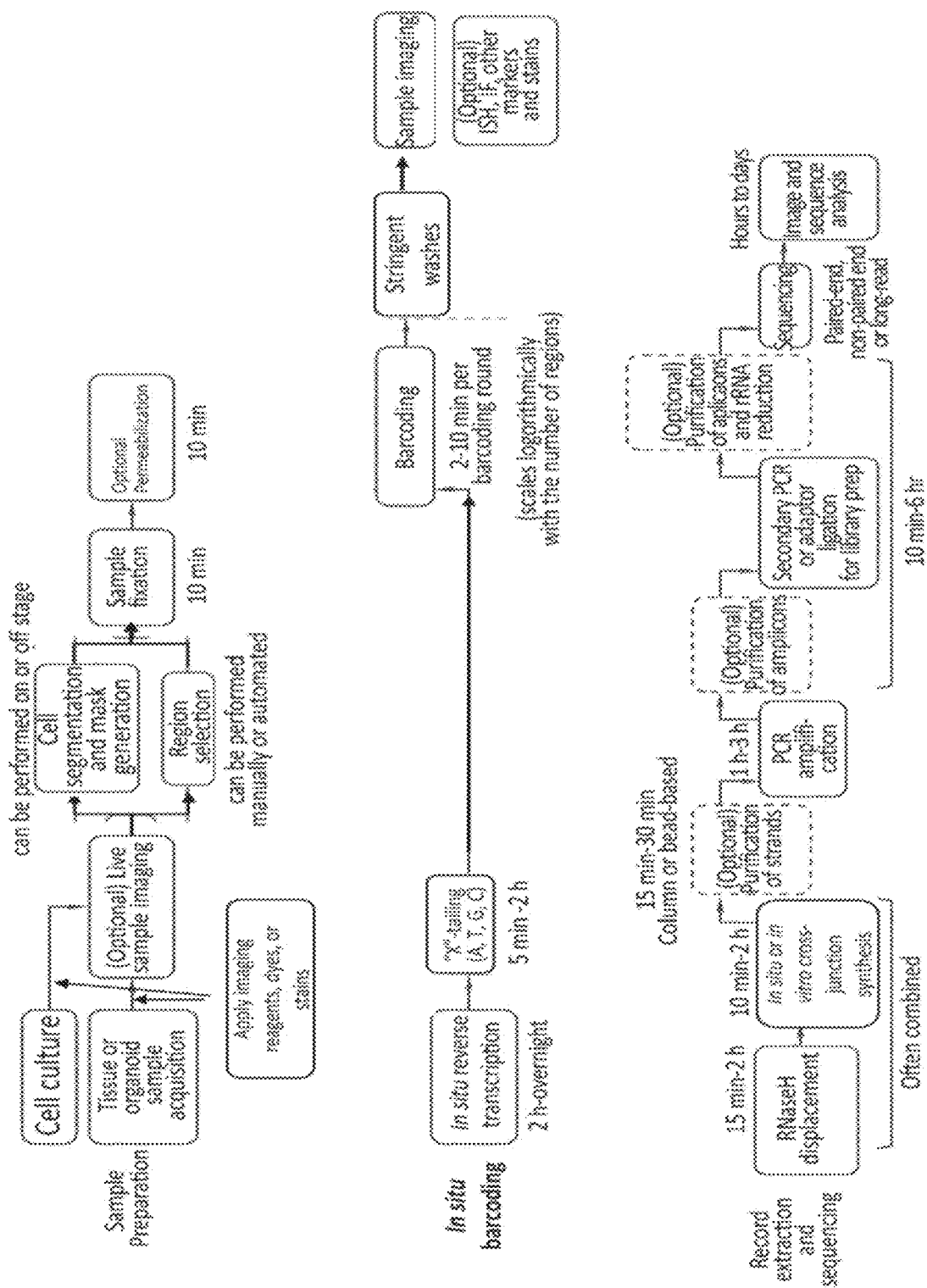
FIGS. 13A and 13B illustrate a process workflow, incorporating sample preparation, light-based in situ barcoding of a population of cells, and record extraction and sequencing.

Described further herein, are features in sample preparation, in situ imaging and barcoding, and record extraction and sequencing. An exemplary workflow for analysis of a biological cell is provided in FIG. 13A. Briefly, a step of sample preparation (e.g., a tissue sample or a population of cells) is performed. The sample preparation step may include culture of cells or acquisition of tissue or organoids followed by imaging. Dyes and/or probes to enhance visualization of cells and/or structures therein may be applied to the sample. Subsequent optional staining and/or imaging provides morphological and architectural information of the sample to assist with region selection, cell segmentation, and mask generation. The sample is then optionally permeabilized. In some embodiments, permeabilization is performed before imaging the sample or concurrently with fixation of a sample. Permeabilization is performed, in some embodiments, for analysis of intracellular biomolecules.

Following the workflow, to analyze the biological cell in situ, reverse transcription of RNA is performed, optionally followed by tailing of the resulting cDNA. Spatially directed barcoding within selected regions of interest is then performed utilizing photomasks, with region selection for masking, optionally, based on the earlier sample imaging. The biological cell is, optionally, further imaged to show incorporation of barcodes. Following the process described in FIG. 13A, Record extraction and sequencing comprises displacement of barcoded nucleic acids. Displacement is optionally achieved with application of RNaseH. Cross-junction synthesis to generate continuous nucleic acids can also effect displacement of the barcoded nucleic acids. Enzymatic displacement and synthesis reactions can be combined or performed sequentially. After sequences have been extracted from the sample, further imaging or other assays (e.g., mass spectrometry, H&E staining) may be performed on the sample. Subsequent Polymerase Chain Reaction (PCR) amplification and optional purification is followed by optional library preparation and next generation sequencing). The resulting sequence analysis is merged with the captured imaging data to provide integrated spatial and sequence-based information output.

Figure 13B:
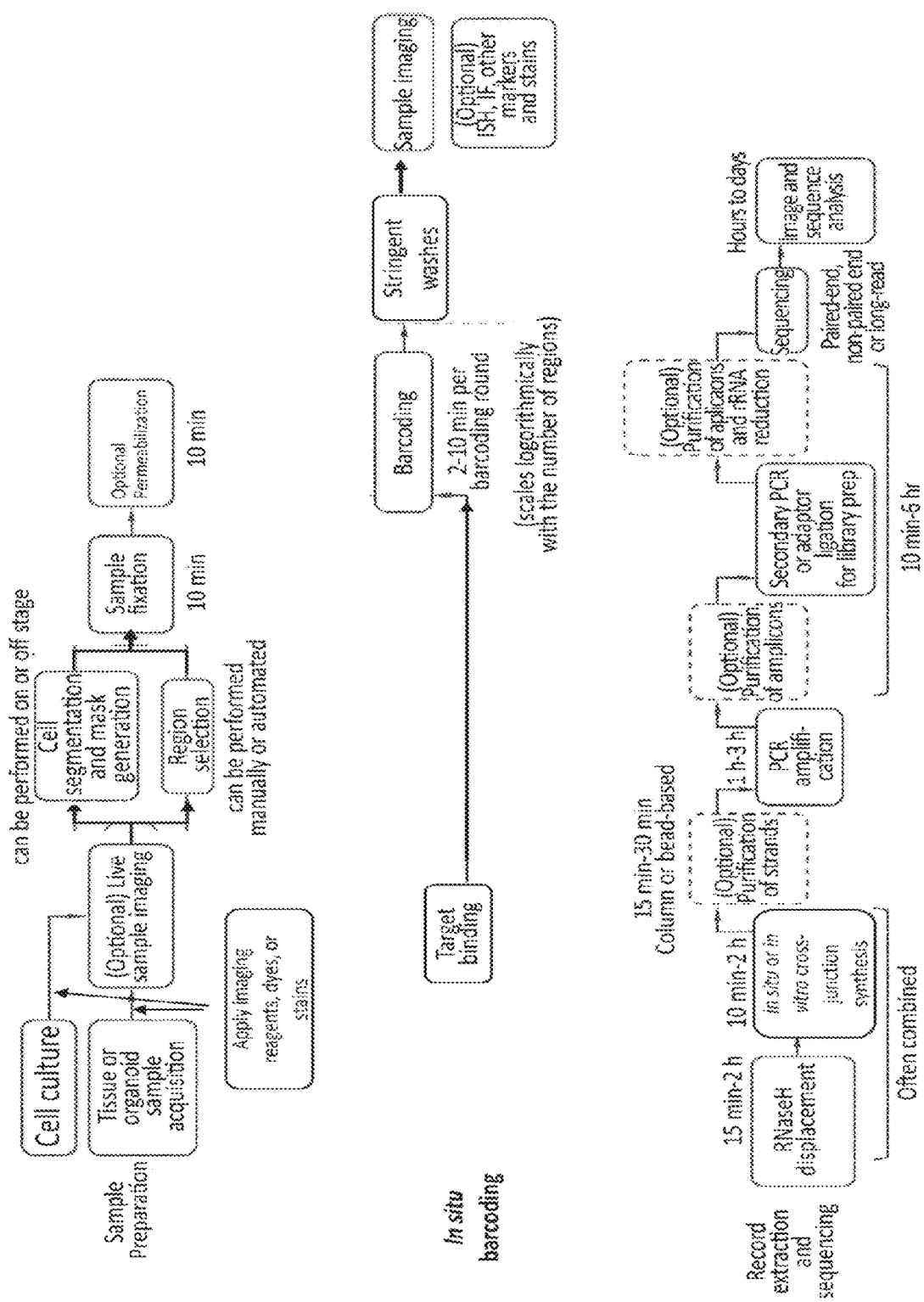

A further exemplary workflow is illustrated in FIG. 13B. Briefly, a step of sample preparation (e.g., a tissue sample or a population of cells) is performed. The sample preparation step may include culture of cells or acquisition of tissue or organoids followed by imaging. Dyes and/or probes to enhance visualization of cells and/or structures therein may be applied to the sample. Subsequent imaging provides morphological and architectural information of the sample to assist with region selection, cell segmentation, and mask generation. The sample is then optionally permeabilized.

As described in FIG. 13B, barcoding of a sample comprises target binding. In some embodiments, the target binding is affinity binding. Affinity binding can comprise binding to a ligand, an epitope, or any other specific recognition binding. In some embodiments, the target binding is hybridization. Hybridization can comprise hybridization of nucleic acid strands, including but not limited to deoxyribonucleic acid (DNA) strands, ribonucleic acid (RNA) strands, peptide nucleic acid (PNA) strands, locked nucleic acid (LNA) strands, and combinations thereof. For example, hybridization can comprise hybridization of RNA to RNA, DNA to DNA, RNA to DNA, RNA to PNA, DNA to PNA, PNA to PNA, or any combination thereof.

Figure 13C:
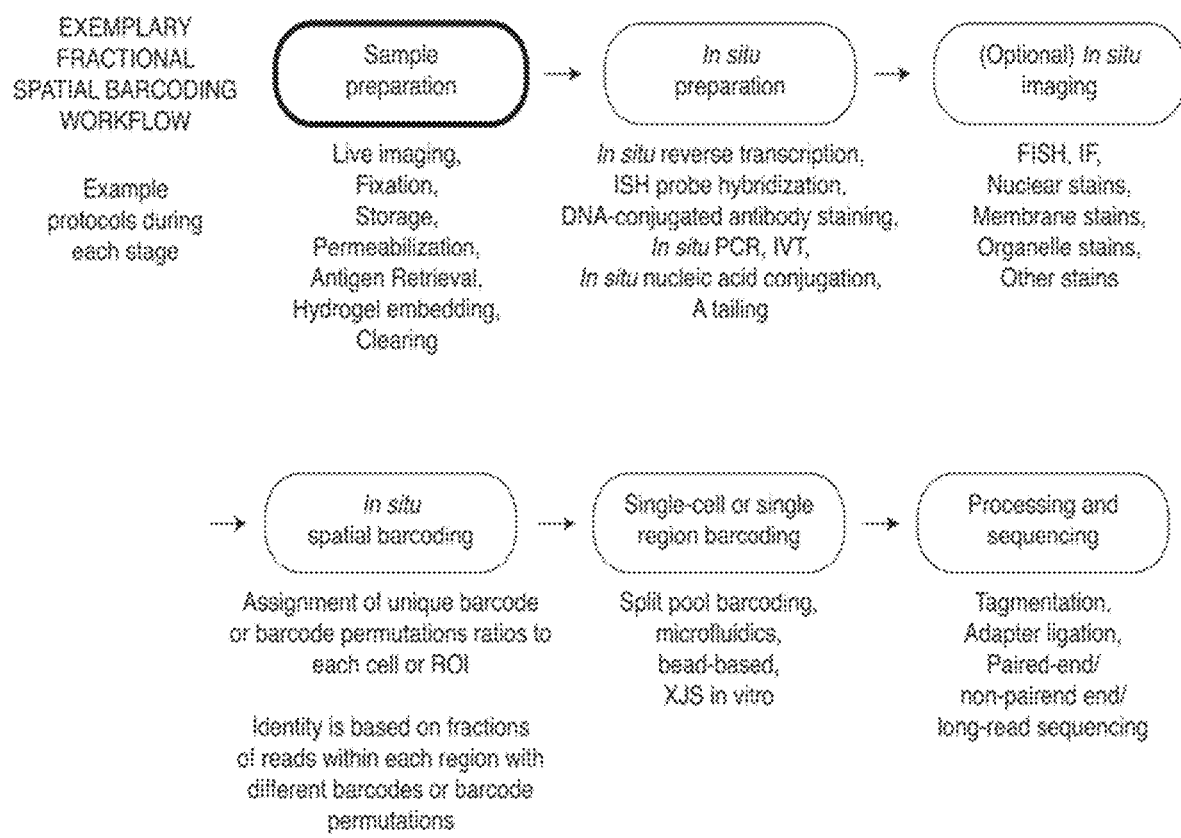
FIG. 13C illustrates a workflow providing for fractional spatial barcoding.
Figure 14A:
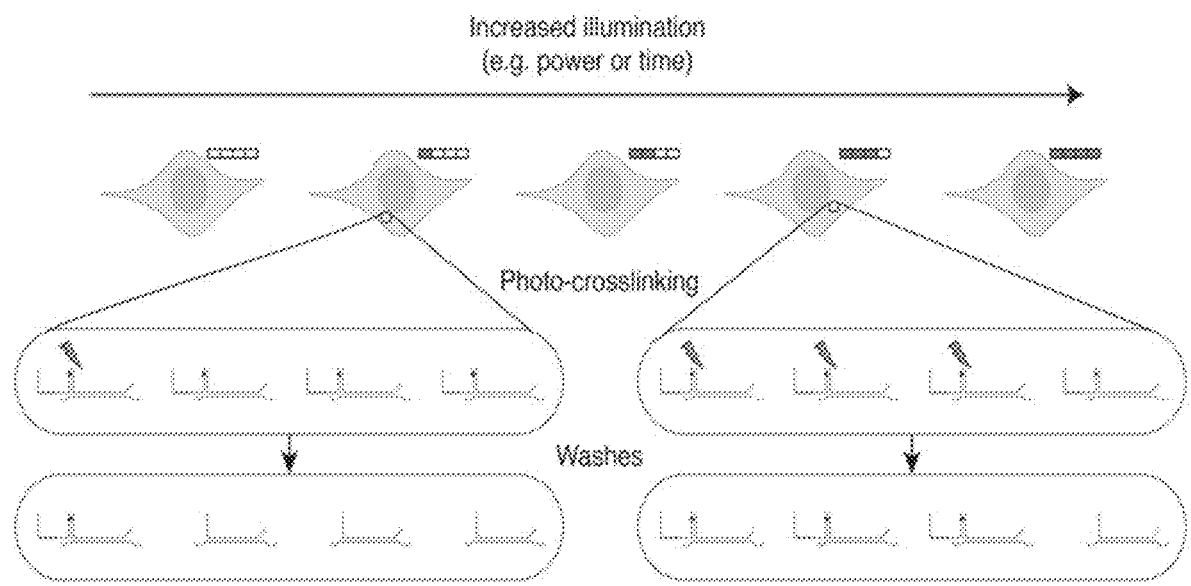
FIGS. 14A and 14B illustrate a fractional barcoding schema during or following the workflow described in FIG. 13C
Figure 14B:
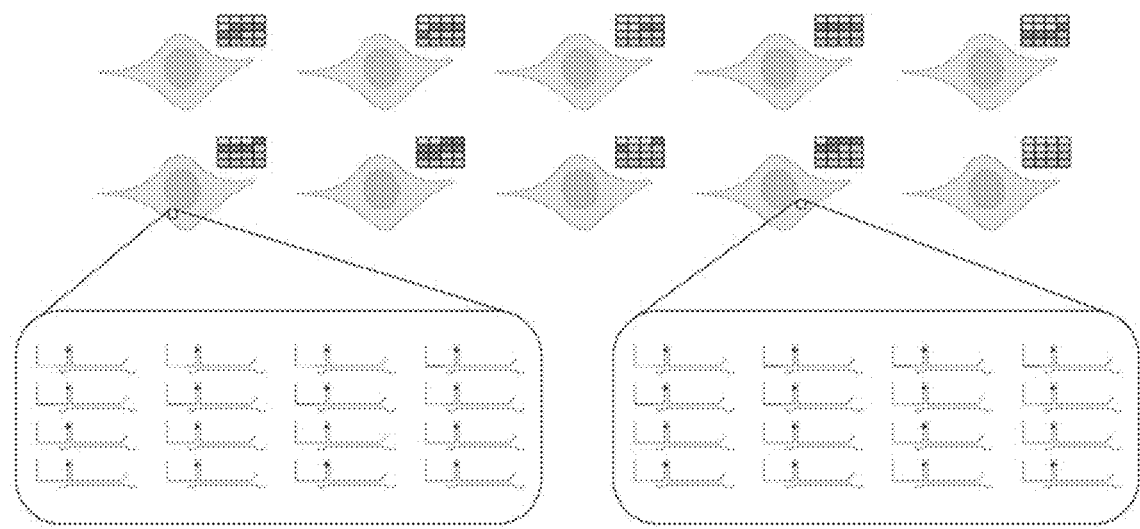

A fractional spatial barcoding workflow is illustrated in FIG. 13C. Sample preparation and optional imaging steps comprise methodologies similar to previous workflows. In this case, a unique ratio of barcode or barcode permutations is assigned to a specific cell or region of interest (ROI). Duration or power of applied radiation energy is controlled in order to define the fraction of available targets which will crosslink with the contacted barcode. FIG. 14A is an exemplary depiction of controllably increasing illumination time to induce more crosslinking events in a specific region, in this case, a cell. Multiple rounds of fractional barcode crosslinking can be applied across a sample, allowing differentiation and identification of cells or regions of interest. FIG. 14B illustrates example combinations of four barcodes sequences applied across a cell or region. Each cell or region of interest can be assigned a unique split of barcode sequences across its reads, so that after subsequent single cell or region barcoding and sequencing, the original spatial location of cells can be recovered based on the fraction of reads from each barcode measured with next generation sequencing. Cells or regions are separately barcoded, in some instances after dissociation of the sample. In some embodiments, sorting methods to separate distinct regions are applied, for example split pool barcoding, microfluidics, barcoded beads, or other single-cell barcoding techniques, prior to sequencing. Each cell or ROI can be identified based on the fraction of photo-crosslinked barcodes within reads corresponding to nodes or combinations thereof.

Figure 15:
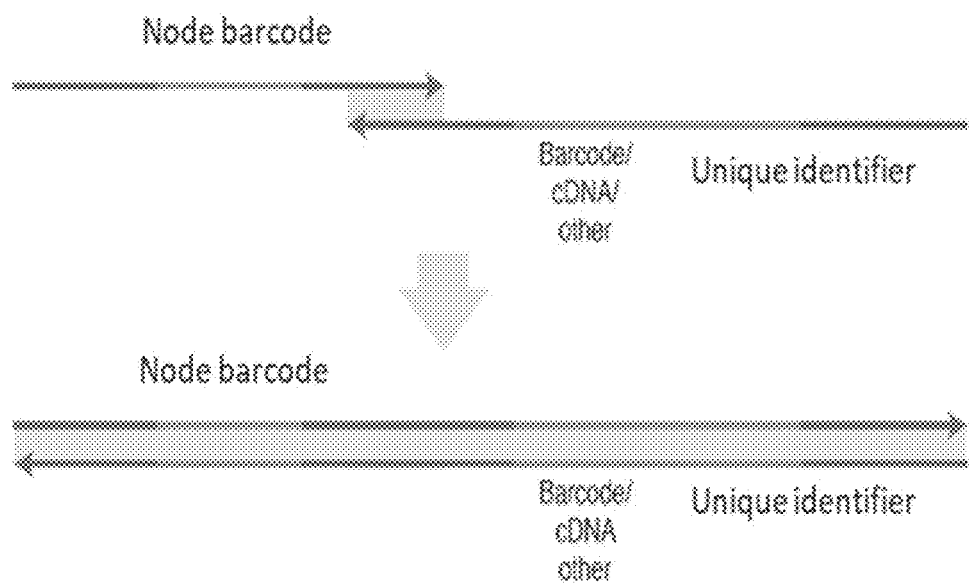
FIG. 15 illustrates an exemplary combination of node barcode strand and a target barcode strand further comprising a unique identifier.

Generated node barcode strands described herein may combine with a target sequence. In some embodiments, a target sequence comprises one or more cDNA, nucleic acid barcodes, ISH probes, other unique identifier sequences, or any combination thereof. FIG. 15 shows an exemplary embodiment of a combination of a node barcode strand with a target barcode and a unique identifier to record proximity information about which node is near a molecule of interest. Complementary regions on the strands hybridize and strands are extended using polymerization methods described herein. Proximity information can be used to computationally reconstruct the original spatial orientation of the node locations in the sample or substrate. Spatial orientation can be mapped based on a frequency of target nucleic acids and node barcodes present in the concatenated nucleic acids.

Figure 16:
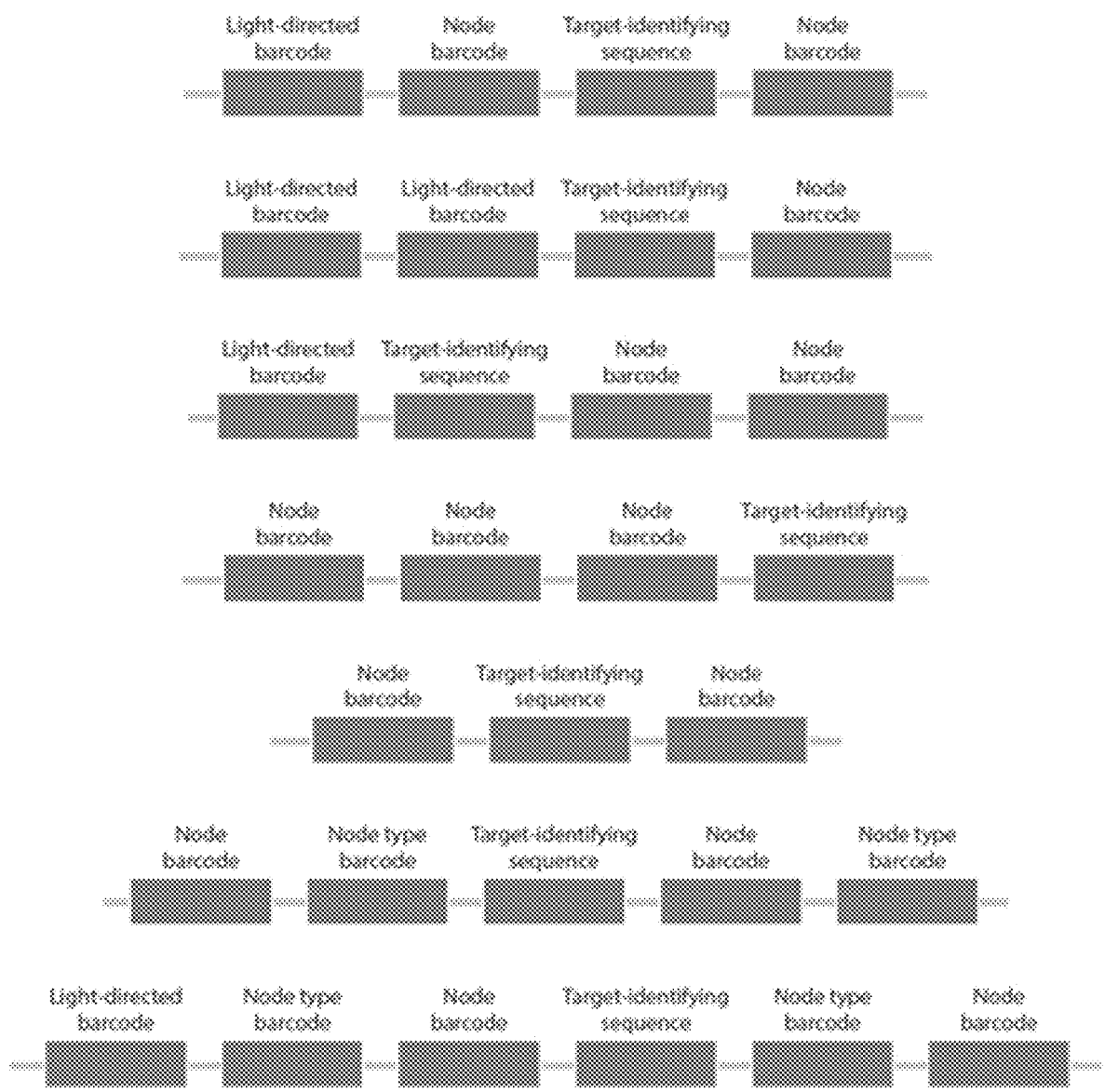
FIG. 16 provides possible combinations and barcode sequences in a concatemer.

Contemplated herein are any combination of conjugated nucleic acids comprising node nucleic acids, factory target nucleic acids, and target barcodes. Methods described herein are not limited to an order of conjugation of barcoded nucleic acids. Additionally, barcoded strands described herein comprise, in different embodiments, any combination, order, and repetition of target barcodes, node barcodes, factory target barcodes, node-type barcodes, unique modifiers, or any other identifier described herein. Exemplary order and number of barcodes is depicted in FIG. 16. Intervening spaces between barcodes depicted in FIG. 16 optionally comprise nothing, a linker, a primer, an L or R flanking sequence, or a promoter sequence. A "target-identifying sequence", as noted in FIG. 16, refers to any sequence used to identify the 'target' (or targets) being analyzed. In some embodiments, the target sequence is the target itself, for example a fixed nucleic acid could be a sequence attached to the target or reverse complement of that attached sequence. In some embodiments, an ISH probe, aptamer, or nucleic acid conjugated to protein is an attached sequence. In some embodiments, the target sequence could be stacked to multiple levels. For example, a node barcode binds to a probe sequence, which is hybridized to a nucleic acid conjugated to antibody, which is bound to a target protein.

Staining

Provided herein are methods for image capture and enhancement thereof which incorporate application of imaging reagents. Imaging reagents can be used for distinguishing cells, cell types, and/or subcellular structures. In some embodiments, a tissue sample or a population of cells provided herein is contacted with imaging reagents. In some embodiments the imaging reagent is a dye or stain. In some embodiments, the dye or stain comprises 7-AAD, acridine orange, Bismarck brown, calcein, CFSE, carmine, Coomassie blue, cresyl violet, crystal violet, DAPI, eosin, ethidium bromide, acid fuchsin, haematoxylin, Hoechst stains, iodine, malachite green, methyl green, methylene blue, neutral red, Nile blue, Nile red, osmium tetroxide (formal name: osmium tetraoxide), propidium iodide, resazurin, rhodamine, safranin, Trypan Blue, tetrazolium salts, or any combination thereof.

In some embodiments, samples are visualized with immunofluorescent (IF) staining. In some embodiments, the IF staining reagent comprises a fluorophore conjugated streptavidin. In some embodiments, the imaging reagent is a fluorophore. Exemplary fluorophores for inclusion in workflows described herein include, but are not limited to, 1,5 IAEDANS; 1,8-ANS; 4-Methylumbelliferone; 5-carboxy-2, 7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; CMFDA; Coelenterazine; Coelenterazine cp; Coelenterazine f; Coelenterazine fcp; Coelenterazine h; Coelenterazine hep; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Diehl orodihydrofluorescein Diacetate); DDAO; DHR (Dihydrorhodamine 123); Di-4-ANEPPS; Di-8-ANEPPS (non-ratio); DiA (4-Di-16-ASP); DIDS; Dihydorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Eva Green; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxy stilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilb-amidine (FluoroGold); Hydroxytryptamine; Indodicarbo-cyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; LuciferYellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxy coumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitroben-zoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feul-gen); PE-Cy5; PE-Cy7; PerCP; PerCP-Cy5.5; PE-TexasRed (Red 613); Phloxin B (Magdala Red); Phorwite AR; Phor-wite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quina-crine Mustard; Resorufm; RH 414; Rhod-2; Rhodamine; Rhodamine 110; Rhodamine 123; Rhodamine 5 GLD; Rho-damine 6G; Rhodamine B 540; Rhodamine B 200; Rhod-amine B extra; Rhodamine BB; Rhodamine BG; Rhodamine Green; Rhodamine Phallicidine; Rhodamine Phalloidine; Rhodamine Red; Rhodamine WT; Rose Bengal; R-phyco-erythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; SYBR Gold; SYBR Green I; SYBR Green II; SYBR Safe; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; Tricolor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

In some embodiments, sample imaging provides a basis for identification of cellular regions of interest (ROI). An ROI, in some embodiments, comprises an area of a sample targeted for spatially defined barcoding of cDNAs. In some embodiments, the ROI is based on morphology of a sample, for example cells, cellular structures, tissue layers, or sub-cellular structures. In some embodiments, the ROI has a regular or irregular boundary. In some embodiments, the ROI describes a boundary for spatially-defined barcoding in a sample. In some embodiments, the ROI is grid-based. In some embodiments, the ROI is in two dimensions (2D). In some embodiments, the ROI is in three dimensions (3D).

A photomask provides a template to control areas of a sample that receive radiated light. In some embodiments, a photomask is generated to allow radiation of one or more ROIs. In some embodiments, one or more photomasks are generated. In some embodiments, a photomask is generated relevant to each ROI. In some embodiments, each cross-linking step comprises a unique photomask. In some embodiments, the photomask is manually or machine generated. In some embodiments, the photomask is generated according to sample imaging as previously described herein.

In Situ Barcoding

Barcoding provides an information tag in a sample. In some embodiments, a DNA barcode is a short section of DNA wherein individual sequences can be used to identify or differentiate samples, cells, ROIs, cell types, targets, target types, nodes, node types, proximal molecules, spatial information, node information, or combinations thereof. Barcodes, in some instances, are incorporated into a longer length of nucleic acid for further processing. Further processing can comprise extraction, amplification, sequencing, analysis, and any combination thereof.

In some embodiments described herein, methods comprise barcoding a target in a sample. In some embodiments, the target is a nucleic acid, a protein, an antigen, a lipid, a sugar, a cellular structure, a scaffold, or any combination thereof. In some embodiments, the target is a nucleic acid is generated in situ. In some embodiments, cDNA is generated from nucleic acid in a sample through in situ transcription. In some embodiments, the in situ transcription is reverse transcription. In some embodiments, RNA is generated in situ from partially or completely double-stranded DNA through transcription. In some embodiments, an overhang is added to the cDNA by adding a poly-A tail. In some embodiments, the tissue samples or population of cells provided herein are then barcoded by addition of one or more nucleic acid barcodes.

In some embodiments, the target nucleic acid is an amplification product. Nucleic acid amplification can be carried out at constant temperature ("isothermal"), to reduce the use of complex external equipment. In some embodiments, the target nucleic acid is generated by isothermal amplification. In some embodiments, isothermal amplification is performed at ambient temperature and/or room temperature. In some embodiments, ambient temperature and/or room temperature is about 20 to 25° C. In some embodiments, the isothermal amplification is rolling circle amplification (RCA), Loop-Mediated Isothermal Amplification (LAMP), Helicase-Dependent Amplification (HDA), Strand Displacement Amplification (SDA), Multiple Displacement Amplification (MDA), Ligase Chain Reaction (LCR), Recombinase Polymerase Amplification (RPA), Ramification amplification method (RAM), Nucleic Acid Sequence- Based Amplification (NASBA). In some embodiments, the target nucleic acid is generated by signal amplification by exchange reaction (SABER). In some embodiments, the target nucleic acid is generated from a synthesis reaction. In some embodiments, the target nucleic acid is generated by a primer exchange reaction (PER) or RCA. In some embodiments, the PER is a Terminal deoxynucleotidyl transferase (Tdt)-based PER assay. In some embodiments, the target nucleic acid is a long repetitive single-stranded RNA or DNA sequence. In some embodiments, the amplification is performed at multiple temperatures, for example in a cycle. In some embodiments, the amplification is performed using non-isothermal, linear, or exponential amplification methods. In some embodiments, the amplification is PCR. In some embodiments, the PCR is asymmetric PCR. In some embodiments, the amplification is isothermal. Example isothermal amplification methods include strand-displacement amplification (SDA), rolling-circle amplification (RCA), whole-genome amplification (WGA), loop-mediated isothermal amplification (LAMP), helicase-dependent amplification (HDA), and multiple displacement amplification (MDA).

Nucleic acids provided herein can be non-specifically or specifically conjugated to another molecule in a sample. In some embodiments, a nucleic acid is conjugated to a protein, an epitope, a lipid, a liposome, a droplet, a bead, another nucleic acid LNP, AAV, exosome, or a lentivirus. In some embodiments, the barcode is conjugated to the molecule. In some embodiments, a barcode comprises a nucleic acid conjugated to an antibody, antibody fragment, protein, nanobody, small molecule, nucleic acid therapeutic, lipid, nanoparticle, lipid nanoparticle or other affinity reagent. In some embodiments, an antibody fragment, as described herein, is a $F(ab')_2$ fragment, an Fab' fragment, an Fab fragment, an Fv fragment, an IgG fragment, an Fc fragment, or any combination thereof. In some embodiments, the lipid is an emulsion, a liposome, a particle, or any combination thereof. In some embodiments, the antibody is an IgA, IgG, or IgM antibody or a functional fragment thereof. In some embodiments, the tissue samples or population of cells provided herein are imaged after barcoding.

In some embodiments, the target nucleic acid is conjugated to a molecule. In some embodiments, the target nucleic acid and/or a molecule conjugated to said target nucleic acid is detected by a proximity ligation assay (PLA). PLA permits detection of protein-protein interactions in situ at distances of about less than 40 nanometers. In some embodiments, the target nucleic acid is a PLA oligonucleotide. In some embodiments, a barcode nucleic acid provided herein further comprises a PLA oligonucleotide. In some embodiments, the target nucleic acid comprises a first PLA oligonucleotide, wherein the first PLA oligonucleotide is conjugated to a first protein of interest. In some embodiments, the first PLA oligonucleotide hybridizes to a second PLA oligonucleotide, wherein the second PLA oligonucleotide is conjugated to a second protein of interest. In some embodiments, the first protein of interest or the second protein of interest are selected from the group consisting of: an antibody, an antibody fragment, a cell surface receptor, a cell surface protein, and intracellular protein, a mitochondrial protein, a nuclear protein, a transcription factor, or a scaffold protein. In some embodiments, the first PLA oligonucleotide and the second PLA oligonucleotide are ligated to form a circular DNA. In some embodiments, the circular DNAs are amplified. In some embodiments, the circular DNA comprises a barcode strand provided herein. In some embodiments, the circular DNA is contacted with a barcode strand provided herein. In a PLA reaction, the barcodes can be used to identify unique protein-protein or nucleic acid and protein interaction within a sample.

In some embodiments, a concatemer described herein is linked to a protein. In further embodiments, a proteinase is applied to release the concatemer from the surface. In some embodiments, a barcode described herein is linked to a protein. In further embodiments, a proteinase is applied to release the barcode from the surface. Example proteinases for inclusion include, without limitation, proteinase K. In some embodiments, the proteinase is applied prior to an antigen retrieval reaction (e.g., reverse transcription), prior to a barcoding reaction, prior to a concatemerization reaction, and/or prior to the concatemer retrieval reaction.

In some embodiments, the target nucleic acid is DNA. In some embodiments, the DNA is nuclear DNA. In some embodiments, the DNA is mitochondrial DNA. In some embodiments, the target nucleic acid is RNA. In some embodiments, the target nucleic acid is an intron. In some embodiments, the target nucleic acid is an exon. In some embodiments, the RNA is messenger RNA (mRNA). In some embodiments, the target nucleic acid is a regulatory RNA. In some embodiments, the RNA is circular RNA (circRNA), ribosomal RNA (rRNA), 16S ribosomal RNA (16S rRNA), transfer RNA (tRNA), small nucleolar RNA (snoRNA), small nuclear RNA (snRNA), a non-coding RNA, long non-coding RNA (lncRNA), or microRNA (miRNA).

In some embodiments, a target nucleic acid is exposed to a DNA or RNA polymerase. In some embodiments, a polymerase refers to an enzyme that performs template-directed synthesis of polynucleotides. In some embodiments, a DNA polymerase is isolated or derived from *Pyrococcus furiosus, Thermococcus litoralis*, and *Thermotoga maritime*, or modified versions thereof. In some embodiments, polymerase enzymes include, but are not limited to: Klenow fragment (New England Biolabs Inc.), Taq DNA polymerase (QIAGEN), 9° N™ DNA polymerase (New England Biolabs Inc.), Deep Vent™ DNA polymerase (New England Biolabs Inc.), Manta DNA polymerase (Enzymatics), Bst DNA polymerase (New England Biolabs Inc.), or phi29 DNA polymerase (New England Biolabs Inc.). In some embodiments, a polymerase is DNA-dependent. In some embodiments, a polymerase is RNA-dependent. In some embodiments, the polymerase is reverse transcriptase.

In some embodiments, in situ reverse transcription comprises incorporation of a primer. In some embodiments, a primer describes a short nucleic acid sequence. In some embodiments, the primer is DNA. In some embodiments, the primer is RNA. In some embodiments, the primer has a region complementary to a strand of DNA or RNA. In some embodiments, the primer provides a free 3-OH at which a DNA polymerase starts synthesis of a deoxyribonucleotide chain. In some embodiments, the primer contains from about 5 to about 50 or more nucleotides. In some embodiments, the primer contains about 10 to about 30 nucleotides. In some embodiments, a primer as described herein comprises the 3' sequence NNNNNNN (7N's), NNNNNGGG (5N's and 3G's), NNNNNCCC (5N's and 3C's), NNNNNAAA (5N's and 3A's), or NNNNNTTT (5N's and 3T's).

In some embodiments, the primer is attached to an affinity molecule, a scaffold, a substrate, a surface, a bead, or a column. In some embodiments, the substrate. In some embodiments, the primer is in suspension, in solution, or in a hydrogel.

In embodiments a 3' overhang is added to the cDNA transcripts in a tailing step. In some embodiments, tailing is achieved through the use of a terminal transferase enzyme and dXTP (dATP, dCTP, dGTP, dTTP, or any combination thereof). Adding ddXTP (ddATP, ddCTP, ddGTP, ddTTP, or any combination thereof) or another terminating nucleotide at the 3' end prevents subsequent extension during the later cross-junction synthesis step. In some embodiments, ddXTP or another terminating nucleotide is included at a low concentration to randomly terminate the 3' end. In some embodiments, other strategies are used to add a 3' overhang. In some embodiments, an overhang is added by ligation.

Barcodes provided herein generally encode non-genetic data. In some embodiments, the barcode strand is a single-stranded nucleic acid. Introduction of hybridization domains to the barcode strand allows for arbitrary arrangement of barcodes through iterative hybridization, crosslinking, and washing steps. In some embodiments, the nucleic acid barcode strand comprises a barcode domain. In some embodiments, the barcode domain is about 5 to about 10 bases in length. In some embodiments, the barcode domain is flanked by a set of two alternating hybridization domains. In some embodiments, the barcode domain is flanked by unique hybridization domains. In some embodiments, the barcode domain is flanked by an alternating set of 3, 4, 5, 6 or more hybridization domains. In some embodiments, a hybridization domain is a crosslinking domain. In some embodiments, a hybridization domain is a complementary strand. In some embodiments, a set of two alternating hybridization domains comprise one crosslinking strand and one complementary strand. In some embodiments, a nucleic acid barcode comprises a barcode domain linked to (i) a crosslinking strand that comprises a photo-activated nucleotide and (ii) a complementary strand. In some embodiments, the alternating hybridization domains can be at least 5, at least 10, at least 15, or at least 20 bases in length. In some embodiments, the alternating hybridization domains comprise bases to hybridize to a hybridization domain of a second nucleic acid barcode. In some embodiments, a crosslinking strand of one nucleic acid barcode hybridizes with a complementary strand of another.

In some embodiments, barcodes provided herein are deposited onto a sample with a concentration from about 20 nM to about 500 nM. In some embodiments, barcodes provided herein are deposited onto a sample with a concentration up to about 1 nM, 10 nM, 20 nM, 100 nM, 250 nM, 500 nM, 1000 nm, or more. Barcode binding to a target region may be stable or transient.

In some embodiments, a nucleic acid barcode domain is about 5-10 bases in length. In some embodiments, a nucleic acid barcode domain is 4, 5, 6, 7, 8, 9, 10 or more bases in length. In some embodiments, a nucleic acid barcode domain is about 10 or about 10-15 bases in length. Individual unique barcode domains can be assigned a bit value of '0' or '1'. In some embodiments a concatenated string of nucleic acid barcodes is equivalent to a string of '0's and '1's.

A crosslinking strand, in some embodiments, is a single-stranded nucleic acid that is 200 nucleotides or fewer in length. In some embodiments, a crosslinking strand is 5-100, 5-75, 5-50, 5-25, 5-15, or 5-10 nucleotides in length. In some embodiments, a crosslinking strand may be 10-100, 10-50, 10-25, 10-20, 15-25, or 15-25 nucleotides in length. In some embodiments, a crosslinking strand may be 5, 6, 7, 8, 9, or 10 nucleotides in length. In some embodiments, a crosslinking strand comprises at least one photoreactive nucleotide. In some embodiments, a crosslinking strand comprises at least one CNVK or CNVD nucleotide. In some embodiments, a crosslinking strand is complementary to a complementary strand, wherein the crosslinking strand is a component of a first nucleic acid barcode and the complementary strand is a component of a second nucleic acid barcode. In some embodiments, a crosslinking strand is DNA or RNA. In some embodiments, crosslinking strands are further functionalized with moieties such as fluorophores, quantum dots, biotin, streptavidin, functional chemical groups, acrydite, maleimide, lipids, metal isotopes and other tags or nanoparticles.

In some embodiments, a nucleic acid barcode strand is at least 15, 20, 25, 30, 40, 50, 60, 70, 80, 90, or 100 nucleotides in length. In some embodiments, a nucleic acid barcode strand is 20 nucleotides in length. In some embodiments, a nucleic acid barcode strand comprises a barcode domain that is from 2 to 10 nucleotides in length, a crosslinking strand that is from 2 to 12 nucleotides in length, and a complementary strand that is from 2 to 12 nucleotides in length. In some embodiments, a nucleic acid barcode strand comprises a structure in the 5' to 3' direction: 5'-crosslinking strand-to-barcode domain-to-complementary strand-3'. In some embodiments, the nucleic acid barcode strand comprises a structure in the 5' to 3' direction: 5'-complementary strand-to-barcode domain-to-crosslinking strand-3'.

A crosslinking strand can be designed to stably bind or transiently bind to a complementary strand. In some embodiments, a crosslinking strand can be covalently or non-covalently bound to a complementary strand. In some embodiments, a crosslinking strand can be complementary to a complementary strand. A crosslinking strand can be at least 20%, at least 30%, at least 40%, at least 50%, at least 60%, at least 70%, at least 80%, or at least 90% complementary to a complementary strand. Further, a crosslinking strand may bind to a complementary domain of a different nucleic acid barcode. In some embodiments, a crosslinking strand may bind to a complementary domain of a nucleic acid that comprises its own crosslinking strand but does not comprise a barcode strand.

Figure 17:
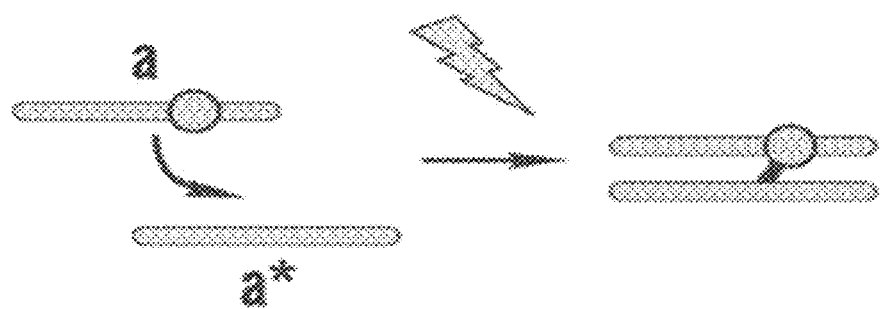
FIG. 17 illustrates the light-directed crosslinking reaction as described herein.

Nucleic acid barcode strands can be concatenated and covalently fixed together by a photo-chemical crosslinking reaction. In some embodiments, the crosslinking reaction is light driven. In some embodiments, the crosslinking reaction is chemically driven. In some embodiments, the crosslinking reaction is pH driven. In some embodiments, the crosslinking reaction can be performed in aqueous solution. In some embodiments, a photoreactive crosslinker is used in the reaction. In some embodiments, a photoreactive nucleobase is used in the reaction. In such embodiments, crosslinking strands of nucleic acid barcodes comprise at least one photo-reactive nucleobase. In some embodiments, the photo-reactive nucleobase can be any modified nucleobase that is capable of forming a crosslink with another nucleobase in the presence of light. In some embodiments, the photo-reactive nucleobase is a modified pyrimidine or purine nucleobase. In some embodiments, the photo-reactive nucleobase comprises 2-hydroxycarbazole, 3-cyanovinylcarbazole phosphoramidite (CNVK) or 3-cyanovinylcarbazole modified d-threoninol (CNVD). In some embodiments, the photo-reactive nucleobase comprises a vinyl, acrylate, N-hydroxysuccinimide, amine, carboxylate or thiol chemical group. In some embodiments, the photo-reactive nucleobase comprises a bromo-deoxyuridine. In some embodiments, the CNVK crosslinking base displays highest crosslinking efficiency with a thymine (T) base that is positioned adjacent to the base on the complementary strand and can be directly incorporated into the DNA hybridization domain itself as a base substitution. In some embodiments, a crosslinking reaction is performed using 365 nm wavelength of light and is completed within 1 second, as depicted in FIG. 17. In some embodiments, a plurality of photo-crosslinker molecules are incorporated, such that different barcodes comprise different photo-crosslinker molecules capable of crosslinking at different wavelengths. Such variance in the barcodes allows for methods varying crosslinking events at one or more regions of interest. In some embodiments, a reverse crosslinking reaction is performed. For example, application of a wavelength of 312 nm for a few minutes provides for crosslink reversal. In some embodiments, a series of crosslink-then-decrosslink reactions is performed to form concatemers. In some embodiments, molecules are deposited on a substrate provided herein to locally generate a light wavelength to support the light sensitive crosslinking reaction.

A crosslinking reaction can be designed to use any wavelength of visible or ultraviolet light. In some embodiments, a crosslinking reaction can be completed within 0.1, 0.25, 0.5, 1, 5, or 10 seconds. In some embodiments, a crosslinking reaction can be completed within 0.5, 1, 5, 10, 20, 30, 40, 50, or 60 minutes. In some embodiments, a crosslinking reaction has negligible effects on bases that neighbor the photoreactive nucleobase. In some embodiments, other photochemical nucleic acid crosslinking agents, including psoralen are used in combination with nucleic acid barcodes.

Figure 18:
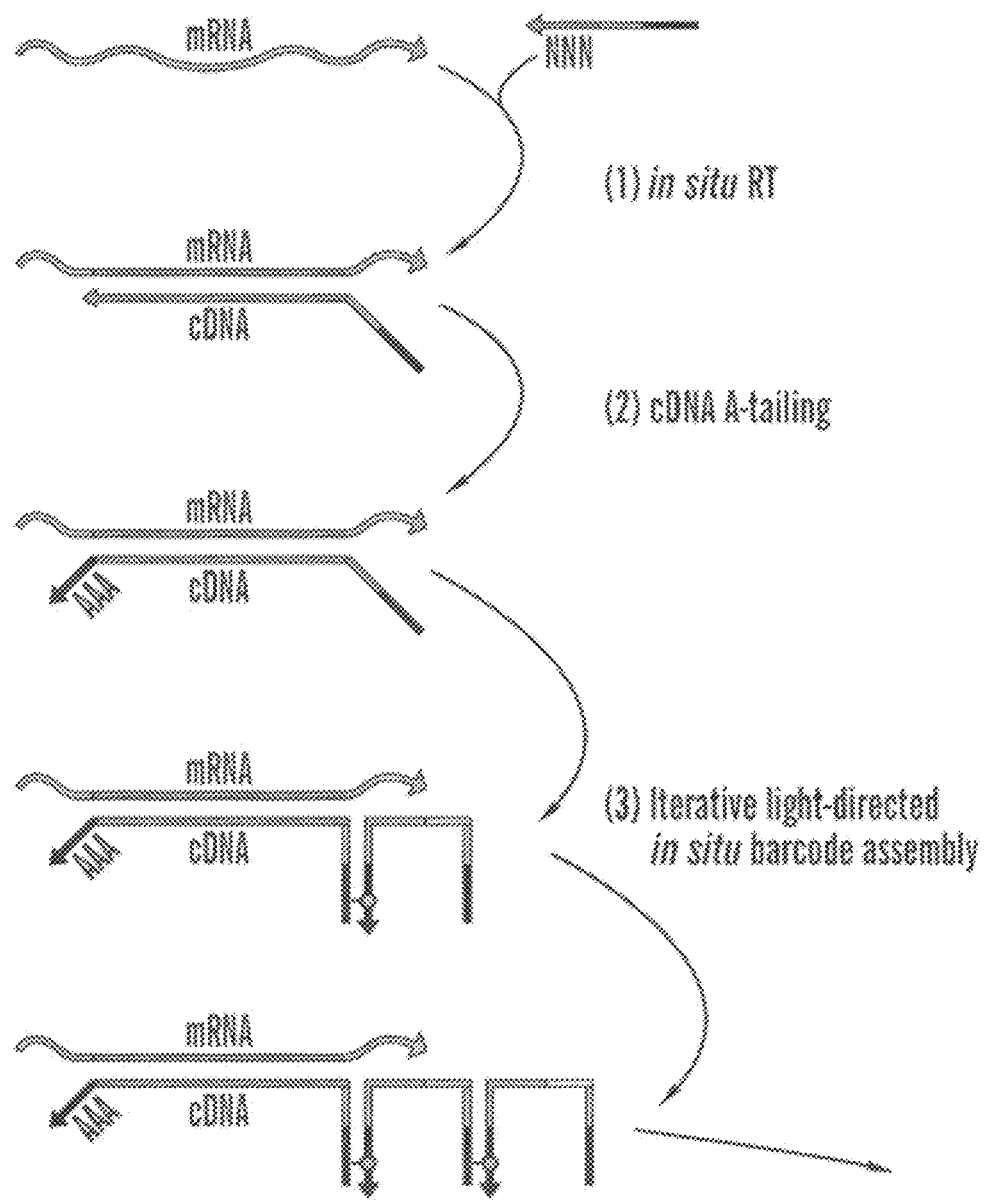
FIG. 18 illustrates an iterative barcode addition method, wherein barcode strands are added to the 5' end of a cDNA.

In some embodiments, a crosslinking reaction is applied to a nucleic acid barcode strand hybridized to the 5' end of a cDNA. In some embodiments, a crosslinking reaction is applied to a nucleic acid barcode strand hybridized to the 3' end of a cDNA. In some embodiments, additional barcode strands are iteratively added to either the 5' or 3' end of the cDNA-nucleic acid barcode structure, using binding and crosslinking as previously described. FIG. 18 shows a process comprising iterative addition of barcode strands to the 5' end of a cDNA according to methods described herein.

In some embodiments, a nucleic acid probe comprises a barcode and a light-sensitive crosslinking molecule. In some embodiments, the nucleic acid probe comprises a barcode and a CNVK molecule. In some embodiments a nucleic acid probe comprises a barcode, a CNVK molecule, and a fluorophore. In some embodiments, the nucleic acid probe hybridizes to a factory target nucleic acid. In some embodiments, the nucleic acid probe hybridizes to a node nucleic acid. In some embodiments, the nucleic acid probe hybridizes to a concatemer of factory target nucleic acids, a concatemer node nucleic acids, or a concatemer of both target binding and node nucleic acids.

Cleaving oligonucleotides are short oligonucleotides, from about 10 to about 50 nucleotides in length, that hybridize to a restriction site on a single-stranded nucleic acid, creating a double-stranded region around the restriction site In some embodiments, functionality an endonuclease requires a double stranded recognition sequence. In some embodiments, short cleaving oligonucleotides are crosslinked to concatemers to generate hybrid node strands that carry a node barcode. In some embodiments, a cleaving oligonucleotide is attached to a single-stranded nucleic acid using light-directed photocaging. In some embodiments, generation of a stable, covalently linked, structure with the in situ generated node strands allows for use of additional functionalization available for synthesized oligonucleotides.

In some embodiments, cleaving oligonucleotides are modified before, during, or after hybridization. In some embodiments, cleaving oligonucleotides are modified to incorporate one or more additional functionalities to the oligonucleotide.

In some embodiments, a crosslinking reaction occurs concurrently with hybridization. In some embodiments, cycles of hybridization and crosslinking are repeated without a washing step to remove barcode strands that are not crosslinked.

Light-directed crosslinking is, in some embodiments, selectively applied to a sample of cells. Crosslinking is selectively performed by shielding areas from radiation, allowing crosslinking only in unshielded areas. A photomask provides a template to shield areas of a sample that receive radiated light. In some embodiments, a photomask is generated to allow radiation of one or more ROIs. In some embodiments, the photomask is manually or machine generated. In some embodiments, the photomask is generated according to sample imaging as previously described herein. In some embodiments a photomask is applied to a sample prior to radiation.

In some embodiments, in addition or in lieu of a photomask, as described herein, light is focused on one or more ROIs. In some embodiments, light is focused using a digital micromirror device (DMD). In some embodiments, light is focused using a confocal microscope. In some embodiments, the confocal microscope is a laser scanning confocal microscope. In some embodiments, light is focused using a DVD writer. In some embodiments, light is focused using a Blu-ray disc writer.

In some embodiments, light is focused on a surface of the tissue samples or population of cells provided herein. In some embodiments, light is focused on a plane comprising at least one portion of the tissue samples or population of cells provided herein. In some embodiments, light is focused on one or more planar surfaces on or within the tissue samples or population of cells provided herein. In some embodiments, the light-directed crosslinking described herein is applied to a surface of the tissue samples or population of cells provided herein. In some embodiments, the light-directed crosslinking described herein is applied across multiple planes within the tissue samples or population of cells provided herein. In some embodiments, the light-directed crosslinking described herein is applied on multiple planes of a 3-dimensional tissue samples or population of cells provided herein.

In some embodiments, radiation is provided at a particular wavelength or range of wavelengths. In some embodiments, the radiation is ultraviolet (UV) radiation. In some embodiments, the radiation is provided at wavelengths in a range from about 300 nanometers (nm) to about 450 nm. In some embodiments, the radiation is provided at a wavelength of about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, about 400 nm, about 405 nm, about 410 nm, about 415 nm, about 420 nm, about 425 nm, about 430 nm, about 435 nm, about 440 nm, about 445 nm, about 450 nm, or any combination thereof. In some embodiments, the radiation is provided at a wavelength of about 365 nm. In some embodiments, the radiation is provided at a wavelength of about 405 nm.

Figure 19A:
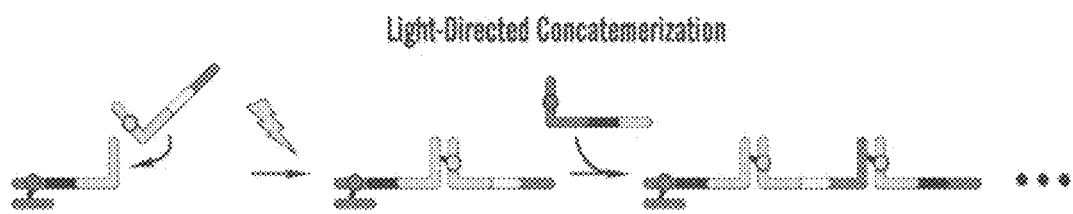
FIG. 19A illustrates light-directed crosslinking to generating barcode concatemers.
Figure 19B:
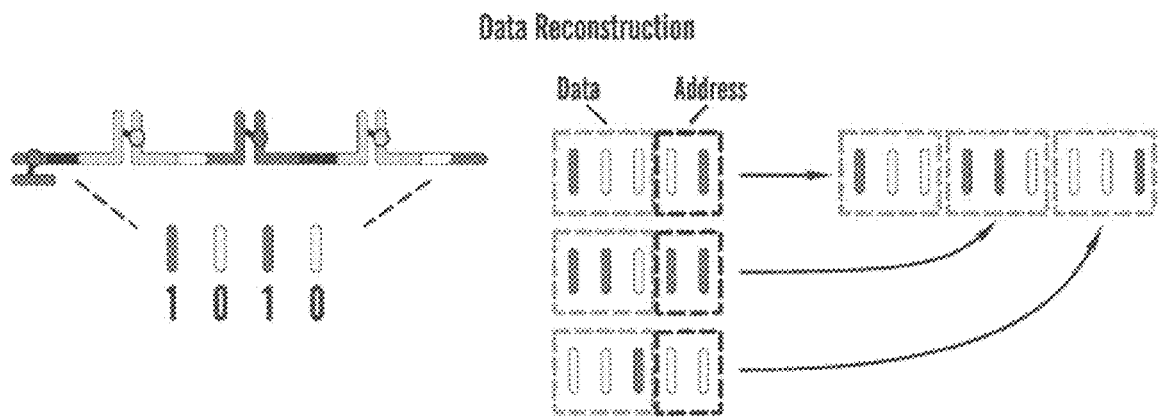
FIG. 19B illustrates data reconstruction from a barcode concatemer.

In some embodiments, radiation is provided for a particular amount of time. In some embodiments, the radiation is provided for about 1 second up to 10 seconds. In some embodiments, the radiation is provided for about 100 milliseconds (ms) up to 10 seconds. In some embodiments, the radiation is provided for at least about 10 ms or more, at least about 100 ms or more, at least about 500 ms or more, at least about 600 ms or more, at least about 700 ms or more, at least about 800 ms or more, at least about 900 ms or more, at least about 1 second or more, at least about 2 seconds or more, at least about 3 seconds or more, at least about 4 seconds or more, at least about 5 seconds or more, at least about 6 seconds or more, at least about 7 seconds or more, at least about 8 seconds or more, at least about 9 seconds or more, at least about 10 seconds or more, at least about 11 seconds or more, at least about 12 seconds or more, at least about 13 seconds or more, at least about 14 seconds or more, at least about 15 seconds or more, at least about 16 seconds or more, at least about 17 seconds or more, at least about 18 seconds or more, at least about 19 seconds or more, at least about 20 seconds or more, or at least about 30 seconds or more. The order and frequency of types of barcodes in a concatemer is not prescribed or limited. A concatemer optionally comprises combinations of target barcodes, node barcodes, The iterative addition of nucleic acid barcodes to a cDNA produces a nucleic acid concatemer. In some embodiments, nucleic acid concatemer comprises at least three nucleic acid barcode strands. A nucleic acid concatemer may comprise nucleic acid barcode strands that are covalently linked to one another via photoreactive nucleotides. In some embodiments, a nucleic acid concatemer may comprise at least 1, at least 2, at least 3, at least 4, at least 5, or at least 10 nucleic acid barcode strands. In some embodiments, a nucleic acid concatemer may comprise at least 1, at least 2, at least 3, at least 4, at least 5, or at least 10 barcode domains that each incorporate data, e.g., each barcode domain may uniquely/independently be assigned to a bit value. One embodiment of digital data storage using light-directed concatemerization of barcodes is shown in FIGS. 19A-19B. Concatemers of nucleic acid barcode can comprise at least two, at least three, at least four, at least five, at least ten, at least 15, at least 20, at least 25, at least 30, or at least 50 nucleic acid barcodes. The order and frequency of types of barcodes in a concatemer is not prescribed or limited. A concatemer optionally comprises combinations of target barcodes, node barcodes, The number of additional barcode strands that can be added is not limited. For example, 1, 2, 3, 4, 5, 6, 7, 8, 9, 10, 11, 12, 13, 14, 15, 16, 17, 18, 19, 20, 21, 22, 23, 24, 25 or more additional barcode strands can be added. In some embodiments, 75, 100, 150, 200, 250 or more additional barcode strands can be added.

In some embodiments, CNVK-labeled strands can be hybridized to docking strands by 1 to 10 bases or by 10 to 20 bases. In some embodiments, salt concentrations, temperature, denaturant concentration, or strand concentration affects stability of strand binding. In some embodiments, stability of strand binding is adjusted such that CNVK-labeled strands bind for less than 1 second, between 1 and 10 seconds, or for less than 1 minute on average. In some embodiments, CNVK-labeled strands can have increased homology domains to docking strands, (20-40 bases, more than 40 bases). In some embodiments, salt is increased, or temperature decreased, thereby adjusting strand binding on average for longer than one minute. In some embodiments, conditions can be adjusted to determine the average bound time of the CNVK-labeled strands to docking strands.

Nucleic acid barcodes optionally comprise additional detectable labels such as fluorophores, luminescent and bioluminescent markers (e.g., biotin, luciferase (e.g., bacterial, firefly, click beetle and the like), luciferin, and aequorin), radiolabels (e.g., 3H, 1251, 355, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. In some embodiments, barcodes described herein are modified to comprise the addition of a small molecule, antibody, enzyme (e.g., Cas9), or metal isotope.

In some embodiments, a nucleic acid described herein is covalently linked to at least one other of nucleic acid through a single photoreactive element of a hybridization domain.

The concatemers of nucleic acid barcodes can be in various positions on the substrate provided herein. For example, concatemers can be linear, have two different orientations, or multiple orientations in different directions. The barcodes can be positioned along x, y, and z coordinates in space.

Methods as described herein comprise application of reagents, including barcode strands, wash sequences, and the like, to a sample. In some embodiments, application methods comprise traditional microfluidics, passive diffusion, electrophoresis, digital microfluidics, acoustic liquid handlers (e.g., Echo Liquid Handler®, Beckman Coulter, Indianapolis, IN) for depositing new solutions, inkjet printers with modified contents, automatic liquid handlers, optionally incorporating pipettors, robotic arms for processing slides between solution baths, or any combination thereof. In some embodiments, application methods are performed on-stage. In some embodiments, application methods are performed off-stage.

Samples can be treated to prevent or reduce nonspecific binding of barcode strands. In some embodiments, a blocking agent is added to the tissue samples or population of cells provided herein prior to application of barcode strands. In some embodiments, a blocking agent is added to the tissue samples or population of cells provided herein concurrently to application of barcode strands. In some embodiments, the blocking agent comprises non-specific nucleic acid sequences, sheared salmon sperm DNA, tRNA, yeast tRNA, single-stranded oligonucleotides, double-stranded oligonucleotides, polysaccharides, charged polysaccharides, negatively charged polysaccharides, negatively charged molecules, charged molecules bovine serum albumin (BSA), dried milk, detergent, a nonionic polymeric surfactant (e.g., Poly (ethyleneoxide)/poly (propyleneoxide) triblock copolymers—PLURONIC™ F-127, Gibco® Pluronic® F-68), crowding agents, or any combination thereof. In some embodiments, ribosomal depletion or targeted depletion of high abundance sequences occurs prior to any of: reverse transcription, barcoding, sequence extraction, cross-junction synthesis, or PCR amplification. In some embodiments, ribosomal depletion or targeted depletion of high abundance sequences occurs after PCR amplification. In some embodiments, in situ hybridization (ISH) probes targeting high abundance sequences are included before or during reverse transcription to block specific the high abundance sequences from acting as binding sites for reverse transcription primers. In some embodiments, ISH probe binding is combined with nuclease activity (e.g. RNaseH) to specifically digest high abundance sequences in situ prior to reverse transcription. In some embodiments, a double-strand specific nuclease (e.g. dsDNAse) is applied after PCR to specifically de-enrich high abundance sequences.

Following radiation and crosslinking reaction, in some embodiments, barcodes that are not crosslinked are removed. In some embodiments, barcodes that are not crosslinked are removed by washing. In some embodiments, barcodes that are not crosslinked are not removed prior to additional cycles of crosslinking. In some embodiments, a sample is washed with a chemical denaturant solution. In some embodiments, the chemical denaturant solution comprises one or more salts. In some embodiments, the salt is NaCl. In some embodiments, the salt concentration is from 0.1 M to 2 M. In some embodiments, the salt concentration is about 0.1 M, about 0.2 M, about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M. In some embodiments, the chemical denaturant is formamide. In some embodiments, the chemical denaturant is ethylene carbonate. In some embodiments, the formamide solution is 50-60% formamide. In some embodiments, the denaturant solution is in a PBS buffer. In some embodiments, the denaturant solution comprises a detergent. In some embodiments, the concentration of detergent in the denaturant solution is about 0.01%, about 0.05%, about 0.1%, about 0.5%, about 1.0%, about 2%, about 3%, about 4%, or about 5% by volume. In some embodiments, the detergent is a polysorbate. In some embodiments, the polysorbate is polysorbate 20 (TWEEN® 20, Merck KGaA, Darmstadt, Germany) or polysorbate 80 (TWEEN® 80, Merck KGaA, Darmstadt, Germany). In some embodiments, the detergent is a nonionic surfactant. In some embodiments, the non-ionic surfactant is a non-ionic polyoxyethylene detergent. In some embodiments, the detergent is polyethylene glycol (PEG), 2-[4-(2,4,4-trimethylpentan-2-yl)phenoxy]ethanol (CAS number: 9002-93-1), N,Ndimethyltetradecylamine N-oxide (TDAO, CAS number: 3332-27-2). In some embodiments, the detergent is Triton X-100, Nereid, TDAO, or a combination thereof. In some embodiments, the washing is performed at room temperature. In some embodiments, the washing is performed at a temperature warmer or cooler than room temperature. In some embodiments, the washing is performed at 4 degrees C., 16 degrees C., 25 degrees C., 37 degrees C., 40 degrees C., 45 degrees C., 50 degrees C., 55 degrees C., 60 degrees C., or higher temperature.

As described earlier herein, barcodes optionally comprise a detectable label. Following washing to remove DNA barcodes that are not crosslinked, bound barcodes can be visualized. In some embodiments, visualization is by colorimetric, fluorescent, ultraviolet, or other means.

A density of barcoded cDNA targets can be measured by the number of unique sequences detected. In some embodiments, the density of barcoded cDNA targets is the number of barcodes generated within one square micrometer ($\mu m^2$) of a tissue sample, a population of cells, or a population of cells. In some embodiments, the density of barcoded cDNA targets is the number of barcodes generated within a cubic micrometer ($\mu m^3$) of a tissue sample, a population of cells, an organoid, or an organ. In some embodiments, the methods provided herein generate about 55 tags or barcodes per square micrometer ($\mu m^2$). In some embodiments, the methods provided herein generate about 5, about 10, about 15, about 20, about 25, about 30, about 35, about 40, about 45, about 50, about 55, about 60, about 65, about 70, about 80, about 90, about 100, about 150, about 200, about 250, about 300, about, about 350, about 400, about 450, about 500, about 550, about 600, about 650, about 700, about 800, about 900, about 1000, about 1200, about 1400, about 1600, about 1800, about 2000, about 2250, about 2500, about 2750, about 3000, about 3500, about 4000, about 4500, about 5000 tags per $\mu m^2$.

In some embodiments, the methods provided herein generate up to about 5, up to about 10, up to about 15, up to about 20, up to about 25, up to about 30, up to about 35, up to about 40, up to about 45, up to about 50, up to about 55, up to about 60, up to about 65, up to about 70, up to about 80, up to about 90, up to about 100, up to about 150, up to about 200, up to about 250, up to about 300, up to about, up to about 350, up to about 400, up to about 450, up to about 500, up to about 550, up to about 600, up to about 650, up to about 700, up to about 800, up to about 900, up to about 1000, up to about 1200, up to about 1400, up to about 1600, up to about 1800, up to about 2000, up to about 2250, up to about 2500, up to about 2750, up to about 3000, up to about 3500, up to about 4000, up to about 4500, up to about 5000 tags per $\mu m^2$.

In some embodiments, the methods provided herein generate about 5, about 10, about 15, about 20, about 25, about 30, about 35, about 40, about 45, about 50, about 55, about 60, about 65, about 70, about 80, about 90, about 100, about 150, about 200, about 250, about 300, about, about 350, about 400, about 450, about 500, about 550, about 600, about 650, about 700, about 800, about 900, about 1000, about 1200, about 1400, about 1600, about 1800, about 2000, about 2250, about 2500, about 2750, about 3000, about 3500, about 4000, about 4500, about 5000, about 6000, about 70000, about 8000, about 9000, about 10,000 tags per cubic micrometer ($\mu m^3$).

In some embodiments, the methods provided herein generate up to about 5, up to about 10, up to about 15, up to about 20, up to about 25, up to about 30, up to about 35, up to about 40, up to about 45, up to about 50, up to about 55, up to about 60, up to about 65, up to about 70, up to about 80, up to about 90, up to about 100, up to about 150, up to about 200, up to about 250, up to about 300, up to about, up to about 350, up to about 400, up to about 450, up to about 500, up to about 550, up to about 600, up to about 650, up to about 700, up to about 800, up to about 900, up to about 1000, up to about 1200, up to about 1400, up to about 1600, up to about 1800, up to about 2000, up to about 2250, up to about 2500, up to about 2750, up to about 3000, up to about 3500, up to about 4000, up to about 4500, up to about 5000, up to about 6000, up to about 70000, up to about 8000, up to about 9000, up to about 10,000 tags per cubic micrometer ($\mu m^3$).

Fractional Barcoding

Modulating irradiation of a sample can control the amount of crosslinking therein. In some embodiments, irradiating for a longer duration or higher intensity increases the number of crosslinks formed in a 1D, 2D, or 3D region. In some embodiments, crosslinking can be controllably increased in a specific region, cell, or on samples or strands in a test tube. Intensity is a radiometric quantity measured in watts per square centimeter (W/cm$^2$). In some embodiments, the fraction of crosslinks formed within a specific area or volume can be precisely controlled (e.g., on a microscope, with an LED or other light source onto a sample or test tube) by controlling radiation exposure time and power levels. Such tuning allows for region specific photosensitive crosslinking of barcode events. In some embodiments, selective radiation control allows for preselected gradation ("fractionation") for any given barcode (or tag) for affixing to a particular region of interest (a tissue region, cell, subcellar region, microwell, tube, etc.). In some embodiments, the light intensity is about 1 to about 5000 W/cm^2. In some embodiments, the light intensity is up to about 1 W/cm^2. In some embodiments, the light intensity is up to about 5000 W/cm^2. In some embodiments, the light intensity is at least 5000 W/cm^2. In some embodiments, the light intensity is more than 5000 W/cm^2. The above intensities are for when intensity is focused on planar light. Similar intensities can be applied in 3D in which case W/cm^3 amounts are applied. When irradiating a solution, the volume of a sample is radiated. In such instances, intensity is applied per volume unit, such as with a UV gun.

Modulation of the duration or power of the radiation exposure can allow for, in some embodiments, controllable tuning the fraction of formed crosslinks in a particular region of interest (ROI). Otherwise stated, the fraction of sequences crosslinked to a barcode in a particular ROI can be controlled by the radiation exposure time or intensity level. In some embodiments, up to about 100% of barcodes are crosslinked following radiation. In some embodiments, 5, 10, 15, 20, 25, 30, 40, 45, 50, 55, 60, 65, 70, 75, 80, 85, 90, 95% of barcode sequences in an ROI are photo crosslinked to target sequence(s) following radiation. In some embodiments, about 10% of barcodes in an ROI are photo crosslinked to a targets sequences following radiation. In some embodiments, about 20% of barcodes in an ROI are photo crosslinked to a targets sequences following radiation. In some embodiments, about 30% of barcodes in an ROI are photo crosslinked to a targets sequences following radiation. In some embodiments, about 40% of barcodes in an ROI are photo crosslinked to a targets sequences following radiation. In some embodiments, about 50% of barcodes in an ROI are photo crosslinked to a targets sequences following radiation. In some embodiments, about 60% of barcodes in an ROI are photo crosslinked to a targets sequences following radiation. In some embodiments, about 70% of barcodes in an ROI are photo crosslinked to a targets sequences following radiation. In some embodiments, about 80% of barcodes in an ROI are photo crosslinked to a targets sequences following radiation. In some embodiments, about 90% of barcodes in an ROI are photo crosslinked to a targets sequences following radiation.

Populations within a sample can be encoded for identification using one or more fractional application of barcodes. Binary, trinary, quaternary, or any smaller fractions of, encodings can be used. In some embodiments, any combination of fractional application of distinct barcodes that allows for differentiation of barcode fractions can be used. In some embodiments, one or more barcodes are applied at defined fractional amounts in ROIs, generating unique combinations of the one or more barcodes in each ROI. Fractional barcodes can be read using sequencing techniques, fluorescence imaging, spectrophotometry, or any other detection method. In an exemplary embodiment, one ROI in a sample contains 40% barcode 1+20% barcode 2+20% barcode 3, while another ROI contains 20% barcode 1+40% barcode 2+20% barcode 3. Fractions need not all add up to 100%, but should be sufficiently differentiable in readout that they can be reliably de-convolved.

Record Extraction and Sequencing

Generated barcode concatemers can be displaced from the tissue samples or population of cells as provided herein. Concatemers can be synthesized to a continuous nucleic acid strand. These steps can occur sequentially or simultaneously. In some embodiments, continuous nucleic acid strands are pooled. In some embodiments nucleic acid strands are then amplified and sequenced. Sequencing data can be incorporated with earlier imaging data to provide spatially defined sequencing information.

Provided herein are methods for concatemer displacement. In some embodiments, concatemers bound to RNA are displaced from the tissue samples or population of cells provided herein. In some embodiments, concatemers are displaced chemically. In some embodiments, concatemers are displaced enzymatically. In some embodiments, concatemers are displaced using an enzyme that specifically cleaves RNA (e.g., RNaseH). In some embodiments, concatemers are displaced using an enzyme that specifically cleaves DNA, a DNAse (e.g., DNAse I). In some embodiments, concatemers are displaced physically. In some embodiments, concatemers are displaced through the process of cross-junction synthesis. In some embodiments, cross-junction synthesis is performed prior to displacement of the barcoded DNA. In some embodiments, cross-junction synthesis is performed after displacement of the barcoded DNA. In some embodiments, displacement and cross-junction synthesis occur concurrently.

Figure 20:
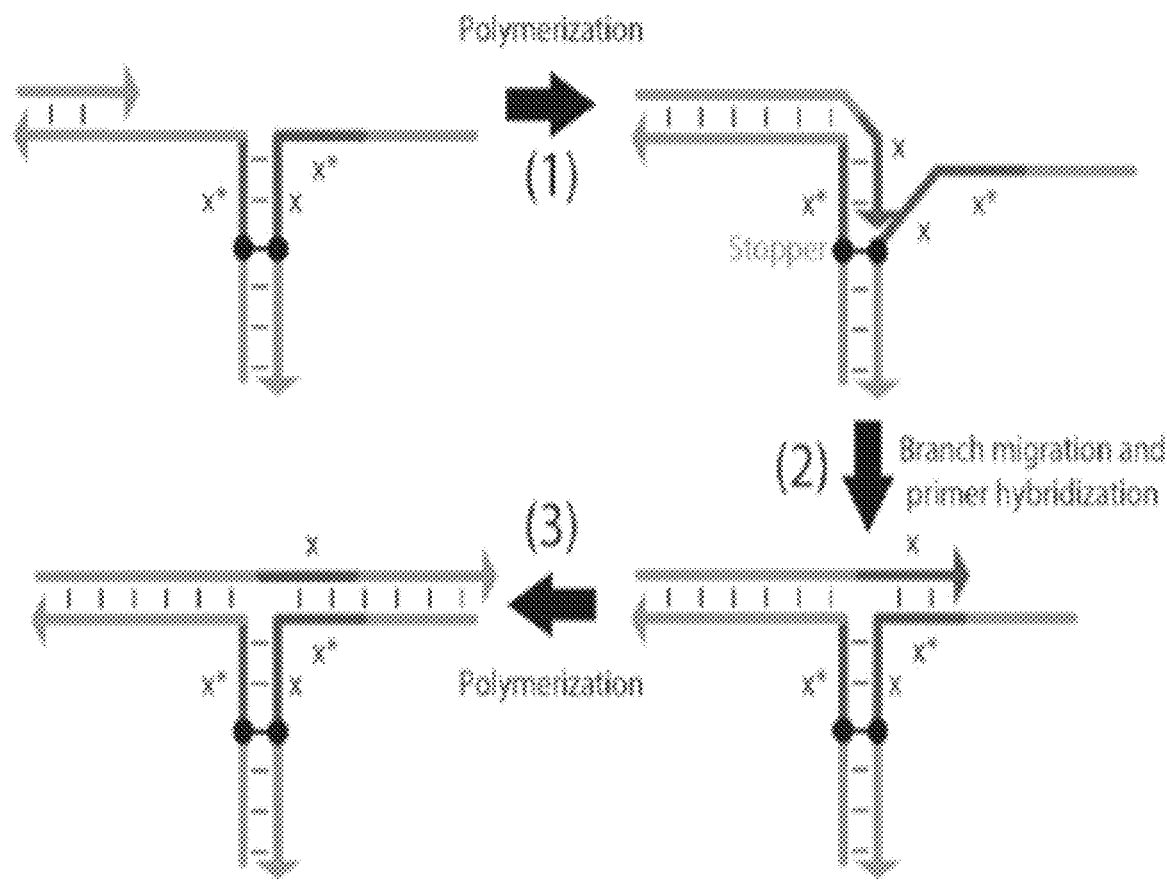
FIG. 20 illustrates the process of cross-junction synthesis.

Provided herein are methods for cross-junction synthesis. Cross-junction synthesis is performed directly in situ, or during/after displacement. The fundamental strategy for cross-junction synthesis is depicted in FIG. 20. Shown are two nucleic acids that have been hybridized together to form a junction. A primer is bound in front of that junction on the first nucleic acid (left). A strand-displacing polymerase is used to copy the x domain (also referred to as a junction domain herein) until it reaches a stopper (shown in black and also referred to as a blocking domain herein). The new and old x domains compete in a random walk branch migration process. Ultimately, the new x domain can bind to the exposed x* domain on the second template strand (right, also referred to as a synthesis region herein). Polymerization can then continue on the second template strand, copying along a new backbone.

In some embodiments, cross-junction synthesis produces a DNA, an RNA, a PNA, or an LNA. In some embodiments, the method of cross-junction synthesis comprises contacting a target nucleic acid or a barcode provided herein with a strand-displacing polymerase. In some embodiments, cross-junction synthesis is performed at room temperature (e.g., at least about 20 degrees C. up to 25 degrees C.). In some embodiments, cross-junction synthesis is performed at temperatures below room temperature (e.g., about 15° C., about 10° C., about 4° C.). In some embodiments, cross-junction synthesis is performed at temperatures above room temperature (e.g., about 30° C., about 37° C.). In some embodiments, nucleic acid amplification or cross-junction synthesis is performed at a constant temperature. In some embodiments, nucleic acid amplification or cross-junction synthesis is performed at different or varied temperature.

Provided herein are methods, wherein a polymerase is prevented or stopped from continuing along the backbone of a template strand and/or copying the template strand by a blocking domain. In some embodiments, the blocking domain comprises one or more modified nucleotides known for increasing $T_m$ of double-stranded nucleic acids. In some embodiments, modified nucleotides include, but are not limited to, locked nucleic acids (LNAs), 2'-0-methoxy-ethyl (2'-MOE) nucleotides, 2,6-diamopurine, G-clamp (an analog of C having 4 hydrogen bonds) and guanidinium G-clamp nucleotides, and the like.

When the nucleic acid template comprises two or more cross-junctions, the first nucleic acid of a first cross-junction can be a second nucleic acid of a second cross-junction. Likewise, the second nucleic acid of a first cross-junction can be a first nucleic acid of a second cross-junction.

It is noted that a nucleic acid described herein, in some embodiments, comprises a barcode domain. In an exemplary embodiment, the second nucleic acid of a junction comprises a barcode domain at the 5'-terminus. In some embodiments, one of the first or second synthesis regions of a nucleic acid comprises a barcode domain.

Figure 21:
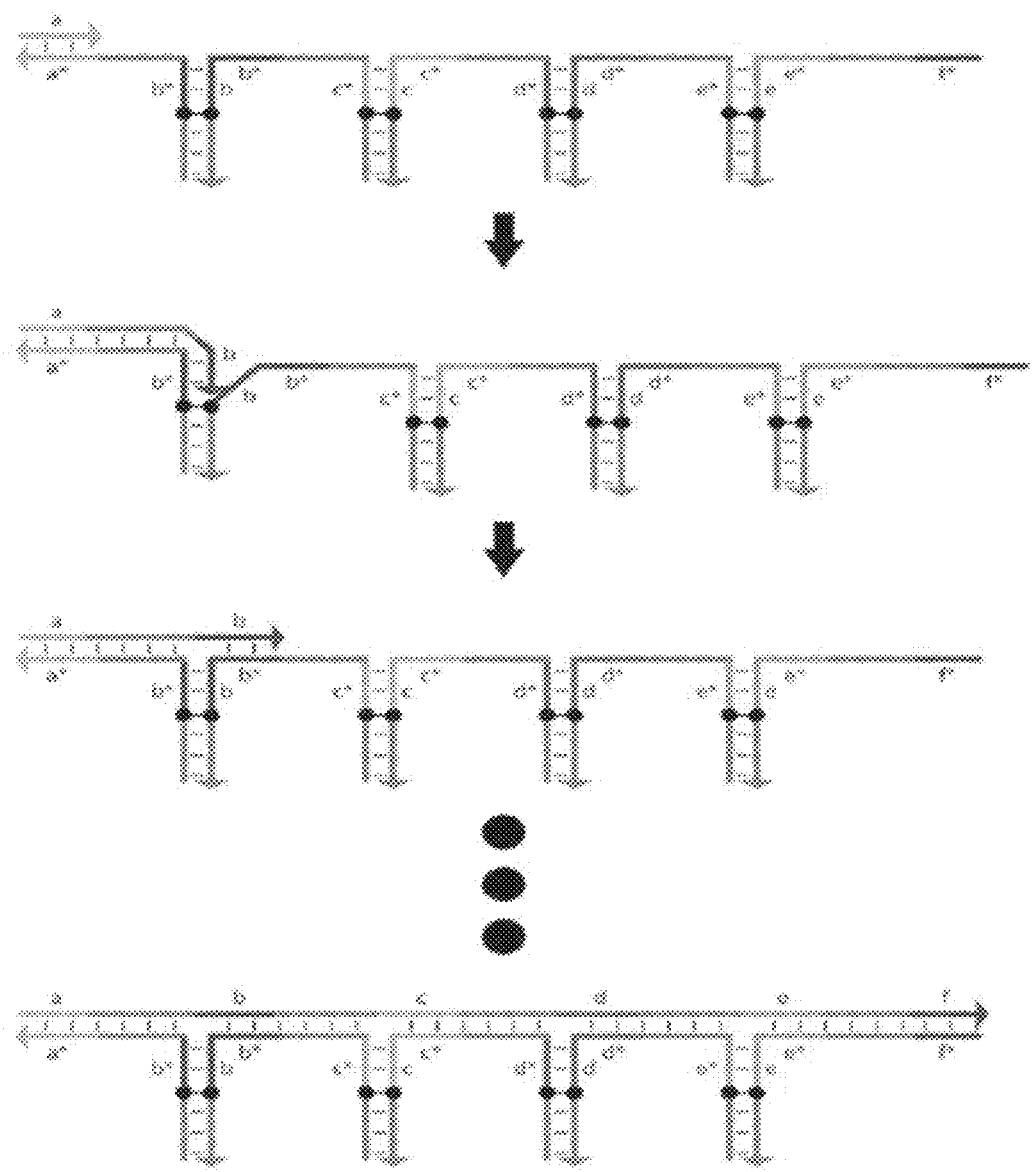
FIG. 21 illustrates a workflow for cross-junction synthesis across a concatemer of barcodes to generate a continuous nucleic acid.

The compositions and methods described herein can be used for synthesis of arbitrary length prescribed sequences. FIG. 21 illustrates an exemplary embodiment, wherein multiple barcode strands are hybridized together and through cross-junction synthesis reactions, are replicated to form longer sequences. Each junction between barcode strands shows the same domain motifs, whereby the strand domains copied on the 3' end of the growing strand before reaching a stopper (b, c, d, e) can reach across the junction and bind to the exposed complementary sequence (b*, c*, d*, e*) on the next barcode strand. Arbitrary sequences can be added in the template regions between the motif domains (shown in gray) to enable longer sequences to be assembled.

In some embodiments, at least one of the blocking domain comprises a poly monomer stretch. For example, the blocking domain comprises a stretch of polyA, polyT, polyC, or polyG.

In some embodiments, the blocking domain can comprise covalent cross-linking of two barcode strands. In some embodiments, the covalent cross-linking is a photo-crosslink or a chemical cross-link. In some embodiments, covalent cross-linking comprises cross-linking the nucleotide at the 5'-terminus of the first barcode strand to the nucleotide at 3'-end of the second template strand. In some embodiments, the cross-linking is at an oligonucleotide or a single nucleic acid backbone linkage. In some embodiments, the cross-linking is by a phosphodiester bond. In some embodiments, the cross-linking reaction is between a CNVK nucleotide and a complementary nucleotide. In some embodiments, the crosslinked nucleotides act as a stopper to a polymerase.

In some embodiments, the blocking region comprises any desired nucleotide sequence or number of nucleotides. In some embodiments, each blocking domain can be of any length. In some embodiments, each blocking domain can be from one nucleotide to 100 nucleotides in length. In some embodiments, each blocking domain is independently one, two, three, four, five, six, seven, eight, nine or ten nucleotides in length. It is noted that a blocking domain can be a single nucleotide.

In some embodiments, in situ hybridization (ISH) is applied. The ISH step generally involves depositing small nucleic acids (e.g., 15-40 mers). In some embodiments, nucleic acid probes recognize a region or regions of genome. In some embodiments, the nucleic acid probes of ISH recognize RNA. In the case of smISH, many small nucleic acids together recognize an RNA, where binding of a single probe results in weak signal, but the ability to obtain a signal from the ensemble of all the probes (directly or via linking of labels to the probes) is robust. In some embodiments, an ISH, or modified ISH, reaction is applied to a sample described herein prior to or following antigen retrieval (e.g., an amplification reaction). In further embodiments, the probes used for ISH are further used for concatemer formation either as the barcode or for barcode binding, followed by methods described herein.

In some embodiments, fluorescent in situ hybridization (FISH) is applied. The FISH step generally involves depositing small nucleic acids (e.g., 15-40 mers) having a label (e.g., a fluorescent label). In some embodiments, nucleic acid fluorescent probes of a FISH recognize a region or regions of genome. In some embodiments, the nucleic acid fluorescent probes of FISH recognize RNA. In the case of smFISH, many small nucleic acids together recognize an RNA, where binding of a single fluorescent probe results in weak signal, but the signal from the ensemble of all the probes is robust. In some embodiments, a FISH, or modified FISH, reaction is applied to a sample described herein prior to or following antigen retrieval (e.g., an amplification reaction). In further embodiments, the probes used for FISH are further used for concatemer formation either as the barcode or for barcode binding, followed by methods described herein.

Provided herein are methods of amplification. In some embodiments, methods comprise PCR amplification. PCR amplification uses a DNA polymerase to synthesize DNA from deoxynucleotide substrates on a single-stranded template. In some embodiments described herein, the PCR method comprises Real-time PCR, Quantitative real time PCR (Q-RT PCR), Reverse Transcriptase PCR (RT-PCR), Multiplex PCR, Nested PCR, Long-range PCR, Single-cell PCR, Fast-cycling PCR, Methylation-specific PCR (MSP), Hot start PCR, High-fidelity PCR, In situ PCR, Variable Number of Tandem Repeats (VNTR) PCR, Asymmetric PCR, Repetitive sequence-based PCR, Overlap extension PCR, Assemble PCR, Intersequence-specific PCR(ISSR), Ligation-mediated PCR, Methylation-specifin PCR, Miniprimer PCR, Solid phase PCR, Touch down PCR, or any combination thereof. In some embodiments, a reverse transcriptase is applied for an amplification described herein. In some embodiments, the reverse transcriptase is a MuLV reverse transcriptase, or Avian myeloblastosis virus (AMV) reverse transcriptase. In some embodiments, a DNA polymerase is applied for an amplification described herein. In some embodiments, the DNA polymerase is a T7 DNA polymerase, thermophilic eubacterial microorganism *Thermus aquaticus* DNA polymerase, Pfu DNA polymerase, or Bst DNA Polymerase. In some embodiments, a DNA ligase is applied for joining strands. In some embodiments, the DNA ligase is EC 6.5. 1.1. In some embodiments, the DNA ligase is a T4 DNA ligase.

In some embodiments, barcode sequences, or primers complementary to such sequences, comprise a polymerase promoter sequence. In some embodiments, the promoter is an RNA polymerase promoter. In some embodiments, the polymerase promoter sequence comprises, without limitation, a T7 RNA polymerase promoter region (SEQ ID NO: 1: TAATACGACTCACTATAG), a T3 RNA polymerase promoter region (SEQ ID NO: 2: AATTAACCCT-CACTAAAG), or a SP6 RNA polymerase promoter region (SEQ ID NO: 3: ATTTAGGTGACACTATAG).

Provided herein are methods for amplicon preparation. In some embodiments, amplicons are purified. In some embodiments, amplicons are analyzed through gel electrophoresis. In some embodiments, amplicons are isolated. In some embodiments, amplicons are fragmented. In some embodiments, amplicons are end-repaired. In some embodiments, amplicons are covalently linked to adapters. In some embodiments, amplicons are tagged.

Provided herein are methods for sequencing. In some embodiments, sequencing comprises next-generation sequencing (NGS) technologies. In some embodiments, sequencing comprises massively parallel sequencing. In some embodiments, sequencing comprises chain termination sequencing, nanopore sequencing, sequencing by ligation, combinatorial probe anchor synthesis, sequencing by synthesis, pyrosequencing, ion semiconductor, or single-molecule real-time sequencing Provided herein are methods for protein analysis. In some embodiments, a protein retrieved from a sample described herein is analyzed by mass spectrometry, an analytical tool for measuring the mass-to-charge ratio (m/z) of one or more molecules present in the sample. Such measurements can be used to calculate the molecular weight of components of the sample.

Provided herein are methods for spatial indexing of transcribed nucleic in selected regions of interest (ROIs) in cells and tissues. In some embodiments, the transcribed nucleic acid is a reverse transcribed DNA or a transcribed RNA. In some embodiments, barcode sequences from sequencing reads provides spatial indexing data. In some embodiments, spatial indexing data combined with imaging methods described earlier herein provides a link between cellular phenotype information and transcriptome information.

In some embodiments, DNA strands are pooled across multiple ROIs. In some embodiments, DNA strands from individual ROI are collected in a region-specific manner. In some embodiments, DNA strands from individual cells are pooled separately. In some embodiments, DNA from individual cells or other defined ROI are barcoded and sequenced separately.

Provided herein are methods of information labeling with nucleic acids. Information labeling, as described herein, provides nongenetic information. In some embodiments, nongenetic information comprises spatial information in a sample. In some embodiments, a sample is a 2-dimensional sample. In some embodiments, a sample is a 3-dimensional sample. In some embodiments, nongenetic information comprises sample information, such as tube number, well number, sample source, charge, mass, or other sample characteristics, or any combination thereof. In some embodiments, nongenetic information comprises digital information. Methods provided herein allow for deposition of barcodes onto a surface. Such barcodes can convey information about the identity of the target, substrate, timing, location, intensity, charge, affinity, etc. As such, the barcode provides for a nucleic acid medium for digital information storage. Methods for barcode deposition provided herein include, without limitation, application of a force to transfer barcodes from a reservoir to the sample. Example forces for application include laminar pressure, capillary pressure, slip flow pressure, magnetic force, electrostatic force, peristaltic force, acoustic force, vibrational force, centripetal force, centrifugal force, or any combination thereof. In some embodiments, a buffer exchange process is employed for barcode deposition. In some embodiments, an electrophoresis process is employed for barcode deposition. In such a process, migration of charged particles (e.g. nucleic acid barcode molecules) in an electric field is due to electrophoresis, and an electrode is near the substrate comprising cells. In some embodiments, electrophoresis is applied to remove a nucleic acid from a surface. In some embodiments, electrophoresis is applied to remove a concatemer described herein from a surface. The electrode may create a uniform field across a surface, or specific electrodes may be used for each region of interest. In some embodiments, a temperature change is employed for barcode disposition. In further embodiments, the barcode sequences comprise a temperature sensitive feature and an increase in temperature renders available a hybridization region unavailable at a lower temperature. In some embodiments, a ROI comprises a warming unit or electrode adjacent to the ROI sufficient to increase temperature at the ROI. In further embodiments, the barcodes comprise a melting temperature and the ROI is heated to reach the barcode melting temperature, thereby allowing for selective hybridization of the barcode(s).

Exemplary methods described herein may be further combined to incorporate any combination of described methods. For example, samples barcoded with iterative construction of barcodes are further tagged using fractional barcoding methods described herein.

In some embodiments, barcodes are deposited to ROI in a preselected pattern across a surface provided herein. In some embodiments, the pattern forms a grid of repeating shapes spanning a region and alternating shapes are preselected for barcode deposition. In some embodiments, the pattern forms a grid of repeating shapes spanning a region and less than all shapes are preselected for barcode deposition. In some embodiments, the shapes are squares, rectangles, triangles, ovals, diamonds, or spheres.

Provided herein are methods, wherein cells (or subcellular compartments such as nuclei) of a sample are sorted by defined characteristics prior to or after barcoding or tagging. In some embodiments, cells are sorted prior to every iteration of barcoding. In some embodiments, cells are sorted prior to any barcoding steps. In some embodiments, cells are sorted after all barcoding steps. In some embodiments, cells are sorted in one step based on a characteristic, for example surface receptor. In further embodiments, cells are sorted in a second step based on a second characteristic, for example gene expression. In some embodiments, cells are sorted based on a first characteristic and barcoded using methods described herein. In a further embodiment, barcoded cells are further sorted based on a second characteristic and optionally further barcoded.

Provided herein are methods for nucleic acid barcoding comprising cell sorting. Cell sorting, in some embodiments, is performed using fluorescent activated cell sorting (FACS) analysis. In some embodiments, cell sorting is performed with a microfluidic device. In some embodiments, cell sorting is performed using flow cytometry. In some embodiments, cell sorting is performed using magnetic cell sorting. In some embodiments, nuclei or multi-cellular arrangements are sorted rather than individual cells.

Figure 22:
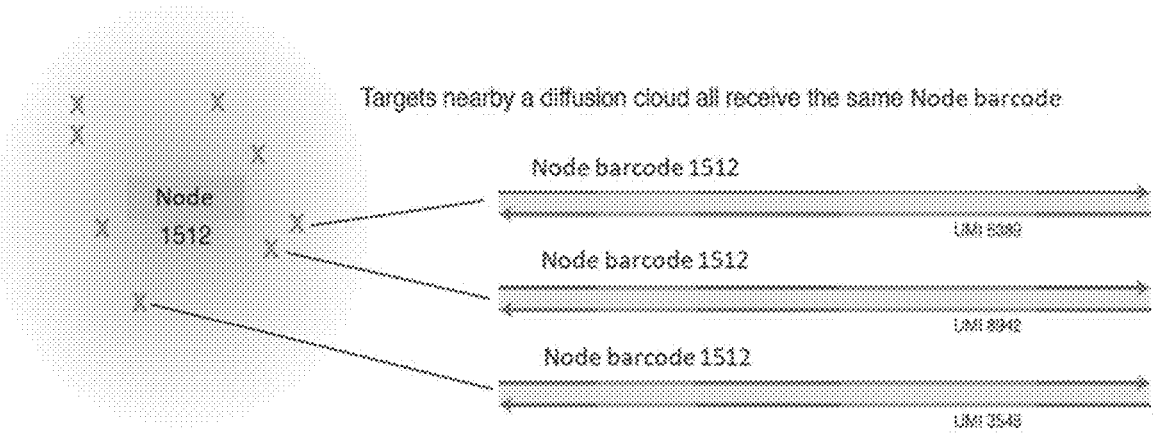
FIG. 22 illustrates the combination of unique identifiers from different areas within a node barcode diffusion cloud with the amplified node barcode strand.

Diffusing node barcode strands can interact with nucleic acid barcodes from target molecules. Target molecules comprise one or more cDNA, nucleic acid barcodes, ISH probes, other unique identifier sequences, or any combination thereof. The combination of node barcodes and target identifiers creates records of spatial correlation between node locations and targets. FIG. 22 shows an exemplary embodiment of a node barcodes in a diffusion cloud combining with target nucleic acids with different unique identifiers. Node barcode 1512 is generated in a strand and diffuses out from the node. The node barcode strand combines with target nucleic acid strands, each comprising a different unique identifier (UMI 5389, UMI 8942, and UMI 3548 in the figure). All combined nucleic acids comprise the same node barcode sequence and have different target unique identifiers. In some embodiments, target nucleic acids are diffused or are immobilized to a molecule of interest.

Figure 23A:
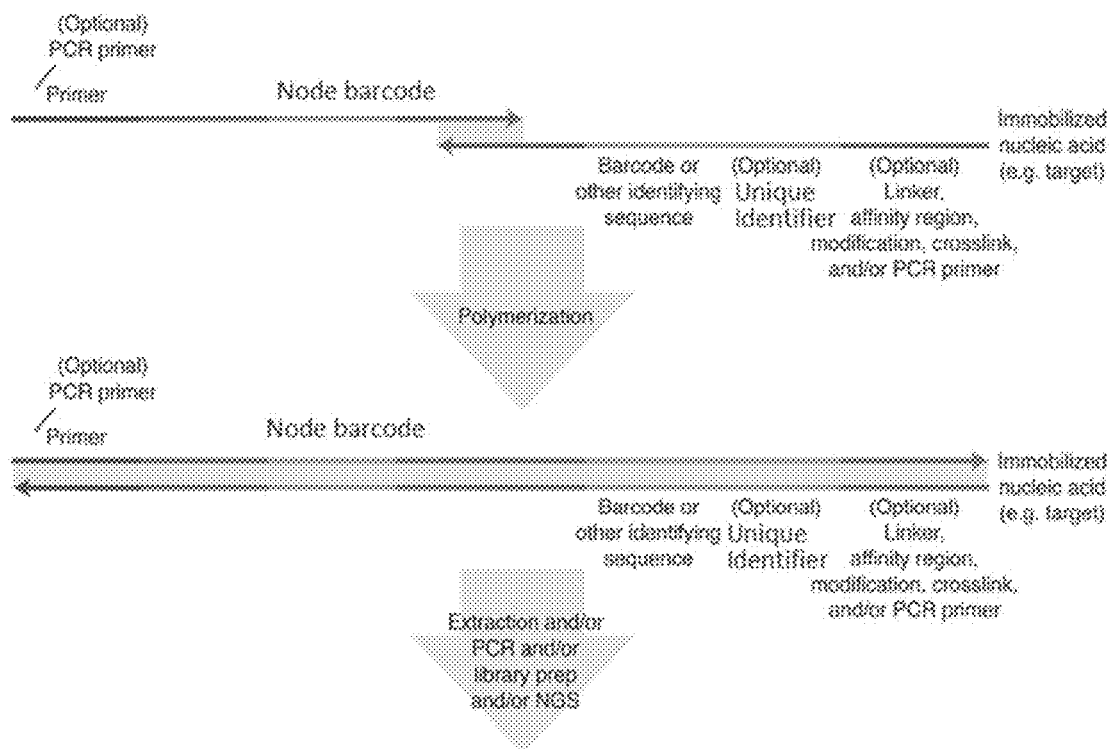
FIG. 23A illustrates polymerization of a node barcode strand comprising a primer and a node barcode hybridized to an immobilized target nucleic acid strand comprising a target barcode, a unique identifier, and a linker, affinity region, modification, crosslink, and/or PCR primer to generate a double-stranded nucleic acid comprising regions from both strands.
Figure 23B:
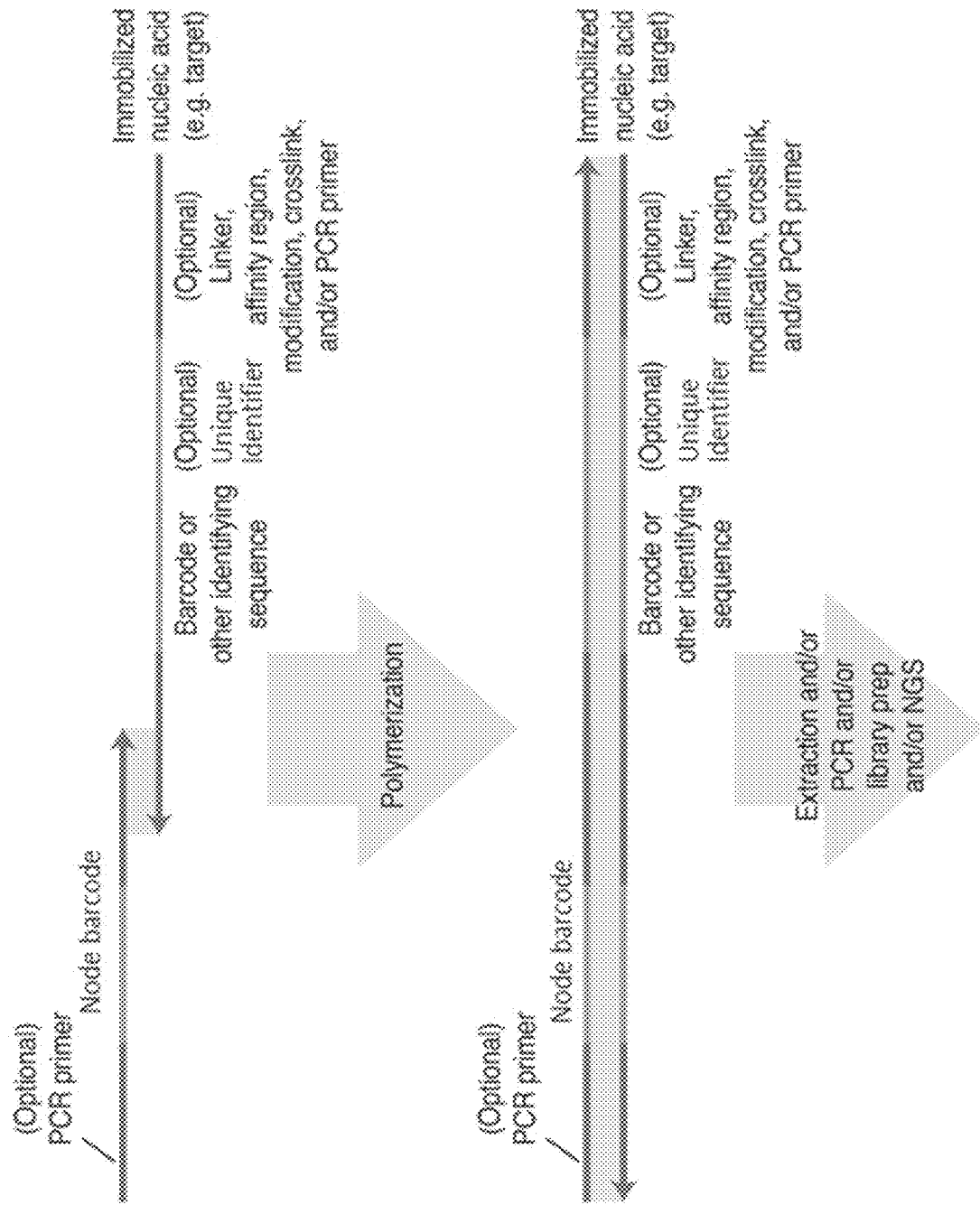
FIG. 23B illustrates polymerization of a node barcode strand comprising a node barcode hybridized to an immobilized target nucleic acid strand comprising a target barcode, a unique identifier, and a linker, affinity region, modification, crosslink, and/or PCR primer to generate a double-stranded nucleic acid comprising regions from both strands.
Figure 23C:
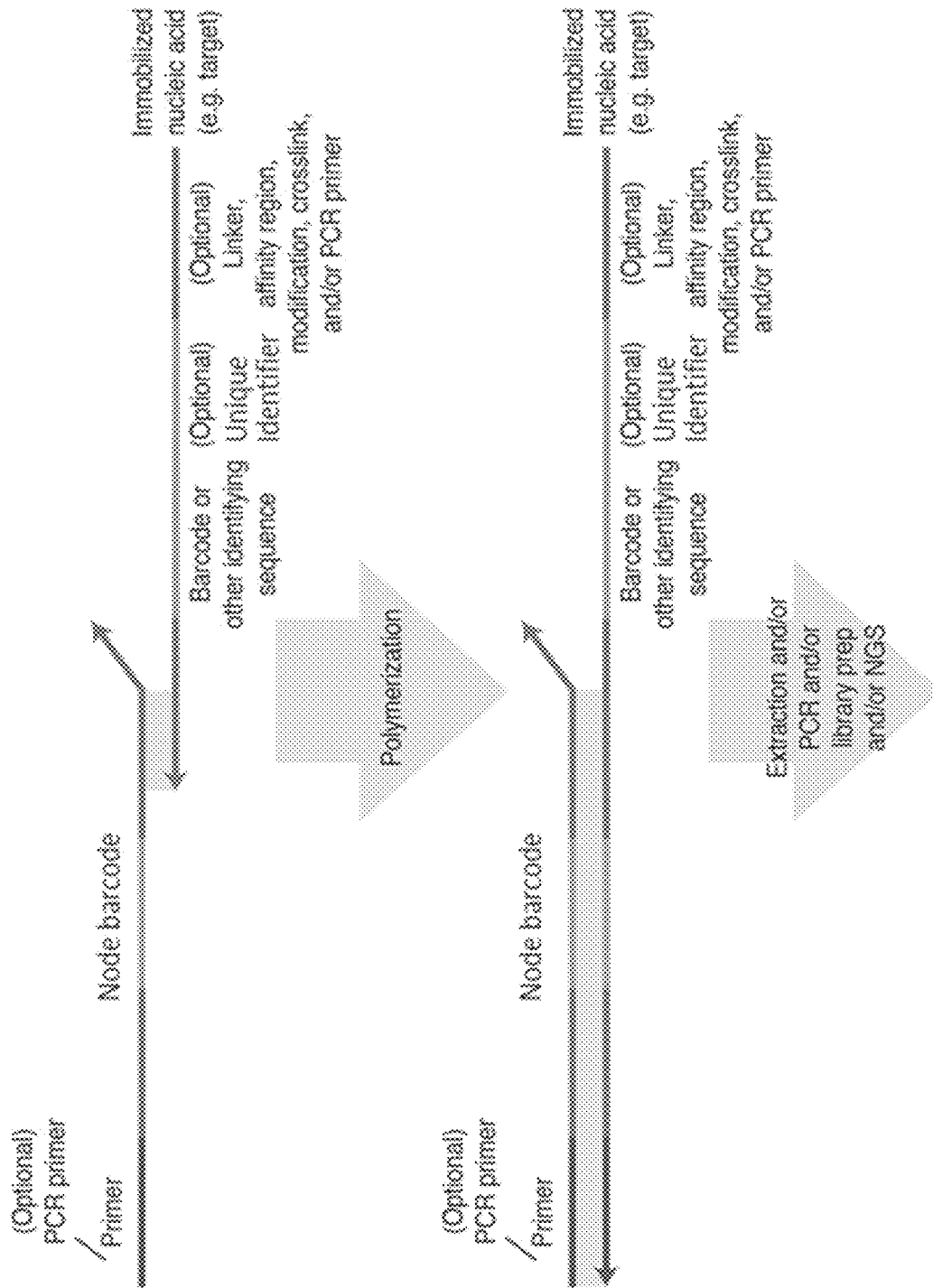
FIG. 23C illustrates polymerization of a node barcode strand comprising a primer, a node barcode and a non-hybridized domain 3' of the hybridization sequence hybridized to an immobilized target nucleic acid strand comprising a target barcode, a unique identifier, and a linker, affinity region, modification, crosslink, and/or PCR primer, wherein the target nucleic acid strand is extended to generate a single stranded combined sequence.
Figure 23D:
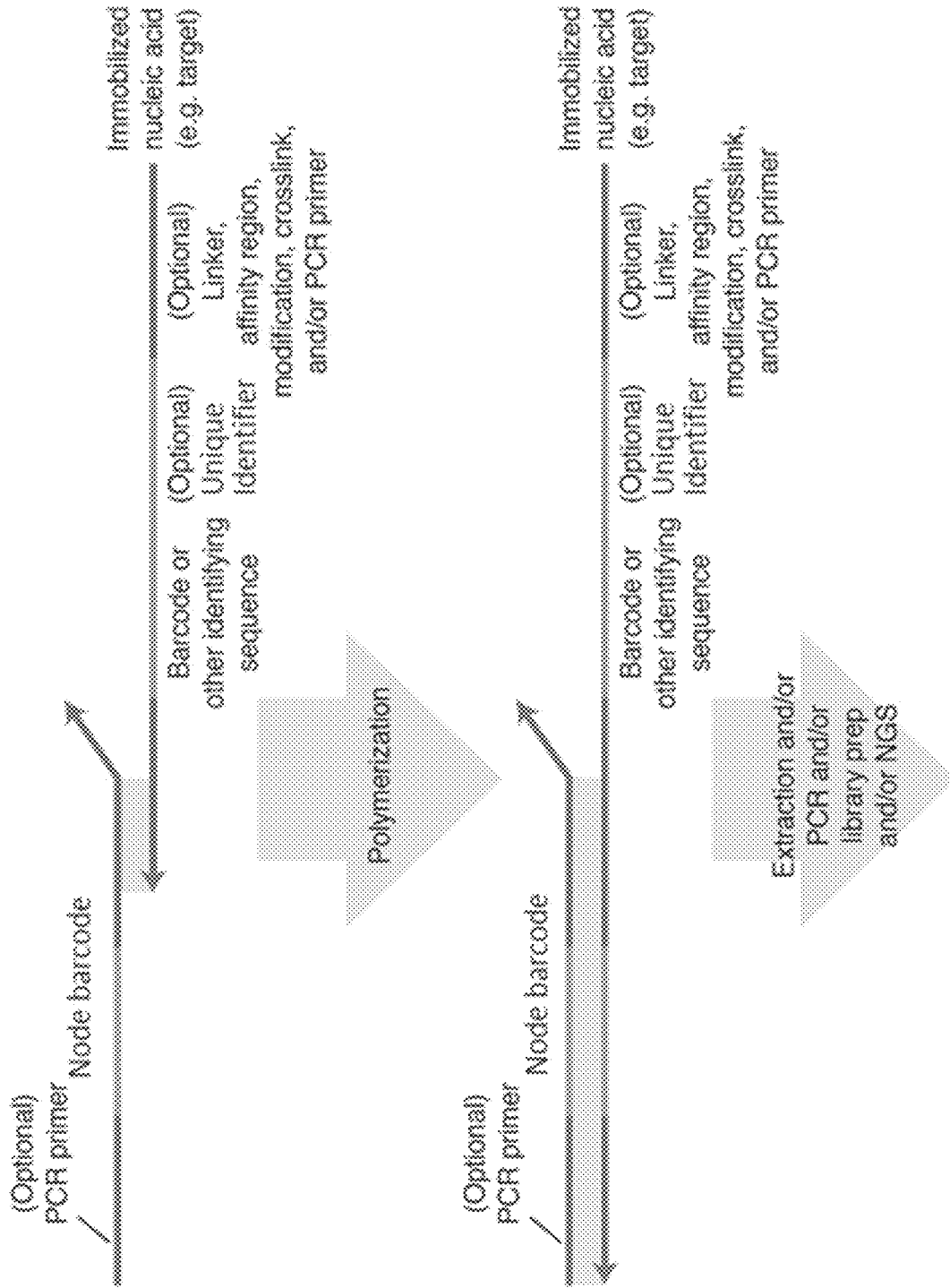
FIG. 23D illustrates polymerization of a node barcode strand comprising a node barcode with no primer, and a non-hybridized domain 3' of the hybridization sequence hybridized to an immobilized target nucleic acid strand comprising a target barcode, a unique identifier, and a linker, affinity region, modification, crosslink, and/or PCR primer, wherein the target nucleic acid strand is extended to generate a single stranded combined sequence.
Figure 23E:
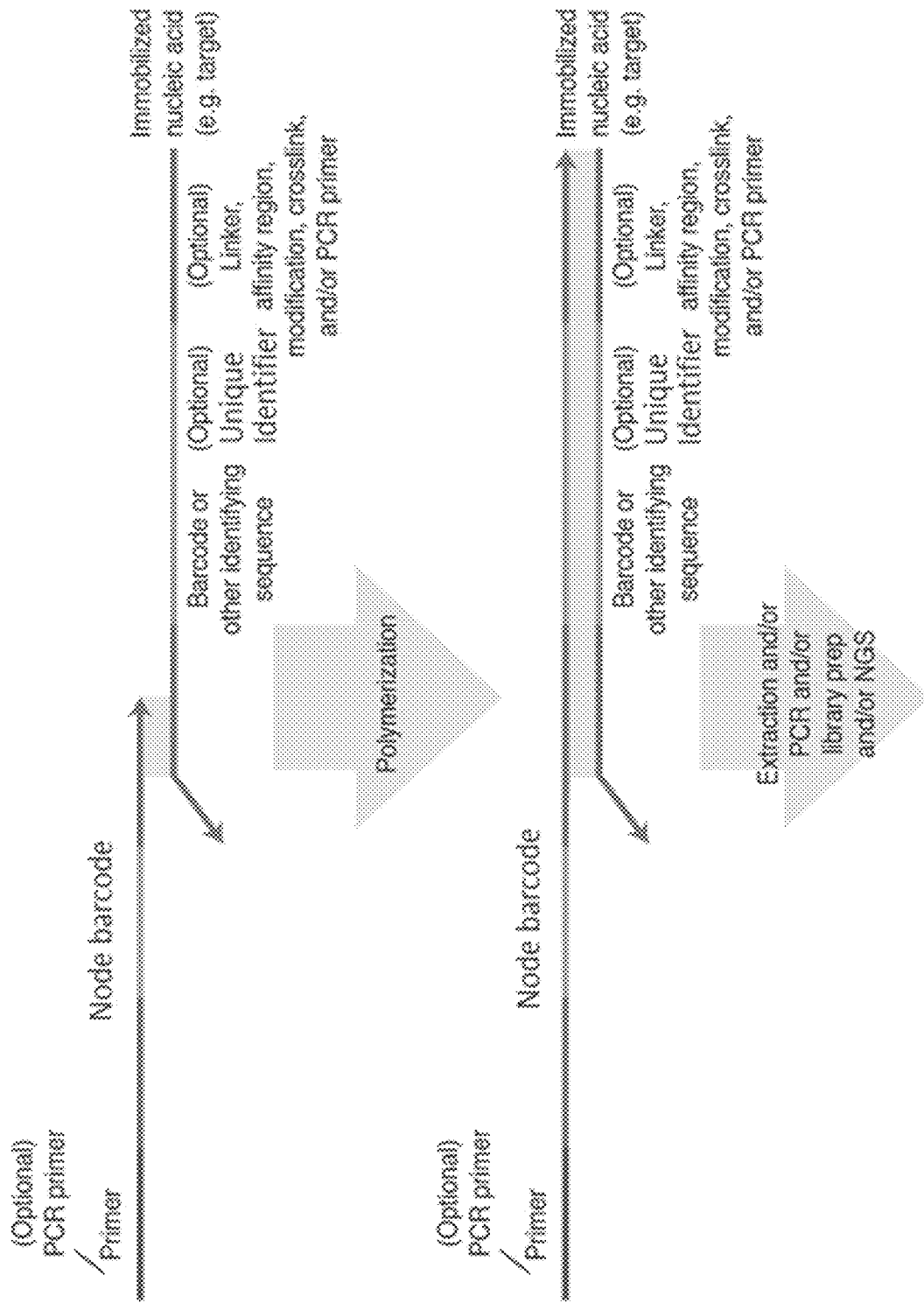
FIG. 23E illustrates polymerization of a node barcode strand comprising a primer and a node barcode hybridized to an immobilized target nucleic acid strand comprising a non-hybridized domain 3' of a hybridization sequence, a target barcode, a unique identifier, and a linker, affinity region, modification, crosslink, and/or PCR primer, wherein the node barcode strand is extended to generate a single stranded combined sequence.
Figure 23F:
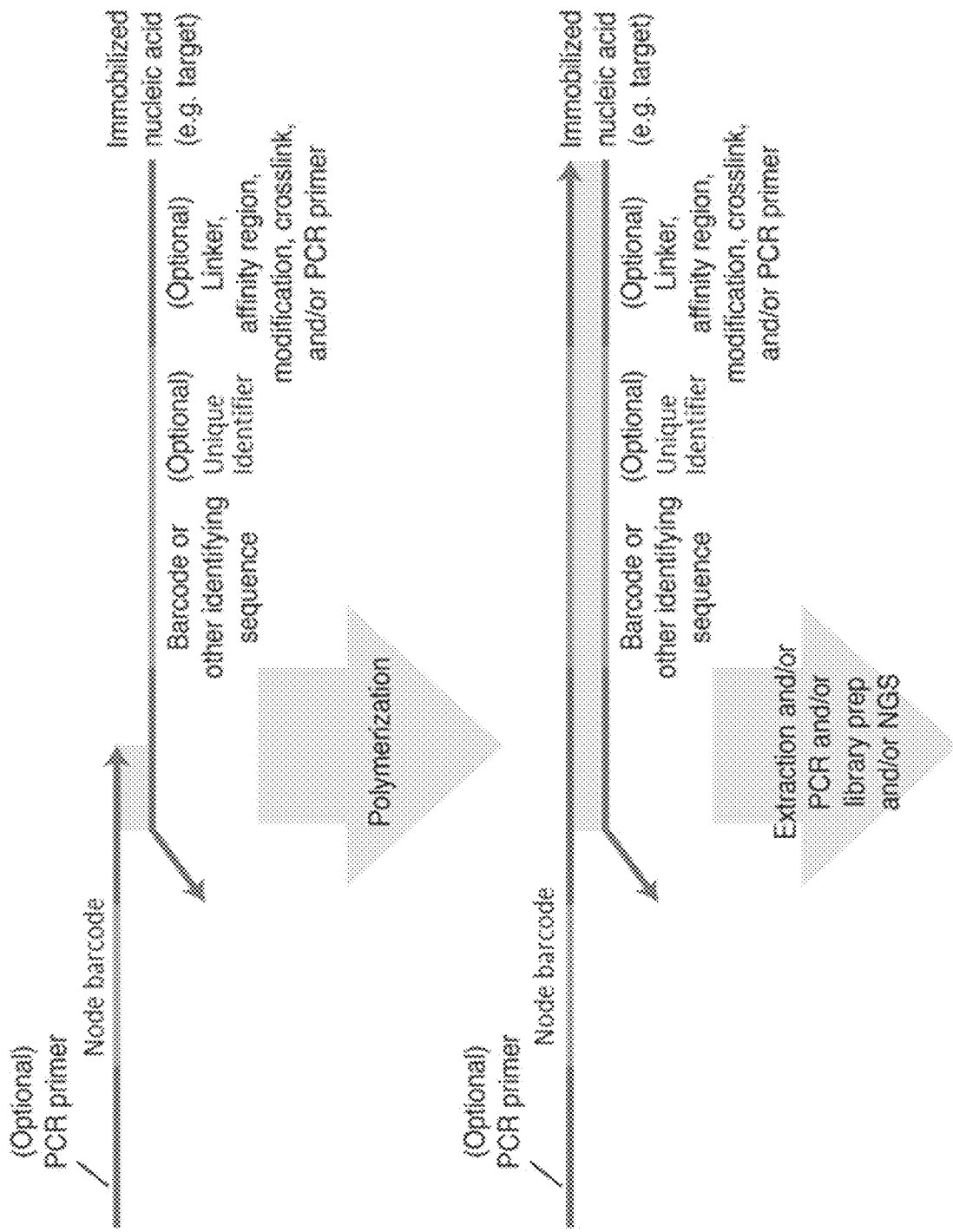
FIG. 23F illustrates polymerization of a node barcode strand comprising a node barcode with no primer hybridized to an immobilized target nucleic acid strand comprising a non-hybridized domain 3' of a hybridization sequence, a target barcode, a unique identifier, and a linker, affinity region, modification, crosslink, and/or PCR primer, wherein the target nucleic acid strand is extended to generate a single stranded combined sequence.

In methods described herein, nucleic acids can be combined to provide proximity information. In some embodiments, combined nucleic acids are generated by ligating node barcode strands to target molecules or unique identifiers. Ligation may include a splint molecule. Ligation may comprise extending one or more of the strands through polymerization. In some embodiments, sequences are assembled using Primer Exchange Reaction (PER), cross-junction synthesis, asymmetric PCR, Gibson assembly, transposase-based concatenation, for example, using Tn5 transposition for RNA-DNA hybrids, or any combination thereof. FIGS. 23A-23F show exemplary embodiments of polymerization-based proximity recording ligation reactions. FIG. 23A shows a node barcode strand comprising a primer and a node barcode hybridized to an immobilized target nucleic acid comprising a target barcode, a unique identifier, and a linker, affinity region, modification, crosslink, and/or PCR primer. Both strands are extended by polymerization to generate a double stranded combined sequence. The double stranded combined sequence is then processed through extraction and/or PCR and/or library prep and/or NGS. FIG. 23B shows a node barcode strand comprising a node barcode without a primer hybridized to an immobilized target nucleic acid comprising a target barcode, a unique identifier, and a linker, affinity region, modification, crosslink, and/or PCR primer. Both strands are extended by polymerization to generate a double stranded combined sequence. The double stranded combined sequence is then processed through extraction and/or PCR and/or library prep and/or NGS. FIG. 23C shows a node barcode strand comprising a primer, a node barcode, and a non-hybridized domain 3' of a hybridization sequence hybridized to an immobilized target nucleic acid comprising a target barcode, a unique identifier, and a linker, affinity region, modification, crosslink, and/or PCR primer. The target nucleic acid strand is extended by polymerization to generate a single stranded combined sequence. The combined sequence is then processed through extraction and/or PCR and/or library prep and/or NGS. FIG. 23D shows a node barcode strand comprising a node barcode without a primer, and a non-hybridized domain 3' of a hybridization sequence hybridized to an immobilized target nucleic acid comprising a target barcode, a unique identifier, and a linker, affinity region, modification, crosslink, and/or PCR primer. The target nucleic acid strand is extended by polymerization to generate a single stranded combined sequence. The combined sequence is then processed through extraction and/or PCR and/or library prep and/or NGS. FIG. 23E shows a node barcode strand comprising a primer and a node barcode hybridized to an immobilized target nucleic acid comprising a non-hybridized domain 3' of a hybridization sequence, a target barcode, a unique identifier, and a linker, affinity region, modification, crosslink, and/or PCR primer. The node barcode strand is extended by polymerization to generate a single stranded combined sequence. The combined sequence is then processed through extraction and/or PCR and/or library prep and/or NGS. FIG. 23F shows a node barcode strand comprising a node barcode without a primer an immobilized target nucleic acid comprising a non-hybridized domain 3' of a hybridization sequence hybridized to a target barcode, a unique identifier, and a linker, affinity region, modification, crosslink, and/or PCR primer. The node barcode strand is extended by polymerization to generate a single stranded combined sequence. The combined sequence is then processed through extraction and/or PCR and/or library prep and/or NGS.

Unique identifying sequences are optionally added as an intrinsic part of the template sequence, or extrinsically. In some embodiments, a unique identifier is incorporated in to a sequence as a oligonucleotide that is added to generated strands. In some embodiments, extrinsic addition occurs prior to replication. In some embodiments, extrinsic addition occurs after strands are generated.

Exemplary Applications

Methods described herein provide for proximity recording of various types of targets. In some embodiments, the target is DNA, RNA, protein, or any other material to which a nucleic acid can be immobilized. Detection can be through cDNA synthesis, ISH probe binding, antibody detection, any other means for detecting target nucleic acids, or any combination thereof. Proximity recording of node barcodes to target molecules can occur on target molecules that have been separately (previously, concurrently, or subsequently) barcoded using other assays (e.g., through binding, cross-linking, photo-crosslinking, hybridization, tagmentation).

Figure 24A:
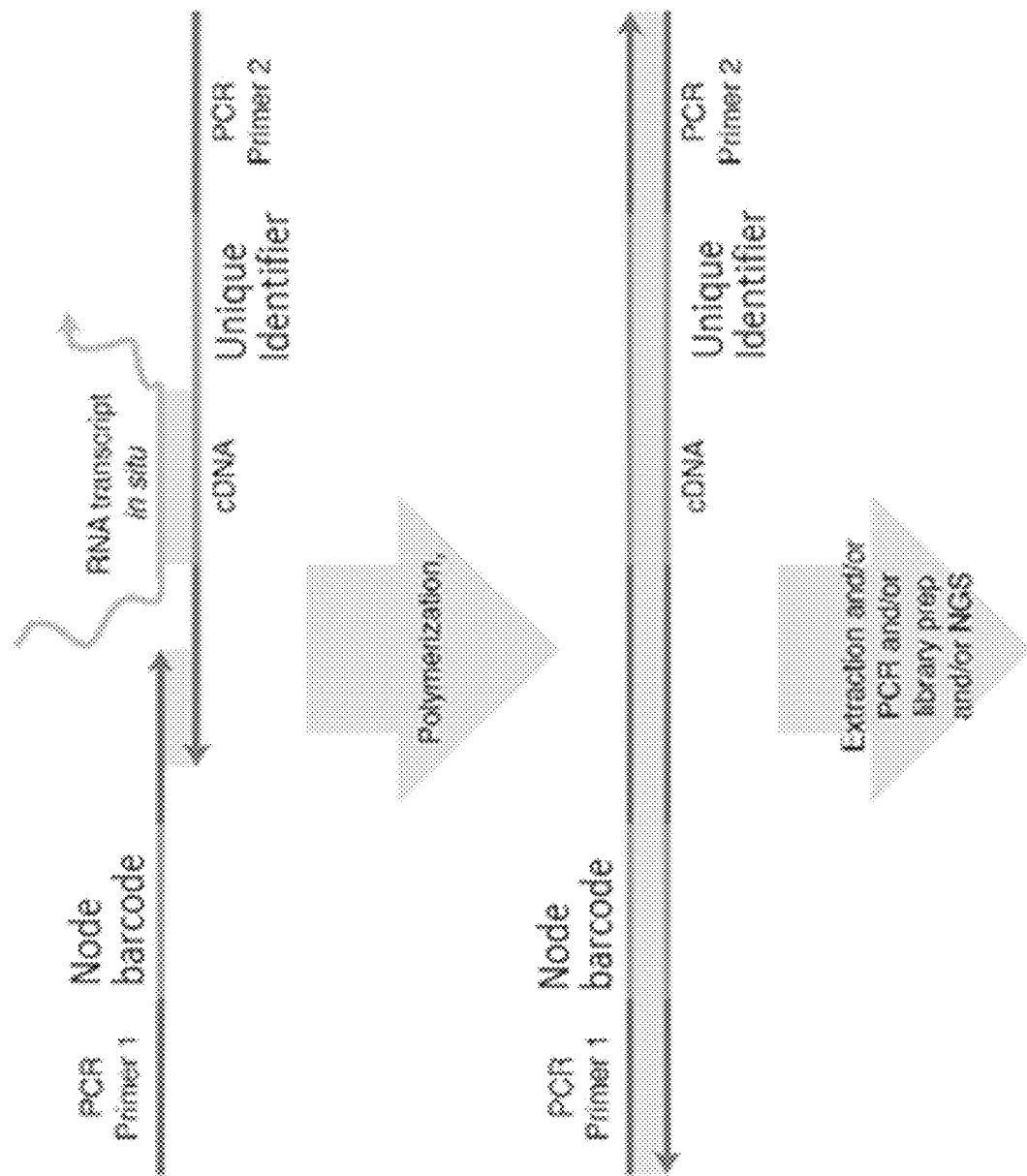
FIGS. 24A-24C illustrate exemplary embodiments of proximity recording of target RNA transcripts in situ using cDNA, wherein a node barcode nucleic acid comprising a first primer, a node barcode, and a hybridization sequence is hybridized to a target nucleic acid comprising a hybridization sequence, cDNA te to a target RNA, a unique identifier and a second PCR primer.
Figure 24B:
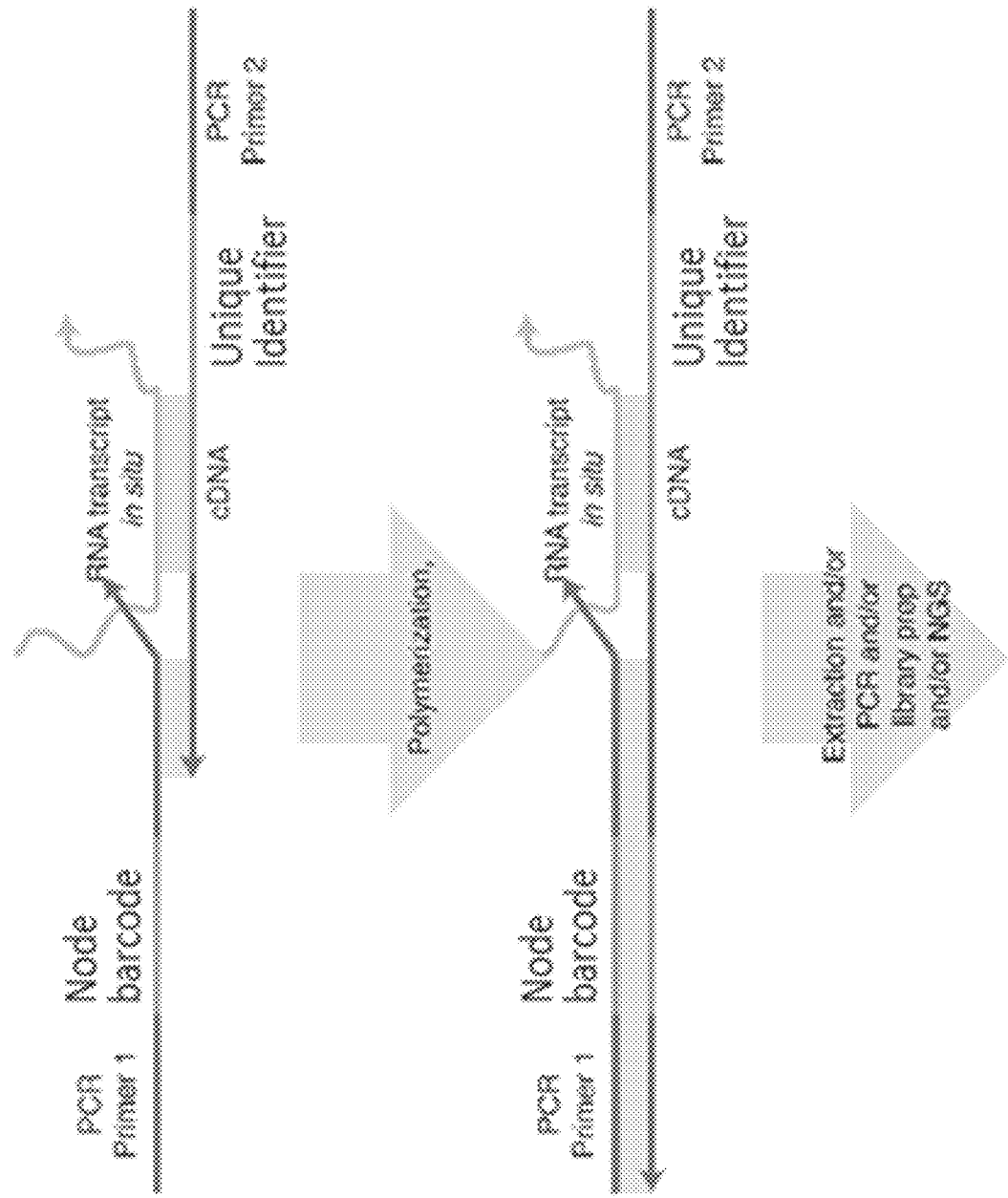
Figure 24C:
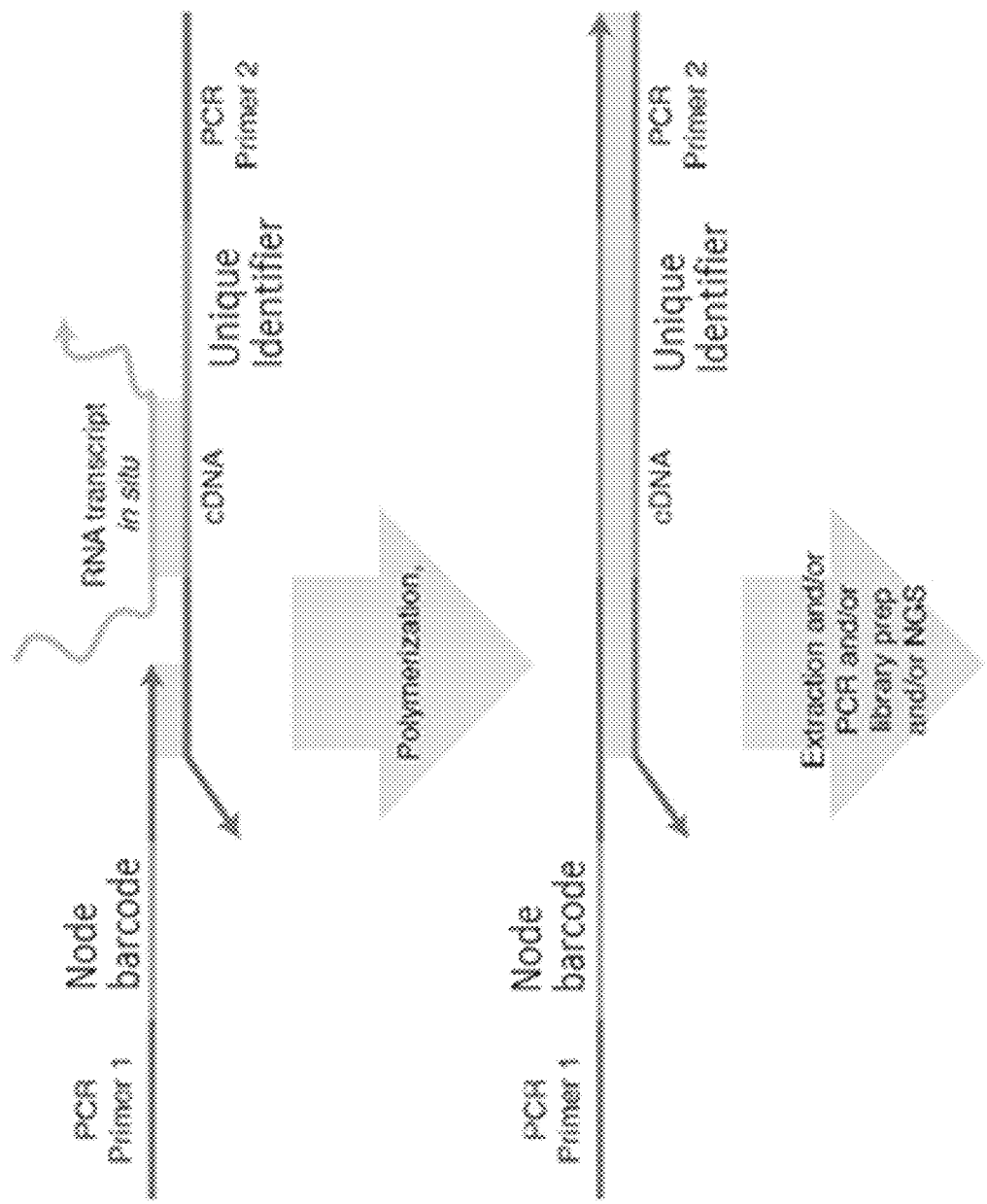
Figure 24D:
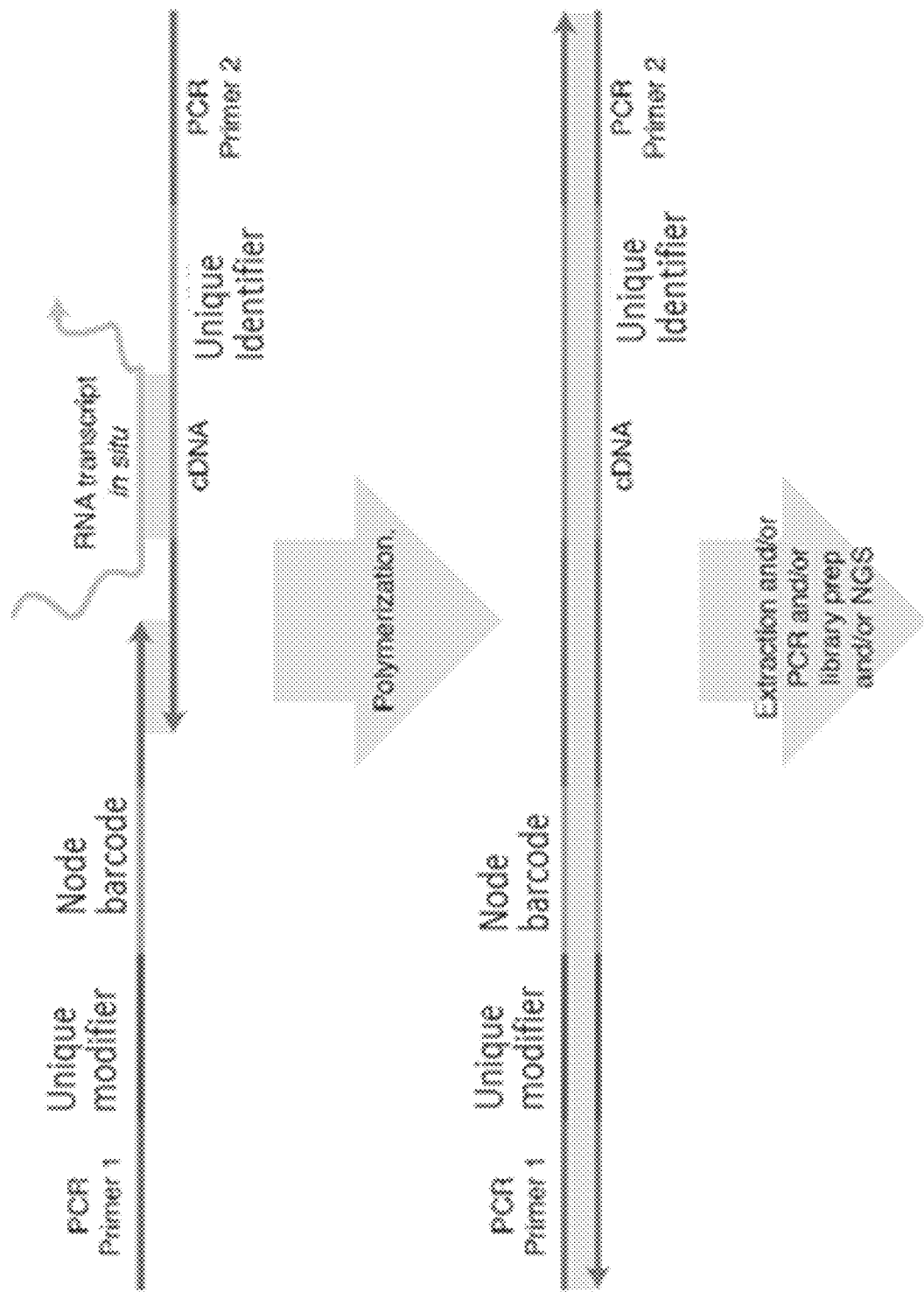
FIGS. 24D-24F illustrate exemplary embodiments of proximity recording of target RNA transcripts in situ using cDNA, wherein a node barcode nucleic acid comprising a first primer, a unique identifier, and a node barcode is hybridized to a target nucleic acid comprising a cDNA complement to a target RNA, a unique identifier and a second PCR primer.
Figure 24E:
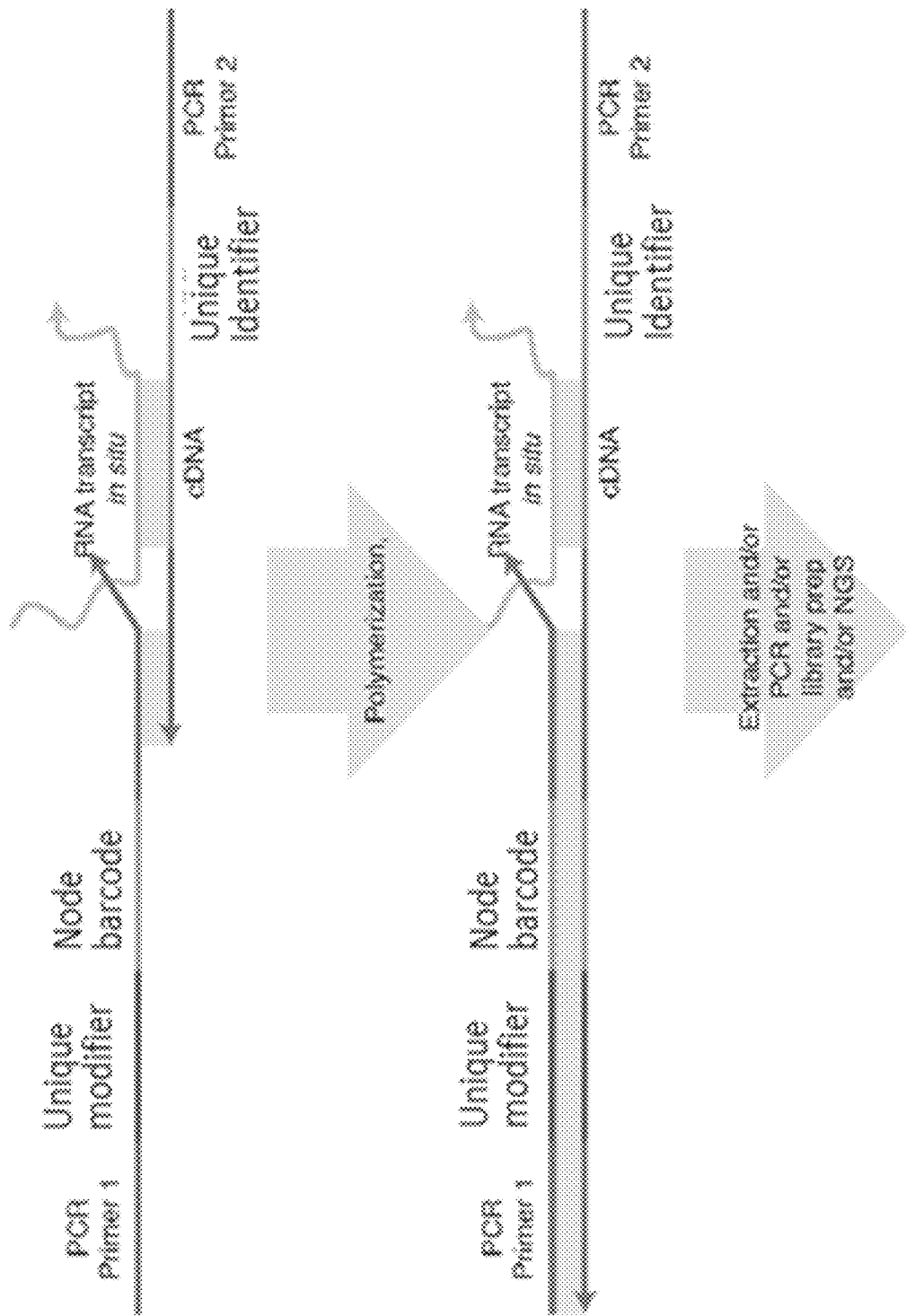
Figure 24F:
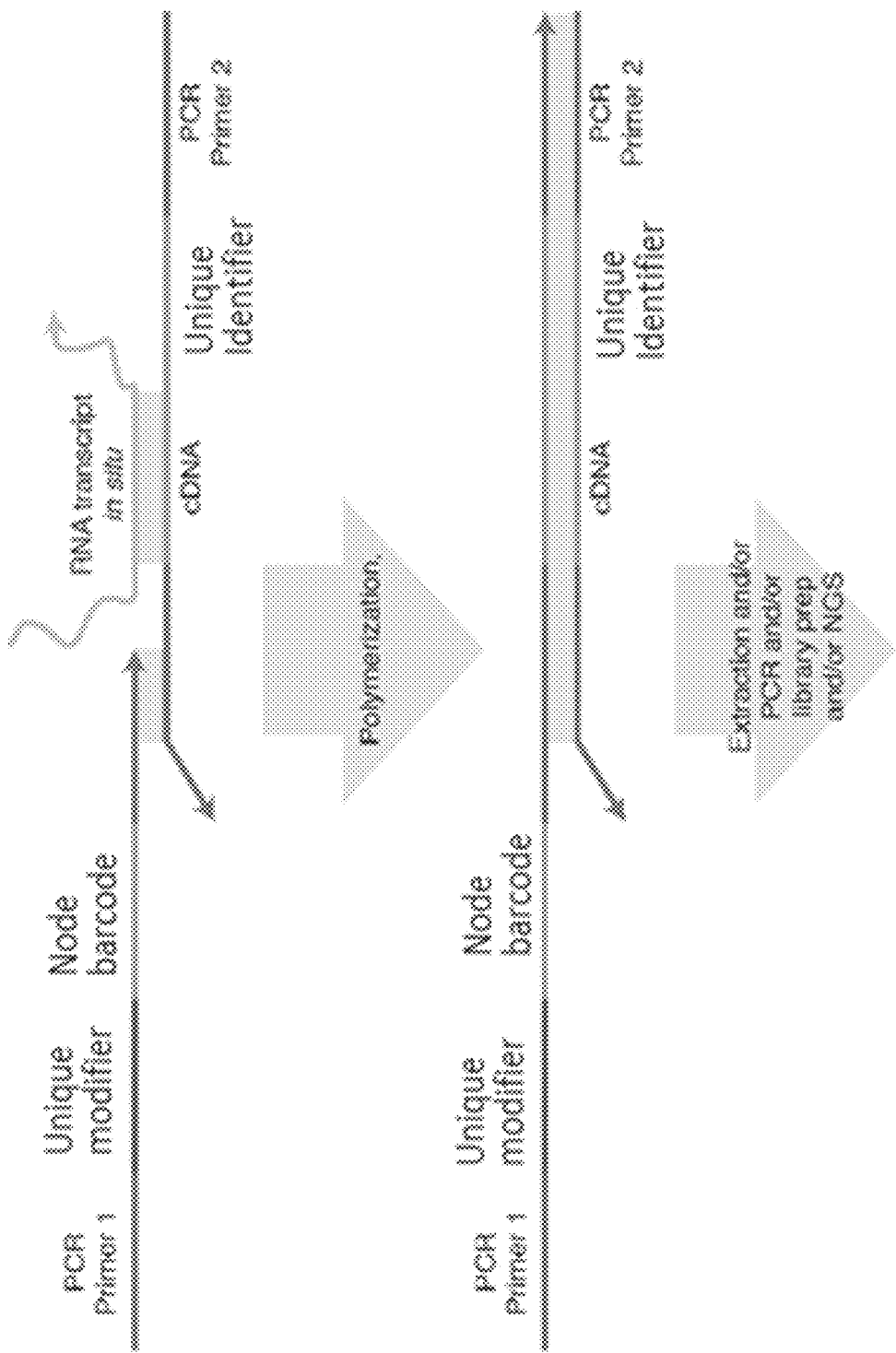

FIGS. 24A-24F show exemplary embodiments of proximity recording of target RNA transcripts in situ using cDNA. FIG. 24A shows a node barcode strand further comprising a first PCR primer hybridizing with a target barcode strand comprising a cDNA, a unique identifier, and a second PCR primer. Both strands are extended by polymerization to generate a double stranded combined sequence. The double stranded combined sequence is then processed through extraction and/or PCR and/or library prep and/or NGS. FIG. 24B shows a node barcode strand further comprising a first PCR primer, a node barcode, a hybridization sequence and a non-hybridized domain 3' of the hybridization sequence, hybridizing with a target barcode strand comprising a cDNA, a unique identifier, and a second PCR primer. The target nucleic acid strand is extended by polymerization to generate a single stranded combined sequence. The combined sequence is then processed through extraction and/or PCR and/or library prep and/or NGS. FIG. 24C shows a node barcode strand further comprising a first PCR primer and a hybridization sequence hybridizing with a target barcode strand comprising a hybridized domain 3' of a hybridization sequence, cDNA sequence, a unique identifier, and a second PCR primer. The node barcode strand is extended by polymerization to generate a single stranded combined sequence. The combined sequence is then processed through extraction and/or PCR and/or library prep and/or NGS. FIG. 24D shows a node barcode strand further comprising a first PCR primer and a unique modifier hybridizing with a target barcode strand comprising a cDNA, a unique identifier, and a second PCR primer. Both strands are extended by polymerization to generate a double stranded combined sequence. The double stranded combined sequence is then processed through extraction and/or PCR and/or library prep and/or NGS. FIG. 24E shows a node barcode strand further comprising a first PCR primer, a unique modifier, a node barcode, a hybridization sequence and a non-hybridized domain 3' of the hybridization sequence hybridizing with a target barcode strand comprising a cDNA, a unique identifier, and a second PCR primer. The target nucleic acid strand is extended by polymerization to generate a single stranded combined sequence. The combined sequence is then processed through extraction and/or PCR and/or library prep and/or NGS. FIG. 24F shows a node barcode strand further comprising a first PCR primer and a hybridization sequence hybridizing with a target barcode strand comprising a hybridized domain 3' of a hybridization sequence, cDNA sequence, a unique identifier, and a second PCR primer. The node barcode strand is extended by polymerization to generate a single stranded combined sequence. The combined sequence is then processed through extraction and/or PCR and/or library prep and/or NGS.

Figure 25A:
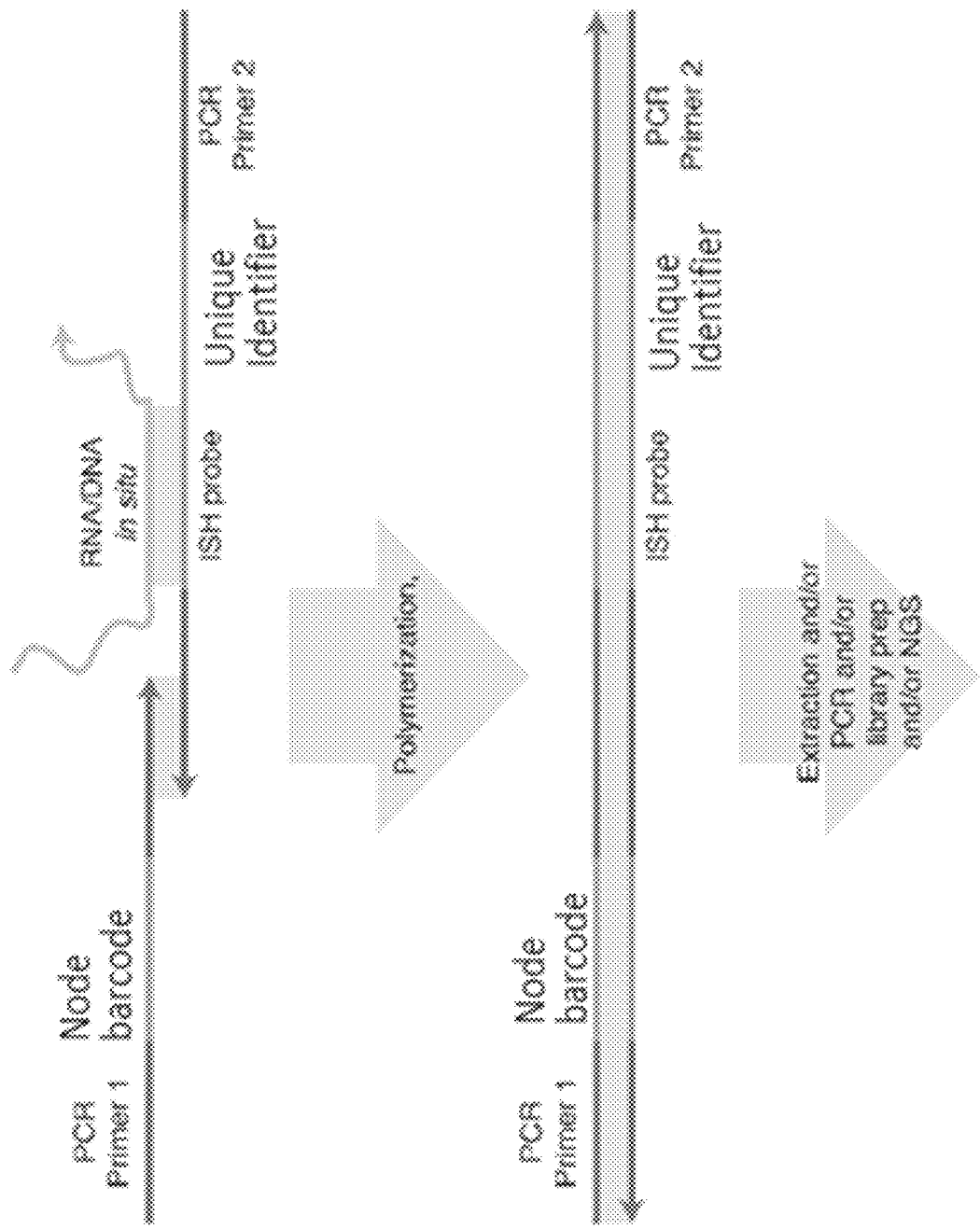
FIGS. 25A-25C illustrate exemplary embodiments of proximity recording of target RNA transcripts in situ using ISH probes, wherein a node barcode nucleic acid comprising a first primer, a unique identifier, and a node barcode is hybridized to a target nucleic acid comprising a cDNA complement to a target RNA, a unique identifier and a second PCR primer.
Figure 25B:
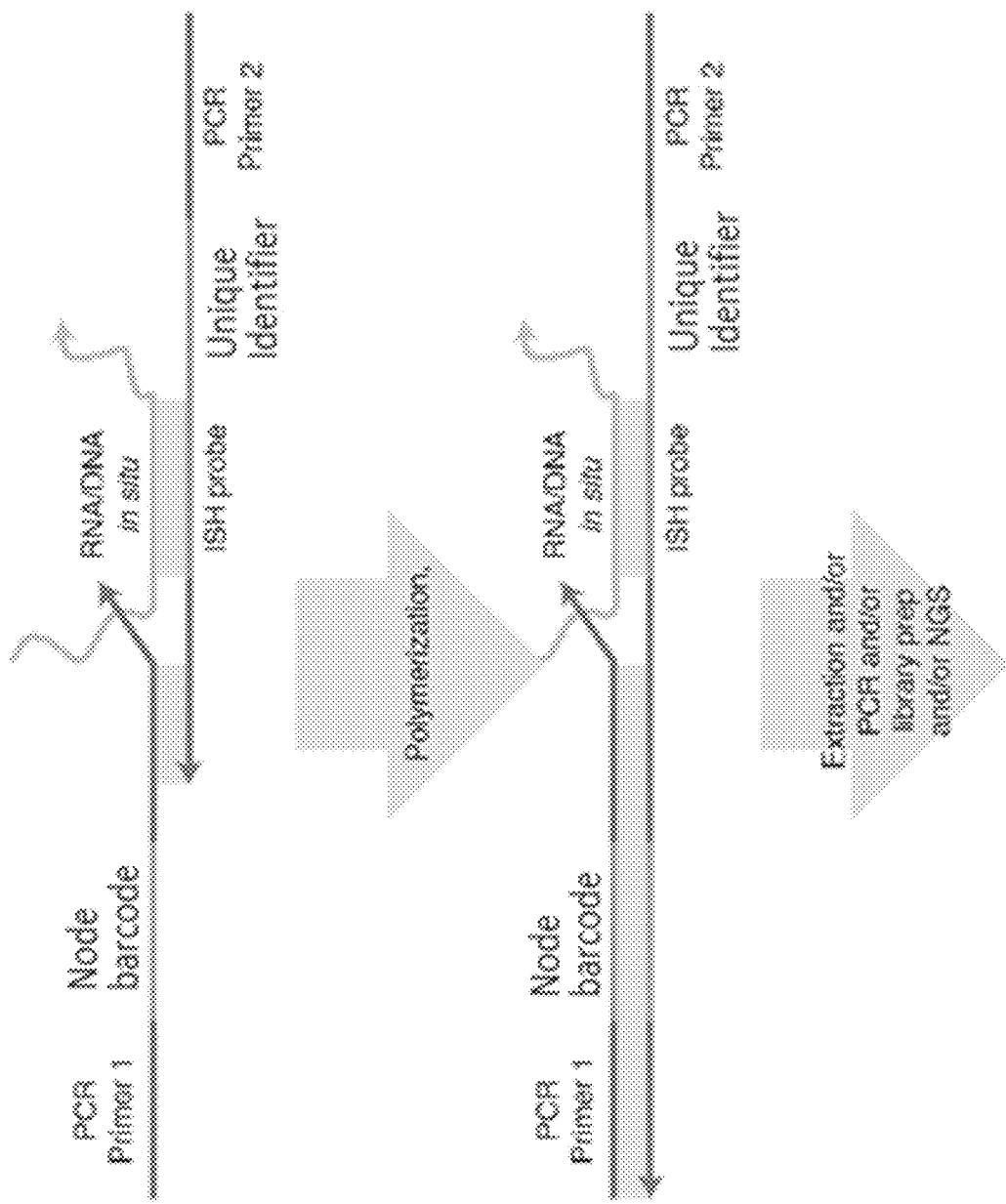
Figure 25C:
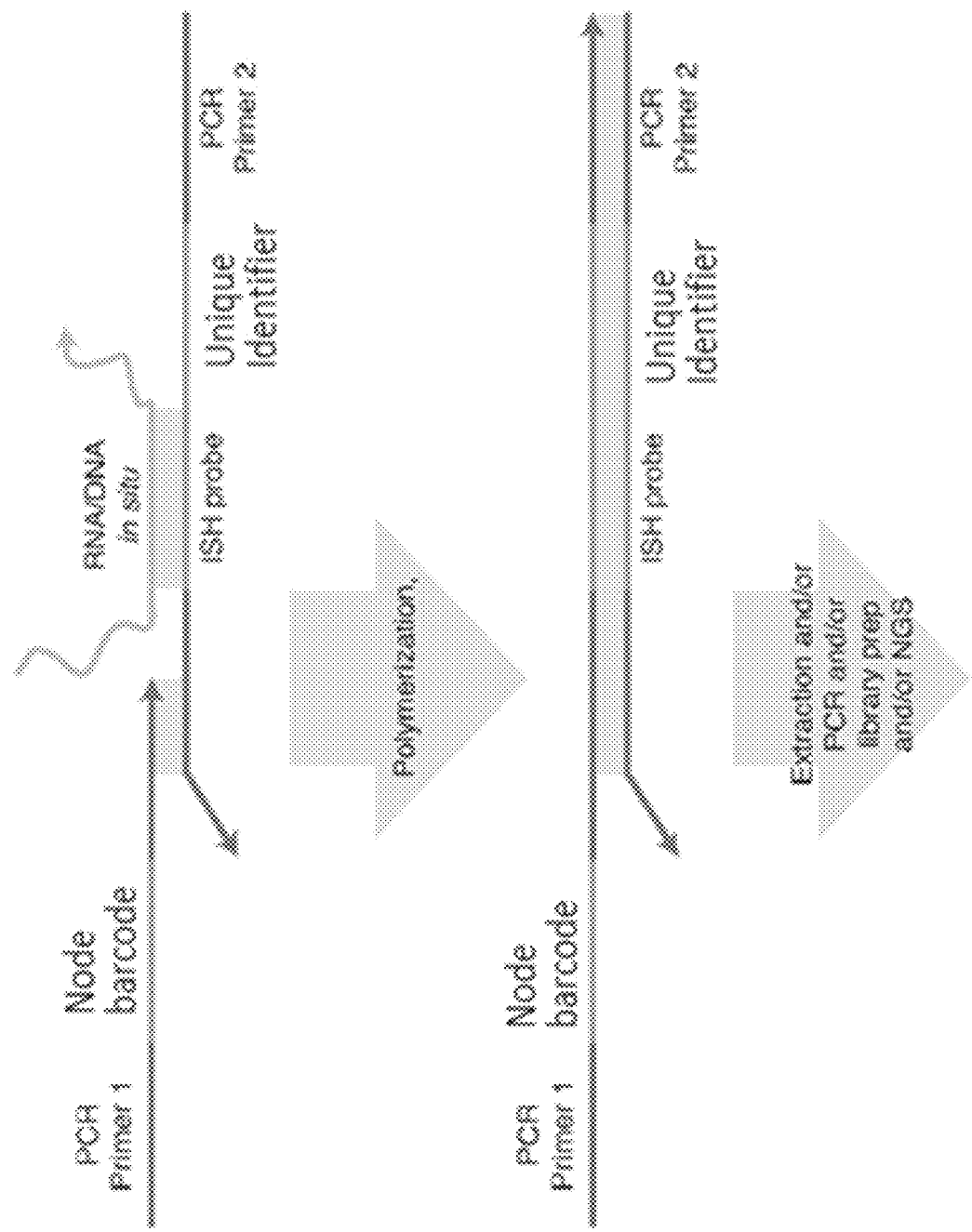
Figure 25D:
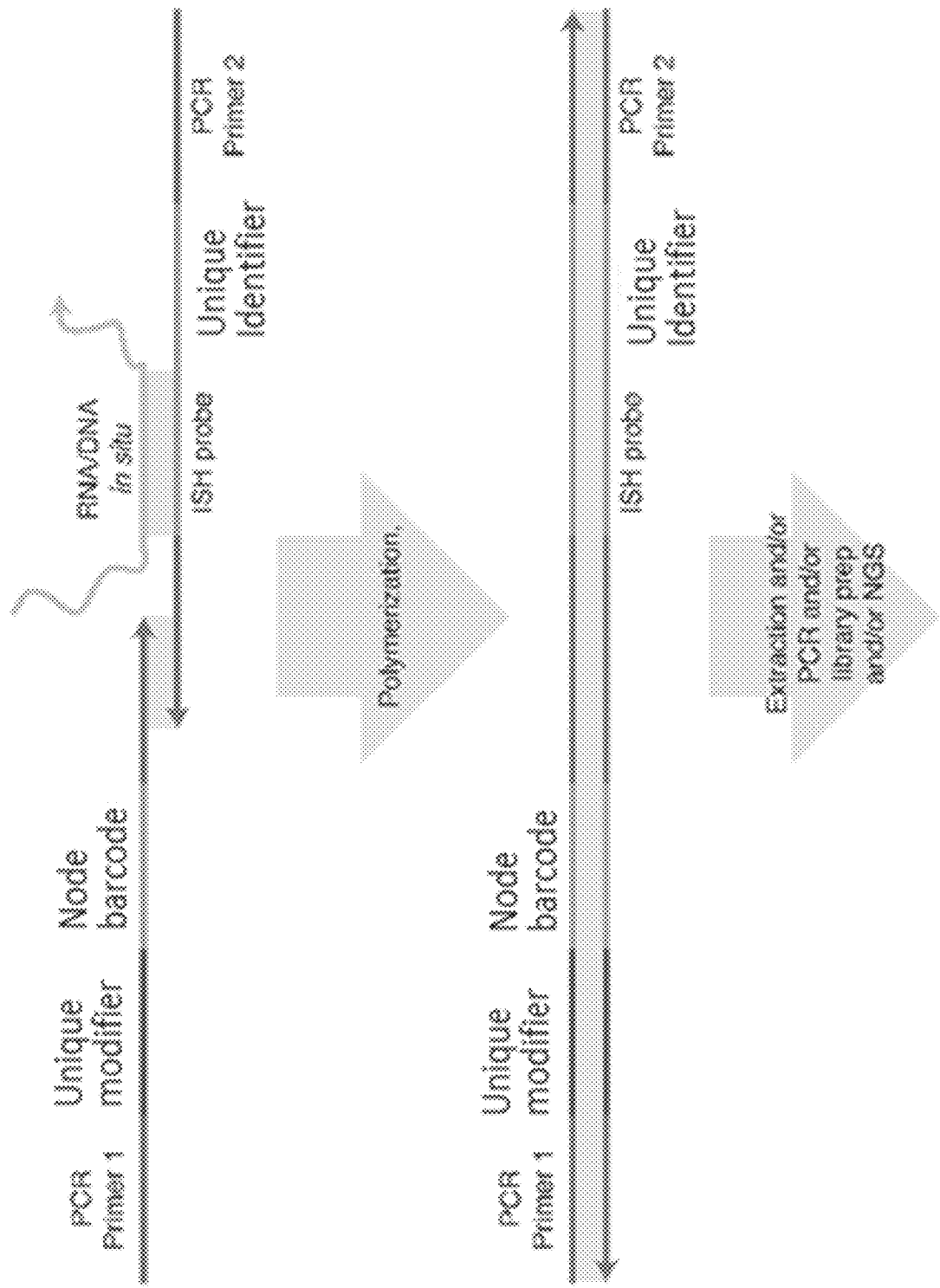
FIGS. 25D-25F illustrate exemplary embodiments of proximity recording of target RNA transcripts in situ using ISH probes, wherein a node barcode nucleic acid comprising a first primer, a unique identifier, a node barcode, and a hybridization sequence is hybridized to a target nucleic acid comprising a hybridization sequence, an ISH probe complement to a target RNA, a unique identifier and a second PCR primer.
Figure 25E:
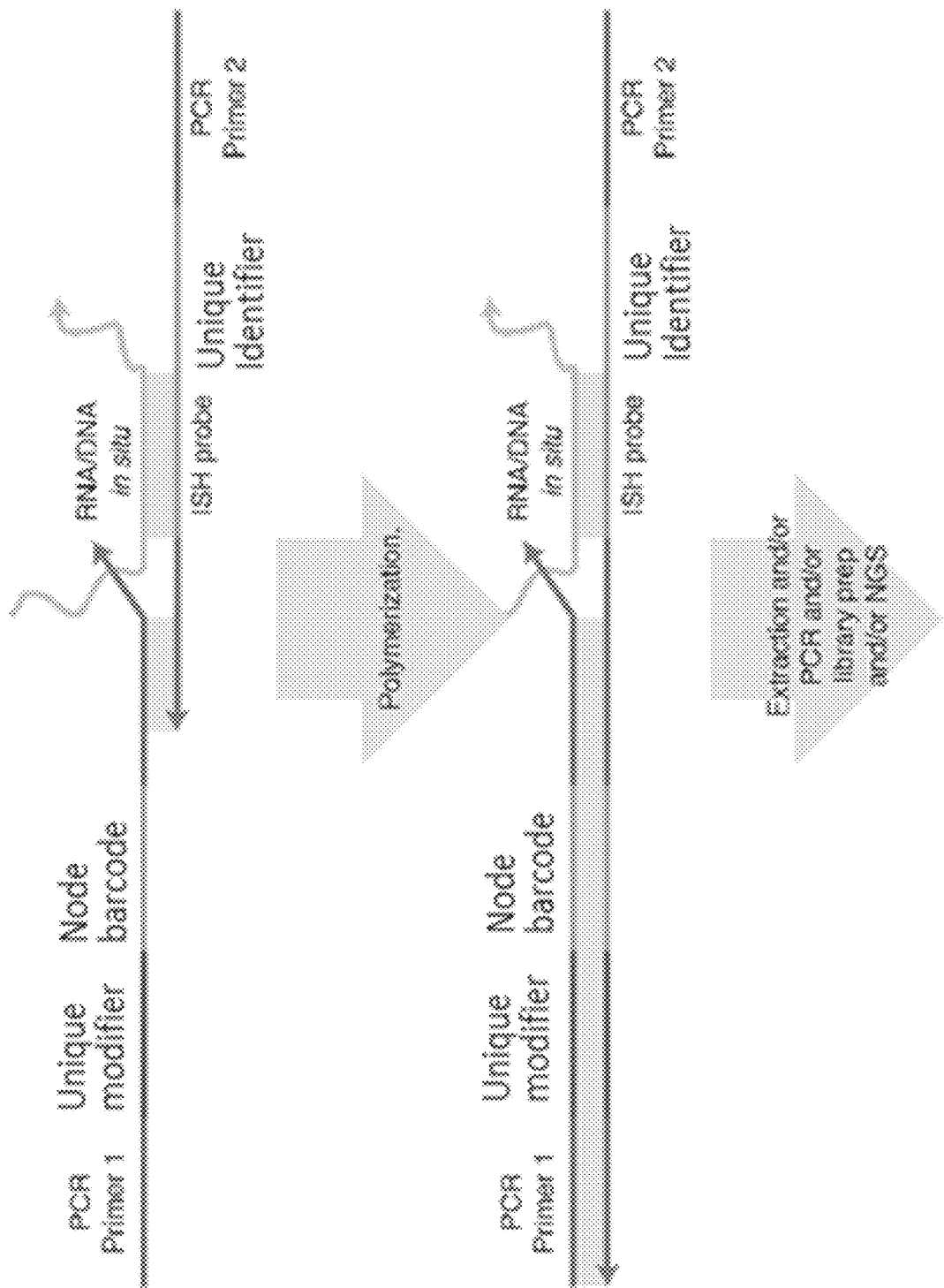
Figure 25F:
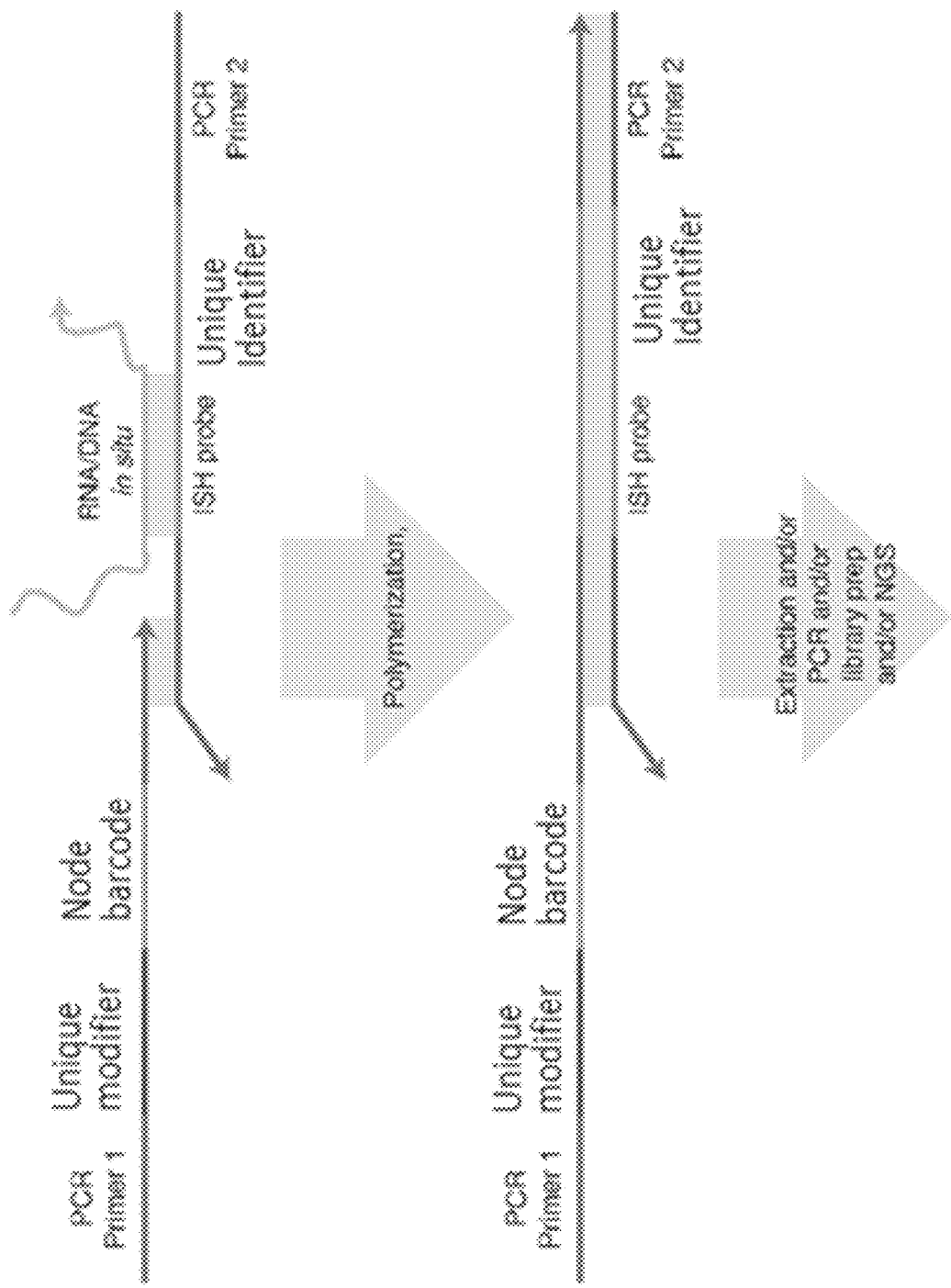

FIGS. 25A-25F show exemplary embodiments of proximity recording of target RNA transcripts using ISH probes. FIG. 25A shows a node barcode strand further comprising a first PCR primer hybridizing with a target barcode strand comprising an ISH probe, a unique identifier, and a second PCR primer. Both strands are extended by polymerization to generate a double stranded combined sequence. The double stranded combined sequence is then processed through extraction and/or PCR and/or library prep and/or NGS. FIG. 25B shows a node barcode strand comprising a first PCR primer, a node barcode, a hybridization sequence, and a non-hybridized domain 3' of a hybridization sequence hybridizing with a target barcode strand comprising an ISH probe, a unique identifier, and a second PCR primer. The target nucleic acid strand is extended by polymerization to generate a single stranded combined sequence. The combined sequence is then processed through extraction and/or PCR and/or library prep and/or NGS. FIG. 25C shows a node barcode strand comprising a first PCR primer, a node barcode, and a hybridization sequence hybridizing with a target barcode strand comprising a non-hybridizing domain 3' of a hybridization sequence, an ISH probe, a unique identifier, and a second PCR primer. The node barcode strand is extended by polymerization to generate a single stranded combined sequence. The combined sequence is then processed through extraction and/or PCR and/or library prep and/or NGS. FIG. 25D shows a node barcode strand further comprising a first PCR primer and a unique modifier hybridizing with a target barcode strand comprising an ISH probe, a unique identifier, and a second PCR primer. Both strands are extended by polymerization to generate a double stranded combined sequence. The double stranded combined sequence is then processed through extraction and/or PCR and/or library prep and/or NGS. FIG. 25E shows a node barcode strand comprising a first PCR primer, a unique modifier, a node barcode, a hybridization sequence, and a non-hybridized domain 3' of a hybridization sequence hybridizing with a target barcode strand comprising an ISH probe, a unique identifier, and a second PCR primer. The target nucleic acid strand is extended by polymerization to generate a single stranded combined sequence. The combined sequence is then processed through extraction and/or PCR and/or library prep and/or NGS. FIG. 25F shows a node barcode strand comprising a first PCR primer, a unique modifier, a node barcode, and a hybridization sequence hybridizing with a target barcode strand comprising a non-hybridizing domain 3' of a hybridization sequence, an ISH probe, a unique identifier, and a second PCR primer. The node barcode strand is extended by polymerization to generate a single stranded combined sequence. The combined sequence is then processed through extraction and/or PCR and/or library prep and/or NGS.

Figure 26A:
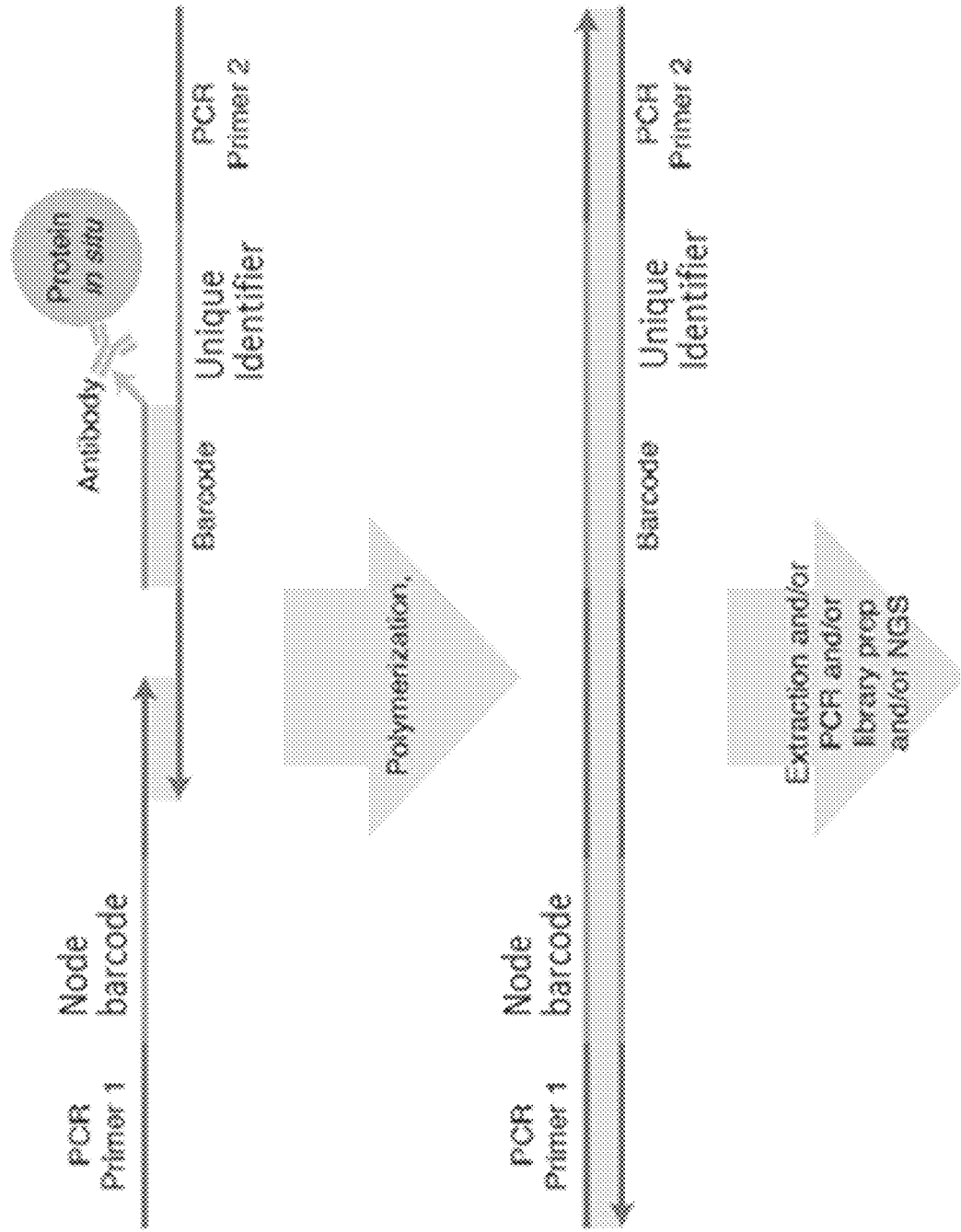
FIGS. 26A-26C illustrate exemplary embodiments for proximity recording of a protein in situ through binding an antibody to a target protein, wherein the antibody is conjugated to a hybridization sequence, and wherein a node barcode nucleic acid comprising a first primer and a node barcode is hybridized to a target nucleic acid comprising a barcode complement to the conjugated hybridization sequence, a unique identifier, and a second PCR primer.
Figure 26B:
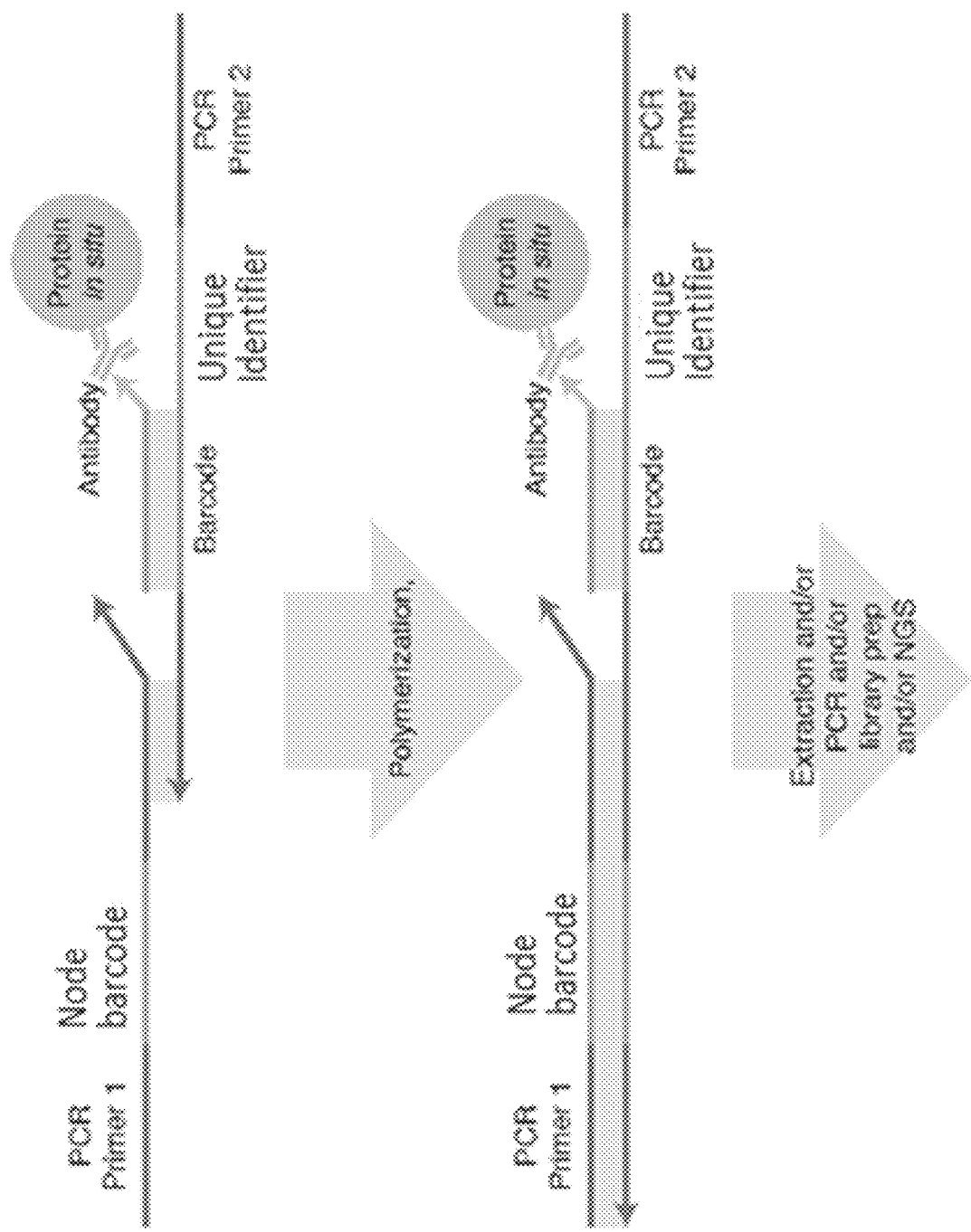
Figure 26C:
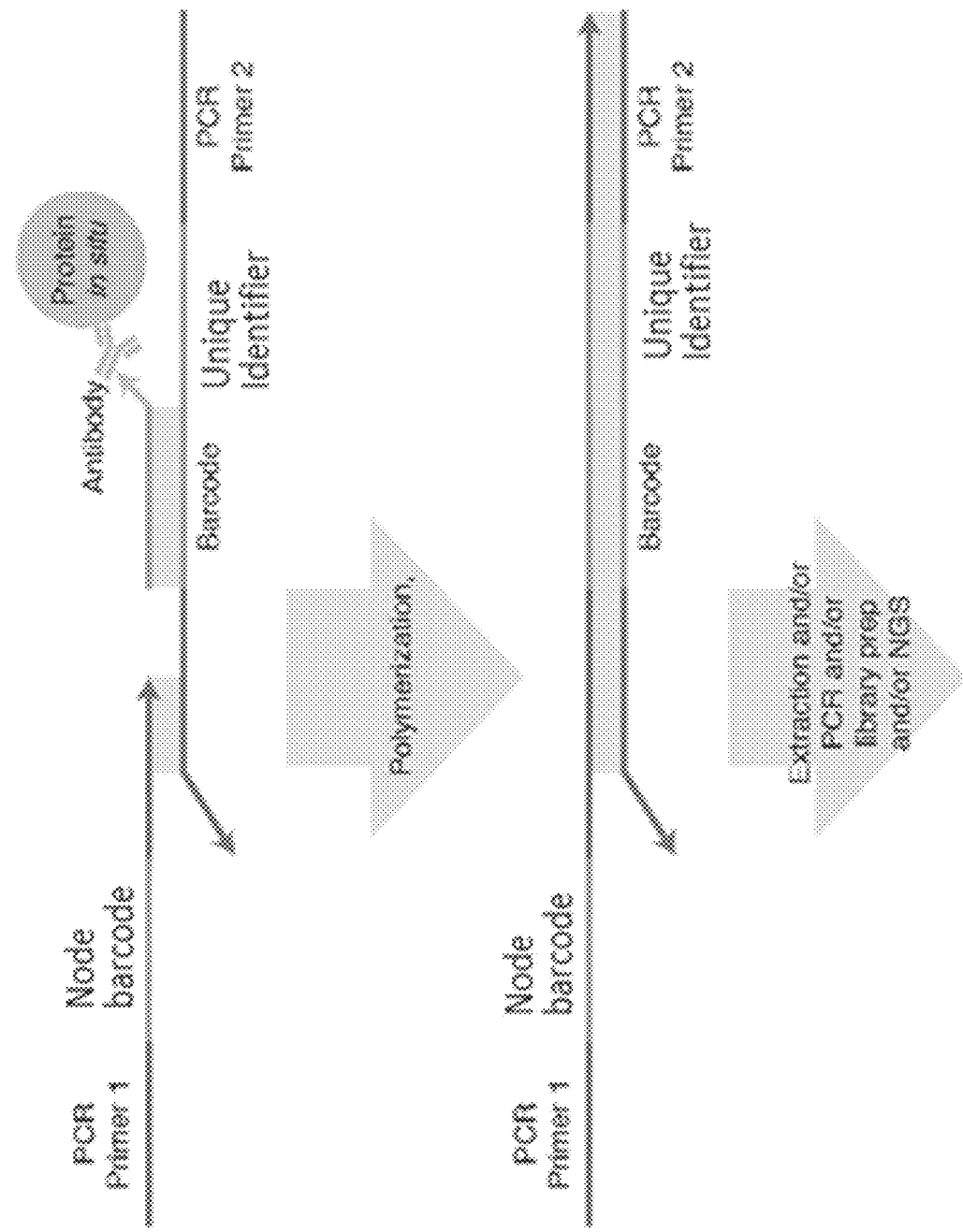

FIGS. 26A-26C show exemplary embodiments of proximity recoding of a protein in situ. An antibody conjugated to a hybridization sequence binds the protein through affinity binding. The antibody-conjugate hybridizes to a barcode sequence on a strand, wherein the barcode sequence strand further comprises a unique identifier and a primer. FIG. 26A shows a node barcode strand comprising a first PCR primer, a node barcode, hybridizing with a target barcode strand comprising an barcode, a unique identifier, and a second PCR primer. Both strands are extended by polymerization to generate a double stranded combined sequence. The double stranded combined sequence is then processed through extraction and/or PCR and/or library prep and/or NGS. FIG. 26B shows a node barcode strand comprising a first PCR primer, a node barcode, and a non-hybridized domain 3' of a hybridization domain hybridizing with a target barcode strand comprising a barcode, a unique identifier, and a second PCR primer. The target nucleic acid strand is extended by polymerization to generate a single stranded combined sequence. The combined sequence is then processed through extraction and/or PCR and/or library prep and/or NGS. FIG. 26C shows a node barcode strand comprising a first PCR primer, a node barcode, and a hybridization domain hybridizing with a target barcode strand comprising a non-hybridizing domain 3' of a hybridization sequence, a barcode, a unique identifier, and a second PCR primer. The node barcode strand is extended by polymerization to generate a single stranded combined sequence. The combined sequence is then processed through extraction and/or PCR and/or library prep and/or NGS.

Figure 26D:
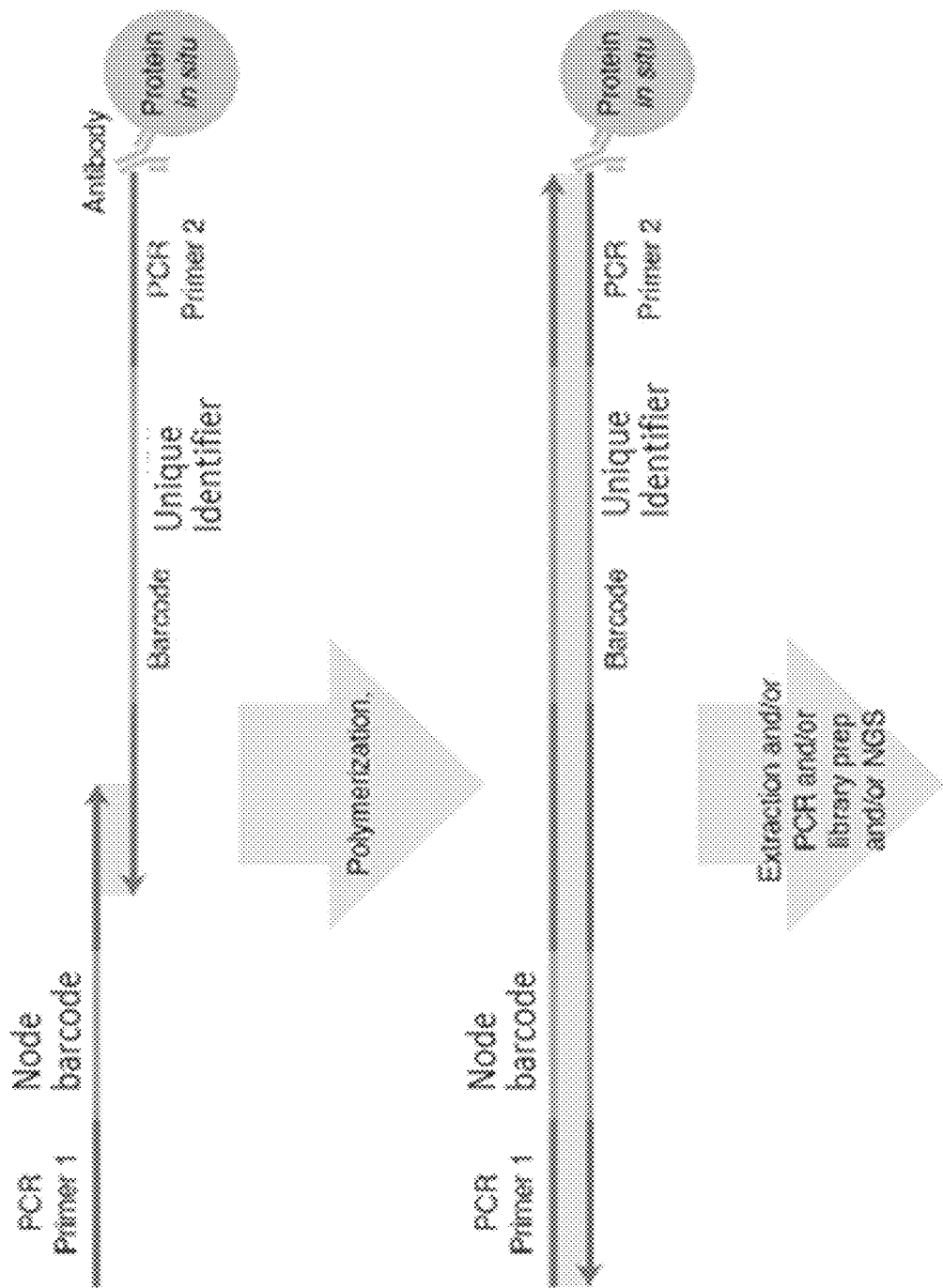
FIGS. 26D-26F illustrate exemplary embodiments of proximity recording of a protein in situ through binding an antibody to a target protein, wherein the antibody is conjugated to a target nucleic acid, wherein a node barcode nucleic acid comprising a first primer and a node barcode is hybridized to the target nucleic acid comprising a barcode, a unique identifier, and a second PCR primer.
Figure 26E:
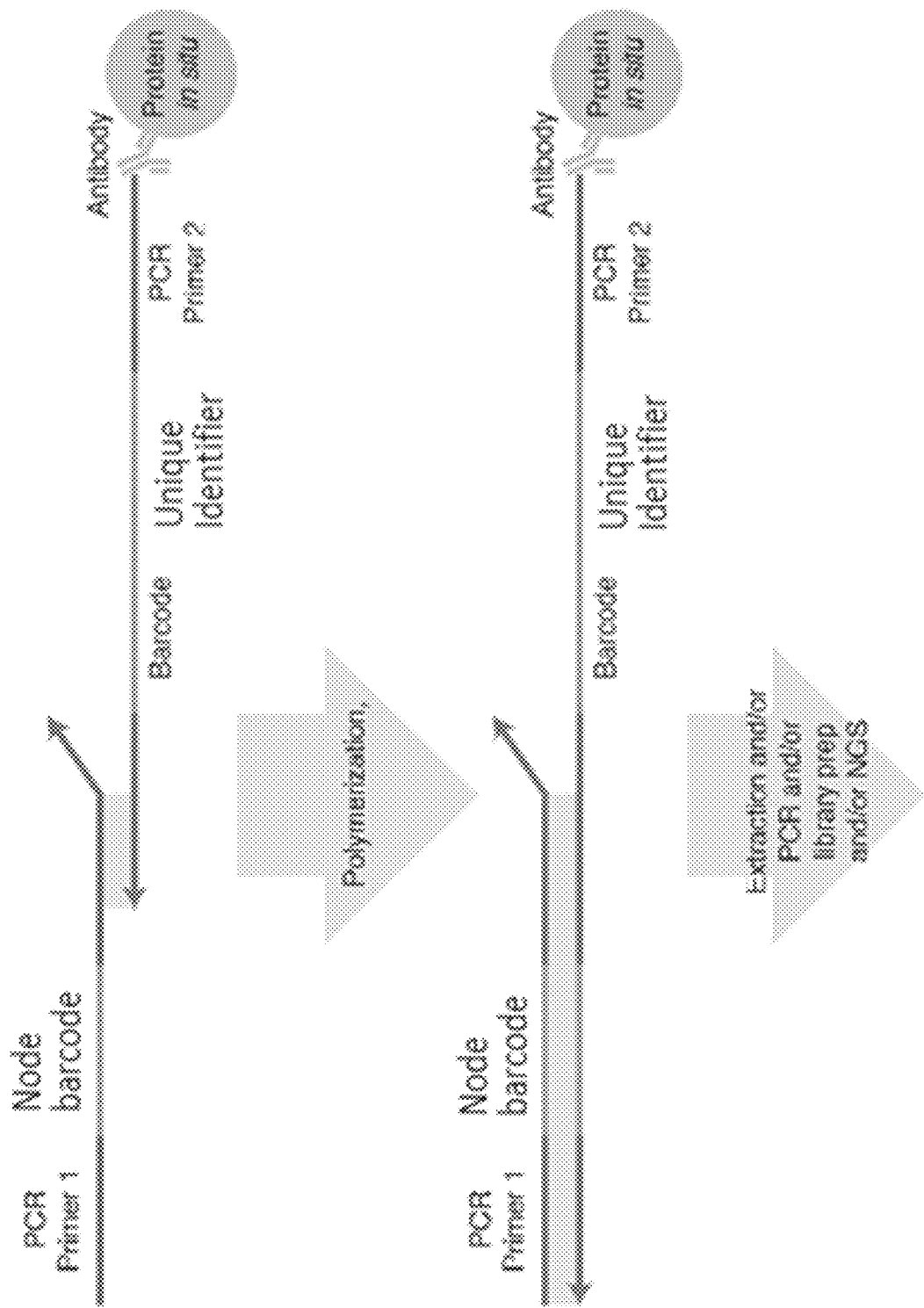
Figure 26F:
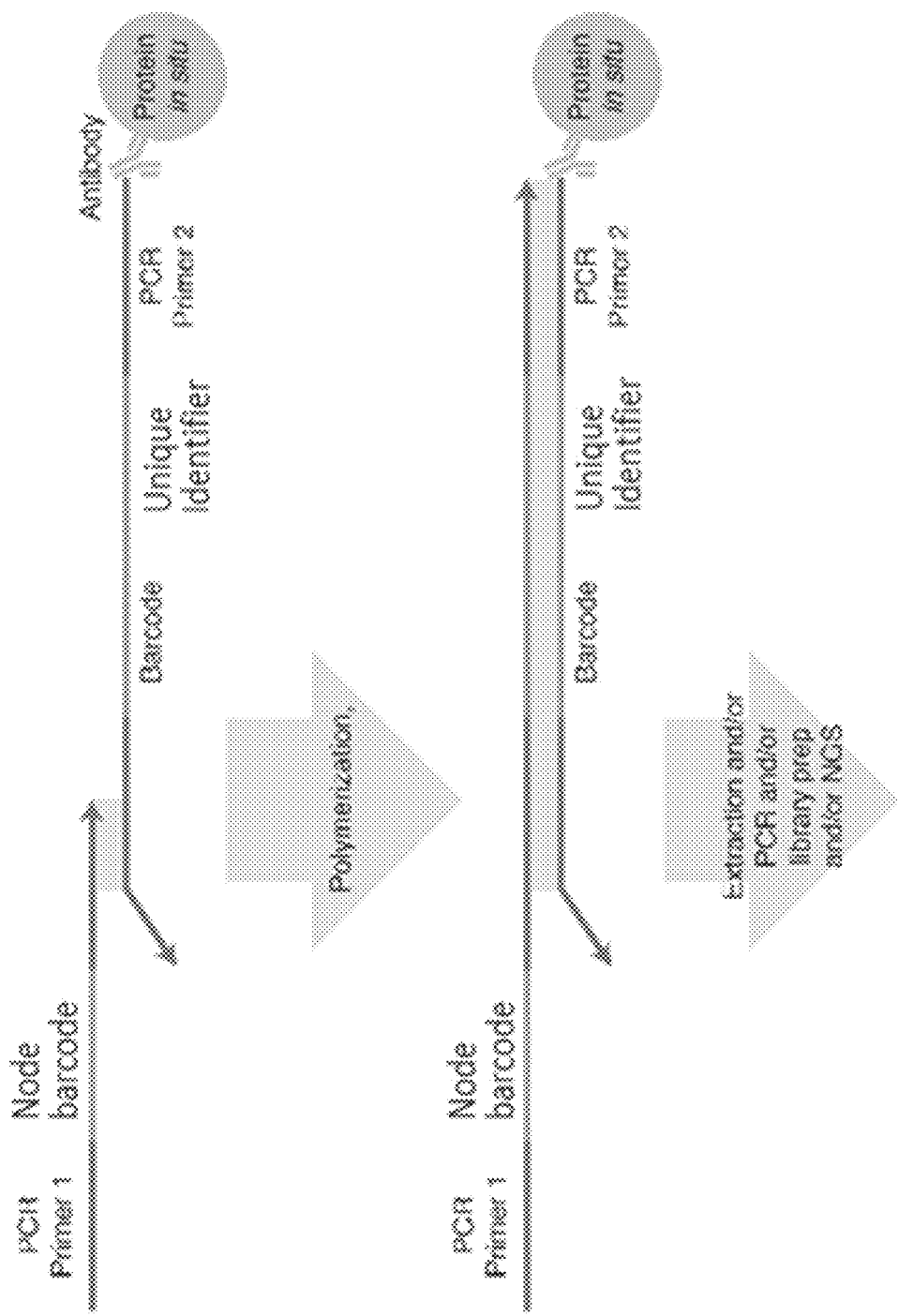

FIGS. 26D-26F show exemplary embodiments of proximity recoding of a protein in situ, wherein an antibody conjugated to a target nucleic acid binds the protein through affinity binding. FIG. 26D shows a node barcode strand further comprising a first PCR primer hybridizing with the antibody-conjugated target barcode strand comprising a barcode, a unique identifier, and a second PCR primer. Both strands are extended by polymerization to generate a double stranded combined sequence. The double stranded combined sequence is then processed through extraction and/or PCR and/or library prep and/or NGS. FIG. 26E shows a node barcode strand comprising a first PCR primer, a node barcode, a hybridization sequence, and a non-hybridized domain 3' of a hybridization sequence hybridizing with the antibody-conjugated target barcode strand comprising a barcode, a unique identifier, and a second PCR primer. The target nucleic acid strand is extended by polymerization to generate a single stranded combined sequence. The combined sequence is then processed through extraction and/or PCR and/or library prep and/or NGS. FIG. 26F shows a node barcode strand comprising a first PCR primer. a node barcode, and a hybridization sequence hybridizing with the antibody-conjugated target barcode strand comprising a non-hybridizing domain 3' of a hybridization sequence, a barcode, a unique identifier, and a second PCR primer. The node barcode strand is extended by polymerization to generate a single stranded combined sequence. The combined sequence is then processed through extraction and/or PCR and/or library prep and/or NGS.

Figure 26G:
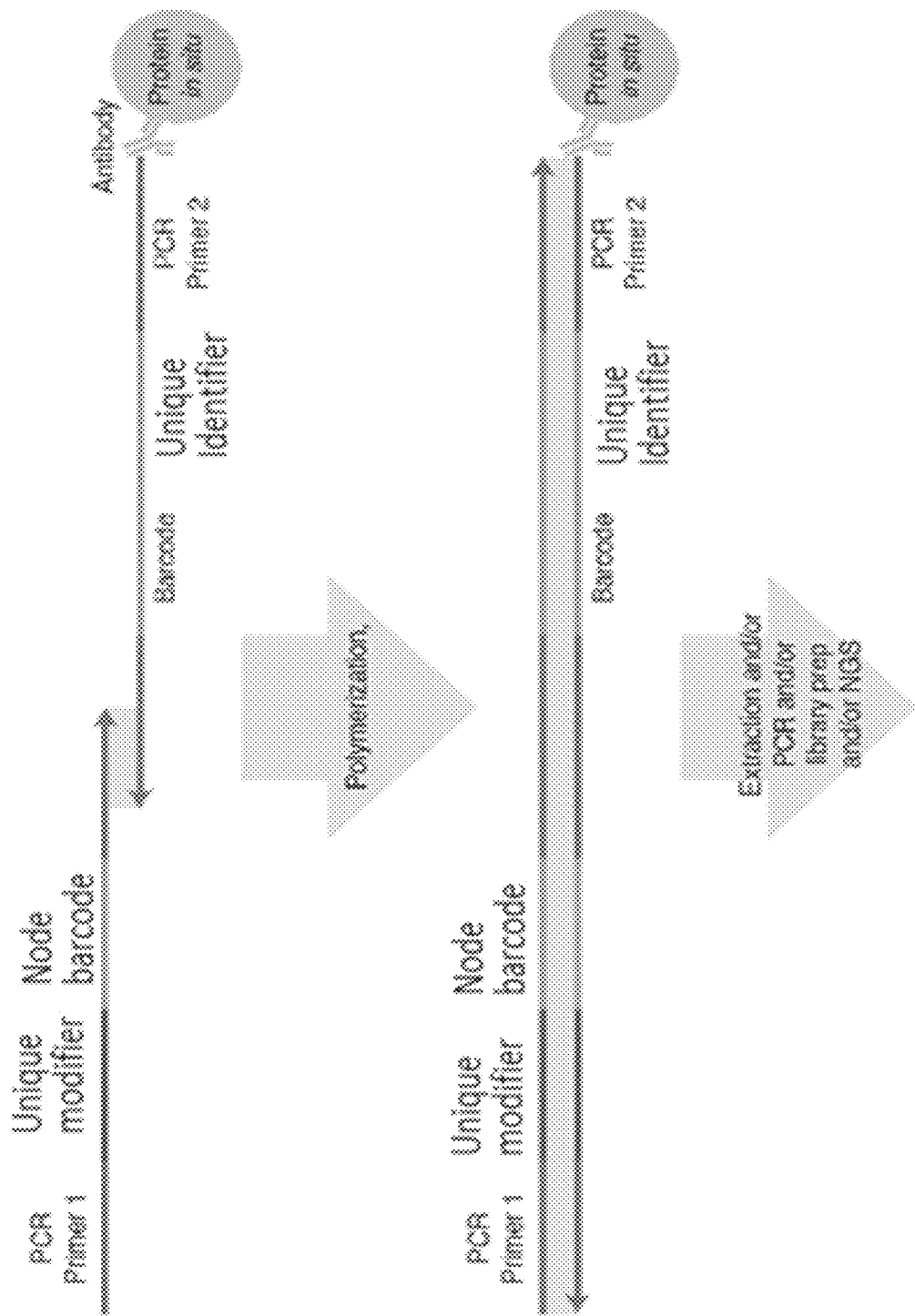
FIGS. 26G-26I illustrate exemplary embodiments of proximity recording of a protein in situ through binding an antibody to a target protein, wherein the antibody is conjugated to a target nucleic acid, wherein a node barcode nucleic acid comprising a first primer, a unique modifier, a node barcode and a hybridization sequence is hybridized to the target nucleic acid comprising a hybridization sequence, a barcode, a unique identifier, and a second PCR primer.
Figure 26H:
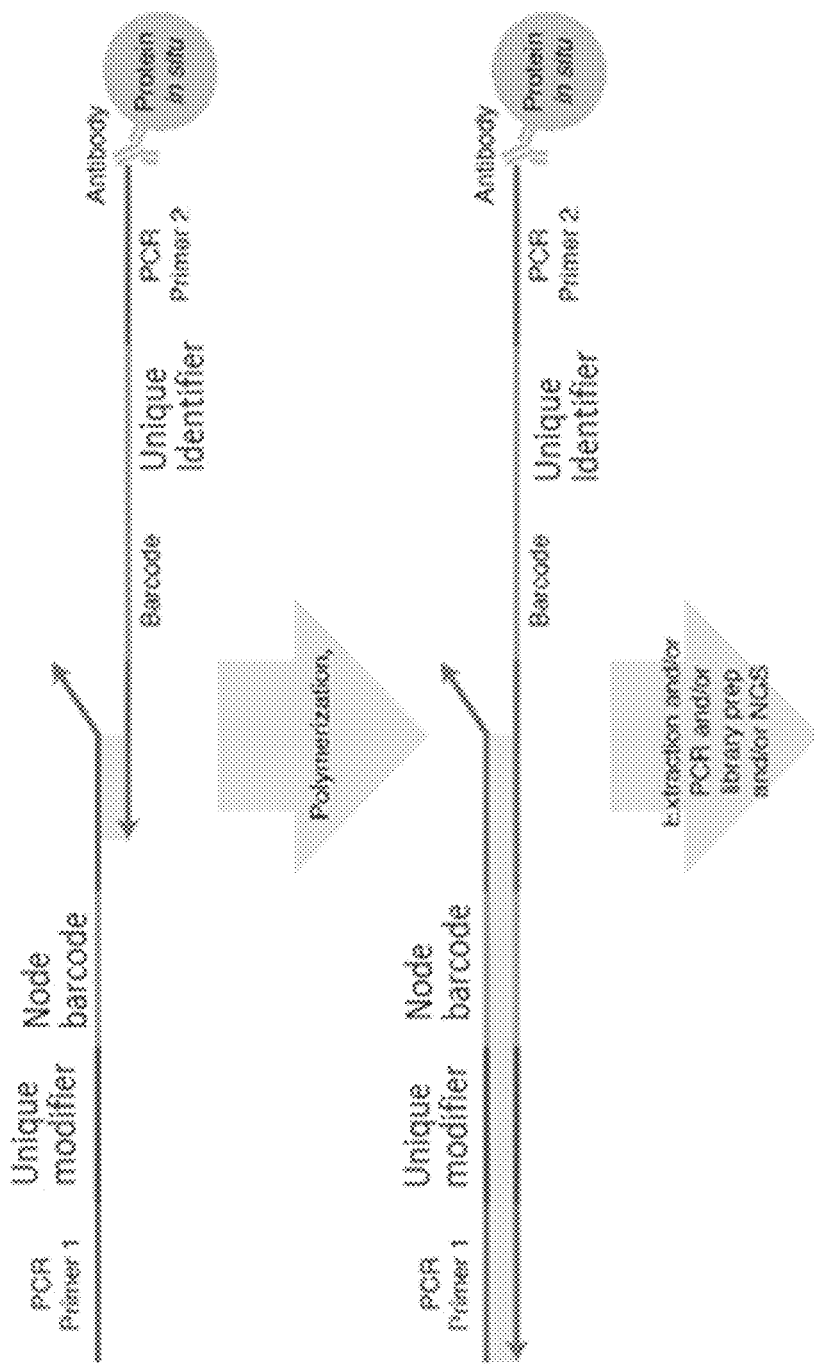
Figure 26I:
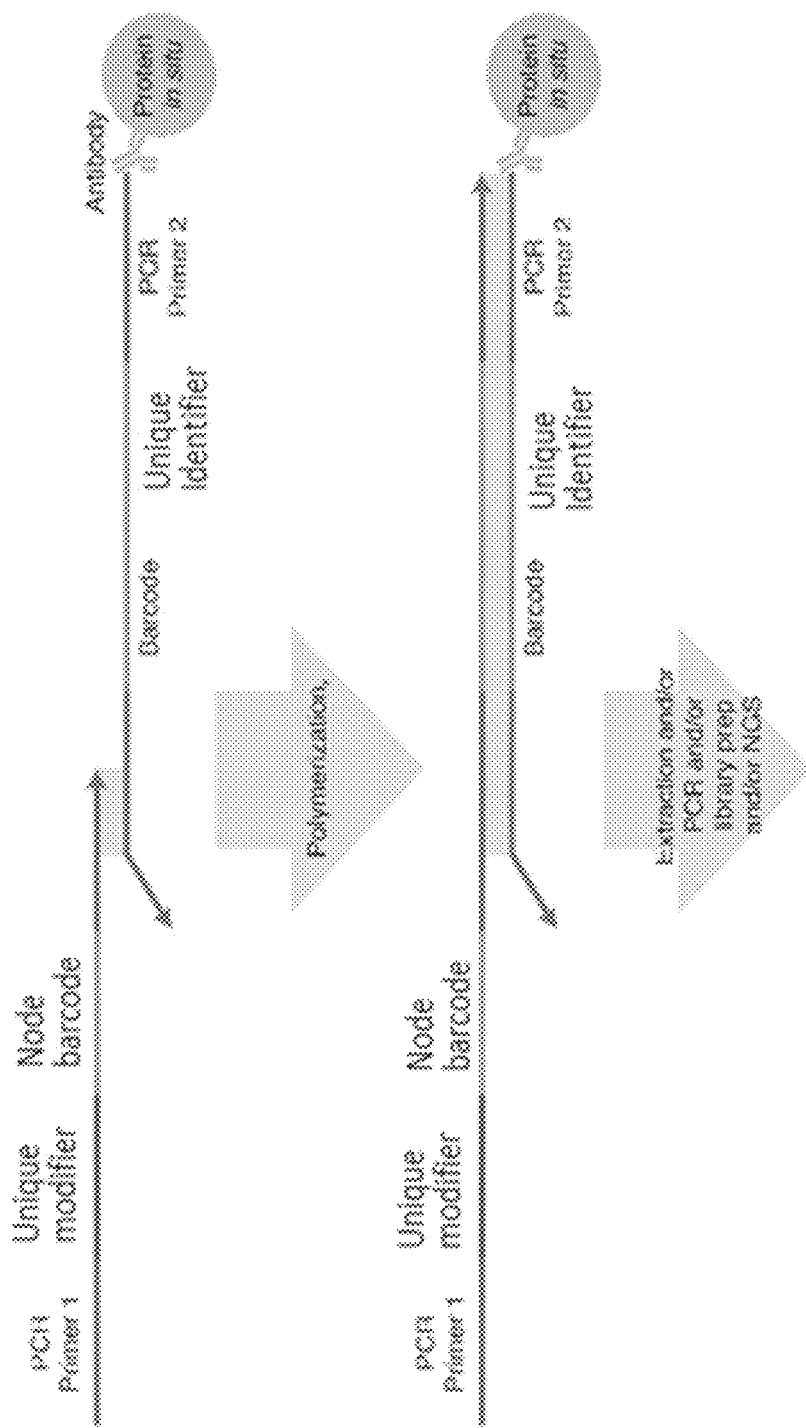

FIGS. 26G-26I show exemplary embodiments of proximity recoding of a protein in situ, wherein an antibody conjugated to a target nucleic acid binds the protein through affinity binding. FIG. 26G shows a node barcode strand further comprising a first PCR primer and a unique modifier hybridizing with the antibody-conjugated target barcode strand comprising a barcode, a unique identifier, and a second PCR primer. Both strands are extended by polymerization to generate a double stranded combined sequence. The double stranded combined sequence is then processed through extraction and/or PCR and/or library prep and/or NGS. FIG. 26H shows a node barcode strand comprising a first PCR primer, a unique modifier, a node barcode, a hybridization sequence, and a non-hybridized domain 3' of the hybridization sequence hybridizing with the antibody-conjugated target barcode strand comprising a barcode, a unique identifier, and a second PCR primer. The target nucleic acid strand is extended by polymerization to generate a single stranded combined sequence. The combined sequence is then processed through extraction and/or PCR and/or library prep and/or NGS. FIG. 26I shows anode barcode strand further comprising a first PCR primer, a unique modifier. a node barcode, and a hybridization sequence hybridizing with the antibody-conjugated target barcode strand comprising a non-hybridizing domain 3' of a hybridization sequence, a barcode, a unique identifier, and a second PCR primer. The node barcode strand is extended by polymerization to generate a single stranded combined sequence. The combined sequence is then processed through extraction and/or PCR and/or library prep and/or NGS.

Figure 27A:
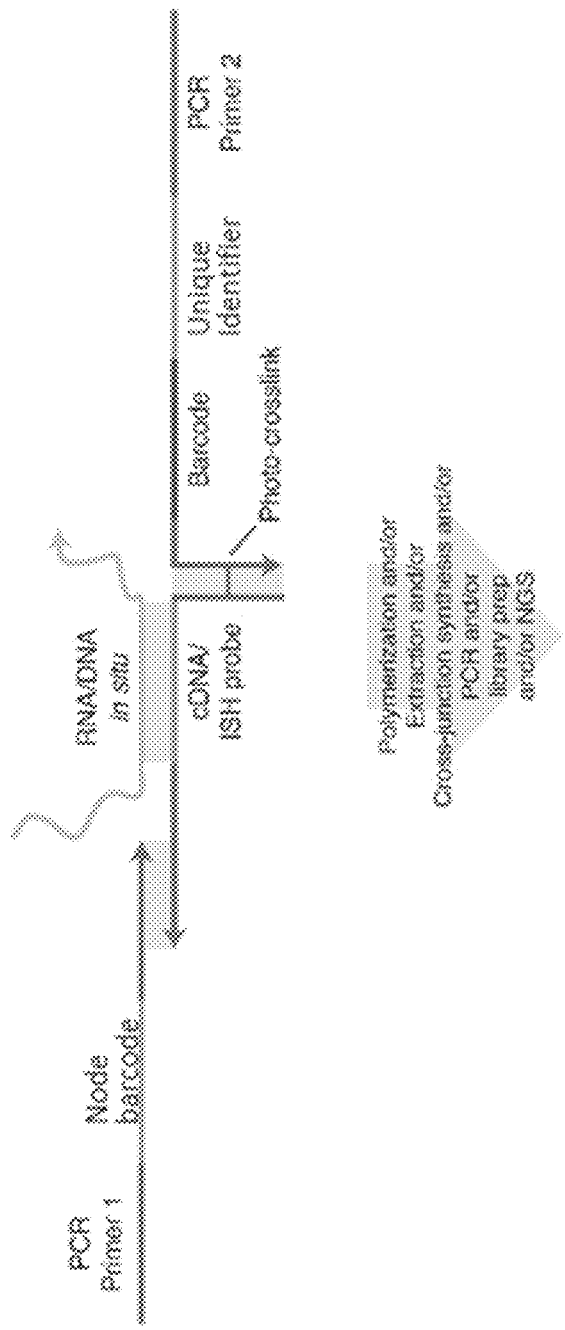
FIGS. 27A-27G illustrate exemplary embodiments of proximity recording of target RNA or DNA transcripts in situ using cDNA or ISH probes, wherein a node barcode nucleic acid comprising a first primer, a node barcode, and a hybridization domain is hybridized to a target nucleic acid comprising a hybridization domain and a cDNA or ISH probe complement to a target RNA, and the probe is photo-crosslinked to a strand comprising a barcode, and additional unique identifier and a second PCR primer.
Figure 27B:
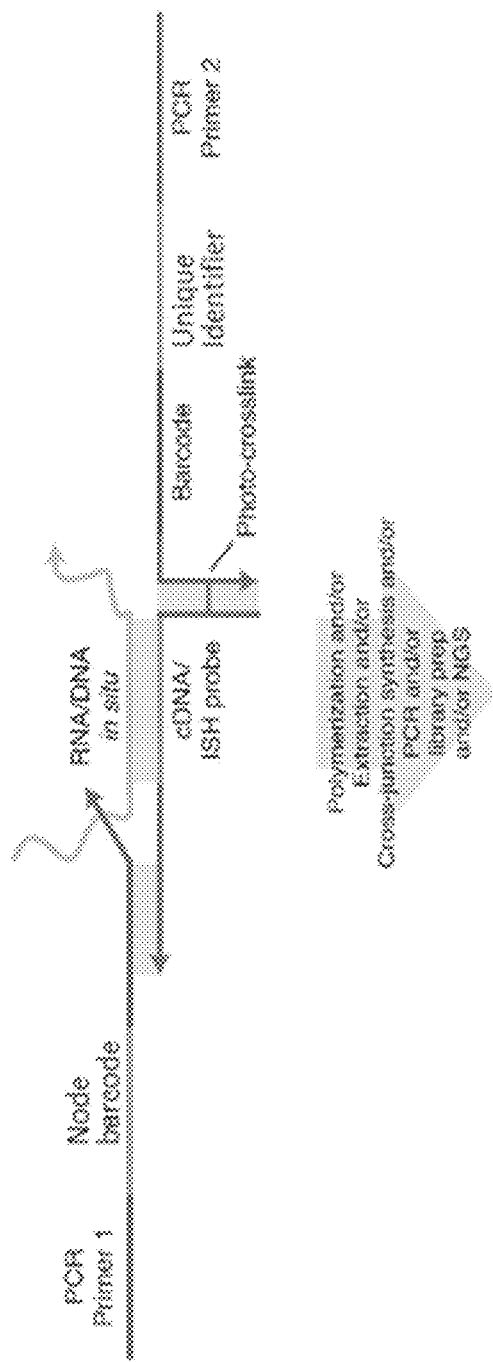
Figure 27C:
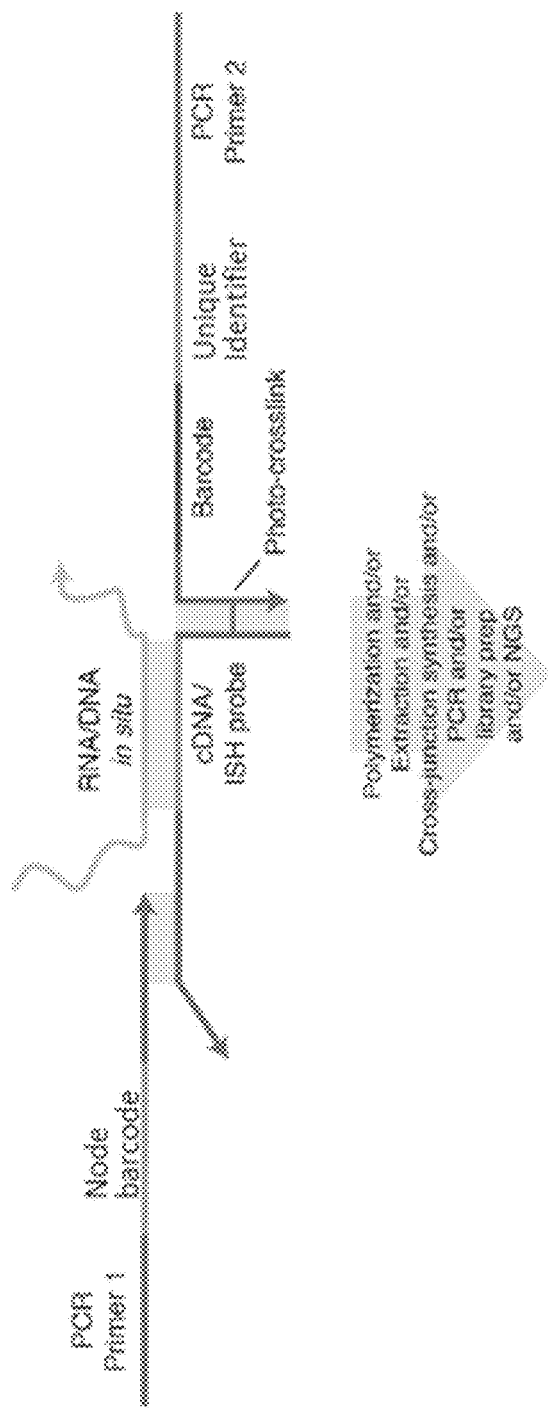
Figure 27D:
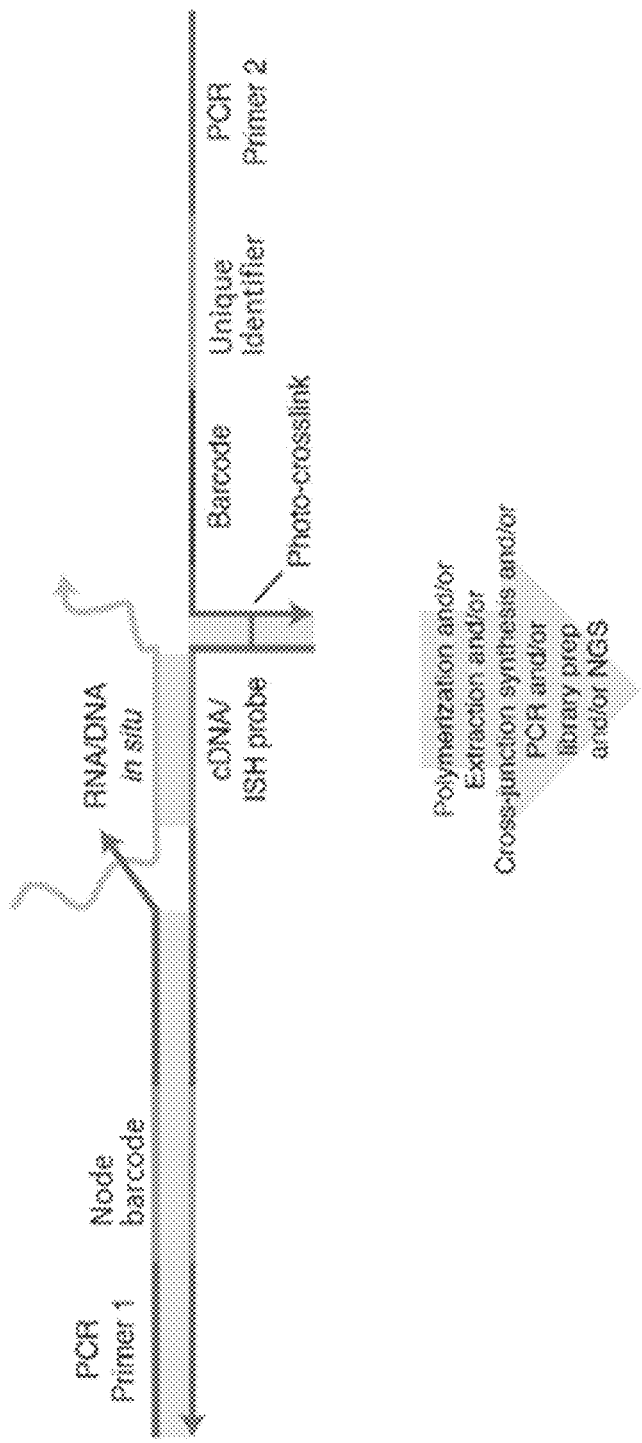
Figure 27E:
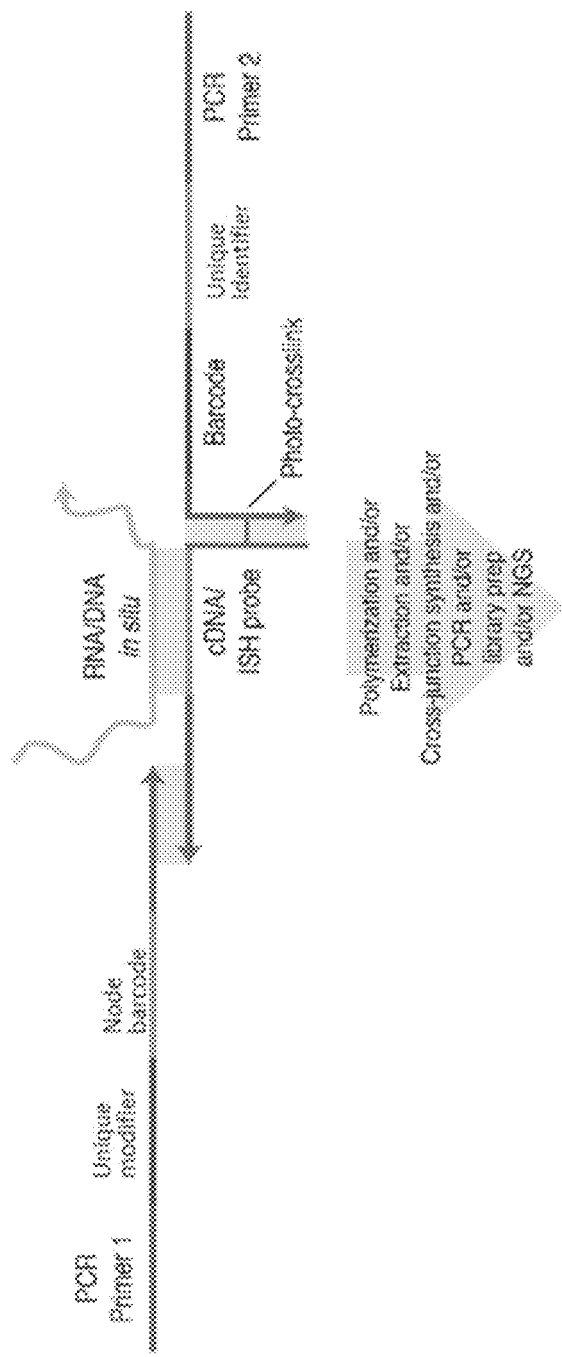
Figure 27F:
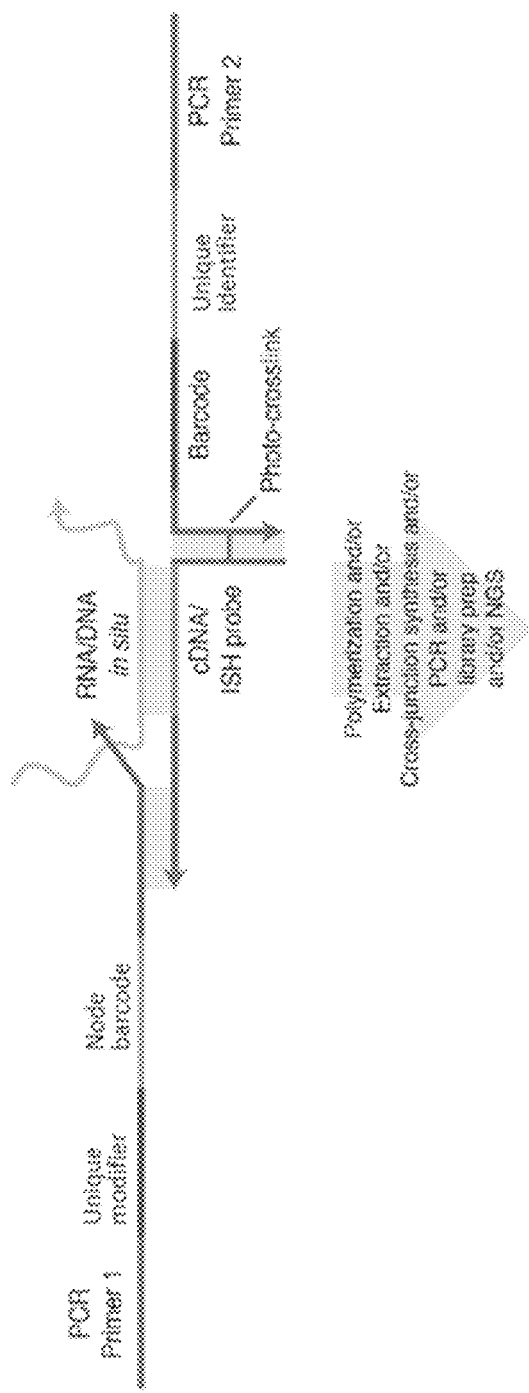
Figure 27G:
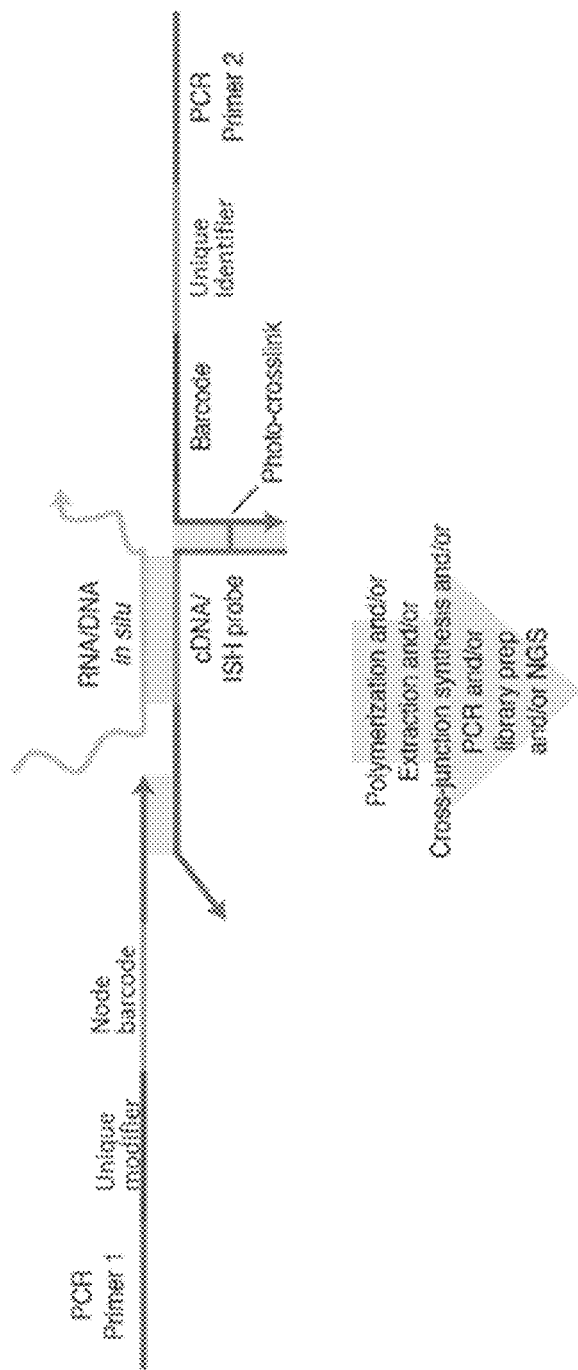

FIGS. 27A-27G show exemplary embodiments of proximity recording of target RNA transcripts using cDNA transcripts. FIG. 27A shows a node barcode strand comprising a first PCR primer. a node barcode, and a hybridization domain hybridizing with a target barcode strand comprising a hybridization domain and a cDNA or ISH probe complementary to a target RNA or DNA sequence photo crosslinked to a target barcode, a unique identifier, and a second PCR primer. FIG. 27B shows a node barcode strand comprising a first PCR primer, a node barcode, a hybridization domain, and a non-hybridization domain 3' of the hybridization domain hybridizing with a target barcode strand comprising a hybridization domain and a cDNA or ISH probe complementary to a target RNA or DNA sequence photo crosslinked to a target barcode, a unique identifier, and a second PCR primer. FIG. 27C shows a node barcode strand comprising a first PCR primer, a node barcode, and a hybridization domain hybridizing to a target barcode strand comprising a non-hybridization domain 3' of a hybridization domain and a cDNA or ISH probe complementary to a target RNA or DNA sequence photo crosslinked to a target barcode, a unique identifier, and a second PCR primer. FIG. 27D shows a node barcode strand comprising a first PCR primer, a node barcode, and a non-hybridizing domain 3' of the node barcode region hybridizing with a target barcode strand comprising a hybridization domain complementary to the node barcode and the first primer, a cDNA or ISH probe region complementary to a target RNA or DNA sequence photo crosslinked to strand comprising a target barcode, a unique identifier, and a second PCR primer. FIG. 27E shows a node barcode strand comprising a first PCR primer, a unique modifier, a node barcode, and a hybridization domain hybridizing with a target barcode strand comprising a hybridization domain and a cDNA or ISH probe region complementary to a target RNA or DNA photo-crosslinked to a strand comprising a barcode, a unique identifier, and a second PCR primer. FIG. 27F shows a node barcode strand comprising a first PCR primer, a unique modifier, a node barcode, a hybridization domain, and a non-hybridized region 3' of the hybridization domain hybridizing with a target barcode strand comprising a hybridization domain and a cDNA or ISH probe region complementary to a target RNA or DNA photo-crosslinked to a barcode, a unique identifier, and a second PCR primer. FIG. 27G shows a node barcode strand comprising a first PCR primer, a unique modifier, a node barcode and a hybridization domain hybridizing to a target barcode strand comprising a non-hybridized region 3' of a hybridization domain and a cDNA or ISH probe region complementary to a target RNA or DNA photo-crosslinked to a barcode, a unique identifier, and a second PCR primer.

Figure 28A:
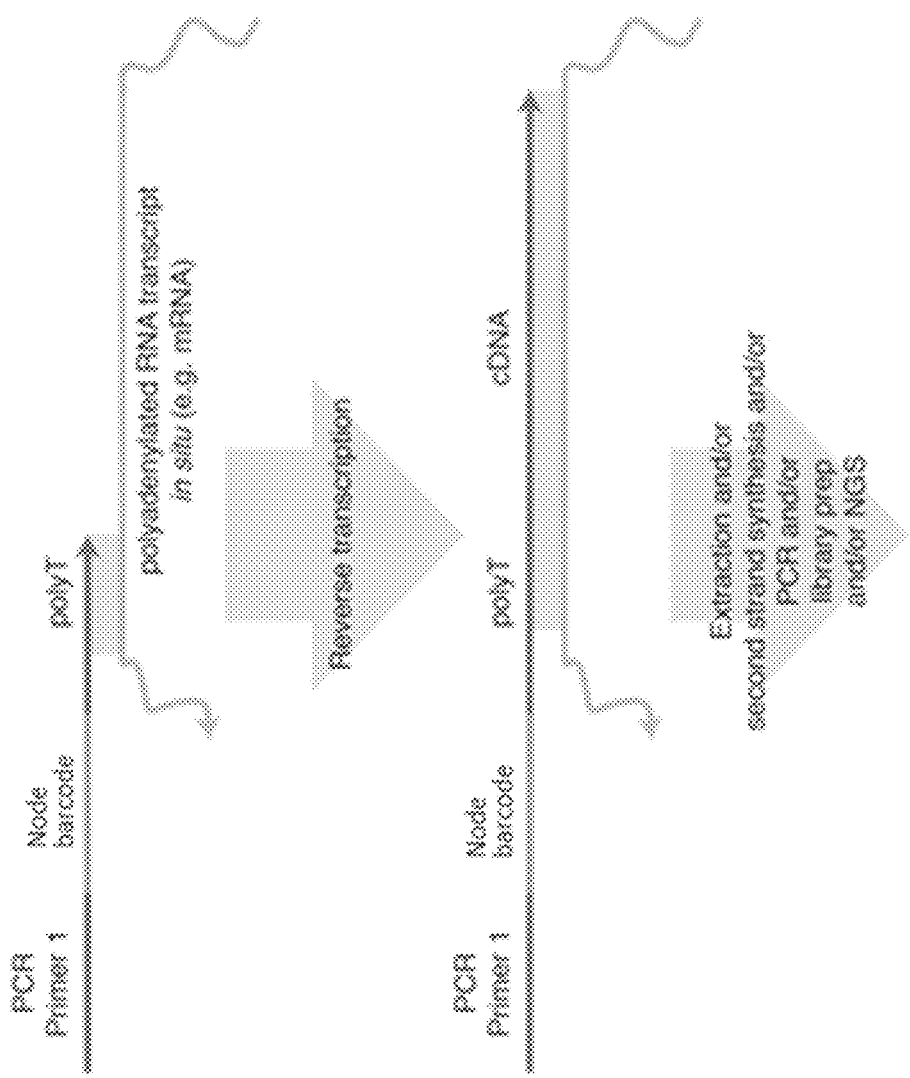
FIG. 28A illustrates a node barcode strand comprising a PCR primer, a node barcode region, and a polyT 3' tail acting as a primer for reverse transcription of an mRNA sequence.
Figure 28B:
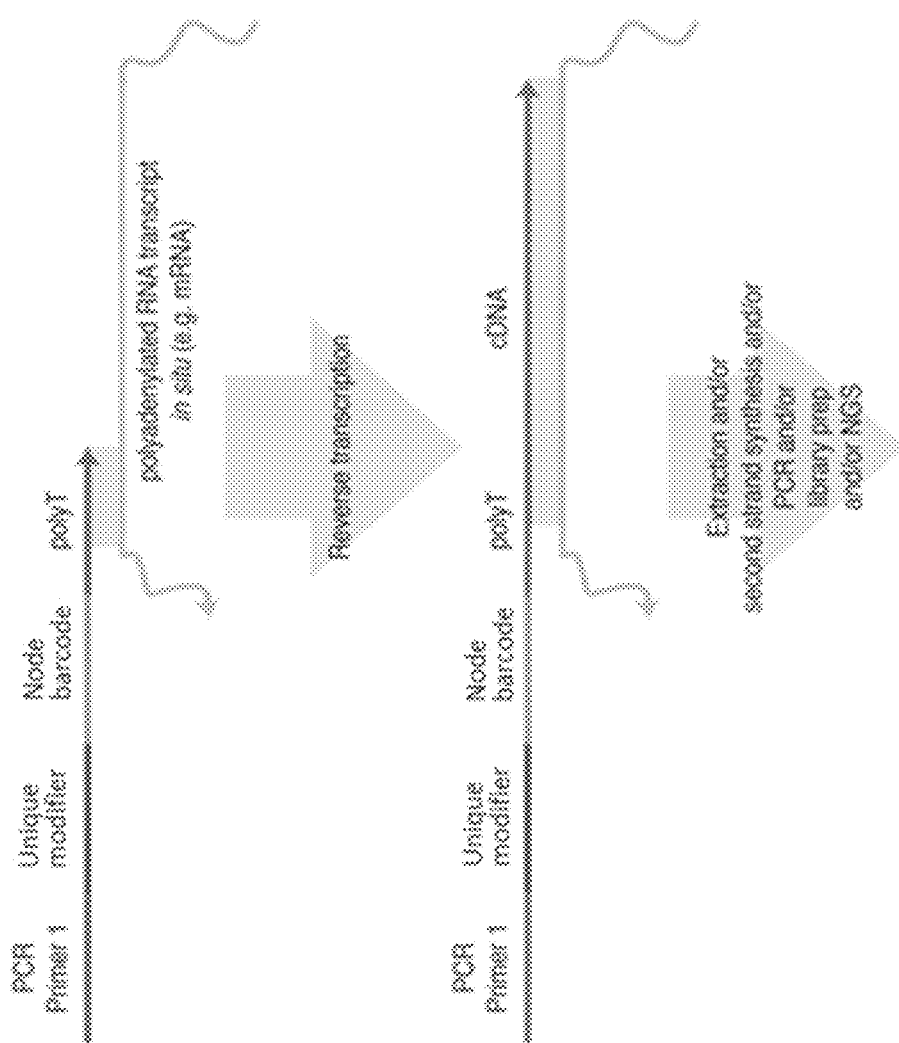
FIG. 28B illustrates a node barcode strand comprising a PCR primer, a unique modifier, a node barcode region, and a polyT 3' tail acting as a primer for reverse transcription of an mRNA sequence.
Figure 28C:
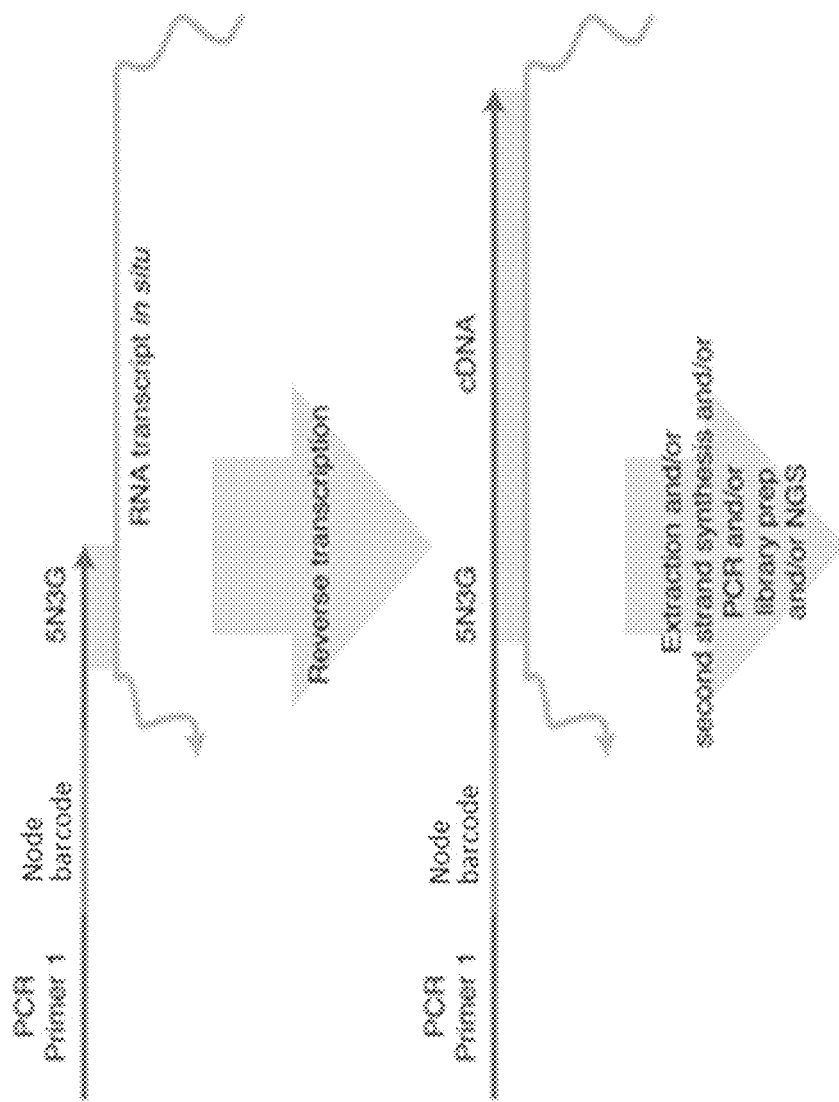
FIG. 28C illustrates a node barcode strand comprising a PCR primer, a node barcode region, and a 5N3G 3' tail acting as a primer for reverse transcription of an mRNA sequence.
Figure 28D:
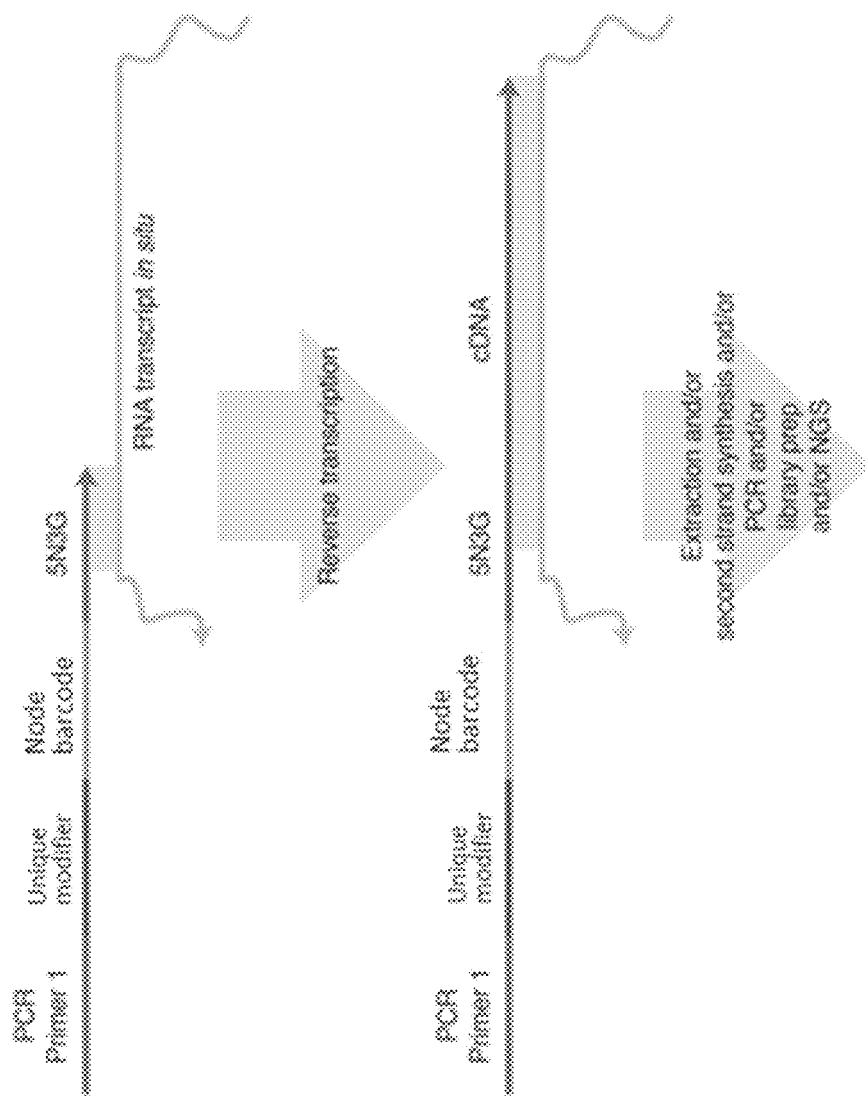
FIG. 28D illustrates a node barcode strand comprising a PCR primer, a unique modifier, a node barcode region, and a 5N3G 3' tail acting as a primer for reverse transcription of an mRNA sequence.

In some embodiments, the node barcode strand functions as a primer on a target nucleic acid strand. Transcription from the primer region generates a template cDNA region on the node barcode strand. FIGS. 28A-28D show exemplary embodiments using a node barcode strand as a primer for reverse transcription of a target mRNA. FIG. 28A shows a node barcode strand comprising a PCR primer and a node barcode with a 3' polyT domain hybridized to a polyA tail on an mRNA target. Reverse transcription from the polyT domain generates a cDNA strand extension associated with the node barcode strand. FIG. 28B shows a node barcode strand comprising a PCR primer, a unique modifier, and a node barcode with a 3'polyT domain hybridized to a polyA tail on an mRNA target. Reverse transcription from the polyT domain generates a cDNA strand extension associated with the node barcode strand. FIG. 28C shows a node barcode strand comprising a PCR primer and anode barcode with a random sequence (5N3G) for priming on an RNA sequence. Reverse transcription from the 5N3G domain generates a cDNA strand extension associated with the node barcode strand. FIG. 28D shows a node barcode strand comprising a PCR primer, a unique modifier, and a node barcode with a random sequence (5N3G) for priming on an RNA sequence. Reverse transcription from the 5N3G domain generates a cDNA strand extension associated with the node barcode strand. In some embodiments, primer sequences are random or specific. In some embodiments, the primer sequence comprises TTTTTTTTTT, TTTTTTTTTTTTTTTTTTTT, TTTTTTTTTTTTTTTTTTTTVN, NNNNNNN, NNNNNNNN, NNNNNGGG, NNNNNCCC, NNNNNTTT, or any combination thereof. In some embodiments, the priming sequences is specific to an RNA of interest. In some embodiments, the primer sequence is a CRISPR guide RNA sequence, an mRNA therapeutic sequence, a T or B cell receptor sequence, or any combination thereof. In some embodiments, second strand synthesis is applied to the reverse transcription product. In some embodiments, template switching oligos (TSO) are used in the second strand synthesis. In some embodiments, second strand synthesis generates a strand comprising PCR primers flanking one or more barcode and cDNA sequences.

Figure 29A:
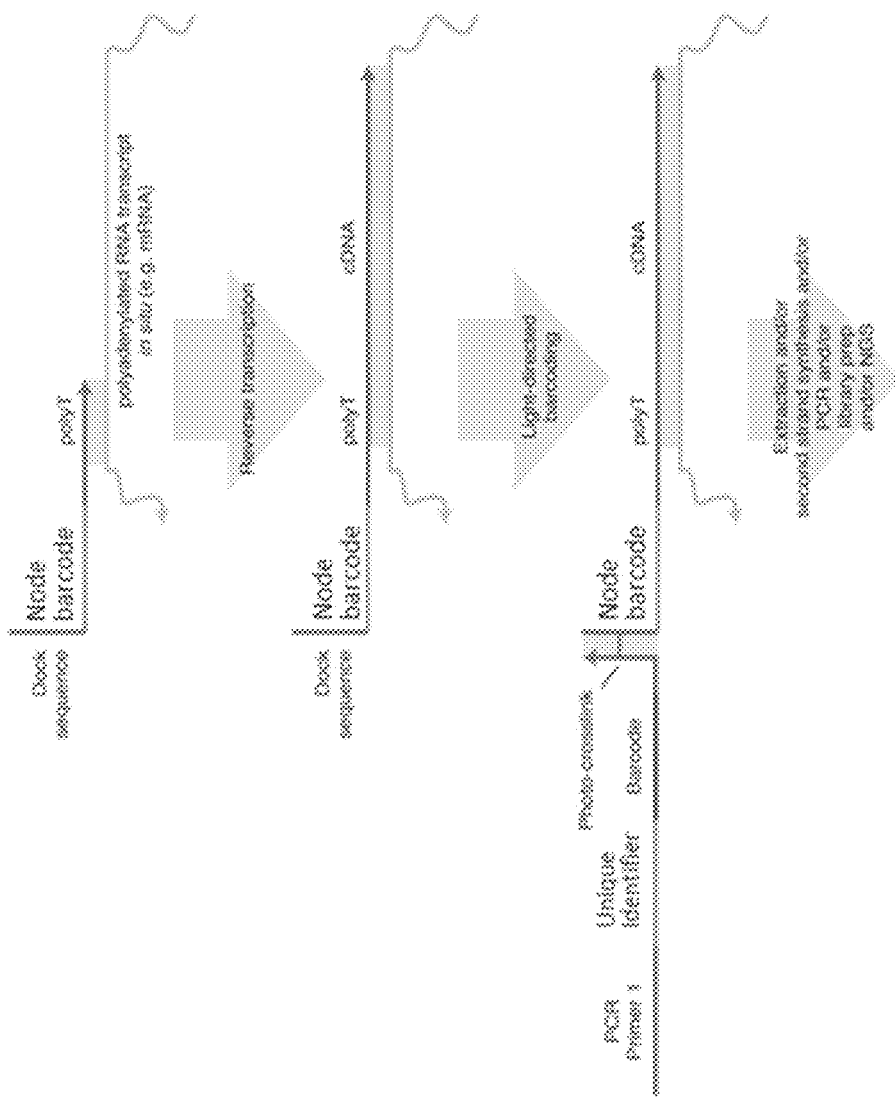
FIG. 29A illustrates a node barcode strand comprising a dock sequence, a node barcode region, and a polyT 3' tail acting as a primer for reverse transcription of an mRNA sequence, followed by light directed barcoding to photo-crosslink a strand comprising a PCR primer, a unique identifier, and another barcode sequence.
Figure 29B:
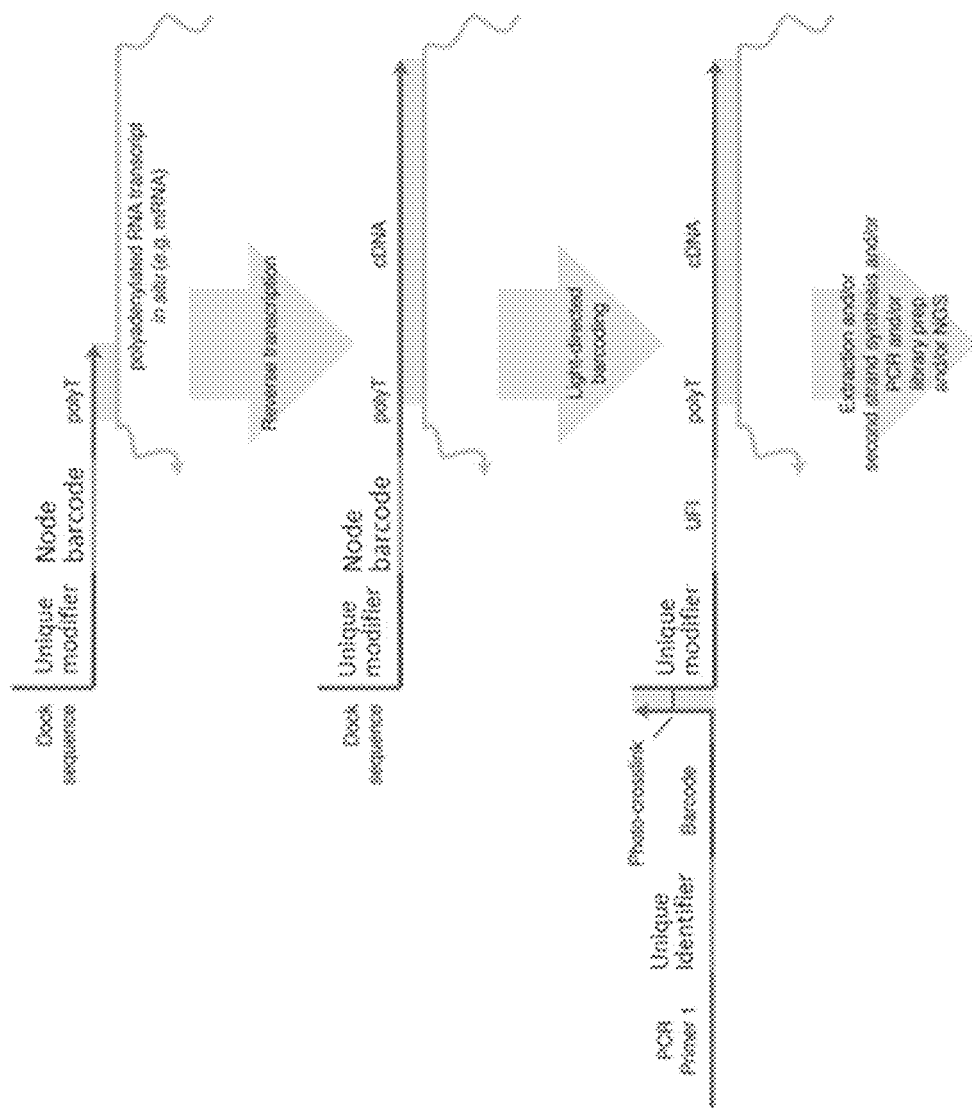
FIG. 29B illustrates a node barcode strand comprising a dock sequence, a unique modifier, a node barcode region, and a polyT 3' tail acting as a primer for reverse transcription of an mRNA sequence, followed by light directed barcoding to photocrosslink a strand comprising a PCR primer, a unique identifier, and another barcode sequence.
Figure 29C:
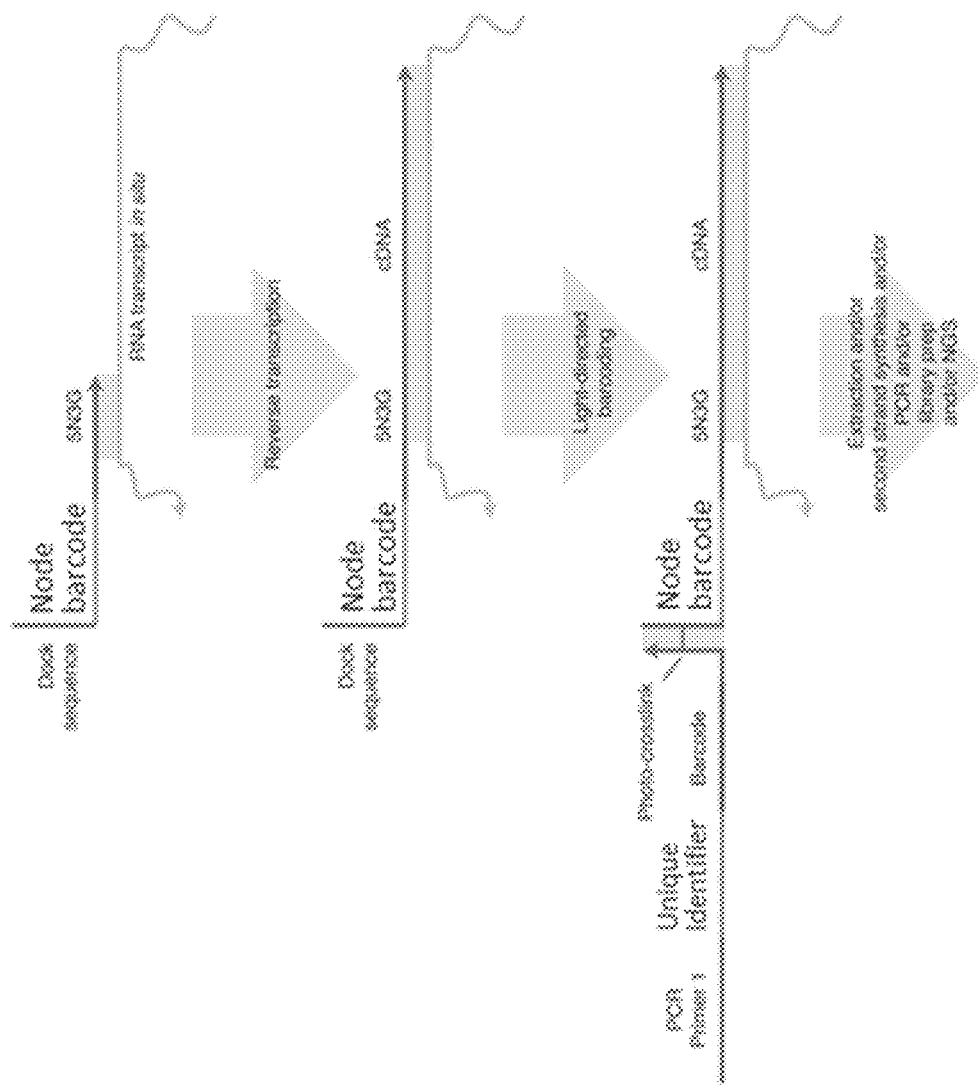
FIG. 29C illustrates a node barcode strand comprising a dock sequence, a node barcode region, and a 5N3G 3' tail acting as a primer for reverse transcription of an mRNA sequence, followed by light directed barcoding to photo-crosslink a strand comprising a PCR primer, a unique identifier, and another barcode sequence.
Figure 29D:
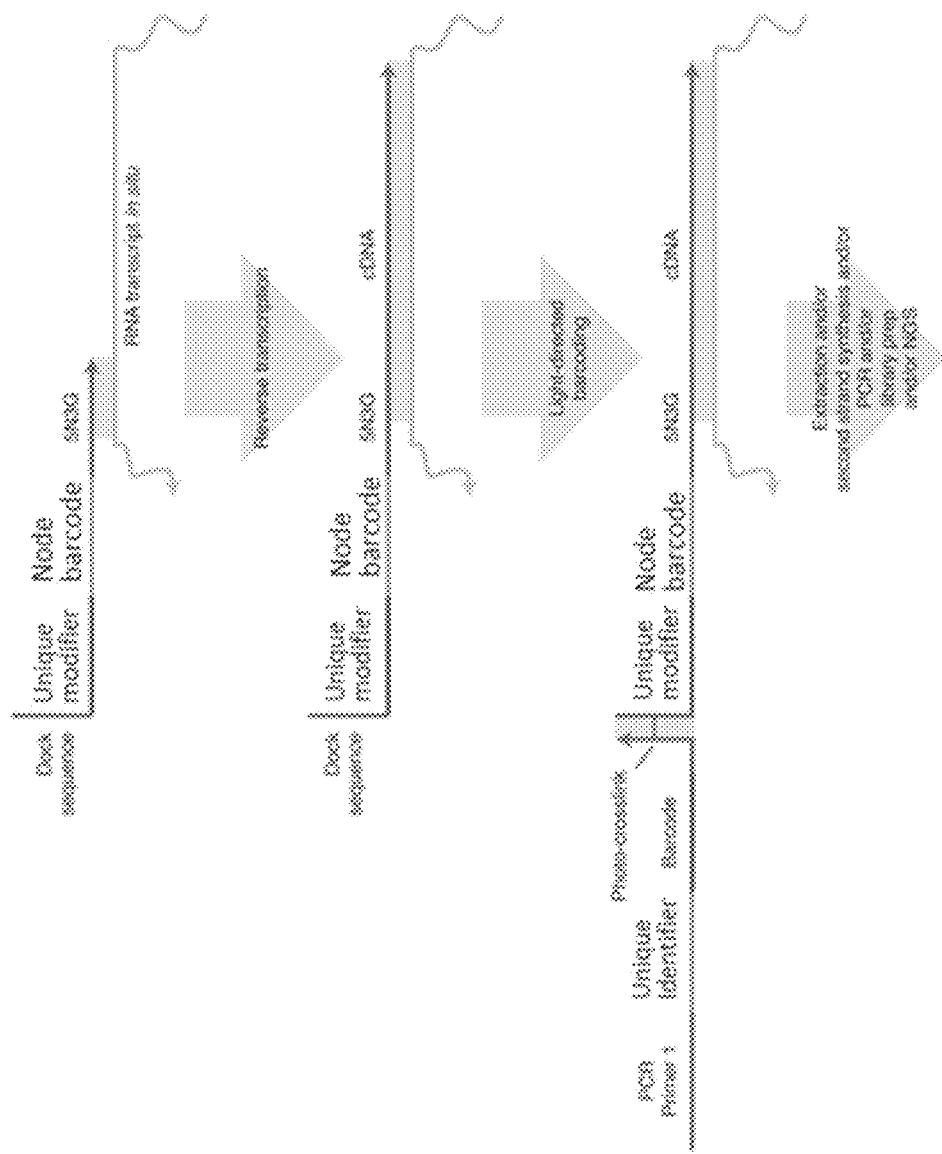
FIG. 29D illustrates a node barcode strand comprising a dock sequence, a unique modifier, a node barcode region, and a 5N3G 3' tail acting as a primer for reverse transcription of an mRNA sequence, followed by light directed barcoding to photocrosslink a strand comprising a PCR primer, a unique identifier, and another barcode sequence.

In some embodiments, node barcode strands described herein function as a primer and further comprise a docking sequence. FIGS. 29A-29D show exemplary embodiments using anode barcode strand as a primer for reverse transcription of a target mRNA, wherein the node barcode strand further comprises a docking sequence. FIG. 29A shows a node barcode strand comprising a dock sequence and a 3'polyT domain hybridized to a polyA tail on an mRNA target. Reverse transcription from the polyT domain generates a cDNA strand extension associated with the node barcode strand. A barcode strand comprising a PCR primer, unique identifier, and an additional barcode is photo-crosslinked with the dock sequence. FIG. 29B shows a node barcode strand comprising a dock sequence and a 3'polyT domain hybridized to a polyA tail on an mRNA target. Reverse transcription from the polyT domain generates a cDNA strand extension associated with the node barcode strand. A barcode strand comprising a PCR primer, unique identifier, and an additional barcode is photo-crosslinked with the dock sequence. FIG. 29C shows a node barcode strand comprising a dock sequence and a node barcode with a random sequence (5N3G) for priming on an RNA sequence. Reverse transcription from the 5N3G domain generates a cDNA strand extension associated with the node barcode strand. A barcode strand comprising a PCR primer, unique identifier, and an additional barcode is photo-crosslinked with the dock sequence. FIG. 29D shows a node barcode strand comprising a dock sequence, a unique modifier, and a node barcode with a random sequence (5N3G) for priming on an RNA sequence. Reverse transcription from the 5N3G domain generates a cDNA strand extension associated with the node barcode strand. A barcode strand comprising a PCR primer, unique identifier, and an additional barcode is photo-crosslinked with the dock sequence.

Re-Constructing Spatial Landscape from Diffusion Clouds

The frequency and combination of barcodes in concatemers provides information to calculate spatial proximity information. Sequencing of node barcode sequences from different node locations provides handshake or triangulation information on relative locations of nodes. In some embodiments, target nucleic acids are combined with node nucleic acids in concatemers. Sequencing these concatemers provides specific location information for the subject of the target nucleic acids. Node barcode sequences generated from one or more node locations can be concatenated together. In some embodiments, concatenated sequences comprise part or all of 2 or more node barcode sequences. Concatenated sequences may comprise additional sequences, including unique modifiers and other additional sequences of 1 to 50 nt or longer. These concatenated node barcode strands are referred to as node barcode concatemers. Node barcode strands may comprise additional sequences introduced or eliminated during the concatenation. Concatenation of node barcode strands into pairwise or multiple node barcode concatemers can indicate proximity of node locations at a specific or nonspecific time, by direct interaction, such as by base-pairing, or indirect interaction, such as enzyme-mediated or splint-mediated combining. The node barcode concatemers can be sequenced. In some embodiments, the sequence is read using next-generation sequencing, ISH, microarrays, or any variation or combination thereof. In some embodiments, sequencing results are used to reconstruct which node barcode strands were concatenated. Association of the node barcode sequences within or excluded from concatenated strands to their node locations (e.g., originating from a single or multiple biomolecules) can enable reconstruction of the spatial landscape of the sample.

In some embodiments, these node barcode strands have originated from one or more strands, either or both of which may be immobilized on a substrate, in a substrate, or within an immobilized or live sample. In some embodiments, concatenating node barcode strands include, but are not limited to, ligation, splinted ligation, cross-junction synthesis, ligation and cross-intercrosslink synthesis, cross-intercrosslink and nick synthesis, and pairwise hybridization and copying (see, FIG. 18). Alternatively, PER, asymmetric PCR, Gibson assembly, transposase-based concatenation (e.g., Tn5 transposition for RNA-DNA hybrids), or any other strategy for assembling sequences may be used.

In some embodiments, concatenated node barcode strands are amplified and prepared for sequencing, node barcode specific readout (e.g., ISH), or other methods to identify the original node barcodes which were concatenated.

The spatial relationship between node locations can be deconvolved from the coincidence of node barcode sequences within concatemers and the associated unique identifiers, barcodes, and/or additional information gathered from the same tissues/cells/substrate. In some embodiments, the association of node barcodes and target barcodes is used to reconstruct location of node locations relative to one another in the sample. This additional information may relate to protein or RNA detection, morphological imaging, spatial delivery of barcode sequences, or other sample information. Interaction of node barcode strands from node locations can be controlled by titration of diffusion rates within the sample, which can alter the incidence of concatemerization. In some embodiments, one or more of imaging data of nodes, node concatemers, diffusion clouds, light-directed ROI size, or light-directed ROI shape are used in any combination to aid in computational deconvolution.

Layered Processes

Methods described herein can be used separately or in combination. In some embodiments, additional layers of spatial and expression information are advantageous. Described embodiments comprise sequencing from distinct diffusion clouds, overlapping diffusion clouds, light-directed barcoding, fractional light-directed barcoding, or any combination thereof. Election of a method or combination as described herein is guided, in various embodiments, by the capabilities of each method.

Mapping using distinct diffusion clouds provides relative location mapping of node locations to targets. Use of distinct diffusion clouds from node locations allows sub-cellular resolution of an entire sample with no special equipment. The integrity of a tissue sample remains intact. Additionally, reaction is completed without having to perform multiple wash cycles, in other words, it is a "one-pot" reaction.

In some embodiments, diffusion of generated node barcode nucleic acid strands from a plurality of node locations is modulated such that diffusion clouds from separate node locations overlap. Node barcode nucleic acids from separate node locations combine by hybridization, extension, ligation, splinted ligation, cross-junction synthesis, ligation and cross-interstrand crosslink (ICL) synthesis, cross ICL and nick synthesis, pairwise copying, or any combination thereof to form concatemers of node barcode nucleic acids. Concatenated node barcode nucleic acid strands from overlapping diffusion clouds allow for complete reconstruction of the spatial atlas of an entire sample. The method also is a "one-pot" reaction.

Mapping samples using light-directed barcoding of cells allows for location mapping in intact sample tissues. Photomasking during light-directed barcoding allows for sequencing only cells or regions of interest. Fractional barcoding, as described herein, provides for identification of cells or regions of interest using light-directed barcoding with fractions of barcodes across a population of reads from the same area. Fractional barcoding allows for location mapping with minimal fluid exchange sequences. Fractional barcoding can comprise binary, trinary, quaternary, or any other fractional percentage of one or more barcodes.

In some embodiments, a barcoding method is optionally combined with a diffusion cloud labelling method. Combination of methods allows for location mapping with minimal fluid exchanges at sub-cellular resolution. Combining methods allows for mapping only in cells or regions of interest. Additionally, samples remain intact following barcoding. In some embodiments, spatial analysis is performed using light-directed barcoding. In some embodiments, spatial analysis is performed using one or more types of fractional barcoding. In some embodiments, spatial analysis is performed using light-directed barcoding and one or more types of fractional barcoding. In some embodiments, spatial analysis is performed using distinct diffusion clouds. In some embodiments, spatial analysis is performed using overlapping diffusion clouds. In some embodiments, spatial analysis is performed using light-directed barcoding and distinct diffusion clouds. In some embodiments, spatial analysis is performed using light-directed barcoding and overlapping diffusion clouds. In some embodiments, spatial analysis is performed using one or more types of fractional barcoding and distinct diffusion clouds. In some embodiments, spatial analysis is performed using one or more types of fractional barcoding and overlapping diffusion clouds. In some embodiments, spatial analysis is performed using any combination of light-directed barcoding, one or more types of fractional barcoding, distinct diffusion clouds, and overlapping diffusion clouds.

Screening

Further provided herein are methods of screening regions of interest impacted by an intervention compared to regions of interest not impacted. In some embodiments, methods comprise screening one or more regions of interest within a sample. In some embodiments, methods comprise screening one or more regions of interest across one or more samples. In some embodiments, one or more regions of interest are impacted with an intervention prior to screening, after screening, or between multiple screens. In some embodiments, the impacting comprises application of a small molecule, a peptide, an antibody, cells, a protein, an energy, or any combination thereof. In some embodiments, the energy comprises thermal energy, radiant energy, chemical energy, nuclear energy, electrical energy, motion energy, sound energy, or any combination thereof.

Nucleic Acid-Based Information Storage

Provided herein are compositions, methods, and systems utilizing the above innovations in the context of writing and reading DNA for storage of digital information. Briefly, the utilization of DNA "writing" technologies described herein, optionally, combined with "reading" by methods such as fluorescence microscopy or next generation sequencing allows for efficient and scaled data storage. In some embodiments, digital information is converted to nucleic acid information. In some embodiments, the nucleic acid information comprises nucleic acid sequences. In some embodiments, an item of digital information is converted to a sequence of nucleic acids. In some embodiments, an item of information is converted to a nucleic acid sequence of one or more nucleic acids. In some embodiments, an item of information is converted to a sequence of about 2, about 5, about 10, about 20, about 30, about 40, about 50, about 100, about 200, about 300, about 400, about 500, about 600, about 700, about 800, about 900, or about 1000 nucleic acids. In some embodiments, barcodes, as described herein, each comprise an item of information.

polymer from each pixel, showing covalently linked DNA strands. These strands are generated using light-directed assembly as described herein, utilizing ultrafast scanners or digital micromirror devices.

In some embodiments, the barcoded information is deposited on a surface a node locations. In some embodiments, multiple copies of the barcoded information is provided and diffuses out from the node location. In some embodiments, copies of the barcoded information are generated and diffuse out from the node location. Concatenation of barcodes from node locations are assembled and translated according to methods described herein.

Figure 36A:
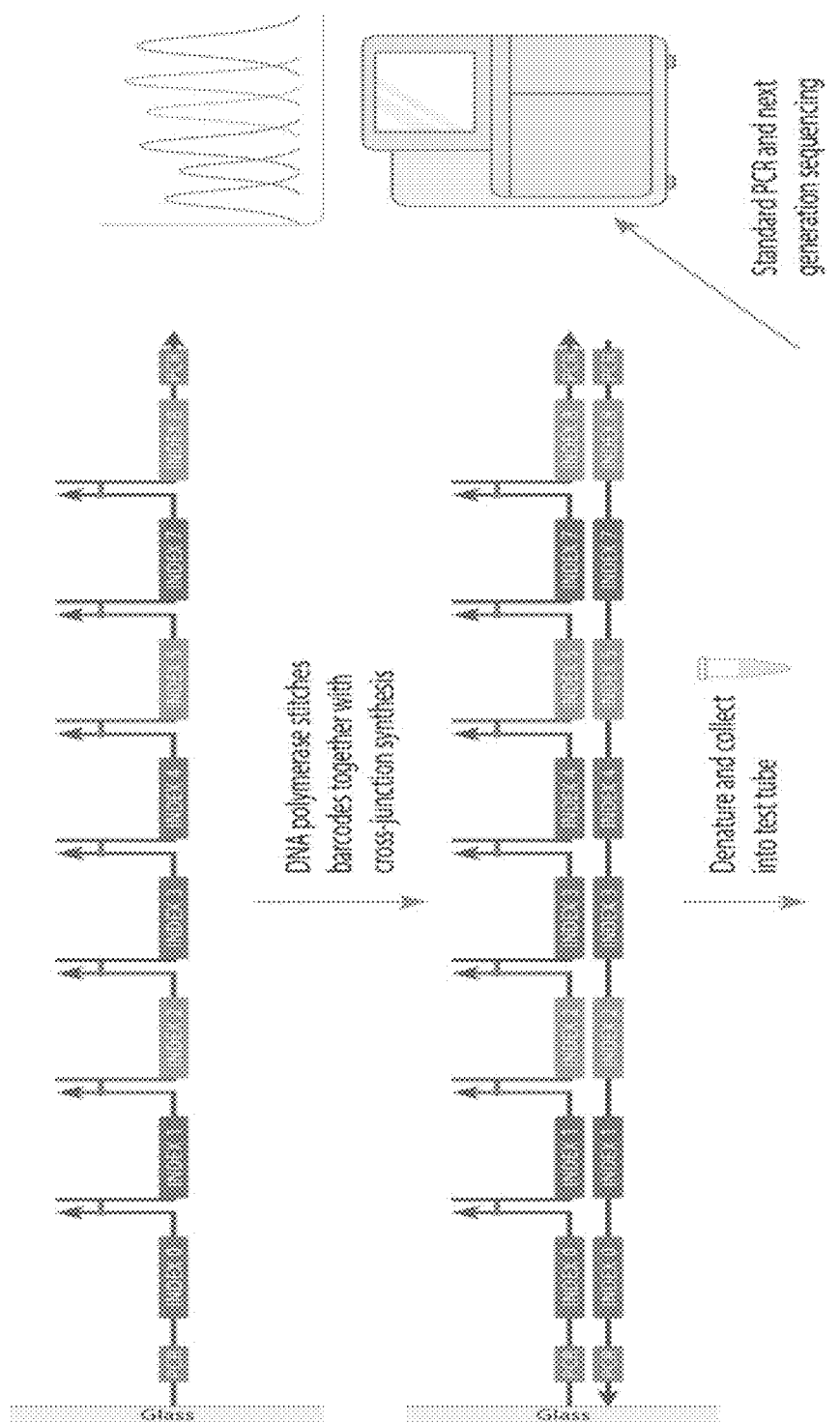
FIG. 36A illustrates a readout workflow using the cross-junction stitching reaction, copies of the encoded concatemers can be made using a DNA polymerase, and then sent for sequencing.
Figure 36B:
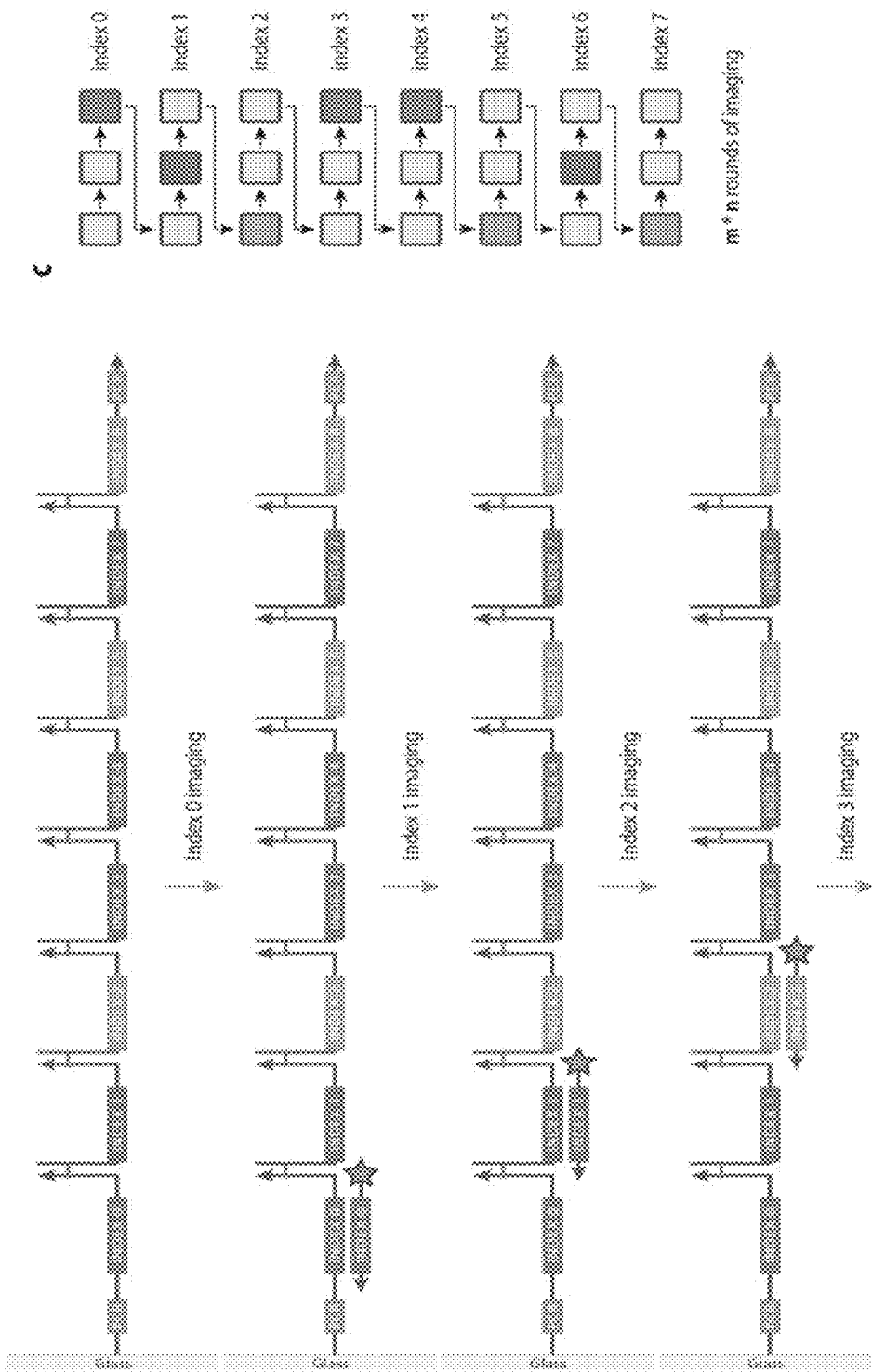
FIG. 36B illustrates a readout workflow using concatemers can be directly imaged on using complementary fluorophore-labeled strands.

Extraction of stored information to digital information is possible by different methods. In some embodiments, sequencing methods are applied to access nucleic acid information for conversion to digital information. In some embodiments, fluorescent tagging methods are applied to a sample to translate the stored information. Two exemplary strategies for extraction of molecularly encoded information are depicted as follows. In one embodiment, as shown in FIG. 36A, a one-pot cross-junction synthesis stitching reaction is used to copy the information into continuous strands that can be amplified with PCR and sequenced using next generation sequencing. In a second embodiment, as shown in FIG. 36B, molecular identities are read out through fluorescence, such as by the same ultrafast scanning device that was used to write the information.

Table 1 lists example writing and reading strategies.

TABLE 1

| | Blu-ray | "DNA-ray" (imaging readout) | "DNA-ray" (sequencing readout) |
|---|---|---|---|
| Writing strategy | Photo-lithography with 405 nm laser | m * n rounds of DNA photo-lithography with 365 nm-405 nm laser | Several rounds of DNA photo-lithography with 365 nm-405 nm laser |
| Reading strategy | Imaging 405 nm laser | Imaging in any channel, including 405 nm | Stitching of sequences with DNA polymerase, then standard sequencing |
| Additional material for reading | None | DNA | DNA + DNA polymerase + PCR + sequencing |

Figure 33:
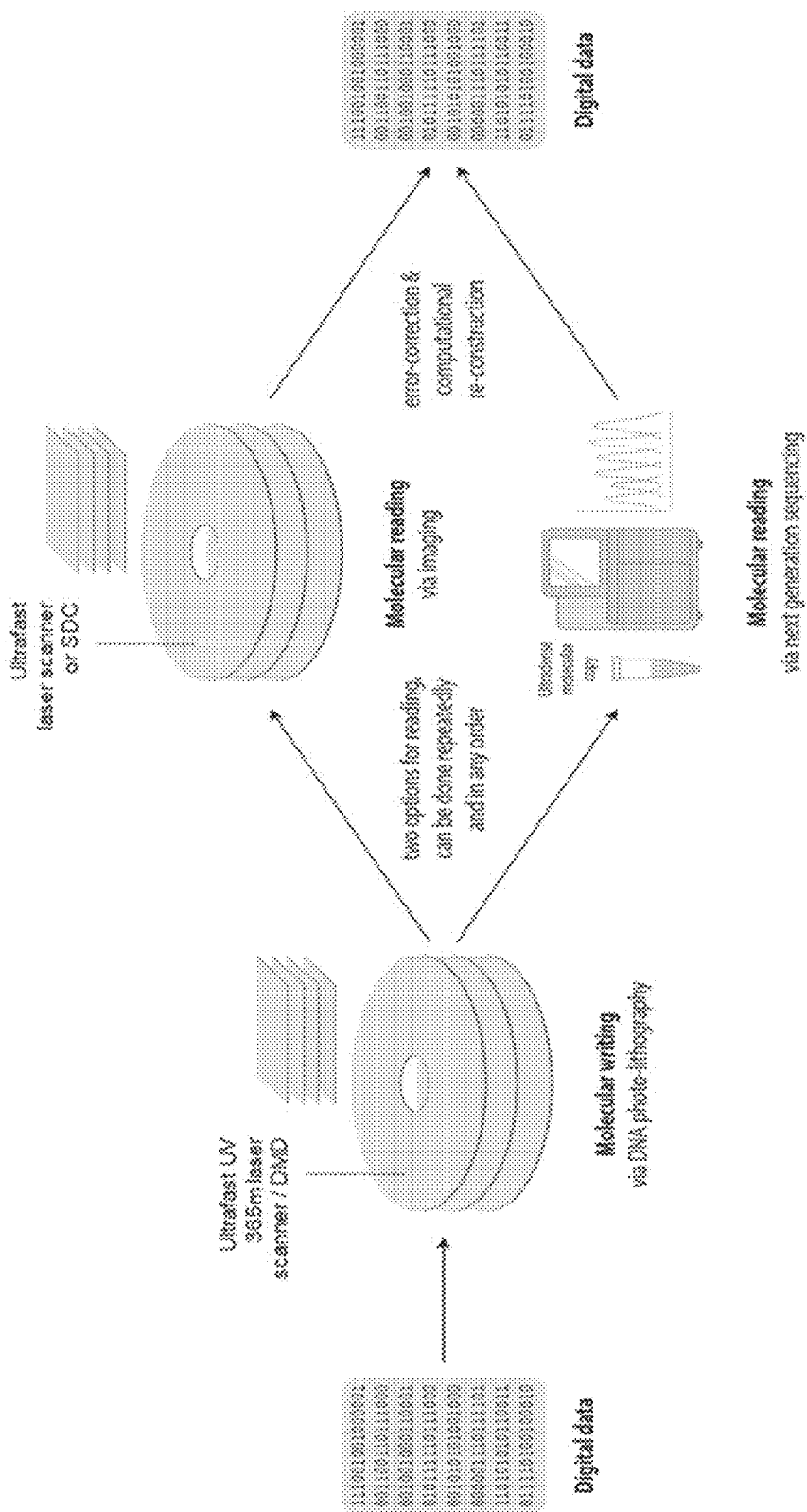
FIG. 33 illustrates a process workflow for a DNA array-based tech stack. Digital data is converted to nucleic acids, then subjected to molecular writing via DNA photo-lithography. Subsequently, options for reading include molecular reading via imaging or molecular reading via next generation sequencing. Following error correction, the information generated is converted back to digital data.
Figure 34:
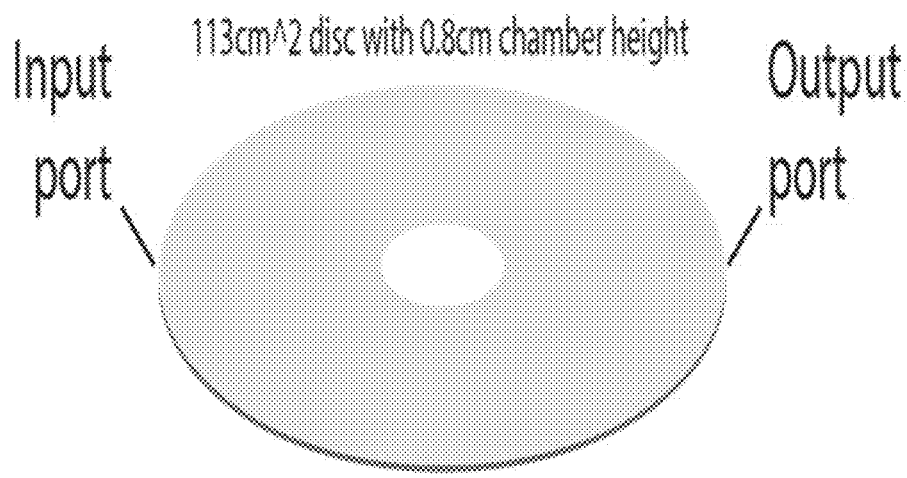
FIG. 34 illustrates a sample disc design, having an input port and an output port.

An exemplary depiction of data writing to DNA and subsequent reading is depicted in FIG. 33. Digital information is converted to nucleic acid information. Nucleic acid information is partitioned into barcodes. Barcodes comprising the partitioned information are assembled into nucleic acid strands on a glass disc, similar to a Blu-ray disc, according to the generated information, using light-directed barcoding methods described herein. A representative disc for sequence assembly is shown in FIG. 34. The disc comprises input and output ports, having about 113 cm² surface area. Reading the generated bar code strands can be performed using imaging or next generation sequencing techniques. Information from the molecular reading step can then be used to reconstruct the digital data.

Figure 35:
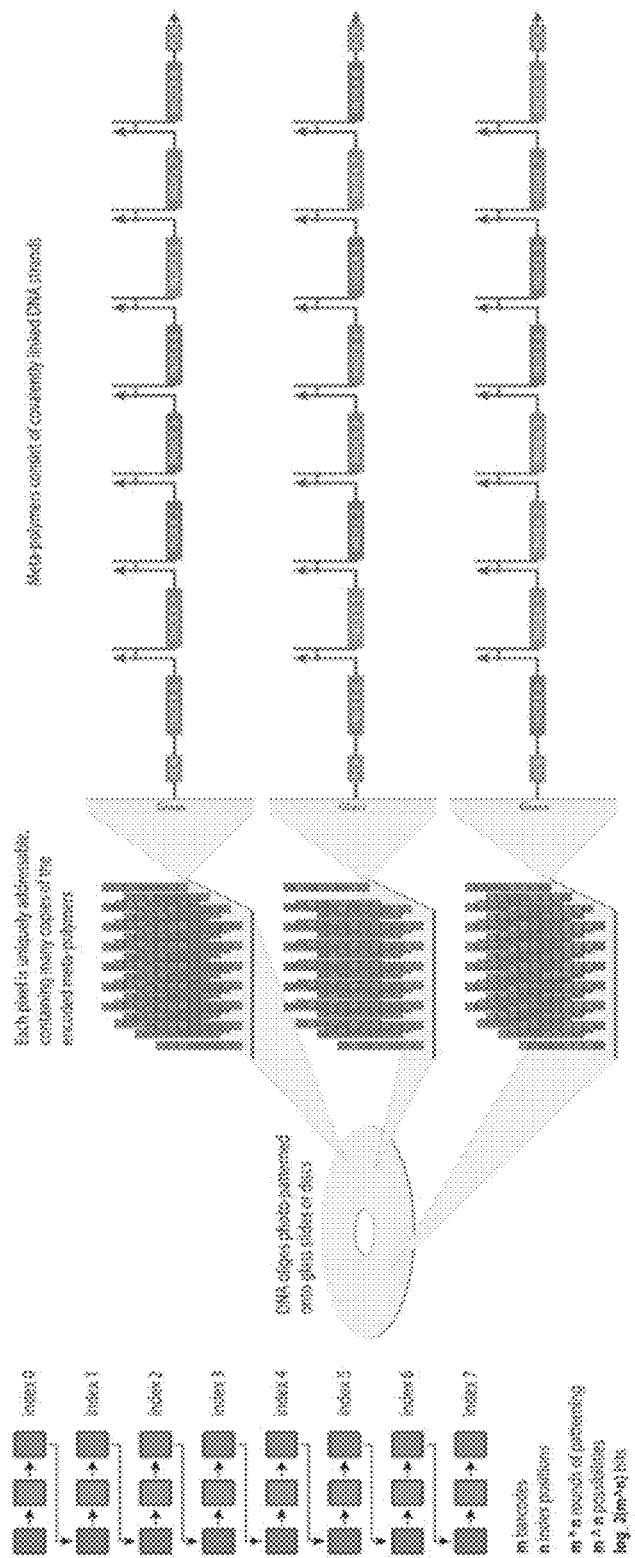
FIG. 35 illustrates a workflow for light-directed oligo-by-oligo synthesis for data encoding with m distinct barcode sequences per n rounds, log_2(m^n) bits of information can be encoded with just m*n rounds of photo-patterning (left section of image). Within each spatially programmable pixel, many copies of the same 'meta-polymer' sequence are assembled (right section of image).

Combinatorial libraries of sequences are assembled using light-directed oligo-by-oligo synthesis. An exemplary depiction for the magnitude of information that can be stored using this method is shown in FIG. 35. Providing m barcodes at n index positions provides for m*n rounds of patterning. This results in m^n possible combinations, or log_2(m^n) bits of information possible. As shown in the center of FIG. 35, each pixel on the substrate contains many copies of the same "meta-polymer" sequence. Proceeding to the right side of the figure, showing a representative meta- Estimates of Capacity, Cost, and Time General estimates include storage capacity, reading time, and approximate cost. With a 2 μm×2 μm pixel size, it is estimated that 10^6 sequences could be assembled per field of view (FOV) and up to ~3 billion sequences could be assembled on a glass substrate approximately the size of a Blu-ray disc.

If m=8 barcodes and n=8 index positions are used per pixel for data encoding, then this would correspond to 24 bits of information per pixel, or 8.5 GB per glass disc. Sequence length is flexible depending on the design of the library. With about 20 nucleotide barcode sequences to accommodate error correction+imaging, it is estimated that assembled sequences of about 300 nucleotides in length, or up to twice that depending on the indexing strategy used.

Early studies demonstrated that exposure times of as little as 100 microseconds resulted in barcoding, and it is expected that using a powerful laser can lower this time substantially, such that an ultrafast scanner can be developed that minimizes movement times to reach the speed of a 16× Blu-ray drive (such as by employing either a spinning disc format), and hybridization and wash steps of approximately 2 minutes each per round. It is suspected that the time for writing each 8.5 GB disc could be as low as 10 minutes per round or 10.7 hours per disc. For imaging-based readout, the same scanning system could be used to read out fluorescence signals. With such a scanner, it is expected the time for reading each 8.5 GB disc through imaging could be comparable (10.7 hours per disc).

The cost and time for sequencing-based reading of the stored data is expected to approach similar levels as that for writing. Additionally, sequencing-based reading allows for molecular copies to be detached from the substrate and stored in a super dense format.

If sequencing-based readouts will not be used, then single bit writing and imaging-based reading could employ a spatial encoding strategy even more similar to Blu-ray, with an expected resolution, reading, and writing time comparable to Blu-ray for around 100 times less total in cost for writing and reading costs. The single bit strategy is also compatible with more sophisticated molecular encryption chemistry that would data security.

Oligonucleotide Library Generation

In some embodiments, light-based concatemerization methods described herein are used to generate libraries of oligonucleotides. In some embodiments, sequences of oligonucleotides are generated using computational generation methods. In further embodiments, oligonucleotide sequences are synthesized on a surface according to methods described herein. Synthesized oligonucleotides are cleaved from the support. Further steps, comprising removal of protecting groups, purification, or isolation, are optionally performed.

Surface Materials

In some embodiments, surfaces of nucleic acid storage provided herein surface comprise a flexible or a rigid material. Exemplary rigids materials include, without limitation: glass; fused silica; silicon such as silicon dioxide or silicon nitride; metals such as gold or platinum; plastics such as polytetrafluoroethylene, polypropylene, polystyrene, polycarbonate, and a combination thereof. A rigid surface can be fabricated from a material selected from the group consisting of silicon, polystyrene, agarose, dextran, cellulosic polymers, polyacrylamides, polydimethylsiloxane (PDMS), and glass, or a combination thereof. Flexible materials are those capable of being bent, folded or similarly manipulated without breakage. In some cases, a flexible material is bent at least 30 degrees around a roller. In some cases, a flexible material is bent at least 180 degrees around a roller. In some cases, a flexible surface is bent at least 270 degrees around a roller. In some instances, a flexible material is bent about 360 degrees around a roller. In some cases, the roller is less than about 10 cm, 5 cm, 3 cm, 2 cm or 1 cm in radius. Exemplary flexible materials include, without limitation: nylon (unmodified nylon, modified nylon, clear nylon), nitrocellulose, polypropylene, polycarbonate, polyethylene, polyurethane, polystyrene, acetal, acrylic, acrylonitrile, butadiene styrene (ABS), polyester films such as polyethylene terephthalate, polymethyl methacrylate or other acrylics, polyvinyl chloride or other vinyl resin, transparent PVC foil, transparent foil for printers, Poly(methyl methacrylate) (PMMA), methacrylate copolymers, styrenic polymers, high refractive index polymers, fluorine-containing polymers, polyethersulfone, polyimides containing an alicyclic structure, rubber, fabric, metal foils, and any combination thereof. Nylon and PMAA surfaces herein, in some instances, are provided as a sheet or alternatively provided as a layer that is coated over another material, such as silicon. Various plasticizers and modifiers may be used with polymeric substrate materials to achieve selected flexibility characteristics. In some instances, the flexible material is a hydrogel such as agarose or polyacrylamide.

In some embodiments, nucleic acid strands are covalently or non-covalently attached to the surface. In some embodiments, a surface is first coated with biotin, then streptavidin. In further embodiments, biotinylated nucleic acids are attached to the coated surface. In some embodiments, a surface is coated with copolymers of N, N-dimethylacrylamide. In some embodiments, nucleic acid are baked onto a glass surface using desiccation and UV light. In some embodiments, nucleic acid strands contain an acrydite modification and are covalently linked to a hydrogel. In some embodiments, nucleic acid strands are attached to beads that are immobilized on the surface. In further embodiments immobilized strands are UV-cleavable from the beads. In some embodiments, beads are hydrogel beads, metallic beads, streptavidin beads, magnetic beads, magnetic streptavidin beads, gold nanoparticles, metallic nanoparticles, or any combination thereof. In some embodiments, nucleic acid strands are encapsulated by a bead, LNP, AAV, virus, exosome in the biological sample. In some embodiments, the biological sample is a fixed tissue or cells. In some embodiments, the biological sample is live cells.

In some embodiments, the surface is silanized. In further embodiments nucleic acid strands comprise bases modified by amination, or other reactive groups, and are covalently bound to the silanized surface. In some embodiments, attachment to the silanized surface is direct by reaction with an epoxy group. In some embodiments, attachment to the silanized surface is indirect, using crosslinkers such as 1,4-phenylenedisiothiocyanate (PDC). In some embodiments, nucleic acid strands are covalently bound to the surface using click chemistry, wherein strands are modified with either azide or alkyne reactive groups, that react with alkyne or azide groups, respectively, on the surface, for example in the presence of copper.

Exemplary Embodiments

Provided herein are methods biological information generation, the methods comprising: providing node factories on a biological sample at node locations, wherein the node factories comprise one or more node nucleic acids, and wherein each node nucleic acid comprises: a node barcode region; one or more flanking node barcode hybridization regions; and optionally, a node primer region; amplifying the one or more node nucleic acids to generate concatemers of node nucleic acids, wherein the concatemers diffuse away from the node locations over time; cleaving the concatemers into a plurality of node nucleic acids; attaching two or more node nucleic acids generated by the node factories to generate multinode nucleic acids; and analyzing for a frequency of association of the two or more node nucleic acids, wherein the frequency of association provides information for spatial mapping of the biological sample. Further provided herein are methods, wherein the node factories further comprise one or more factory target nucleic acids, wherein each factory target nucleic acid comprises: a target binding region; a target barcode region; one or more flanking target binding hybridization regions; and optionally, a target primer region; wherein each factory target nucleic acid is contiguous to a node nucleic acid, and wherein the amplifying generates concatemers comprising repeats of node nucleic acids and factory target nucleic acids and the cleaving generates a plurality of node nucleic acids and factory target nucleic acids; and wherein the method further comprises: attaching the factory target nucleic acid to a target sequence; and measuring a frequency of association of the factory target nucleic acid and the target sequence, wherein the frequency of association provides information for spatial mapping of the biological sample. Further provided herein are methods, wherein the amplifying comprises rolling circle amplification (RCA), strand-displacement amplification (SDA), Nicking Enzyme Amplification Reaction (NEAR), nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER). Further provided herein are methods, wherein each node factory comprises a padlock probe comprising the node nucleic acid and a node nucleic acid restriction site, the method further comprising: hybridizing the padlock probe to a nucleic acid splint, wherein the nucleic acid splint comprises regions complementary to regions at 3' and 5' ends of the padlock probe; applying a ligase to the sample, wherein the ligase joins the 3' and 5' ends of the padlock probe; applying a rolling circle polymerase to the ligated padlock probe; and generating a concatemer comprising node nucleic acids and node nucleic acid restriction sites by RCA. Further provided herein are methods, wherein the nucleic acid splint comprises at least part of an mRNA sequence in the biological sample. Further provided herein are methods, wherein the nucleic acid splint is conjugated to a surface, a protein, a small molecule, a nucleic acid, a lipid or any combination thereof. Further provided herein are methods, wherein the protein comprises a receptor, a ligand, an antibody, or any functional fragment thereof. Further provided herein are methods, wherein the biological sample further comprises a feature, wherein the feature in the biological sample comprises a cell structure, a receptor, a scaffold, a matrix, a nucleic acid, a tissue, or an organelle. Further provided herein are methods, further comprising depositing a restriction enzyme or nickase on the sample, wherein the restriction enzyme or nickase recognizes the node nucleic acid restriction site, thereby cleaving the concatemer to provide a plurality of node nucleic acids. Further provided herein are methods, further comprising depositing a restriction enzyme or nickase on the sample, wherein the concatemer forms a hairpin comprising the node nucleic acid restriction site. Further provided herein are methods, wherein the restriction enzyme makes a double-stranded cut at the node nucleic acid restriction site. Further provided herein are methods, wherein the nickase makes a single stranded cut at the node nucleic acid restriction site. Further provided herein are methods, further comprising: depositing an oligonucleotide on the sample, wherein the oligonucleotide hybridizes with a region comprising the node nucleic acid restriction site, forming a double-stranded restriction region, depositing a double-strand-specific restriction enzyme on the sample, wherein the restriction enzyme recognizes the node nucleic acid restriction site, thereby cleaving the concatemer to provide a plurality of node nucleic acids. Further provided herein are methods, wherein the plurality of node nucleic acids are generated individually. Further provided herein are methods, wherein the node factories further comprise one or more factory target nucleic acids, wherein each factory target nucleic acid comprises: a target binding region; a target barcode region; one or more flanking target binding hybridization regions; and optionally, a target primer region; wherein each factory target nucleic acid is contiguous to a node nucleic acid, and wherein the amplifying generates concatemers comprising repeats of node nucleic acids and factory target nucleic acids and the cleaving generates a plurality of node nucleic acids and factory target nucleic acids; and wherein the method further comprises: attaching the factory target nucleic acid to a target sequence; and measuring a frequency of association of the factory target nucleic acid and the target sequence, wherein the frequency of association provides information for spatial mapping of the biological sample. Further provided herein are methods, wherein the generated concatemer comprises alternating node nucleic acids, node nucleic acid restriction sites, factory target nucleic acids, and factory target nucleic acid restriction sites. Further provided herein are methods, further comprising depositing a restriction enzyme or nickase on the sample, wherein the restriction enzyme or nickase recognizes the node nucleic acid restriction site and the factory target nucleic acid restriction site. Further provided herein are methods, further comprising depositing a first restriction enzyme on the sample, wherein the first restriction enzyme recognizes the factory target nucleic acid restriction site and does not recognize the node nucleic acid restriction site, thereby generating a plurality nucleic acids comprising the node nucleic acid and the factory target nucleic acid. Further provided herein are methods, further comprising depositing a second restriction enzyme on the sample after the depositing the first restriction enzyme, wherein the second restriction enzyme recognizes the node nucleic acid restriction site, thereby generating a plurality of node nucleic acids and factory target nucleic acids. Further provided herein are methods, wherein the one or more flanking node barcode hybridization regions or the one or more flanking target binding hybridization regions flank the node barcode region or the target binding region. Further provided herein are methods, wherein the providing comprises an affinity reaction, conjugation, incorporation into a hydrogel, crosslinking, or photo-crosslinking. Further provided herein are methods, wherein the template node nucleic acids are conjugated to an antibody, antibody fragment, protein, nanobody, small molecule, nucleic acid therapeutic, lipid, nanoparticle, lipid nanoparticle or other affinity reagent. Further provided herein are methods, wherein the attaching comprises hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, wherein the spatial mapping comprises sequencing the concatemer. Further provided herein are methods, wherein the sequencing comprises chain termination sequencing, nanopore sequencing, sequencing by ligation, combinatorial probe anchor synthesis, sequencing by synthesis, pyrosequencing, ion semiconductor, or single-molecule real-time sequencing. Further provided herein are methods, wherein the node barcodes comprise one or more fluorophore labels. Further provided herein are methods, wherein the spatial mapping comprises imaging the concatemer. Further provided herein are methods, wherein the one or more fluorophore labels are attached to the node barcodes by synthesis or hybridization. Further provided herein are methods, wherein the node locations comprise a pattern. Further provided herein are methods, wherein the node locations are preselected. Further provided herein are methods, wherein the biological sample comprises cells in a synthetic matrix. Further provided herein are methods, further comprising imaging the biological sample. Further provided herein are methods, wherein the biological sample comprises a population of cells, a tissue sample, or a protein. Further provided herein are methods, wherein the node barcode region is from about 3 to about 30 nucleotides. Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, wherein the biological sample is placed on a microscope slide or coverslip. Further provided herein are methods, wherein the diffused node nucleic acids comprise a gradient of decreasing concentration with increased distance from the node location. Further provided herein are methods, wherein the diffused node nucleic acids from different node locations do not overlap. Further provided herein are methods, wherein the node nucleic acids from different node locations overlap. Further provided herein are methods, wherein the node nucleic acids from two or more node locations combine by hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acids further comprise a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the DNA polymerase comprises Phi29, Pol I, Pol II, Pol III, Pol IV, Pol V, T4, Bsm, Bst, Reverse Transcriptase or any combination thereof. Further provided herein are methods, wherein the RNA polymerase comprises T7, T3, or SP6. Further provided herein are methods, further comprising depositing a nickase, wherein the node nucleic acids comprise a nicking site targetable by the nickase. Further provided herein are methods, wherein the node nucleic acids further comprise a unique identification sequence, comprising one or more noncanonical bases, universal bases, other bases which a polymerase will pair randomly or incorrectly, or any combination thereof. Further provided herein are methods, wherein the node nucleic acids are double-stranded, single-stranded, comprises a hairpin structure, or any combination thereof. Further provided herein are methods, further comprising controlling a diffusion factor, wherein a diffusion factor comprises a viscosity, a time, a temperature, a presence of crowding agents, a pH, an electric field, physical features, or any combination thereof. Further provided herein are methods, wherein the viscosity is greater than 1 cP. Further provided herein are methods, wherein the biological sample medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP. Further provided herein are methods, wherein the depositing is at random locations throughout the biological sample. Further provided herein are methods, wherein the depositing is at specific targets in the biological sample. Further provided herein are methods, further comprising generating a second plurality of node nucleic acids from the node nucleic acids.

Provided herein are methods of biological information generation, the method comprising:
depositing template nucleic acids on a biological sample at node locations, wherein the template nucleic acids comprise: a node barcode region; and one or more flanking node barcode hybridization regions; amplifying the template nucleic acids to generate node nucleic acids, wherein the node nucleic acids diffuse away from the node locations over time; depositing factory target nucleic acids onto the biological sample, wherein the factory target nucleic acid comprises: a target binding region; and one or more flanking target binding hybridization regions; and attaching at least one of the node nucleic acids to at least one of the factory target nucleic acids to form a concatemer, wherein a combination of the node nucleic acids and the factory target nucleic acids provides biological information for spatial mapping of the biological sample. Further provided herein are methods, wherein the factory target nucleic acid further comprises a target identification region. Further provided herein are methods, wherein the one or more flanking node barcode hybridization regions or one or more flanking target binding hybridization regions flank the node barcode region or the target binding region. Further provided herein are methods, wherein the providing comprises an affinity reaction, conjugation, incorporation into a hydrogel, crosslinking, or photo-crosslinking. Further provided herein are methods, wherein the template node nucleic acids are conjugated to an antibody, antibody fragment, protein, nanobody, small molecule, nucleic acid therapeutic, lipid, nanoparticle, lipid nanoparticle or other affinity reagent.

Further provided herein are methods, wherein the amplifying comprises rolling circle amplification (RCA), strand-displacement amplification (SDA), Nicking Enzyme Amplification Reaction (NEAR), nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER). Further provided herein are methods, wherein the attaching comprises hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, wherein the spatial mapping comprises sequencing the concatemer. Further provided herein are methods, wherein the sequencing comprises chain termination sequencing, nanopore sequencing, sequencing by ligation, combinatorial probe anchor synthesis, sequencing by synthesis, pyrosequencing, ion semiconductor, or single-molecule real-time sequencing. Further provided herein are methods, wherein the node barcodes comprise one or more fluorophore labels. Further provided herein are methods, wherein the spatial mapping comprises imaging the concatemer. Further provided herein are methods, wherein the one or more fluorophore labels are attached to the node barcodes by synthesis or hybridization. Further provided herein are methods, wherein the node locations comprise a pattern. Further provided herein are methods, wherein the node locations are preselected. Further provided herein are methods, wherein the biological sample comprises cells in a synthetic matrix. Further provided herein are methods, further comprising imaging the biological sample. Further provided herein are methods, wherein the biological sample comprises a population of cells, a tissue sample, or a protein. Further provided herein are methods, wherein the node barcode region is from about 3 to about 30 nucleotides. Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, wherein the biological sample is placed on a microscope slide or coverslip. Further provided herein are methods, wherein the diffused node nucleic acids comprise a gradient of decreasing concentration with increased distance from the node location. Further provided herein are methods, wherein the diffused node nucleic acids from different node locations do not overlap. Further provided herein are methods, wherein the node nucleic acids from different node locations overlap. Further provided herein are methods, wherein the node nucleic acids from two or more node locations combine by hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acids further comprise a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the DNA polymerase comprises Phi29, Pol I, Pol II, Pol III, Pol IV, Pol V, T4, Bsm, Bst, Reverse Transcriptase or any combination thereof. Further provided herein are methods, wherein the RNA polymerase comprises T7, T3, or SP6. Further provided herein are methods, further comprising depositing a nickase, wherein the node nucleic acids comprise a nicking site targetable by the nickase. Further provided herein are methods, wherein the node nucleic acids further comprise a unique identification sequence, comprising one or more noncanonical bases, universal bases, other bases which a polymerase will pair randomly or incorrectly, or any combination thereof. Further provided herein are methods, wherein the node nucleic acids are double-stranded, single-stranded, comprises a hairpin structure, or any combination thereof. Further provided herein are methods, wherein the diffusion factor comprises a viscosity, a time, a temperature, a presence of crowding agents, a pH, an electric field, physical features, or any combination thereof. Further provided herein are methods, wherein the viscosity is greater than 1 cP. Further provided herein are methods, wherein the biological sample medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP. Further provided herein are methods, wherein the depositing is at random locations throughout the biological sample. Further provided herein are methods, wherein the depositing is at specific targets in the biological sample. Further provided herein are methods, further comprising generating a second plurality of node nucleic acid from the node nucleic acids.

Provided herein are methods of biological information generation, the methods comprising: depositing node nucleic acids on a biological sample at node locations, wherein the node nucleic acids comprise: a node barcode region; and one or more flanking node barcode hybridization regions; amplifying the node nucleic acids to generate node amplification products, wherein the node amplification products diffuse away from the node locations; depositing factory target nucleic acids onto the biological sample, wherein the factory target nucleic acids comprise: a target binding region; and one or more flanking target binding hybridization regions; and attaching at least one of the node amplification products to at least one of the factory target nucleic acids to form a concatemer, wherein a combination of the node amplification products and the factory target nucleic acids provides biological information for spatial mapping of the biological sample. Further provided herein are methods, wherein the factory target nucleic acid further comprises a target identification region. Further provided herein are methods, wherein the one or more flanking node barcode hybridization regions or one or more flanking target binding hybridization regions flank the node barcode region or the target binding region. Further provided herein are methods, wherein the depositing comprises an affinity reaction, conjugation, incorporation into a hydrogel, crosslinking, or photo-crosslinking. Further provided herein are methods, wherein the node nucleic acids are attached to another molecule. Further provided herein are methods, wherein the another molecule comprises an antibody, antibody fragment, protein, nanobody, small molecule, nucleic acid therapeutic, lipid, nanoparticle, lipid nanoparticle or other affinity reagent. Further provided herein are methods, wherein the amplifying comprises rolling circle amplification (RCA), strand-displacement amplification (SDA), Nicking Enzyme Amplification Reaction (NEAR), nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER). Further provided herein are methods, wherein the attaching comprises by hybridization, ligation, splinted ligation, cross-junction synthesis, ligation and cross-interstrand crosslink (ICL) synthesis, cross ICL and nick synthesis, pairwise copying, or any combination thereof. Further provided herein are methods, wherein the spatial mapping comprises sequencing the concatemer. Further provided herein are methods, wherein the sequencing is chain termination sequencing, nanopore sequencing, sequencing by ligation, combinatorial probe anchor synthesis, sequencing by synthesis, pyrosequencing, ion semiconductor, or single-molecule real-time sequencing. Further provided herein are methods, wherein the node barcodes comprise one or more fluorophore labels. Further provided herein are methods, wherein the spatial mapping comprises imaging the concatemer. Further provided herein are methods, wherein the one or more fluorophore labels are attached to the node barcodes by synthesis or hybridization. Further provided herein are methods, wherein the node locations comprise a pattern. Further provided herein are methods, wherein the node locations are preselected. Further provided herein are methods, wherein the biological sample comprises cells in a synthetic matrix. Further provided herein are methods, further comprising imaging the biological sample. Further provided herein are methods, wherein the biological sample comprises a population of cells, a tissue sample, or a protein. Further provided herein are methods, wherein the node barcode region is from about 3 to about 30 nucleotides.

Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, wherein the biological sample is placed on a microscope slide or coverslip. Further provided herein are methods, wherein the diffused node amplification products are in a gradient of decreasing concentration with increased distance from the node. Further provided herein are methods, wherein the node amplification products from different node locations do not overlap. Further provided herein are methods, wherein the node amplification products from different node locations overlap. Further provided herein are methods, wherein the node amplification products from two or more node locations combine by hybridization, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acids further comprise a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the DNA polymerase is Pol I, Pol II, Pol III, Pol IV, Pol V, or any combination thereof. Further provided herein are methods, wherein the RNA polymerase is T7, T3, or Reverse Transcriptase. Further provided herein are methods, further comprising a nickase, wherein the node nucleic acids comprise a nicking site targetable by the nickase. Further provided herein are methods, wherein the node nucleic acids further comprise a unique identification sequence, comprising one or more noncanonical bases, universal bases, other bases which a polymerase will pair randomly or incorrectly, or any combination thereof. Further provided herein are methods, wherein the node nucleic acids are double-stranded, single-stranded, comprises a hairpin structure, or any combination thereof. Further provided herein are methods, wherein the biological sample further comprises a biological sample medium, and wherein the biological sample medium comprises a viscosity greater than 1 cP. Further provided herein are methods, wherein the biological sample medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP. Further provided herein are methods, wherein the depositing is at random locations throughout the biological sample. Further provided herein are methods, wherein the depositing is at specific targets in the biological sample. Further provided herein are methods, further comprising: depositing DNA barcodes onto the biological sample, wherein the DNA barcodes comprise a region complementary to a region of the concatemer, and wherein the DNA barcodes comprise a photo-reactive nucleobase capable of crosslinking to another nucleobase; selectively radiating the biological sample to form covalently linked DNA barcode-concatemer complexes; washing the biological sample to remove the DNA barcodes that are not complexed to concatemers; and repeating the depositing, selectively radiating, and washing steps, wherein: the DNA barcodes in a first of the depositing steps comprise a different sequence than the DNA barcodes in a second of the depositing steps, and the selectively radiating occurs at different locations for a first selectively radiating step and a second selectively radiating step. Further provided herein are methods, further comprising synthesizing a continuous DNA strand, wherein the synthesizing comprises contacting the DNA barcode-concatemer complexes with a polymerase. Further provided herein are methods, wherein the synthesizing comprises cross-junction synthesis. Further provided herein are methods, further comprising displacing the continuous DNA strand from the biological sample. Further provided herein are methods, wherein the synthesizing and displacing occur simultaneously. Further provided herein are methods, wherein the displaced continuous DNA strands are pooled. Further provided herein are methods, wherein the pooled continuous DNA strands are amplified. Further provided herein are methods, wherein the pooled continuous DNA strands are sequenced. Further provided herein are methods, wherein the DNA barcodes further comprise a promoter region, a primer region, or any combination thereof. Further provided herein are methods, wherein the primer is one or more random primers or wherein the primer is a non-random primer. Further provided herein are methods, wherein the photo-reactive nucleobase is 3-cyanovinylcarbazole phosphoramidite (CNVK). Further provided herein are methods, wherein the selectively radiating is performed using a photomask. Further provided herein are methods, wherein the photomask is varied in the different selectively radiating steps. Further provided herein are methods, wherein the photomask is generated manually. Further provided herein are methods, wherein the photomask is generated by machine. Further provided herein are methods, wherein the selectively radiating step comprises administering radiation at a wavelength of about 300 nm up to 450 nm. Further provided herein are methods, wherein the selectively radiating step comprises administering radiation at a wavelength of about 350 nm up to 420 nm. Further provided herein are methods, wherein the selectively radiating step comprises administering radiation at a wavelength of about 365 nm up to 405 nm. Further provided herein are methods, wherein the selectively radiating step comprises applying radiation to a preselected region of interest (ROI). Further provided herein are methods, wherein the ROI is cell-specific or sub-cellular specific. Further provided herein are methods, wherein the ROI is based on morphology. Further provided herein are methods, wherein the depositing is performed manually, automatically, robotically, or any combination thereof. Further provided herein are methods, wherein the depositing is performed with a modified inkjet printer. Further provided herein are methods, wherein the depositing or washing is performed using microfluidics, passive diffusion, electrophoresis, digital microfluidics, an acoustic liquid handler, an inkjet printer, an automatic liquid handler, or any combination thereof. Further provided herein are methods, wherein one or more DNA barcodes combine with one or more node barcode strands, wherein the combining is with by hybridization, extension, ligation, splinted ligation, cross-junction synthesis, ligation and cross-interstrand crosslink (ICL) synthesis, cross ICL and nick synthesis, pairwise copying, or any combination thereof.

Provided herein are methods of information storage, the methods comprising: receiving digital information; converting the digital information to nucleic acid information in the form of a plurality of nucleic acid barcodes; depositing template nucleic acids on a surface at node locations, wherein the template nucleic acids comprise: a node barcode region, each corresponding to one of the plurality of barcodes; and one or more flanking node barcode hybridization regions; amplifying the template nucleic acids to generate node nucleic acids; depositing factory target nucleic acids onto the surface, wherein the factory target nucleic acid comprises: a target binding region; one or more flanking target binding hybridization regions; optionally, a target primer region; and attaching at least one of the node nucleic acids to at least one of the factory target nucleic acids to form a concatemer, wherein the combination of node nucleic acids and factory target nucleic acids provides storage information. Further provided herein are methods, wherein the amplifying comprises rolling circle amplification (RCA), strand-displacement amplification (SDA), Nicking Enzyme Amplification Reaction (NEAR), nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER). Further provided herein are methods, wherein the attaching comprises by hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, further comprising converting the nucleic acid information to digital information, wherein the converting comprises sequencing the concatemer. Further provided herein are methods, wherein the sequencing is chain termination sequencing, nanopore sequencing, sequencing by ligation, combinatorial probe anchor synthesis, sequencing by synthesis, pyrosequencing, ion semiconductor, or single-molecule real-time sequencing. Further provided herein are methods, wherein the concatemers comprise one or more fluorophore labels. Further provided herein are methods, wherein the spatial mapping comprises imaging the concatemer. Further provided herein are methods, wherein the one or more fluorophore labels are attached to the concatemers by synthesis or hybridization. Further provided herein are methods, wherein the node locations comprise a pattern. Further provided herein are methods, wherein the node locations are preselected. Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, wherein the diffused node nucleic acids comprise a gradient of decreasing concentration with increased distance from the node location Further provided herein are methods, wherein the node nucleic acids from different node locations do not overlap. Further provided herein are methods, wherein the node nucleic acids from different node locations overlap. Further provided herein are methods, wherein the node nucleic acids from two or more node locations combine by hybridization, extension, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acids further comprise a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the node nucleic acids further comprise a unique identification sequence, comprising one or more noncanonical bases, universal bases, other bases which a polymerase will pair randomly or incorrectly, or any combination thereof. Further provided herein are methods, wherein the node nucleic acids are double-stranded, single-stranded, comprises a hairpin structure, or any combination thereof. Further provided herein are methods, wherein the diffusion factor comprises a viscosity, a time, a temperature, a presence of crowding agents, a pH, an electric field, physical features, or any combination thereof. Further provided herein are methods, wherein the viscosity is greater than 1 cP. Further provided herein are methods, wherein the medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP.

Provided herein are methods of information storage, the methods comprising: receiving digital information; converting the digital information to nucleic acid information in the form of a plurality of nucleic acid barcodes; depositing node nucleic acids on a surface at node locations, wherein the node nucleic acids comprise: a node barcode region, each corresponding to one of the plurality of barcodes; and one or more flanking node barcode hybridization regions; amplifying the node nucleic acids to generate node amplification products, wherein the node amplification products diffuse away from the node locations; depositing factory target nucleic acids onto the surface, wherein the factory target nucleic acids comprise: a target binding region; and one or more flanking target binding hybridization regions; and attaching at least one of the node amplification products to at least one of the factory target nucleic acids to form a concatemer, wherein the combination of node amplification products and factory target nucleic acids provides information for spatial mapping of the node locations. Further provided herein are methods, wherein the amplifying comprises rolling circle amplification (RCA), strand-displacement amplification (SDA), Nicking Enzyme Amplification Reaction (NEAR), nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER). Further provided herein are methods, wherein the attaching comprises by hybridization, ligation, splinted ligation, cross-junction synthesis, ligation and cross-interstrand crosslink (ICL) synthesis, cross ICL and nick synthesis, pairwise copying, or any combination thereof. Further provided herein are methods, wherein the spatial mapping comprises sequencing the concatemer. Further provided herein are methods, wherein the sequencing is chain termination sequencing, nanopore sequencing, sequencing by ligation, combinatorial probe anchor synthesis, sequencing by synthesis, pyrosequencing, ion semiconductor, or single-molecule real-time sequencing. Further provided herein are methods, wherein the concatemers comprise one or more fluorophore labels. Further provided herein are methods, wherein the spatial mapping comprises imaging the concatemer. Further provided herein are methods, wherein the one or more fluorophore labels are attached to the concatemers by synthesis or hybridization. Further provided herein are methods, wherein the node locations comprise a pattern. Further provided herein are methods, wherein the node locations are preselected. Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, wherein the diffused node amplification products are in a gradient of decreasing concentration with increased distance from the node. Further provided herein are methods, wherein the node amplification products from different node locations do not overlap. Further provided herein are methods, wherein the node amplification products from different node locations overlap. Further provided herein are methods, wherein the node amplification products from two or more node locations combine by hybridization, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acids further comprise a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the node nucleic acids further comprise a unique identification sequence, comprising one or more noncanonical bases, universal bases, other bases which a polymerase will pair randomly or incorrectly, or any combination thereof. Further provided herein are methods, wherein the node nucleic acids are double-stranded, single-stranded, comprises a hairpin structure, or any combination thereof. Further provided herein are methods, wherein the node nucleic acids further comprise a medium, and wherein the medium comprises a viscosity greater than 1 cP. Further provided herein are methods, wherein the medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP.

Provided herein are methods for information storage, the method comprising: receiving digital information; converting the digital information to nucleic acid information in the form of a plurality of nucleic acid barcodes; depositing a first oligonucleotide onto a surface, wherein the first oligonucleotide comprises: optionally, a surface binding region; a first barcode region corresponding to a barcode of the plurality of barcodes; and one or more flanking first oligonucleotide hybridization regions, wherein the surface binding region and the one or more flanking hybridization regions optionally comprise a photoreactive nucleobase; optionally selectively radiating the surface to form covalently linked oligonucleotides; depositing a second oligonucleotide on the surface, wherein the second oligonucleotide comprises: a second barcode region corresponding to a barcode of the plurality of barcodes; and one or more flanking second oligonucleotide hybridization regions, wherein the one or more flanking second oligonucleotide hybridization regions comprise a photoreactive nucleobase, and wherein at least one of the one or more flanking first oligonucleotide hybridization regions is complementary to at least one of the one or more flanking second oligonucleotide hybridization regions; and selectively radiating the surface to covalently link the second oligonucleotide to the first oligonucleotide; and optionally repeating the second depositing and radiating steps one or more times, thereby generating a concatemer. Further provided herein are methods, wherein the surface comprises an oligonucleotide comprising a photocleavable nucleobase and a region complementary to at least one of the one or more flanking first oligonucleotide hybridization regions. Further provided herein are methods, wherein the surface comprises a reactive group capable of binding to a nucleoside. Further provided herein are methods, wherein the radiating comprises applying light with a wavelength from about 365 nm to about 405 nm. Further provided herein are methods, wherein the photoreactive nucleobase is 3-cyanovinylcarbazole phosphoramidite (CNVK). Further provided herein are methods, wherein the selectively radiating comprises applying radiation to a preselected region of interest (ROI). Further provided herein are methods, wherein the ROI is described with a photomask. Further provided herein are methods, wherein the photomask is varied in each selectively radiating step. Further provided herein are methods, wherein the photomask is generated manually. Further provided herein are methods, wherein the photomask is generated by machine. Further provided herein are methods, wherein the selectively radiating step comprises administering radiation at a wavelength of about 300 nm up to 450 nm. Further provided herein are methods, wherein the selectively radiating step comprises administering radiation at a wavelength of about 365 nm up to 405 nm. Further provided herein are methods, further comprising washing after each selectively radiating step to remove unbound oligonucleotides. Further provided herein are methods, wherein the concatemer further comprises a primer region, a promoter region, or any combination thereof. Further provided herein are methods, further comprising depositing a polymerase on the concatemer. Further provided herein are methods, wherein a continuous complementary nucleic acid strand of the concatemer is generated by cross-junction synthesis, hybridization, extension, ligation, splinted ligation, ligation and cross-interstrand crosslink (ICL) synthesis, cross ICL and nick synthesis, pairwise copying, or any combination thereof. Further provided herein are methods, wherein the continuous complementary nucleic acid strand is amplified and sequenced, thereby generating sequencing data. Further provided herein are methods, wherein the sequencing data allows for translating the nucleic acid information to the digital information. Further provided herein are methods, wherein the concatemers are contacted with fluorophore-labelled sequences complementary to the barcode regions of the oligonucleotides to generate a fluorophore-concatemer complex. Further provided herein are methods, wherein the fluorophore-concatemer complexes are imaged. Further provided herein are methods, wherein the imaging comprises applying light with a wavelength from about 365 nm to about 405 nm. Further provided herein are methods, wherein the imaging allows for translating the nucleic acid information to the digital information.

Provided herein are methods of biological information generation, the methods comprising: depositing node factories comprising a matrix on a biological sample at node locations, wherein each node factory comprises a plurality of node nucleic acids, and wherein each node nucleic acid comprises: a node barcode region; one or more flanking node barcode hybridization regions; optionally, a node primer region, a target binding region; a target barcode region; one or more flanking target binding hybridization regions; and optionally, a target primer region, releasing at least one of the node nucleic acids from the node factory, wherein the releasing provides biological information for spatial mapping of the biological sample. Further provided herein are methods, wherein the node factories comprise a plurality of node nucleic acids reversibly immobilized to a carrier. Further provided herein are methods, wherein the carrier comprises a liposome, a droplet, a bead, LNP, AAV, exosome, lentivirus, or a protein. Further provided herein are methods, wherein the carrier comprises a bead. Further provided herein are methods, further comprising releasing the node nucleic acids from the carrier. Further provided herein are methods, wherein each node nucleic acid further comprises a restriction site, and wherein the plurality of node nucleic acids are provided in a concatemer. Further provided herein are methods, further comprising depositing a restriction enzyme on the sample, wherein the restriction enzyme recognizes the restriction site, thereby cleaving the concatemer to provide a plurality of node nucleic acids. Further provided herein are methods, further comprising depositing an oligonucleotide on the sample, wherein the oligonucleotide hybridizes with a region comprising the restriction site on the node nucleic acid, and wherein the restriction enzyme recognizes the double-stranded cleavage site on the sample, thereby cleaving the concatemer to provide a plurality of node nucleic acids.

Provided herein are methods of biological information generation, the methods comprising: depositing node template nucleic acids onto a sample at node locations, wherein the node nucleic acids comprise: a node barcode region; and flanking hybridization regions; depositing factory target nucleic acids onto the population of cells, wherein the factory target nucleic acids comprise: a target identification region; a target binding region; and flanking hybridization regions; and hybridizing at least one of the node nucleic acids to at least one of the factory target nucleic acids.

Provided herein are methods of biological information generation, the methods comprising: depositing factory target nucleic acids onto a sample at node locations comprising node nucleic acids; performing a plurality of polymerase-based amplifications to generate amplification products, wherein the amplification products comprise at least one node nucleic acid and a plurality of factory target nucleic acids; wherein the amplification products provide information for spatial mapping of the population of cells based on a frequency of the factory target nucleic acids and the node nucleic acids present in the amplification products.

Provided herein are methods of biological information generation, the methods comprising: depositing node nucleic acids onto a node locations in a sample, wherein the locations comprise a pattern, wherein the tissue sample comprises cells in a synthetic matrix, and wherein the node nucleic acids comprise: a node barcode region; and flanking hybridization regions; depositing factory target nucleic acids onto the population of cells, wherein the factory target nucleic acids comprise: a target identification region; a target binding region; and flanking hybridization regions; and hybridizing at least one of the node nucleic acids to at least one of the factory target nucleic acids, wherein density of the synthetic matrix modulates hybridization rate.

Provided herein are methods of biological information generation, the methods comprising: depositing node nucleic acids onto a sample at preselected node locations, wherein the node nucleic acids comprise: a node barcode region; and flanking hybridization regions; depositing factory target nucleic acids onto the population of cells, wherein the factory target nucleic acids comprise: a target identification region; a target binding region; and flanking hybridization regions; performing polymerase-based amplification to generate amplification products, wherein the amplification products comprise at least one node nucleic acid and a plurality of factory target nucleic acids; sequencing the amplification products to generate sequencing data; and generating a spatial map based on the sequencing data.

Further provided herein are methods as described herein, wherein the sample comprises a population of cells, a tissue sample, or a protein. Further provided herein are methods, wherein the node barcode region is from about 3 to about 30 nucleotides. Further provided herein are methods, wherein the node nucleic acid is from about 20 to about 50, from about 50 to about 100, from about 100 to about 200, from about 200 to about 500, from about 500 to about 1000, or more than 1000 nucleotides. Further provided herein are methods, further comprising amplifying the node nucleic acids, wherein the amplification products diffuse away from the node. Further provided herein are methods, wherein the diffused amplification products are in a gradient of decreasing concentration with increased distance from the node. Further provided herein are methods, wherein the amplification products from different node locations do not overlap. Further provided herein are methods, wherein the amplification products from different node locations overlap. Further provided herein are methods, wherein the node barcode strands from two or more node locations combine by hybridization, ligation, splinted ligation, cross-junction synthesis, ligation and cross-interstrand crosslink (ICL) synthesis, cross ICL and nick synthesis, pairwise copying, or any combination thereof. Further provided herein are methods, wherein the node nucleic acid further comprises a promoter region, a primer region, or any combination thereof. Further provided herein are methods, further comprising depositing a polymerase on the node nucleic acids. Further provided herein are methods, wherein the polymerase is a DNA polymerase or an RNA polymerase. Further provided herein are methods, wherein the DNA polymerase is Pol I, Pol II, Pol III, Pol IV, Pol V, or any combination thereof. Further provided herein are methods, wherein the RNA polymerase is T7, T3, or Reverse Transcriptase. Further provided herein are methods, further comprising a nickase, wherein the node barcode strand comprises a nicking site targetable by the nickase. Further provided herein are methods, wherein the node nucleic acid further comprises a unique identification sequence, comprising one or more noncanonical bases, universal bases, other bases which a polymerase will pair randomly or incorrectly, or any combination thereof. Further provided herein are methods, wherein the node nucleic acid is double-stranded, single-stranded, comprises a hairpin structure, or any combination thereof. Further provided herein are methods, wherein the sample medium comprises a viscosity greater than 1 cP. Further provided herein are methods, wherein the sample medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP. Further provided herein are methods, wherein the depositing is at random locations throughout the sample. Further provided herein are methods, wherein the depositing is at specific targets in the sample.

Provided herein are methods as described herein, further comprising: contacting a population of cells with a nucleic acid polymerase and a primer to generate amplification products; depositing DNA barcodes onto the population of cells, wherein the DNA barcodes comprise a region complementary to a region of the amplification products, and wherein the DNA barcodes comprise a photo-reactive nucleobase capable of crosslinking to another nucleobase; selectively radiating the population of cells to form covalently linked DNA barcode-amplification product complexes; washing the population of cells to remove the DNA barcodes that are not complexed to amplification products; and repeating the depositing, selectively radiating, and washing steps, wherein: the DNA barcodes in a first of the depositing steps comprise a different sequence than the DNA barcodes in a second of the depositing steps, and the selectively radiating occurs at different locations for a first selectively radiating step and a second selectively radiating step. Further provided herein are methods, further comprising synthesizing a continuous DNA strand, wherein the synthesizing comprises contacting the DNA barcode-amplification product complexes with a polymerase. Further provided herein are methods, wherein the synthesizing comprises cross-junction synthesis. Further provided herein are methods, further comprising displacing the continuous DNA strand from the population of cells. Further provided herein are methods, wherein the synthesizing and displacing occur simultaneously. Further provided herein are methods, wherein the displaced continuous DNA strands are pooled. Further provided herein are methods, wherein the pooled continuous DNA strands are amplified. Further provided herein are methods, wherein the pooled continuous DNA strands are sequenced. Further provided herein are methods, wherein the primer is one or more random primers. Further provided herein are methods, wherein the primer is a non-random primer. Further provided herein are methods, wherein the photo-reactive nucleobase is 3-cyanovinylcarbazole phosphoramidite (CNVK). Further provided herein are methods, wherein the selectively radiating is performed using a photomask. Further provided herein are methods, wherein the photomask is varied in the different selectively radiating steps. Further provided herein are methods, wherein the photomask is generated manually. Further provided herein are methods, wherein the photomask is generated by machine. Further provided herein are methods, wherein the selectively radiating step comprises administering radiation at a wavelength of about 300 nm up to 450 nm. Further provided herein are methods, wherein the selectively radiating step comprises administering radiation at a wavelength of about 350 nm up to 420 nm. Further provided herein are methods, wherein the selectively radiating step comprises administering radiation at a wavelength of about 365 nm up to 405 nm. Further provided herein are methods, wherein the selectively radiating step comprises applying radiation to a preselected region of interest (ROI). Further provided herein are methods, wherein the ROI is cell-specific or sub-cellular specific. Further provided herein are methods, wherein the ROI is based on morphology. Further provided herein are methods, wherein the depositing is performed manually, automatically, robotically, or any combination thereof. Further provided herein are methods, wherein the depositing is performed with a modified inkjet printer. Further provided herein are methods, wherein the depositing or washing is performed using microfluidics, passive diffusion, electrophoresis, digital microfluidics, an acoustic liquid handler, an inkjet printer, an automatic liquid handler, or any combination thereof. Further provided herein are methods, wherein one or more DNA barcodes combine with one or more node barcode strands, wherein the combining is with ligation, splinted ligation, cross-junction synthesis, ligation and cross-interstrand crosslink (ICL) synthesis, cross ICL and nick synthesis, pairwise copying, or any combination thereof.

EXAMPLES

The examples below further illustrate the described embodiments without limiting the scope of this disclosure.

Example 1: Fixation of Samples

MRC-5 (human, ATCC CCL-171) and HEK293T cells (human, ATCC CRL-1573) are grown in Dulbecco's modified Eagle medium (Gibco #10564) supplemented with 10% (vol/vol) serum (Gibco #10437 for MRC-5 and Peak Serum PS-FB2 for HEK293 Ts), 50 U/mL penicillin, and 50 µg/mL streptomycin (Gibco #15070). EY.T4 embryonic fibroblasts (mouse) 49 are grown in Dulbecco's modified Eagle medium supplemented with 15% (vol/vol) serum, 50 U/mL penicillin, and 50 µg/mL streptomycin. Cells are cultured at 37 degrees C. in the presence of 5% $CO_2$.

Cells are pre-washed with phosphate buffer (PBS), 0.1% TWEEN® 80 in PBS, 0.1% polysorbate 20 (TWEEN® 20) in PBS or Hank's Balanced Salt Solution (HBSS). Samples are fixed in 1-10% formaldehyde followed by washes with PBS or HBSS. Cells are optionally permeabilized with 0%-2.5% Triton X-100+0.1% TWEEN® 20. The fixed sample can be maintained at a temperature of 4 to 45 degrees Celsius. Samples are fixed at room temperature (20 to 25 degrees C.) for approximately 5 to 20 minutes prior to barcode hybridization. Alternatively, samples are fixed at lower temperatures at 4 degrees C. and stored for up to two weeks before barcoding. After fixation, the samples are washed with PBS or 0.1% TWEEN® 20 in PBS. Bovine serum albumin (BSA) is used as a blocking agent to reduce non-specific detection of the target nucleic acids and proteins. Other blocking agents or detergents can be used. When blocking, the cells are incubated in the BSA or detergent at room temperature.

Example 2: Barcode Hybridization and Imaging

To a fixed tissue sample, such as that generated in Example 1, barcodes are hybridized to the target nucleic acids using the reagents listed in Table 2. The reagent conditions include the range of concentrations that permit DNA barcode hybridization to a target.

TABLE 2

| Barcode Hybridization Reagents | | |
|---|---|---|
| Reagent Type | Reagents | Reagent Concentration Ranges |
| Salt | Phosphate buffer solution (PBS) | 0.1× to 1× |
| | Sodium Chloride (NaCl); | 0 to 1M |
| | Magnesium Chloride ($MgCl_2$) | 10 mM to 100 mM |
| Detergents | Triton X-100 and | 0% to 2.5% (w/v) |
| | polysorbate 20 (TWEEN ® 20) | 0% to 1% (w/v) |
| Blocking | dextran sulfate | 0 to 20% (w/v) |
| | bovine serum albumin (BSA) | 1% to 10% (w/v) |
| | sheared salmon sperm DNA | 0% to 15% (w/v) |

TABLE 2-continued

Barcode Hybridization Reagents

| Reagent Type | Reagents | Reagent Concentration Ranges |
|---|---|---|
| Additional agents | tRNA, yeast tRNA | 0.1 pg to 5 µg |
| Barcode | Barcode 1 strand and/or Barcode 2 strand | 100 nM to 500 nM |
| RNAse | RNase H (New England Biolabs ®) | 200 to 300 U/ml |
| Cross-junction Synthesis Buffer | ThermoPol Reaction buffer (New England Biolabs)<br>dNTP (New England Biolabs)<br>BST LF polymerase (New England Biolabs) | 1×<br>100 µM<br>800 U/ml |

A barcoding solution consisting of 250 nM Barcode 1 strand is admixed in PBS and TWEEN® 20 (PBST) with 2 mg/ml sheared salmon sperm DNA (Invitrogen AM9680), 10% dextran sulfate (wt/vol, Sigma Aldrich S4030), and 500 mM NaCl is applied to the fixed tissue sample for 20 min up to 1 hour. Samples are washed with PBST with 1 M NaCl 3 times for approximately 1 min each. Fixed samples can be maintained in the barcoding solution at a temperature of approximately 20 up to 60 degrees Celsius prior to photo-stimulation.

Using microscopy, the desired regions on the tissue sample are visually identified in brightfield or fluorescent images. Hand-drawn masks are set as photostimulation regions. A high-power liquid light guide coupled LED source is applied at 365 nm to a selected region of interest on the sample per barcoding round. The microscope focus is set to a desired layer on the sample and photomask regions are manually selected. Samples are photo-stimulated, imaged and then washed with approximately 0.1×-1× PBS; 25 to 80% formamide; and 0% up to 1% TWEEN® 20.

Additional barcode strands can be added to the barcoding solution after finding the same cell area within the fixed sample. After barcoding, samples are optionally treated with a cross-junction synthesis solution consisting of RNase H, and reverse transcription buffer. cDNAs can be extracted by washing the cells with PBST and collecting the supernatant in a tube for amplification and/or next generation sequencing. cDNAs can be pooled together or in separate sequential barcoding steps for sequencing analysis.

Example 3: Binary Encoding

Figure 30:
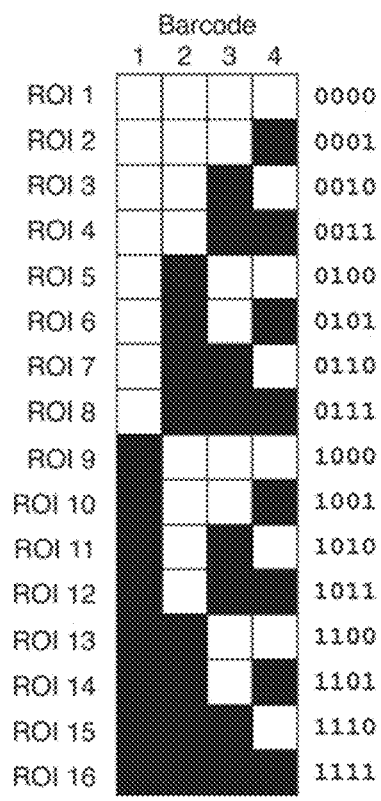
FIG. 30 illustrates coding combinations with 4 barcode strands using a binary encoding method.

A sample is spatially defined with 16 regions of interest (ROI). Four unique barcodes are applied in 4 rounds of crosslinking iterations. In each of the four crosslinking rounds, light is applied to half the ROI. Any illuminated fraction in each round comprises approximately ¼ (25%) or less saturation, providing for $2^4=16$ unique combinations of the 4 barcode strands being crosslinked or not crosslinked in each region. This is represented in FIG. 30, with a filled square representing some fraction of reads in a region containing the barcode corresponding to that column, and an empty white square representing no illumination during that barcoding round. On the right, a binary encoding for the four barcodes can be assigned to each of these combinations.

Example 4: Quaternary Encoding

Figure 31:
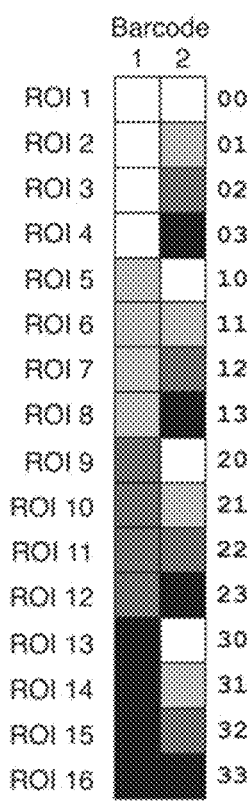
FIG. 31 illustrates coding combinations with 2 barcode strands using a quaternary encoding method.

A sample is spatially defined with 16 regions of interest (ROI). Two unique barcodes are applied in two rounds of crosslinking iterations. In each of the two crosslinking rounds, light is applied to 75% of the ROI at one of three different levels such that the most illuminated fraction in each round comprises approximately ½ (50%) or less cross-link saturation of sites. This provides for $4^2=16$ unique combinations of the 2 barcode strands crosslinked fractions. Combinations are illustrated in FIG. 31, with gradations of filled squares representing different fraction of reads in a region containing the barcode corresponding to that column, and an empty white square representing there was no illumination during that barcoding round. On the right, a quaternary encoding for the two barcodes can be assigned to each of these cases.

Example 5: Fractional Encoding

Figure 32:
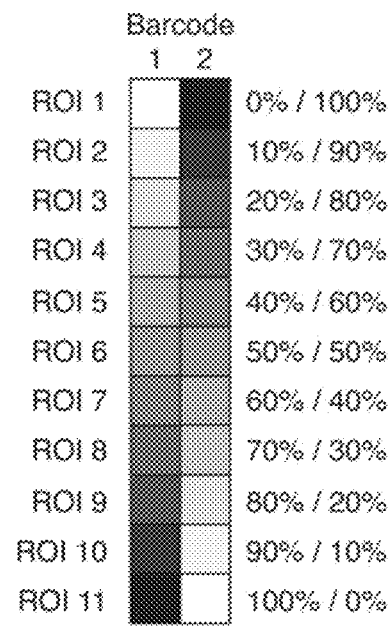
FIG. 32 illustrates coding combinations with 2 barcode strands using a fractional encoding method.

A sample is spatially defined with 11 regions of interest (ROI). Two unique barcodes are applied in two rounds of crosslinking iterations. In each of the crosslinking rounds, light is applied to each ROI at 10 different gradations such that there is a unique ratio of barcode fractions. Light is applied at gradations providing for 0%, 10%, 20%, 30%, 40%, 50%, 60%, 70%, 80%, 90%, and 100% barcoded fraction. These 11 unique ratios of the two barcode strands are illustrated in FIG. 32, with gradations of filled squares representing different fractions of reads in a region containing the barcode corresponding to that column, and empty white squares representing there was no illumination during that barcoding round. On the right, a ratio-based encoding for the two barcodes can be assigned to each of these cases.

Example 6: Node Strand Generation

Figure 37A:
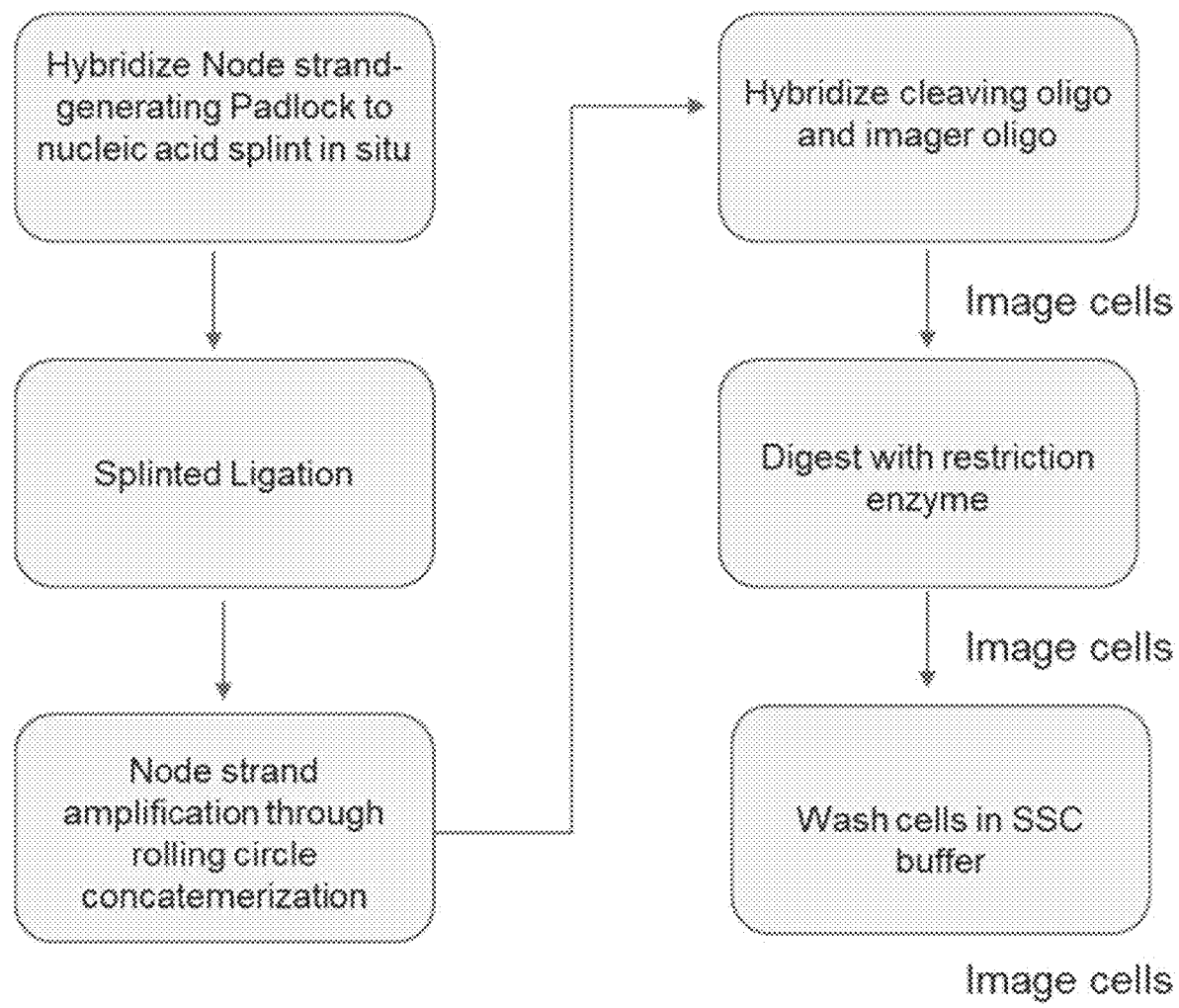
FIG. 37A is a schematic illustrating a workflow for node strand/node nucleic acid generation in situ, directed by oligonucleotide hybridization.

Diffusive strands from single stranded rolling circle amplification (RCA) repeats (concatemers) in cells were generated by hybridizing short oligos to make a double stranded restriction enzyme (RE) site that can be cut to release strands. An exemplary schematic of the workflow is shown in FIG. 37A.

Cell Seeding and Fixation

3T3 cells were seeded and grown overnight in glass-bottom chambers on glass slides. The next day, media was removed and the cells were washed with pre-warmed DPBS (no calcium, no magnesium) before fixation with 4% paraformaldehyde solution in 1×PBS (4% PFA). Cells were incubated in fixative for 5 minutes at room temperature before washing twice for 2 minutes in 1×PBS with 0.1% Tween-20 (PBST).

Cells were then permeabilized with 1×PBS with 0.25% Triton-X-100 (PBSTx) for 10 minutes, then washed twice for 1 min in 1×PBS. Finally, cells were washed with PBST twice for 2 minutes.

Blocking solution was comprised of 1× Ampligase Buffer (ThermoFisher), 0.05 M KCl, 20% formamide, 0.1 µM blocking oligo, 0.2 µg/mL of BSA, 1 U/µl RiboLock (ThermoFisher), 0.2 µg/µl yeast tRNA (ThermoFisher). Blocking solution was incubated with the sample for 30 minutes at room temperature and then washed twice for 1 minute with PBST.

Splint Ligation and RCA

Figure 37B:
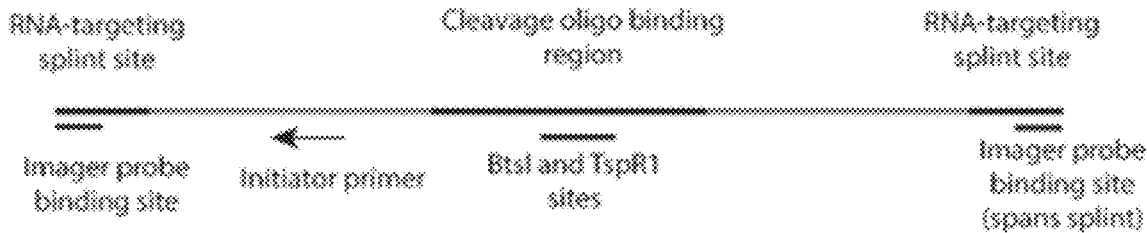
FIGS. 37B and 37C are schematics illustrating node strand generating padlocks used in splinted ligation, which form node templates upon ligation.
Figure 37C:
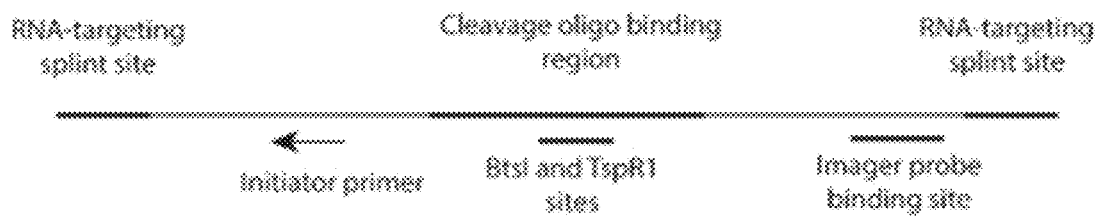
Figure 37D:
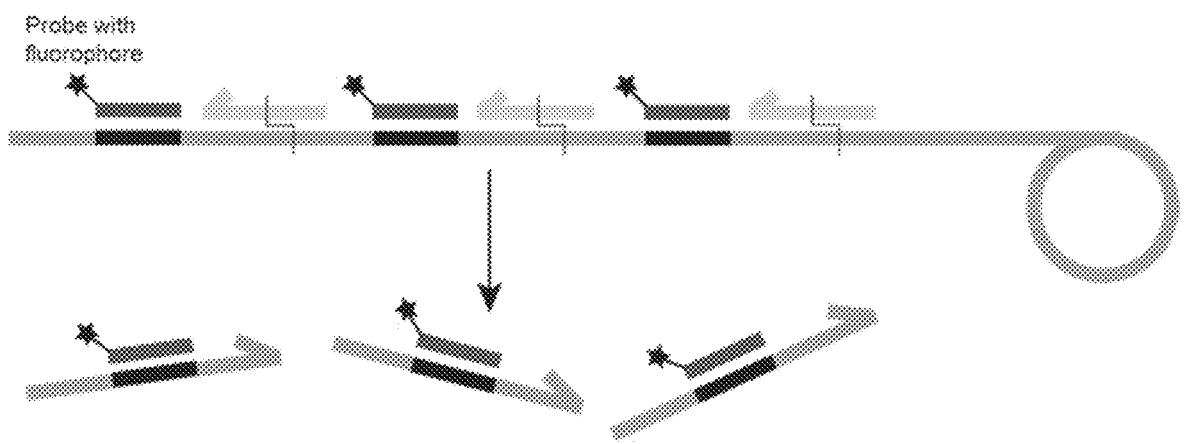
FIG. 37D is a schematic illustrating rolling circle amplification (RCA) concatemers with fluorescent probe detection (top) and released strands using cleaving oligos of various lengths (bottom), which reconstitute the double-stranded restriction enzyme sites.
Figure 37E:
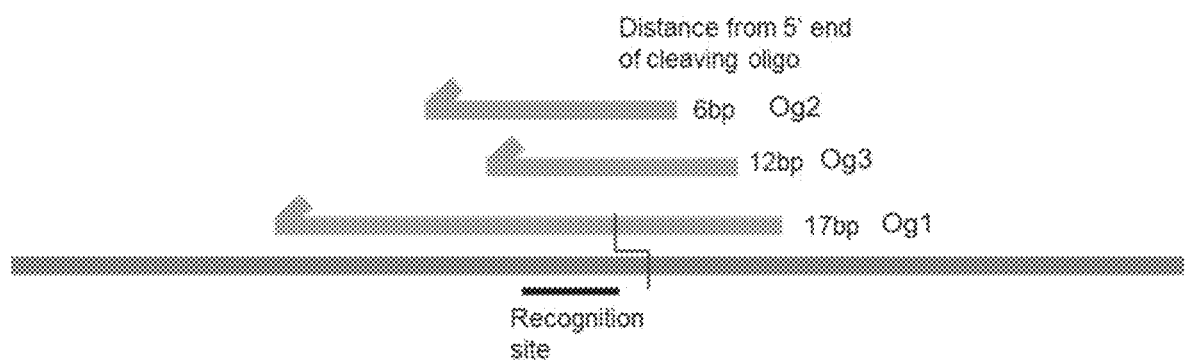
FIG. 37E is a schematic illustrating cleaving oligos of various lengths and various distances from recognition site sequence.
Figure 37F:
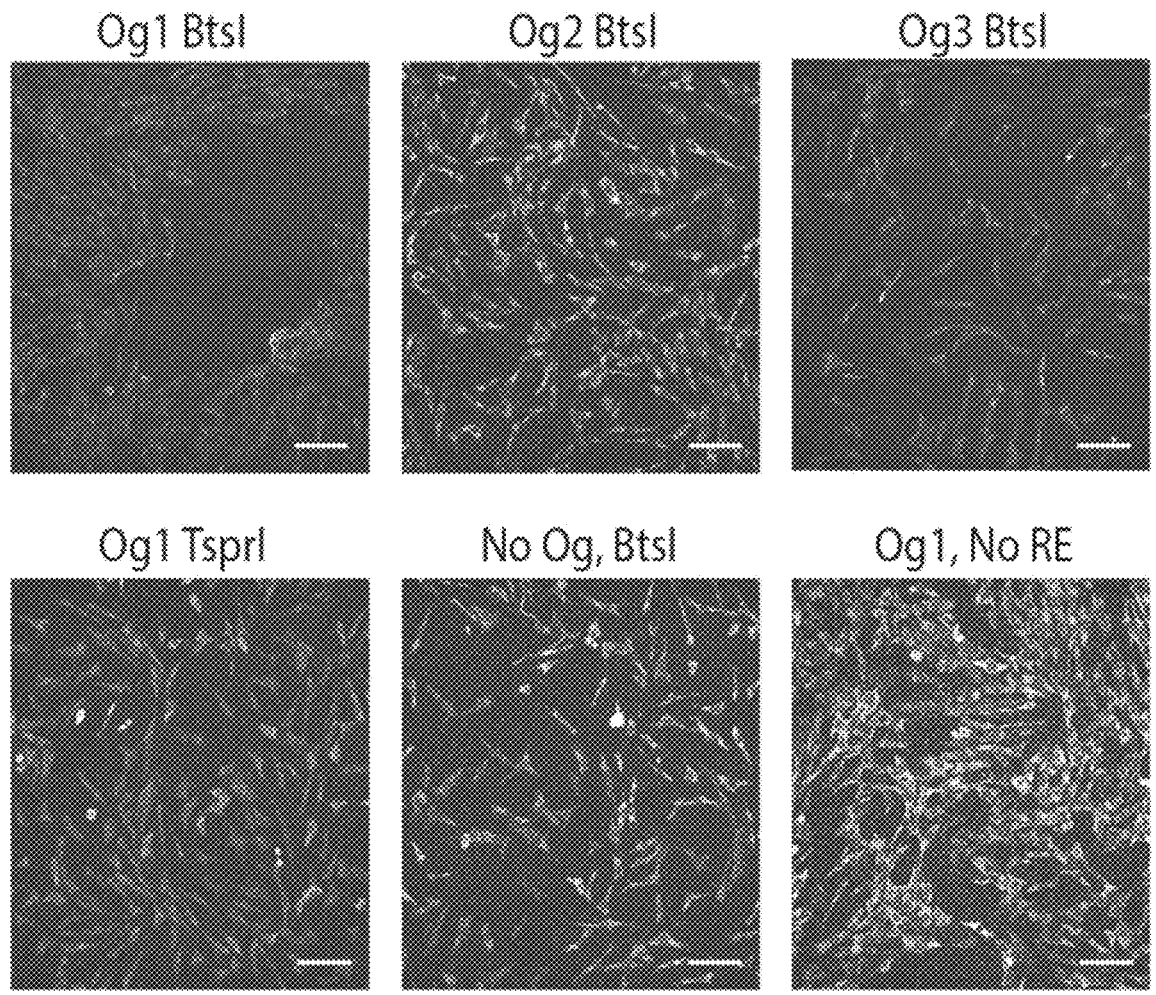
FIG. 37F are images illustrating puncta intensity after cleaving using various oligos and restriction enzymes, compared to controls (Og=oligo, RE=restriction enzyme). Scale bars: 100 µm.

Padlock probe hybridization to generate FIG. 37F was performed with padlock probe (FIG. 37B) concentration of 0.05 µM in the blocking solution, without addition of the blocking oligo. Three padlock probes (FIG. 37C) were hybridized to the sample to generate FIG. 37G, each at a final incubation concentration of 0.02 µM during padlock hybridization in blocking solution, without addition of blocking oligonucleotide. Cells were incubated for padlock hybridization at 55° C. for 15 minutes, followed by 45° C. for 120 minutes. Slides were then washed three times for 5 minutes with Wash Buffer (10% formamide in 2× SSC) at room temperature, followed by three 1 minute washes in PBST.

Node strand-generating Padlocks are shown in FIGS. 37B and 37C, which were hybridized to a nucleic acid sequence in situ and splint ligated to form a circular construct. Padlock probes were ligated in Ligation Solution comprising 1× T4 RNA ligase buffer, 0.01 mM ATP, 0.2 µg/µl BSA, from 0.005 to 0.5 U/µL SplintR (FIG. 37E with 0.5 U/µl, FIG. 37F with 0.005 U/µl), and 1 U/µl RiboLock. Incubation time was overnight at room temperature, followed by two 1 minute washes with PBST.

Rolling circle amplification was then performed using a primer complementary to the padlock with phosphorothioate bonds on the 3' nucleotides (RCA initiator primer) in a solution of 1× Phi29 Buffer, 5% glycerol, 0.2 µg/µl BSA, 0.25 mM dNTP mix, 0.1 µM RCA initiator primer, and 0.5 U/µl Phi29 Polymerase.

Chamber slides were incubated at 30° C. for 2 hours and washed twice for 1 minute with PBST. Slides were then fixed with 4% PFA in 1×PBS for 5 minutes at room temperature, followed by three 1 minute washes with PBST, then three 5 minute washes with 65% formamide at 30° C., then two 1 minute washes with PBST. Slides were stored overnight at 4° C. in PBST.

Cleavage of RCA Products

Hybridization of cleavage oligonucleotides to the RCA products was then performed prior to treatment with restriction enzymes, to make the RCA products double stranded at the restriction enzyme sites. Cleaving oligonucleotides (light grey harpoons in FIGS. 37D and 37E) were tested that differ in length and number of bases between the recognition site of the enzyme and the end of the oligonucleotide (also tested were 2 restriction enzymes that have a recognition site in the duplex). The same cleavage oligonucleotide was used for both TsprI (restriction site: NNCASTGNN) and BstI-v2 (restriction site: GCAGTGNN), since their restriction enzyme recognition sites are overlapping (where N is any nucleotide and S is either G or C). Slides were first treated with 10 mM EDTA solution in water and incubated at 65° C. for 15 minutes, followed by three 1 minute washes with 1×PBS. Cleavage oligonucleotides were hybridized in 1× SSC, 5% formamide, 0.06 µM cleavage oligonucleotide, and 0.1 µg/mL BSA. Slides were incubated for cleavage oligonucleotide hybridization for 20 minutes at 33° C., followed by three 5 minute washes in 10% formamide in 2× SSC at 33° C., followed by three 1 minute washes with 6× SSC.

For the 'Pre-Cut', 'Post-Cut, Pre-Wash', and 'Post-Wash' conditions (FIG. 37G), cleavage oligonucleotides and fluorescent probes were then hybridized to the samples in a single solution containing 1× SSC, 5% formamide, 0.02 µM of each probe (one for detection of RCA products of each padlock), and 0.1 µg/mL BSA, 0.06 µM of a cleavage oligonucleotide. Samples were incubated for 33° C. for 30 minutes and then washed three times for 5 min with 10% formamide in 2× SSC, followed by three 1 min washes with 6× SSC. The 'Pre-Cut' samples were imaged after hybridization and prior to washing with 20× spinning disk confocal imaging.

Figure 37G:
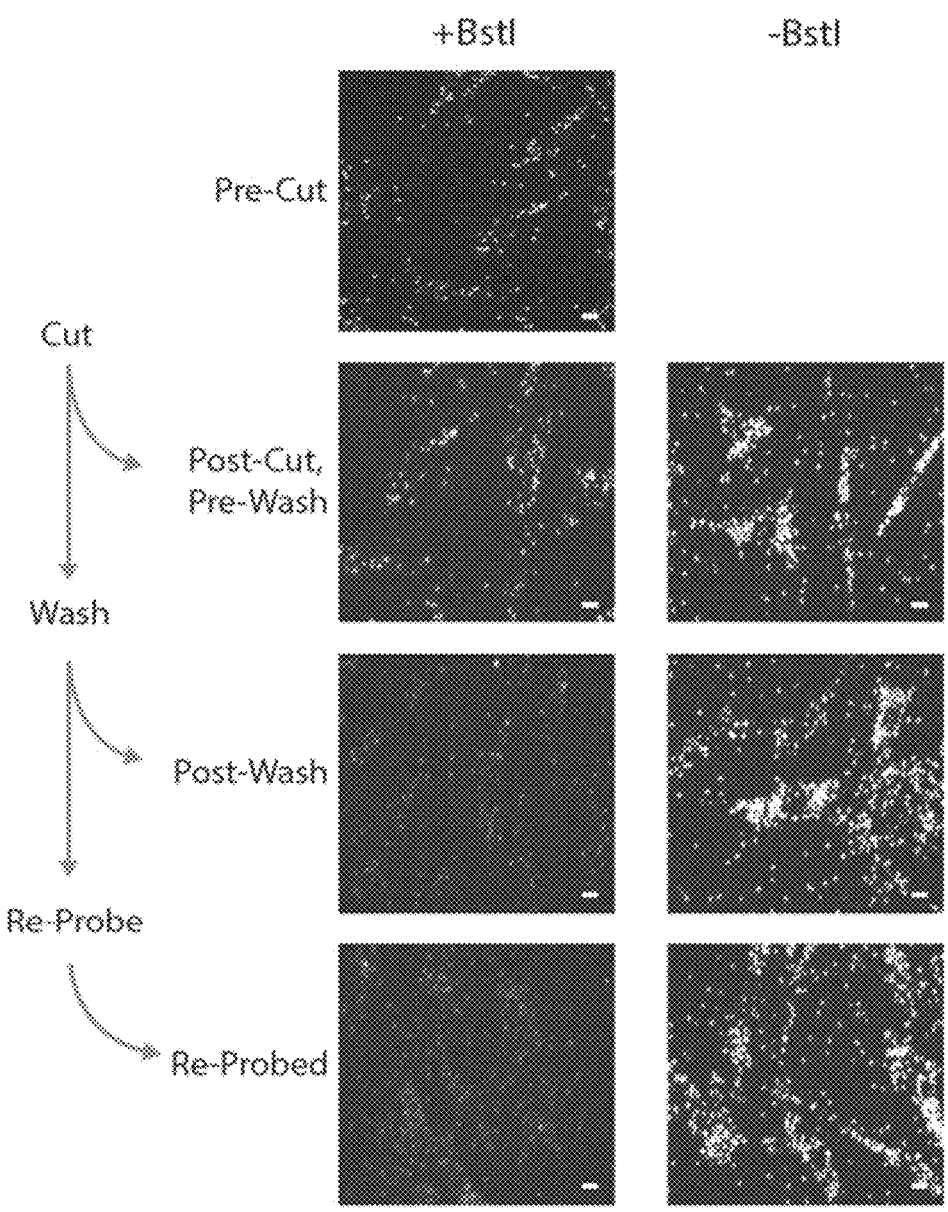
FIG. 37G are images illustrating probe signal for concatemers and cleaved concatemers before and after wash steps.

Restriction enzymes (either BtsI-v2 or TsprI) were then added in 1× CutSmart Buffer for 1 hour at 55° C. Samples were then washed three times for 1 minute with PBST (FIG. 37F) or cleaving was performed with 0.2 U/µl BtsI-v2 (+BtsI) or water (-BtsI condition) in 1× CutSmart buffer and incubated for 30 minutes at 50° C. 'Post-Cut, Pre-Wash' samples were then imaged (FIG. 37G). Samples were then washed three times with 6× SSC. 'Post-Wash' conditions were then imaged with 20× spinning disk confocal imaging.

The 'No Og' control (no oligonucleotide control) was treated with this same protocol, with the exception of water to replace the cleavage oligonucleotide. The 'No RE' control (no restriction enzyme control) similarly followed this same protocol, but water was used in lieu of the restriction enzymes during the cleavage step. 'Re-probed' samples underwent fluorescent probe hybridization after cleavage and washing. Fluorescent probes were incubated in 1× SSC, 5% formamide, 0.02 µM of each fluorescent probe, and 0.1 µg/mL BSA. Incubation occurred at 33° C. for 30 minutes, followed by three 5 minute washes in 10% formamide in 2× SSC at 33° C. and three 1 minute washes with 6× SSC at room temperature. 'Re-probed' samples were then imaged with 20× spinning disk confocal imaging.

Images were acquired with equivalent acquisition parameters for all samples and maximum intensity projections of z-stack images are shown in the figures.

Detection of RCA Products and Imaging

Detection of cleaved products was performed through hybridization of fluorescent oligos to the target sequence within the RCA products (FIGS. 37F and 37G). 3' Cy3-labeled probe oligo was incubated in a hybridization solution containing 1× SSC, 5% formamide, 0.06 µM fluorescent probe, and 0.1 µg/mL BSA for 20 minutes at room temperature, protected from light. Slides were then washed three times for 5 minutes with 10% formamide in 2× SSC at 33° C., followed by three 1 minute washes with 6× SSC at room temperature. Slides were then imaged at 20× with a spinning disc confocal imager to visualize the RCA products post-cleavage.

Figure 37H:
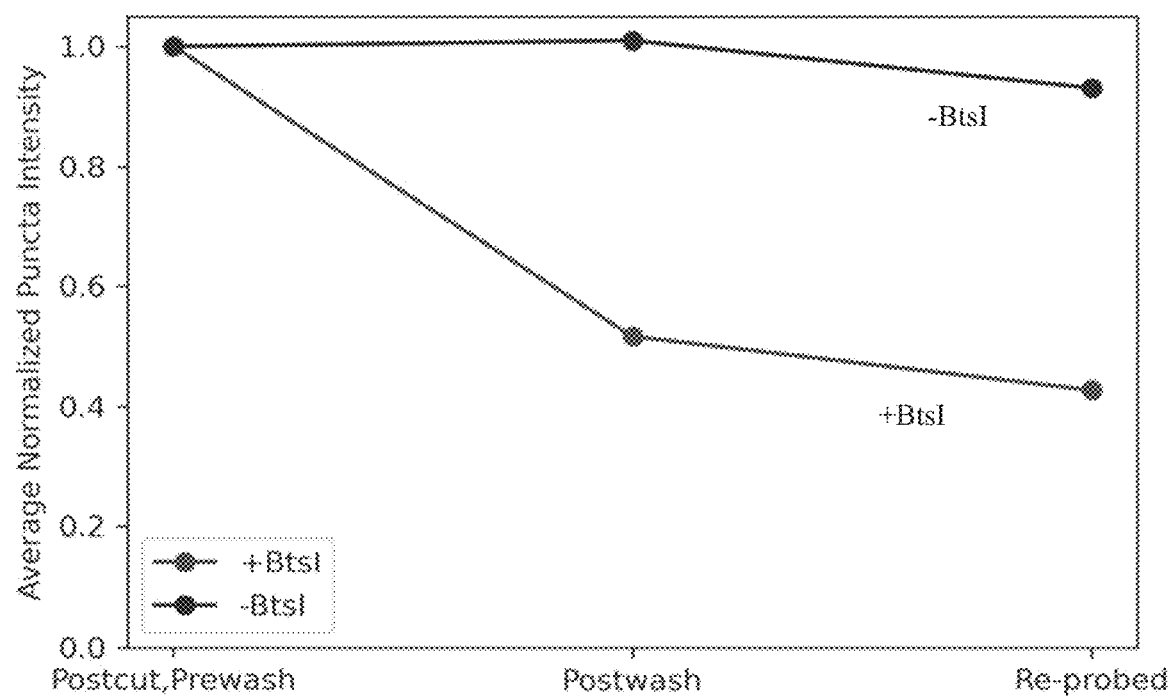
FIG. 37H is a line graph illustrating the average puncta intensities for 'Postcut, Prewash', 'Postwash', and 'Reprobed' samples, which were divided by the average puncta intensity for the 'Postcut, Prewash' condition, taken as the baseline signal before diffusion. This resulted in the 'Normalized Average Puncta Intensity' value for each condition. The no restriction enzyme control (-BtsI) is plotted separately from the cleavage condition (+BtsI) in the line plot to display the difference in punctate fluorescence retention with and without cleavage by BtsI.

Quantification of average fluorescent puncta intensity and area were performed on the maximum intensity projections of acquired z-stack images and shown in FIG. 37H. A Laplacian of Gaussian method was used to segment individual puncta, with Otsu's thresholding to define puncta image pixels. The total puncta area and the average intensity of all segmented puncta pixels was calculated for each punctum.

To generate the line plot (FIG. 37H), the average puncta intensities for 'Postcut, Prewash', 'Postwash', and 'Re-probed' samples were divided by the average puncta intensity for the 'Postcut, Prewash' condition, taken as the baseline signal before diffusion. This resulted in the 'Normalized Average Puncta Intensity' value for each condition. The no restriction enzyme control (-BtsI) is plotted separately from the cleavage condition (+BtsI) in the line plot to display the difference in punctate fluorescence retention with and without cleavage by BtsI.

Example 7: Node Strand Generation

Figure 38A:
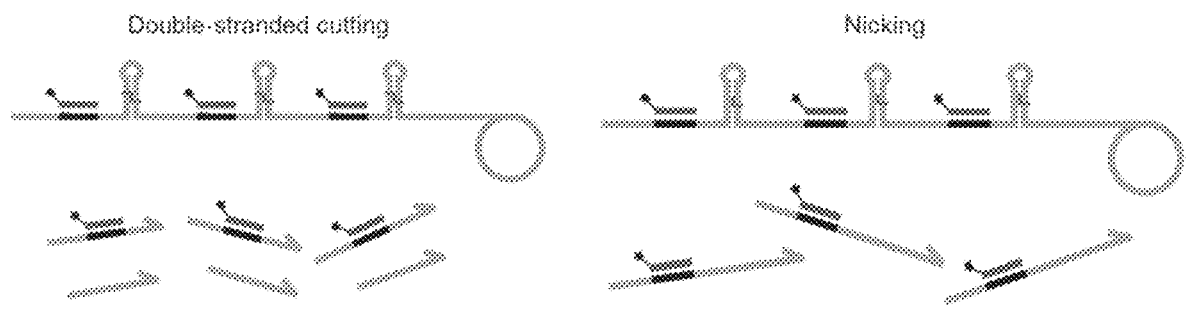
FIG. 38A is a schematic illustrating release of diffusive node strands from concatemers through cleaving of hairpin secondary structure by either double stranded cutting or nicking of hairpin structures.
Figure 38B:
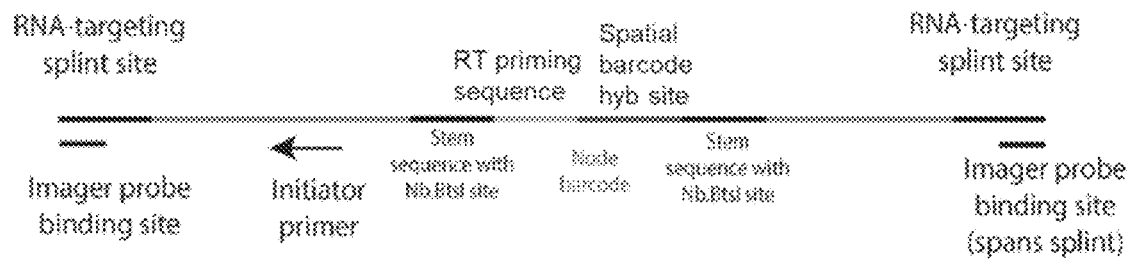
FIG. 38B is a schematic illustrating node strand generating padlock used in splinted ligation to generate the images in FIG. 38C.

While Example 6 demonstrated strand release by hybridizing an oligonucleotide, this example showed strand release by cleaving a hairpin that forms entirely from a nucleotide sequence in the padlock (FIG. 38B) and retained in the single stranded product of rolling circle amplification (FIG. 38A). This example also showed that this structure can be cleaved by either a restriction enzyme, which cuts both strands of the hairpin stem, or a nickase, which cuts only one strand. The two types of cuts resulted in the release of 2 strands or 1 strand per repeat, respectively (shown schematically in FIG. 38A).

Figure 38C:
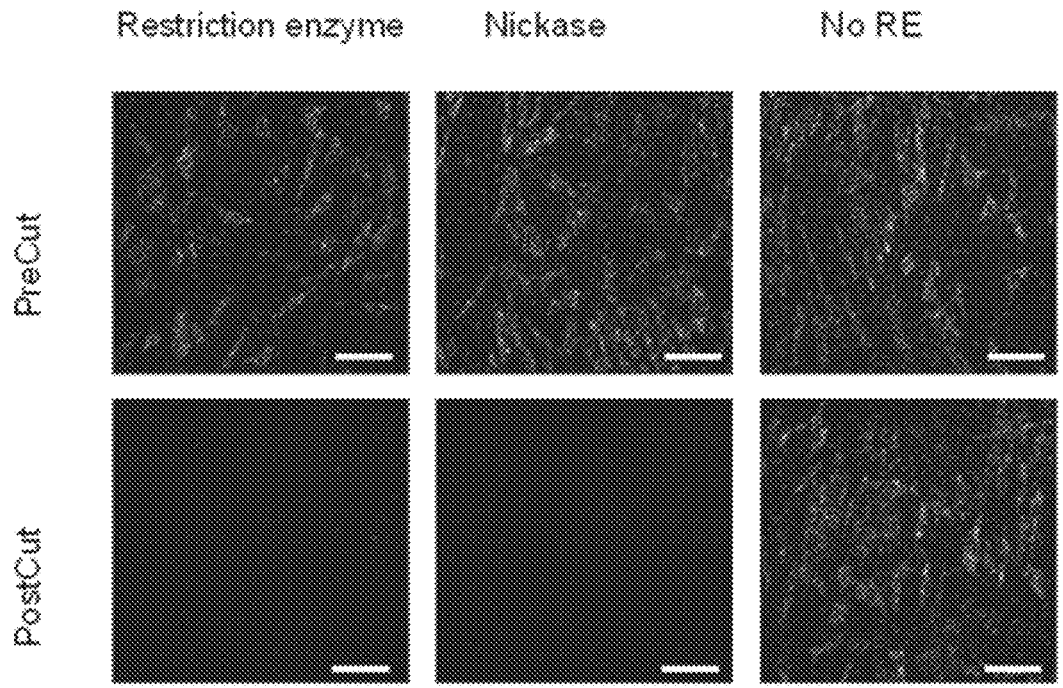
FIG. 38C are images illustrating cleaving at the hairpin compared to control without enzyme using either a double-stranded cutter (restriction enzyme) or a nickase. Temperature cycling and wash step were applied from 8° C. to 55° C. Scale bars: 100 µm.

The same methods were used as in Example 6 except as noted below. 'PreCut' images were acquired at 20× using a spinning disk confocal imager. A fluorescent probe was hybridized to the sample in a 1× SSC, 5% formamide, 0.1 μg/mL BSA solution with 0.06 μM probe concentration. Probe hybridization occurred at 33° C. for 30 minutes. Samples were then washed three times for 5 minutes with 10% formamide in 2× SSC at 33° C. and then three times for 1 minute with 6× SSC at room temperature. 'PreCut' images were acquired to view the RCA products before cleavage (FIG. 38C).

Samples were then treated with either a nickase (Nb.BtsI), restriction enzyme (Bts1-v2), or water (no restriction enzyme control) to cleave the RCA products in situ. Both enzymes recognize the oligonucleotide recognition site, GCAGTGNN. Samples were incubated in 2× CutSmart buffer with 300 μM dNTPs, 0.5% Triton-X-100, 6 mM RNaseOUT, and either 0.2 U/μL Nb.BtsI for the Nickase condition, 0.2 U/μL BtsI-v2 for the Restriction Enzyme condition, or water. Samples were placed in a thermocycler and run on the following program: 15 cycles of 55° C. for 30 s, 50° C. for 30 s, 8° C. for 30 s, 15° C. for 30 s, 25° C. for 30 s, 30° C. for 1 min, 37° C. for 1 min, 42° C. for 2 min, followed by 50° C. for 30 min.

Samples were then washed with 6× SSC, 2×1 minute 60% formamide in 1×PBST, 2×1 minute in 1× PBT with 1 M NaCl, followed by 2×1 minute in PBST. The same imaging probe hybridization as described above was performed again to detect and image the RCA products post-cleavage. Slides were imaged with the same acquisition conditions to capture the Cy3 imaging channel with spinning disk confocal imaging. PreCut and PostCut images were equally acquired, zoomed, and contrasted for display in the figure (FIG. 38C).

Example 8: Ligase Concentration Modulates Strand Generation

This example shows that the density of node sources can be controlled by modulating the concentration of ligase used to transform the padlock probe into a closed circle, on which Phi29 can perform RCA. Control of node source density is particularly useful for spatial inference of relative cellular and subcellular localization through handshakes (interaction of node strands from the same and/or different node locations). For instance, denser nodes may improve resolution, while increasing the depth of handshake sequencing required; whereas, sparse nodes may provide sufficient information for larger scale spatial reconstruction, while reducing the sequencing depth required to achieve reliable spatial reconstruction.

The same methods were used as in Example 6 except as noted below. Padlock probe hybridization was performed with padlock probe (FIG. 39B) concentration of 0.05 μM in the Blocking solution, without addition of blocking oligo. Padlock probes were ligated in Ligation Solution consisting of 1× T4 RNA ligase buffer, 0.01 mM ATP, 0.2 μg/μl BSA, 1 U/μl RiboLock, and varying concentrations of SplintR ligase as shown in the figure. Incubation time was for either 1 hour or 16 hours (overnight) at room temperature, followed by two 1 minute washes with PBST.

RCA was then performed in a mix with 1× Phi29 buffer, 5% glycerol, 0.2 μg/μL of BSA, 0.25 mM dNTPs, 0.1 μM of RCA primer and 0.5 U/μl of Phi29 Polymerase. Samples were incubated for 2 hours at 30° C. and then washed twice for 1 minute with PBST. Samples were then fixed with 4% PFA in 1×PBS for 5 minutes at room temperature, and were washed 3 times for 1 minute with PBST, three times for 5 minutes with 65% formamide at 30° C., and twice for 1 minute with PBST.

RCA products were then detected through hybridization of a 3' Cy3 labeled fluorescent probe complementary to the RCA product. Probe was hybridized to the sample in a 1× SSC, 5% formamide, 0.1 μg/mL BSA solution with 0.06 μM probe concentration. Probe hybridization occurred at 33° C. for 30 minutes. Samples were then washed three times for 5 minutes with 10% formamide in 2× SSC and then three times for 1 minute with 6× SSC.

Figure 39A:
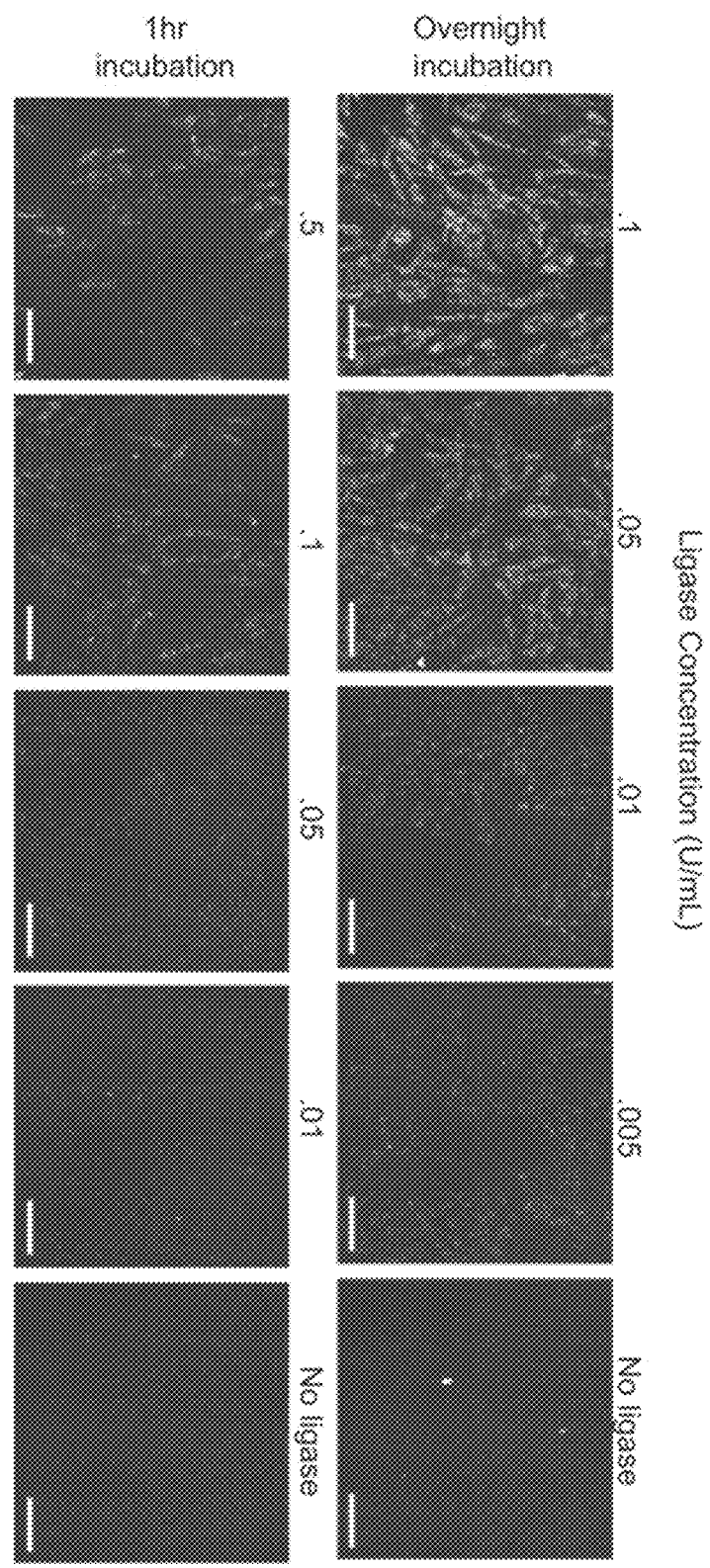
FIG. 39A are images illustrating node strand-generating concatemer density through ligation parameters showing differences in puncta (concatemer) density across concentrations of SplintR Ligase in the reaction for 2 different incubations times—1 hr and Overnight (~16 hours). Scale bars: 100 µm.
Figure 39B:
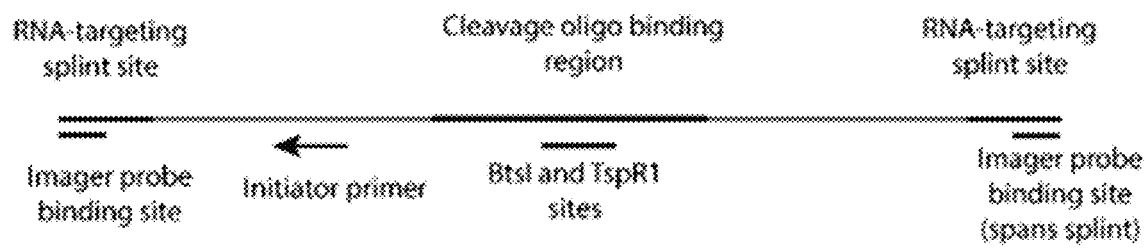
FIG. 39B is a schematic illustrating node strand generating padlock used in splinted ligation to generate the line graph in FIG. 39C.
Figure 39C:
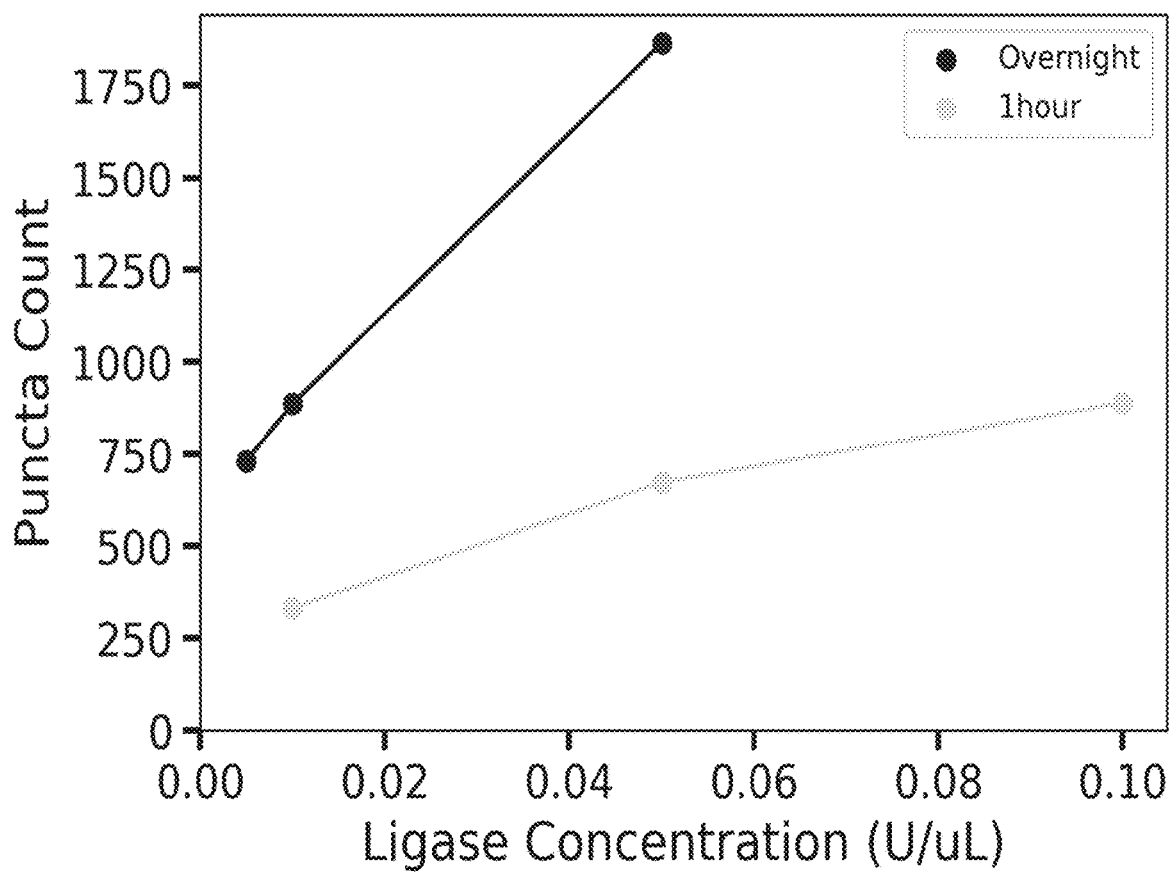
FIG. 39C is a graph illustrating quantification of puncta per field of view across lower ligase concentration conditions with resolvable puncta. Higher ligase concentration conditions are excluded from quantification due to inability to resolve individual puncta in the imaging conditions.

Images were acquired with equivalent acquisition parameters for all samples and maximum intensity projections of z-stack images are shown in the figures (FIG. 39A). The images showed differences in puncta (concatemer) density across concentrations of SplintR Ligase in the reaction for 2 different incubation times—1 hr and Overnight (~16 hours). FIG. 39C showed quantification of puncta per field of view across lower conditions with resolvable puncta. Higher concentration conditions were excluded from quantification due to the inability to resolve individual puncta in the imaging conditions used.

Example 9: Minimal Off Target Amplification

A risk in generating node strands with polymerases in situ is that they may amplify undesirable templates (for example genomic DNA), producing background. One limitation of detecting nodes using probes is that the probes are sequence specific and don't allow visualization of unknown, unintended targets. To circumvent this, a modified dNTP (DIG-dUTP) was used, which had a DIG hapten recognizable by an antibody. The antibody is conjugated to HRP, and produces a fluorescent signal deposition in the presence of fluorescently-labeled tyramine and peroxide. Any significant amplification of a background template that includes A bases should be visible. The results demonstrated that minimal off-target amplification was detected. Many other types of modified dUTP bases exist, which may also be useful for incorporation during node strand generation. For example, incorporation of modifications that enable efficient cross-linking of strands. These additional types of modifications are not shown.

Figure 40A:
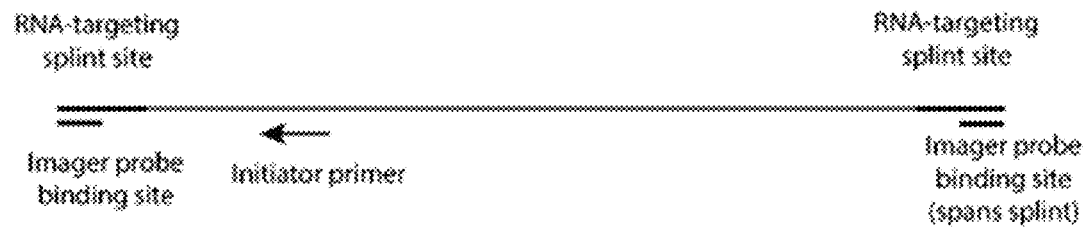
FIG. 40A is a schematic illustrating node strand generating padlock used in splinted ligation to generate the images in FIG. 40B.

The same methods were used as in Example 6 except as noted below. A padlock probe (FIG. 40A) was hybridized at 1 μM concentration. Controls (-Padlock (no padlock) conditions) comprised water in lieu of the padlock probe. Padlock probes were then ligated for 16 hours at 25° C.

Figure 40B:
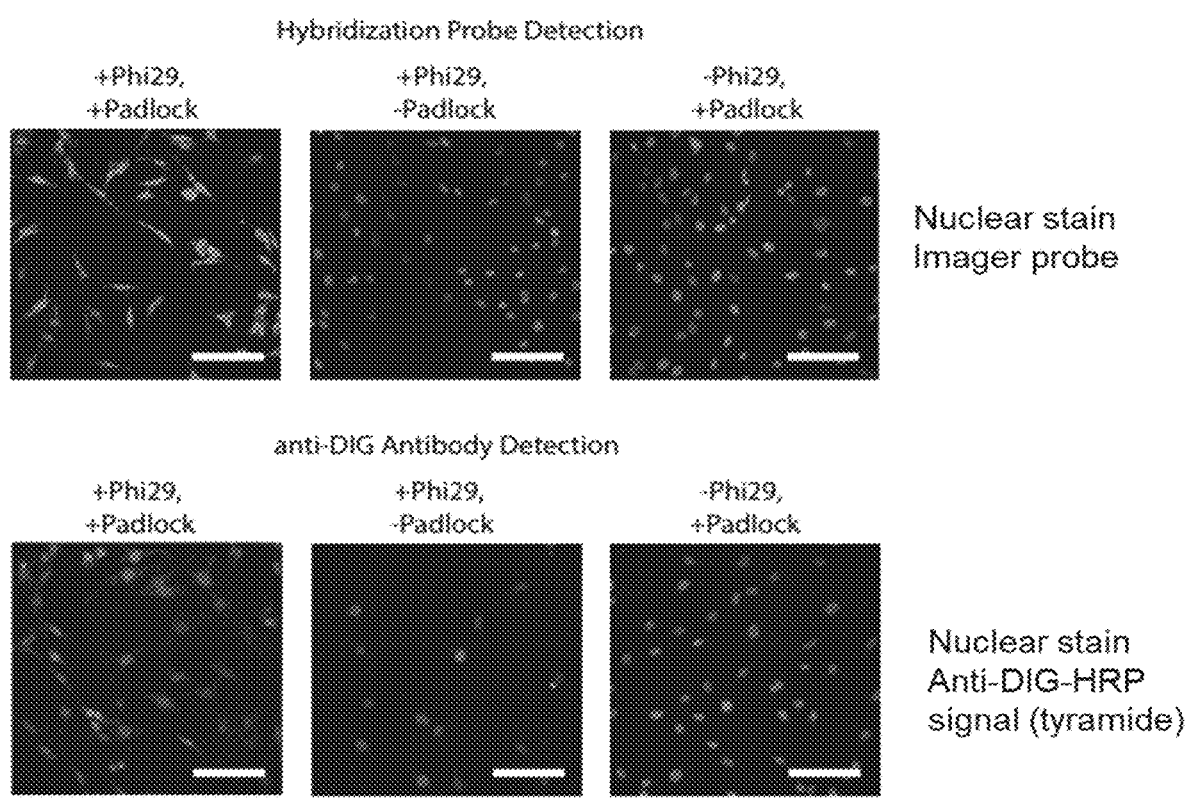
FIG. 40B are images illustrating hybridization probe detection and anti-DIG antibody detection. Scale bars: 100 µm.

The samples shown in the top row of FIG. 40B were treated with normal dTTP in the RCA reaction, while the samples on the bottom received DIG-modified uracil deoxynucleotides (DIG DNA labeling mix, Millipore Sigma) to incorporate into the RCA product during polymerization. The mix contained 1 mM dATP, 1 mM cCTP, 1 mM dGTP, 0.65 mM dTTP, 0.35 mM DIG-dUTP. This enabled detection of the RCA products by anti-DIG antibodies downstream, for an amplified detection readout (FIG. 40B).

RCA reaction was carried out at 30° C. for 2 hours, and slides were washed twice for 1 minute with PBST. Slides were fixed with 4% PFA in 1×PBS for 5 minutes at room temperature, followed by three 1 minute washes with PBST. Slides were then washed three times for 5 minutes with 65% formamide at 30° C., followed two 1 minute washes with PBST.

RCA products were then detected by fluorescent probe hybridization (top row) or anti-DIG antibody (bottom row). For probe detection, a 3' Cy3 labeled probe oligo complementary to the RCA product was hybridized to the sample in a solution of 1× SSC, 5% formamide, 0.06 μM Probe, 0.1 μg/mL BSA for 20 minutes at room temperature, protected from light. Slides were then washed three times for 5 minutes with 10% formamide in 2× SSC and three times for 1 minute with 6× SSC comprising DAPI added at 1:1000 dilution from a 2 mg/mL stock solution. Slides were then imaged in SlowFade mounting media with a spinning disk confocal microscope, as described below.

For DIG-based detection, samples were incubated with Blocking Buffer. First, TNT-x buffer was made with 100 mM Tris-HCl, 150 nM NaCl, and 0.25% Triton-X-100. Then, 1% Block Powder Solution was created by dissolving block powder (Roche in situ hybrdiziation blocking reagent, Millipore Sigma) to 1% in TNT-x buffer (w/v). Finally, a 1:1 solution of 1% Block Powder Solution:5% Normal Donkey Serum (Fisher Scientific) in TNT-x buffer was made to formulate the Blocking Buffer. Samples were incubated in Blocking Buffer for 10 minutes at room temperature.

Samples were then treated with anti-DIG-HRP (Anti-Digoxigenin-POD, Fab Fragments, Millipore Sigma) antibody at a concentration of 1:2000, incubated for 1 hour at room temperature, followed by four 5 minute washes with TNT-x buffer.

Tyramide staining was performed with 0.5 µM-1 µM of tyramide incubated for 10 minutes at room temperature, protected from light. Samples were then washed three times for 5 minutes with 1×PBS with 0.25% Triton-X-100 (PB-STx) and once with 1×PBS before application of SlowFade mounting media and imaging.

Cells were imaged with an inverted Nikon Ti2-E microscope equipped with a Yokogawa CSU-W1 single disk spinning disk (50 µm pinhole size) using a 20× objective. Fluorescence was acquired from 405 nm and 560 nm through spinning disk confocal imaging, labeling nuclei and RCA product-detecting fluorescent probes, respectively. Z-stack images were acquired through the depth of the cells. For display in the figure, z-stack images were maximum intensity projected and equally contrasted. Images were acquired near the boundary of illumination, to capture the boundary in fluorescent signal at the boundary of UV-illuminated areas (FIG. 40B).

Figure 41A:
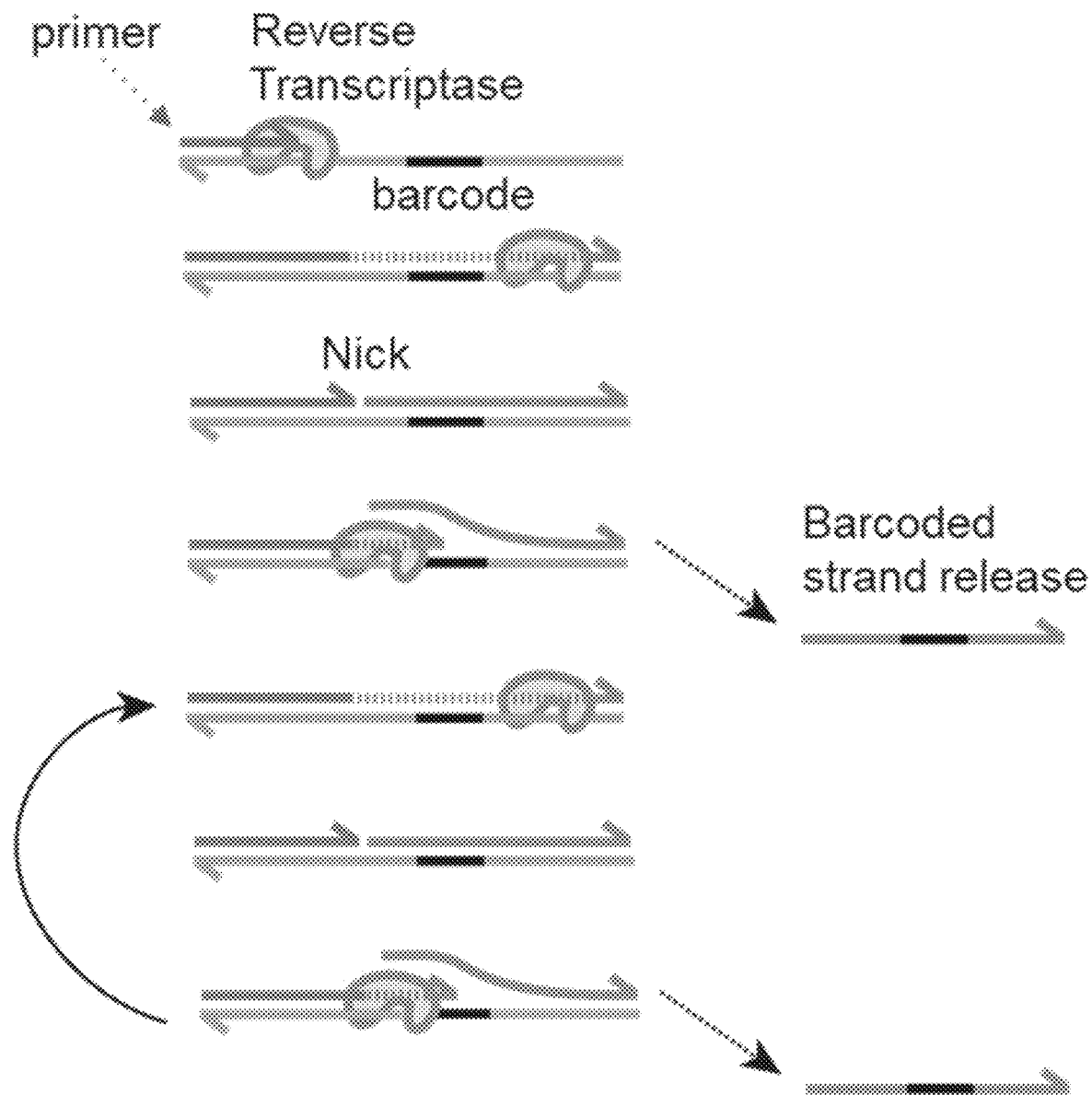
FIG. 41A is a schematic illustrating an exemplary isothermal method for generating barcoded node strands using reverse transcriptase and a nickase.

Example 10: Isothermal Generation of Barcoded Node Strands Using Reverse Transcriptase and Nickase Other mechanisms to generate single stranded DNA node strands may be useful instead of, or in addition to, RCA. Here, it was demonstrated that single stranded DNA strands can be generated by combining a polymerase (specifically a reverse transcriptase) and a nickase (FIG. 41A). The use of the reverse transcriptase is significant because 1) this has the potential to be paired in a single reaction with reverse transcription of mRNA using the generated strands, with no other polymerase required and 2) the product bands have a relatively uniform size compared to methods that involve nicking and conventional strand displacing DNA polymerase (such as BST), which typically results in a large number of byproducts. This was observed whether starting from a double stranded or single stranded template, as well as when the template included a randomized Barcode Sequence.

Figure 41B:
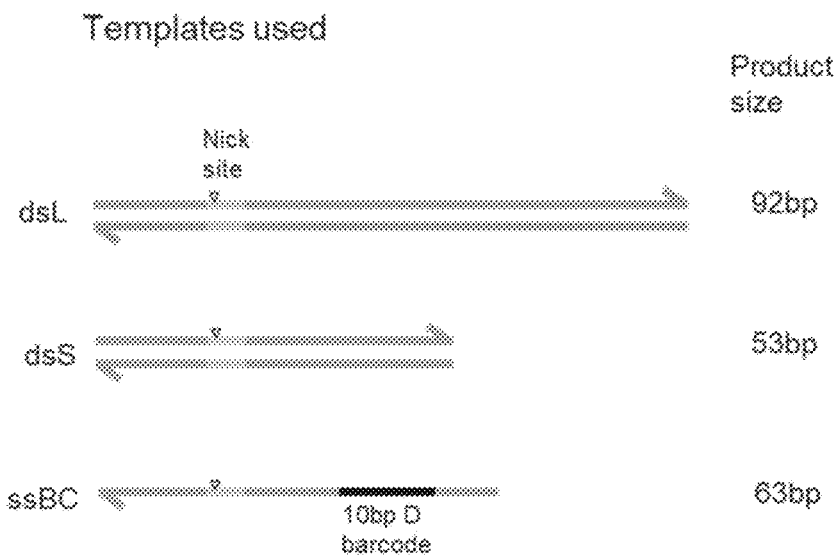
FIG. 41B is a schematic illustrating template strands.
Figure 41C:
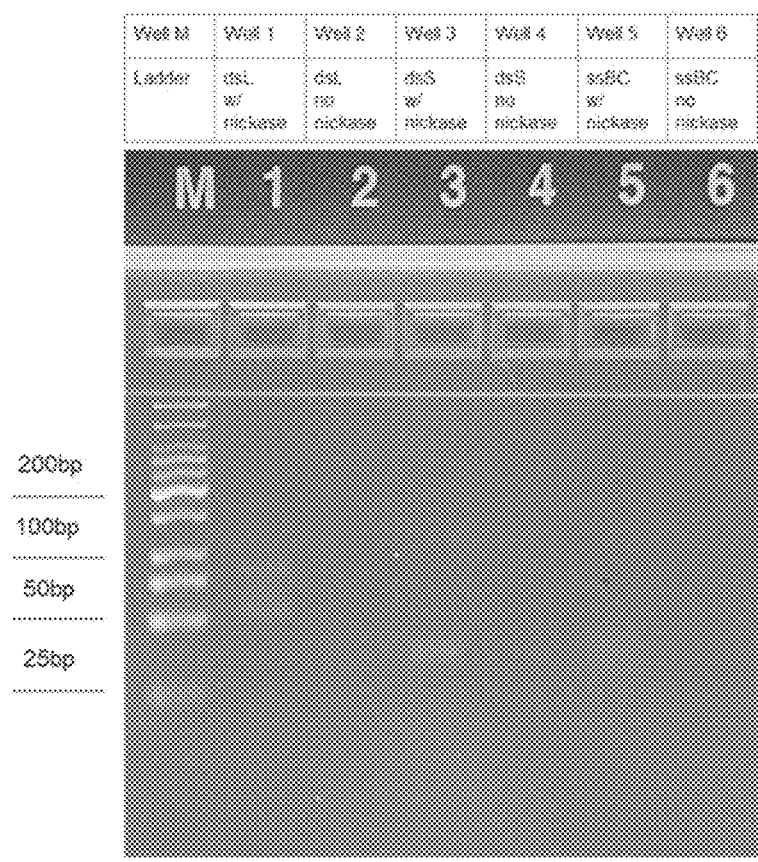
FIG. 41C is a gel illustrating gel products from templates of varying size and starting structure, amplified using an isothermal reaction with reverse transcriptase and nickase.

The three templates (FIG. 41B) were amplified in a reaction comprising of 0.0005 uM template, 1 U/µl Nb.BssSI nickase (NEB), 1 U/µl Maxima RT enzyme (Thermo Fisher), 1× Maxima RT Buffer, 0.625 mM dNTP, and 0.0005 uM of an "initiator primer" with the binding site located upstream of the Nickase site. Nb.BssSI recognized a CACGAG sequence on the templates. No nickase control reactions comprised water in place of the nickase enzyme. The reaction was incubated for 1 hour at 50° C., followed by inactivation at 85° C. for 5 minutes. Products were diluted 1:10 in H20 and analyzed on a 4% ex-gel, against NEB low MW ladder loaded at 100 ng (FIG. 41C). FIG. 41C showed gel products from templates of varying size and starting structure that were amplified using an isothermal reaction with RTase and nickase.

Figure 42A:
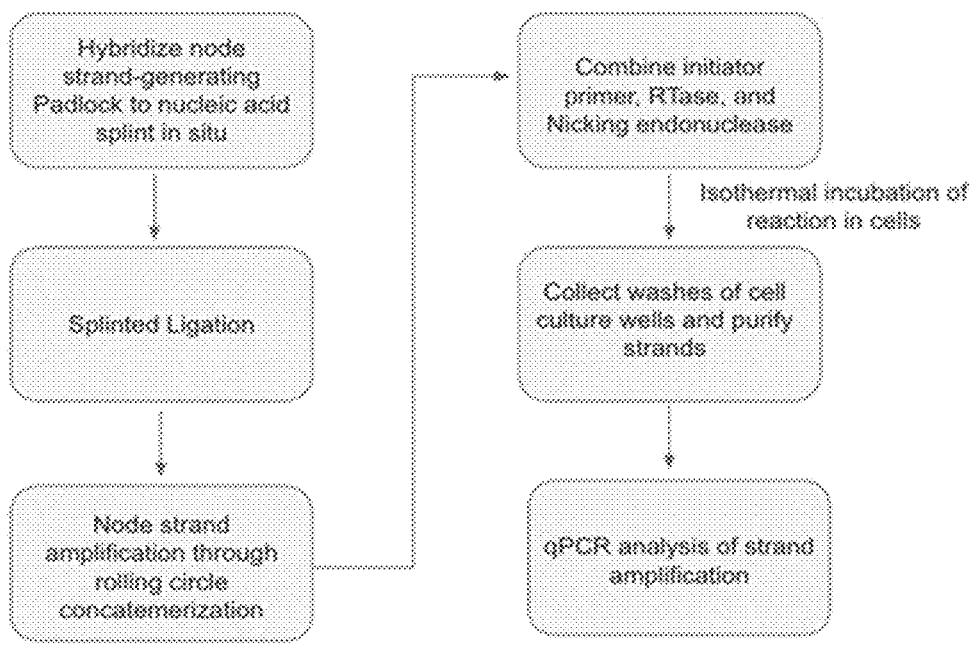
FIG. 42A is a schematic illustrating an isothermal method for generating barcoded node strands using reverse transcriptase and nickase on a concatemer template in situ.
Figure 42B:
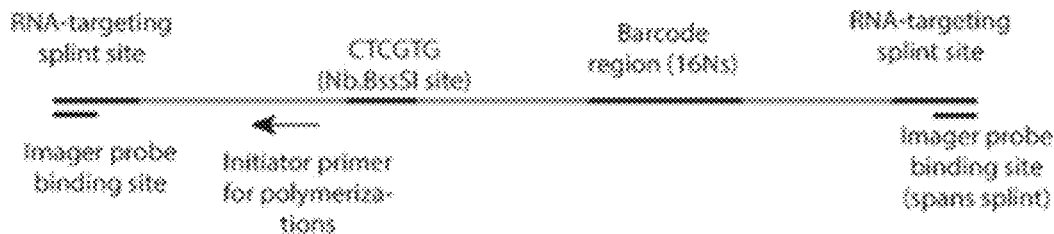
FIG. 42B is a schematic illustrating node strand generating padlock used in splinted ligation to generate the bar graph and gel images in FIGS. 42D and 42E, respectively.
Figure 42C:
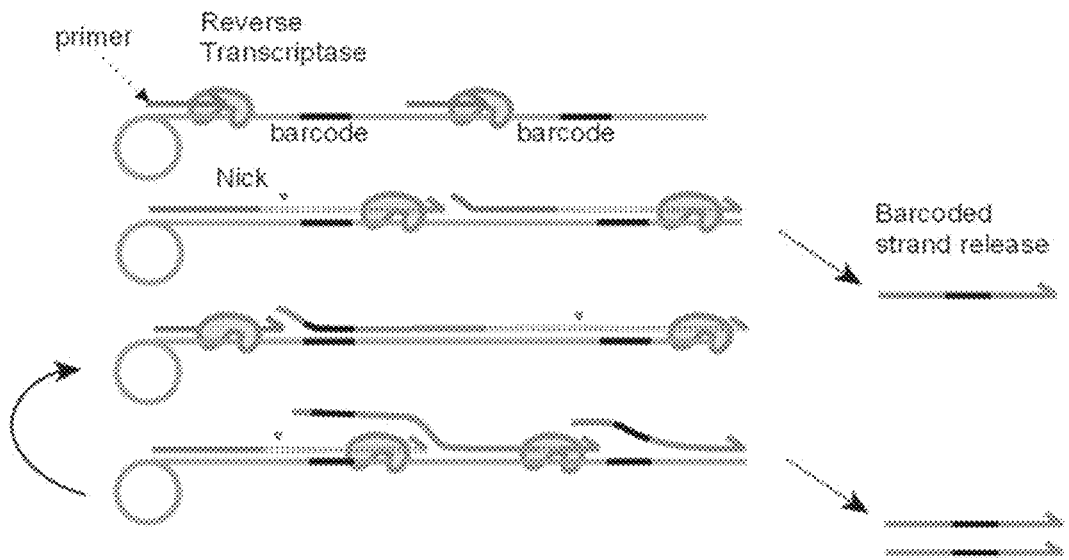
FIG. 42C is a schematic illustrating an isothermal method for generating barcoded node strands using reverse transcriptase and nickase on a concatemer template in situ.

Example 11: Isothermal Generation of Barcoded Node Strands Using Reverse Transcriptase and Nickase on a Concatemer Template In Situ Example 10 established that Reverse Transcriptase and Nickase were effective at generating single stranded products. This example showed that this method workflow (FIG. 42A) can be applied to a single stranded DNA template generated by RCA, and that it can be applied in situ. The combination of these two enzymes can be useful for amplifying the number of node strands that can be generated from a node source (FIG. 42C). A 250-fold or greater increase in the abundance of node strand produced was observed from node sources when the two enzymes are combined in situ in cells. The resulting product has the expected structure as assessed by gel, with some expected banding due to the fact that the reaction is occurring on a repetitive template. The combination of these enzymes is expected to be compatible with simultaneous reverse transcription of mRNA, and may also be useful as a mechanism for generating handshakes. In the latter case, the released strands may initiate polymerization on other node sources (RCA products) and result in conjugation of barcodes (not shown).

The same methods were used as in Example 6 except as noted below. Padlock probes (FIG. 42B) were ligated in Ligation Solution. RCA was then performed in a mix with 1× Phi29 buffer, 5% glycerol, 0.2 µg/µL of BSA, 0.25 mM dNTPs, 0.1 µM of RCA initiator primer and 0.5 U/µl of Phi29 Polymerase. Samples were incubated for 2 hours at 30° C. and then washed twice for 1 minute with PBST, three times for 5 minutes with 65% formamide at 30° C., and twice for 1 minute with PBST. Samples were then treated with 2 mM EDTA for 15 minutes at 70° C., followed by 3 washes in PBS.

Figure 42D:
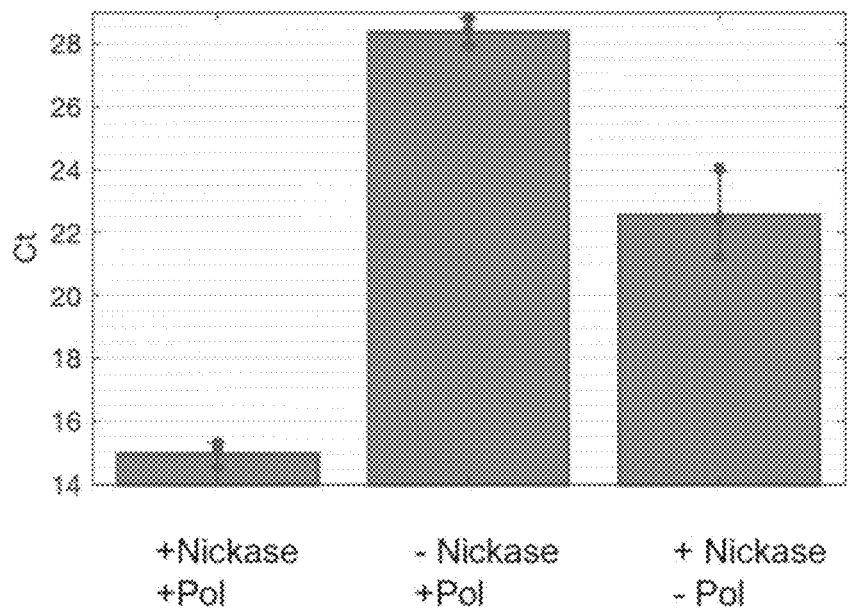
FIG. 42D is a bar graph illustrating qPCR quantification of strand generation in situ from concatemer template, showing a large increase in strand concentration compared to controls that lack essential components of the reaction (Nickase and Reverse transcriptase (Pol)).
Figure 42E:
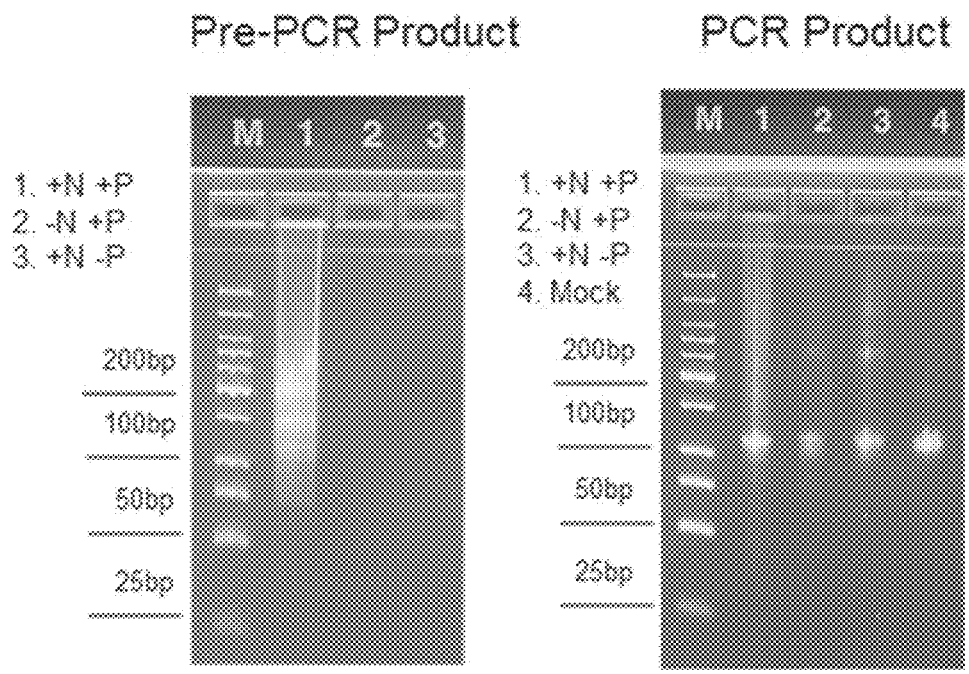
FIG. 42E are gels illustrating product size ranges from purified, unamplified cell supernatant and from PCR amplification. (PCR products are amplified to completion, and intensity does not reflect input abundance). "Mock" lane corresponds to a synthesized DNA strand with the size and sequence structure of the expected amplicon generated from the reaction. The gel shows that sizes correspond between expected control and the reaction products. N=Nickase; P=RT Polymerase.

RCA products were amplified in a reaction comprising of 1 U/µl Nb.BssSI nickase (NEB), 8 U/µl Maxima RT enzyme (Thermo Fisher), 1× Maxima RT Buffer, 0.625 mM dNTP, and 0.625 nM of RCA initiator primer 3. No nickase and no RT controls substituted the respective enzymes with water in the reaction. Reactions were incubated for 2 hours at 50° C., after which the reaction mixture was recovered from the wells and bead purified on Ampure beads at a ratio of 2:1 bead:sample, followed by elution in water. 10 µl of eluted sample was run on a 4% agarose gel for size analysis. FIG. 42E showed product size ranges from purified, unamplified cell supernatant and from PCR amplification.

For qPCR analysis, a FAM-labeled qPCR probe and forward and reverse primers targeting padlock sequence were used in a reaction with Luna universal probe qPCR master mix (NEB). The program was 95° C. 60 s, then 35 cycles at [95° C. 15 s, 60° C. 30 s]. FIG. 42D showed that qPCR quantification of strand generation in situ from concatemer template exhibited a large increase in strand concentration compared to controls that lack essential components of the reaction (Nickase and Reverse transcriptase (Pol)).

Example 12: Single Node to Generate Node Nucleic Acids and Target Nucleic Acids A node factory generated RCA machinery to generate both node nucleic acids and target nucleic acids in alternating repeats in a single concatemer. Restriction sites between each repeat allow for cleavage and release of all generated nucleic acids at the same time.

Padlock probes comprising template sequences encoding alternating repeats of a node nucleic acid and target nucleic acid are generated according to the workflow shown in FIG. 43A. Briefly, padlock probes with two distinct barcode sequences are hybridized in situ to nucleic acid splints. The padlock probes are ligated to circularize the nucleic acid. A polymerase and dNTPs are added to generate concatemers by rolling circle amplification. Short cleaving domain oligonucleotides are then added to reconstruct double-stranded restriction enzyme sites. Samples are then incubated with reverse transcriptase and restriction enzyme and after incubation, the reaction supernatant is collected from the cells. Three sets of nucleic acids are analyzed in downstream steps: 1) cDNAs generated during reverse transcription are A-tailed and released from the cells using an RNAse treatment before purification, amplification, and sequencing, 2) handshake products are purified, amplified, and sequenced, and 3) incompletely cleaved node factory concatemers are amplified across regions containing node-barcode pairs and can be sequenced.

3T3 cells were seeded and grown overnight in glass-bottom chamber slides. The next day, media was removed and the cells were washed with pre-warmed DPBS (no calcium, no magnesium) before fixation with 4% paraformaldehyde solution in 1×PBS (4% PFA). Cells were incubated in fixative for 5 minutes at room temperature before washing 2×2 minutes in 1×PBS with 0.1% Tween-20 (PBST).

Cells were permeabilized with 1×PBS with 0.25% Triton-X-100 (PBSTx) for 10 minutes, then washed with 2×1 minute with 1×PBS. Finally, cells were washed with PBST twice for 2 minutes.

Blocking solution comprised of 1× Ampligase Buffer (Thermo Fisher Scientific, Waltham, MA), 0.05M KCl, 20% formamide, 0.1p M Blocking Oligo, 0.2 µg/mL of BSA, 1 U/µl RiboLock (Thermo Fisher), and 0.2 µg/µl yeast tRNA (Thermo Fisher). Blocking solution was incubated with the sample for 30 minutes at room temperature and then washed twice for 1 minute with PBST.

Two padlock probes (Type 1 and Type 2) were hybridized to the sample, each at a final incubation concentration of 50 nM during padlock hybridization. Padlock Hybridization Solution consisted of: 1× Ampligase Buffer, 0.05M KCl, 20% formamide, 0.2 µg/µl BSA, and 0.2 µg/µl yeast tRNA. Cells were incubated for padlock hybridization at 55° C. for 15 minutes, followed by 45° C. for 120 minutes. Slides were then washed 3×5 minutes with Wash Buffer (10% formamide in 2× SSC), followed by 3 times 1 minute washes in PBST.

Padlock probes were ligated in Ligation Solution consisting of 1× T4 RNA ligase buffer, 10 nM ATP, 0.2 µg/µl BSA, 0.5 U/µL SplintR, and 1 U/µl RiboLock. Incubation time was 2 hours at room temperature, followed by two 1 minute washes with PBST.

RCA was performed with 1× Phi29 Buffer, 5% glycerol, 0.2 µg/µl BSA, 0.25 nM dNTPs, 0.1 µM RCA initiator primer, and 0.5 U/µl Phi29 polymerase. Samples were incubated at 30° C. for 2 hours, then washed 5 times 1 minute with PBST, 3×5 minutes with 65% formamide at 30° C., and two 1 minute washes in PBST. Generated Type 1 and Type 2 concatemers are illustrated in FIG. 43B.

Cleaving Probe Hybridization

Cleavage oligos were hybridized to the sample in a solution of 1× SSC, 5% formamide, 60 nM imaging probe, 0.1 µg/mL BSA, and 60 nM cleavage oligo (Cleave Oligo 1). All cleavage oligos included 3' invdT to prevent degradation and polymerase extension of the cleavage oligos. In 'one-step' reaction with cleaving of both padlock oligos (RT oligo and handshake oligo), two additional cleavage oligos were delivered at 30 nM each (Cleave Oligo 2 and Cleave Oligo 3, for Type 1 and Type 2 nodes respectively). This solution was incubated at 33° C. for 30 minutes, and washed at 33° C. with 2×5 minutes in 10% formamide in 2× SSC, 3×1 minute with 6× SSC. For sequential release oligos, only Cleave Oligo 1 was delivered, to provide a nucleic acids comprising both handshake and RT oligos.

Digestion of RCA Products and Polymerization

A coupled digestion/polymerization reaction mixture was prepared composed of 0.3 mM dNTP (each), 2× CutSmart® Buffer (New England Biolabs (NEB), Ipswich, MA), 2.5% Triton-X, 3 mM RNAseOUT® (Thermo Fisher), 4 U/ul Maxima Reverse Transcriptase (Thermo Fisher), and 0.2 U/ul BtsI-v2 (NEB). No RT control received water in place of Maxima enzyme. "RT oligo added" control reaction received a 57 bp synthesized mimic of the predicted cleaved RT primer strand. Samples were incubated 50° C. 15 minutes, then 15 cycles of [60° C. 30 s, 50° C. 30 s, 8° C. 30 s, 15° C. 30 s, 25° C. 30 s, 30° C. 1 min, 37° C. 1 min, 42° C. 2 min], and 50° C. 15 minutes. The cleavage reaction generates four types of oligos as illustrated in FIG. 43C: two barcoded node nucleic acids with handshake hybridization regions and two barcoded target nucleic acids with RT primer sequences for hybridization to mRNA. Generation of the cDNA for the one step reaction is illustrated in FIGS. 43D-43E. Hybridization of the target node nucleic acid is illustrated in FIG. 43D. RT primer directs association of reverse transcriptase in FIG. 43E. The final generated target barcode/cDNA complex is shown in FIG. 43F. Generation of cDNA using sequentially released barcodes is illustrated in FIG. 43G and FIG. 43H. Hybridization of the combined node nucleic acids and target nucleic acids and association of the reverse transcriptase is shown in FIG. 43G. Completed generation of cDNA and addition of cleavage oligos to cleave the node barcode sequences is shown in FIG. 43H. After the final incubation step, the reaction mixture was collected and stored, and then a 6× SSC wash was performed, which was also collected and stored. Both samples were heat inactivated at 85° C. for 5 minutes. Following the 6× SSC wash, samples were washed 2×1 minute 60% formamide in 1×PBST (0.1% Tween), 2×1 minute in 1×PBST with 1M NaCl followed by 2×1 minute in PBST.

Second Digestion of RCA Products and Polymerization

For samples with sequential release of handshake strands, samples were hybridized as in the first round, but with 30 nM each of Cleave Oligo 2 and 3, and without the imager probe. Digestion/Polymerization reaction and cycling programs were conducted as in the first round. In the second round, "No RT" control samples again received reaction mix without Maxima Reverse Transcriptase. "RT oligo added" control reaction did not receive reaction mix for the second round, and was kept in PBST. Washes and handshake collection was conducted as for the first round.

Preparation of cDNA for NGS cDNA was a-tailed using a reaction mixture comprised of 1× ThermoPol® reaction buffer (NEB), 1 mM dATP, and 2 U/mL of TdT enzyme (NEB). Cells were incubated in the reaction mixture for 45 minutes at 37° C., followed by 3 washes in PBST. Subsequently, cDNA was released by incubating the cells in an RNAseH displacement reaction consisting of 1× ThermoPol® Buffer and 200 U/mL of RNAseH (NEB). Cells were incubated in displacement reaction for 45 minutes at 37° C., and the reaction was recovered from wells and heat inactivated at 75° C. for 20 min, followed by purification with Ampure beads at a 1:1.8 sample:bead ratio, followed by elution in water.

Second strand synthesis was performed using an 'SSS oligo' consisting of 10 Ts on the 3' end, a 6N barcode, and a primer binding sequence for downstream PCR amplification. The second strand synthesis reaction comprised of 1× ThermoPol® Buffer, 0.1 mM dNTP, 0.02 μM SSS oligo, 0.75 U/μL of BST polymerase large fragment (NEB), and ~⅓rd of the recovered cDNA product (11 μL). Samples were incubated at 37° C. for 30 minutes, followed by a 20 minute inactivation at 80° C.

Second strand synthesis product was first amplified by PCR, with one side of the product containing a custom primer sequence for R1 of NGS, and the other side of the product containing the PCR amplification handle introduced at second strand synthesis. PCR reaction was performed with Q5 (NEB) manufacturer recommended PCR conditions. SYBR stain was included in the reaction to assess qPCR Ct values. FIG. 43I is a bar plot of Ct values showing qPCR quantification of cDNA library demonstrating significantly higher concentrations of input cDNA library generated from node strands than in negative controls, and comparable concentrations to library generated by addition of synthesized RT oligos. Synthesized RT oligos share the same RT priming sequence and overhang sequence for amplification and NGS analysis as strands released by nodes: samples receiving an oligo of the predicted cleaved RT primer strand acted as a positive control for high levels of input cDNA. Samples in which no Phi29 polymerase was added showed anticipated low levels of input cDNA.

Samples were run on a 4% agarose gel to assess size. FIG. 43J is an image of the gel showing size range of amplified cDNA in the experimental condition and controls. Negative control indicates that the majority of the product smear cannot be explained as amplification of cellular DNA.

Samples were then diluted 1:3,750 in water, with primers that attach P5 Illumina adapter and i5 indices to the custom primer side of the amplicon, and that attach R2-i7-P7 to the opposite side. Samples were pooled and bead purified using a 1:0.8 sample:bead ratio. Samples were sequenced on the MiniSeq (Illumina) platform using standard manufacturer-recommended settings and custom R1 and i5 sequencing primers. In all PCRs, samples were removed from the cycler at ~0.5 max Rn to prevent overamplification. FIG. 43K is a barplot showing the proportion of node strand-barcoded cDNAs that conform to the expected amplicon structure based on NGS reads. The sample generated by RT from node strands exhibits high levels of expected structure when compared to the positive control, which was generated with mimic oligos added without amplification. Negative control samples which received no reverse transcriptase showed a relatively low proportion of reads with expected amplicon structure.

The proportion of generated barcoded cDNA attributed to Type 1 and Type 2 templates is illustrated in FIG. 43L. both node types contribute in nearly equal proportions to barcoding cDNA, when added to the reaction in an expected 1:1 molar ratio. The Added RT oligo control only exists as a single "type".

Preparation of Handshake Products for NGS

Pairs of generated node nucleic acids for handshake triangulation released from in situ concatemers copied each other's barcodes through annealing and extension. Node nucleic acids comprising complementary handshake sequences hybridized at the handshake region (FIG. 43M). Primers on each nucleic acid direct extension of each nucleic acid (FIG. 43N) to generate a double-stranded sequence comprising both node barcodes (FIG. 43O). Recovered reaction and first wash solutions from the first (one step) or second (sequential) were pooled 1:1 and purified with Ampure beads using a 1:1.8 sample to bead ratio. Products were amplified using Q5 PCR (standard manufacturer recommendations), with PCR primers that introduce a customer primer overhang for NGS.

SYBR stain was included in the reaction to assess qPCR Ct values. Ct values of different reaction conditions are shown in FIG. 43P. Node nucleic acids generated in a one step reaction or with sequential release both showed high levels of expression, represented as low relative Ct count, compared to similar samples without amplification or a negative control with no padlock probe.

Samples were run on a 4% agarose gel to assess size. An image of the gel is reproduced in FIG. 43Q, showing that products have the expected sizes for amplified handshake events. Lane M is a molecular weight ladder, with notations at 50 bp, 100 bp, and 200 bp. Lane 1 received product from a one step release of both node nucleic acids and target nucleic acids in a single nuclease step. Lane 2 received product from a sequential release of target nucleic acid followed by node nucleic acid. Lane 3 received mock template of the expected molecular weight. Band sizes are compared to a mock template (lane 3) that has the expected size and sequence composition of the handshake product. All PCRs are amplified to completion and band intensity is not representative of input concentration. Bands in lanes 1 and 2 show expected size barcodes generated with both methods of cleavage.

Amplified products were then diluted 1:500 in water, and indexed using primers that attach P5 Illumina adapter and i5 indices to the custom primer side of the amplicon, and that attach R2-i7-P7 to the opposite side. Samples were sequenced MiniSeq (Illumina) platform using standard manufacturer-recommended settings and custom R1 and i5 sequencing primers. In all PCRs, samples were removed from the cycler at ~0.5 max Rn to prevent overamplification.

NGS Analysis of cDNA

For cDNA analysis, reads were parsed using a regular expression based on the expected RT priming sequence, including Node Barcode and Node Type ID. Reads were trimmed at the PolyA tail, and reads with >15 bp sequence between the RT priming sequence and A-tail were mapped to the mouse genome. Deduplication was performed using the combination of cDNA sequence, barcode, and Type ID, or cDNA sequence and type ID for the "RT oligo added" control. For each sample, 100,000 reads were drawn randomly and the number of unique genes in the mouse genome that the cDNAs mapped was calculated. This calculation was repeated 30 times for each sample and the average computed. Results are illustrated as a bar plot in FIG. 43R, showing the detected genes by reverse transcription of the target strand is more than 90% of the positive control, using added oligonucleotides. Samples with no reverse transcriptase showed minimal detection. Results demonstrated that gene recovery is comparable between in situ generated node strand-priming and priming with RT oligos added to the reaction.

NGS Analysis of Handshake Structure

For Handshake analysis, reads were searched for the following five sequences by pairwise alignment: 1) Handshake PCR primer 1, 2) Handshake PCR primer 2, 3) Handshake sequence, 4) Node 1 ID+the first 10 bases of the Handshake sequence, and 5) the last 10 bases of the Handshake sequence+Node 2 ID. Ten bases of the Handshake sequence were included in the search for Node IDs (each with length of 4 bases) to ensure specificity of the alignment. Alignments were compiled and are shown in FIG. 43S. As shown, reads of the amplified handshake species confirms sequence generation with the expected size and structure of the handshake species.

Results indicate design is effective for generating handshakes. Evidence of abundant handshake structures compared to controls is evident by qPCR. Gel analysis shows handshake structures are of the expected size. Data confirmed that the vast majority of amplified handshakes conform to the expected structure and size of barcodes from two node types conjugated to one another. This demonstrates that one design can generate both barcoding cDNA and also generate nucleic acids for recording spatial information through proximity conjugation.

Example 13: Light-Directed Crosslinking to Node Nucleic Acids

Node-strand generating concatemers can be spatially barcoded using photo-induced crosslinking by CNVK. Light-directed modulation of barcoded nucleic acids allows for flexible control of barcoding with illumination photomasks. This example demonstrates crosslinking fluorescently labeled oligos to in situ-generated concatemers. Additionally demonstrated, cleavage of the concatemer with a nickase in the presence of reverse transcription allows for cross-linking oligos to cells by UV.

3T3 cells were seeded and grown overnight in glass-bottom chamber slides. The next day, media was removed and the cells were washed with pre-warmed DPBS (no calcium, no magnesium) and fixed with 4% paraformaldehyde solution in 1×PBS (4% PFA). Cells were incubated in fixative for 5 minutes at room temperature before washing 2×2 minutes in 1×PBS with 0.1% Tween-20 (PBST).

Cells were permeabilized with 1×PBS with 0.25% Triton-X-100 (PBSTx) for 10 minutes and washed with 2×1 min with 1×PBS. Cells were then washed with PBST 2×2 minutes.

Blocking solution comprised of 1× Ampligase Buffer (Fisher Scientific), 0.05M KCl, 20% formamide, 0.1 μM Blocking Oligo, 0.2 μg/mL of BSA, 1 U/μl RiboLock (Thermo Fisher), and 0.2 μg/μl yeast tRNA (Thermo Fisher). Blocking solution was incubated on the sample for 30 minutes at room temperature and then washed 2×1 minutes with PBST.

Padlock probes were generated as shown in FIG. 44A. The probe comprised 5' and 3' RNA-targeting splint sites, an initiator primer region, flanking stem sequences with an Nb.BtsI site flanking an RT priming sequence, a node barcode, and a spatial barcode hybridization site. 5' and 3' ends further comprised imager probe binding sites. Padlock probe hybridization was performed with padlock probe concentration of 0.05 μM in the Blocking solution, without addition of blocking oligos. Cells were incubated for padlock hybridization at 55° C. for 15 minutes, followed by 45° C. for 120 minutes. Slides were then washed 3×5 minutes with Wash Buffer (10% formamide in 2× SSC), followed by three 1 minute washes in PBST.

Padlock probes were ligated in Ligation Solution consisting of 1× T4 RNA ligase buffer, 0.01 mM ATP, 0.2 μg/μl BSA, 1 U/μl RiboLock, and 0.5 U/ul SplintR ligase. Incubation time was 2 hours at room temperature, followed by two 1 minute washes with PBST.

RCA was performed in a mix with 1× Phi29 buffer, 5% glycerol, 0.2 μg/μL of BSA, 0.25 mM dNTPs, 0.1 μM of RCA initiator primer, and 0.5 U/μl of Phi29 Polymerase. Samples were incubated for 2 hours at 30° C. and washed 2×1 minute with PBST, 3×5 minutes with 65% formamide at 30° C., and 2×1 minute with PBST. Generated concatemers formed secondary hairpin structures, as shown in FIG. 44B. The Nb.BtsI double-stranded recognition site was formed by the hairpin stem region.

A digestion/polymerization reaction mixture was prepared composed of 0.3 mM dNTP (each), 2× CutSmart® Buffer (NEB), 2.5% Triton-X, 3 mM RNAseOUT® (Thermo Fisher), 4 U/ul Maxima Reverse Transcriptase (Thermo Fisher), and 0.2 U/μl BtsI-v2 (NEB). No nickase control received water instead of enzyme. Samples were incubated 15 cycles of [55° C. 30 s, 50° C. 30 s, 8° C. 30 s, 15° C. 30 s, 25° C. 30 s, 30° C. 1 min, 37° C. 1 min, 42° C. 2 min], and 50° C. 15 min. Following incubation, samples received 2×6× SSC washes, 2×1 minute 60% formamide in 1×PBST (0.1% Tween), 2×1 minute in 1×PBST with 1M NaCl followed by 2×1 minute in PBST. cDNA was a-tailed using a reaction mixture comprised of 1× ThermoPol® reaction buffer (NEB), 1 mM dATP, and 2 U/mL of TdT enzyme (NEB). Cells were incubated in the reaction mixture for 45 minutes at 37° C., followed by 3 washes in PBST.

Next, samples were incubated with spatial barcode hybridization mix containing an oligo complementary to step loop in the RCA product as illustrated in FIG. 44C. This oligo contains a barcode, randomer sequence, a 3' Cy5 fluorophore, and a CNVK chemical group for photocrosslinking to the opposing strand. The mix was composed of 2 mg/mL salmon sperm DNA, 1× PBS, 0.5M NaCl, 10% Dextran Sulfate, 0.1% Tween-20, and 0.25 uM of the spatial barcode. Samples were incubated in the hybridization mix for 30 minutes at RT, followed by 3 washes in 1×PBST with 1M NaCl. As noted in FIG. 44C, the tagged oligo hybridized to and crosslinked to both digested and untreated RCA products.

Illumination with ultraviolet light was performed to induce photocrosslinking of the CNVK-containing oligos in select spatial locations using a Nikon Ti2-E microscope with a Mightex Polygon1000 DMD, with a 380 nm LED. Illumination was performed through a 20× objective. In each sample, two large rectangular fields of view were illuminated with 380 nm LED light: one field of view for 10 seconds at 20% power, and one field of view for 20 seconds at 20% power.

After UV illumination, samples were washed 4×60% formamide in 1×PBST (0.1% Tween) and 2×1× PBST with 1M NaCl to remove barcodes that were not photo-crosslinked. Nuclear Green was added to the sample at a concentration 2.5 μM to enable visualization of cells.

Cells were imaged with an inverted Nikon Ti2-E microscope equipped with a Yokogawa CSU-W1 single disk spinning disk (50 μm pinhole size) using a 20× objective. Fluorescence was acquired from 488 nm and 640 nm through spinning disk confocal imaging, acquiring z-stack images through the depth of the cells. For display in the figure, z-stack images were maximum intensity projected and equally contrasted. Images were acquired near the boundary of illumination, to capture the boundary in fluorescent signal at the boundary of UV-illuminated areas.

FIG. 44D provides images of cells treated with the nickase negative control, under low (upper row) and high (lower row) magnification, showing fluorescently stained nuclei (left panels) and, fluorophore-tagged oligos hybridized to node concatemers (right panels). FIG. 44E provides images of cells treated with nickase under high magnification, showing fluorescently stained nuclei (left panel) and fluorophore-tagged oligoes hybridized to node concatemers or released node target barcodes (right panel). The images show UV-induced crosslinking of spatial barcode strands to both cut and uncut concatemers, as evidenced by retention of signal in the illuminated region of interest (right panels in each figure) after stringent washes that melt non-crosslinked duplexes. Scale bars are 100 μm.

Example 14: Enrichment of Node Nucleic Acid Generation

When node templates are enriched within specific cell types (in this example through hybridization of padlock RCA probes to species-specific mRNA transcripts), RT priming from in situ generated node nucleic acids is biased to priming transcripts within the cell type targeted. Associated target nucleic acid barcodes and node nucleic acid barcodes from individual nodes can be amplified from recovered reaction, which can enable sequencing of the barcode associations. The designs produce Handshakes with expected structure and all four possible pairwise interactions. The node RT strand and node Handshake strand generator design was adapted such that two cell types (mouse and human) can be separately targeted with Type 1 and Type 2 padlocks, as presented in FIG. 45A. Two unique padlock probes targeting human Actb mRNA and two unique padlock probes targeting mouse Actb mRNA were generated for deposition on a mixed culture of HeLa and 3T3 cells. All four padlocks were individually ID'd on the target nucleic acid and node nucleic acid. Each padlock probe comprised: 5' and 3' species specific (mouse/human) RNA-targeting splint sites, a cleave oligo 1 binding site, RT primer sequence, specific (mouse/½an and type ½) target ID, 16D barcode, RT PCR primer sequence, cleave oligo 2 binding site and handshake sequence or cleave oligo 3 binding site and reverse complement of handshake sequence, second 16D barcode, specific node (Mouse-targeting, Type 1 and Type 2, Human-targeting, Type 1 and Type 2) ID, and handshake PCR primer. 3' and 5' ends further comprise imager probe binding sites and an initiator primer sequence.

HeLa and 3T3 cells were seeded and allowed to grow overnight in glass-bottom chamber slides. The next day, media was removed and the cells were washed with pre-warmed DPBS (no calcium, no magnesium) before fixation with 4% paraformaldehyde solution in 1×PBS (4% PFA). Cells were incubated in fixative for 5 minutes at room temperature before washing 2×2 minutes in 1×PBS with 0.1% Tween-20 (PBST).

Cells were then permeabilized with 1×PBS with 0.25% Triton-X-100 (PBSTx) for 10 minutes, then washed with 2×1 minute with 1×PBS. Finally, cells were washed with PBST 2×2 minutes.

Blocking solution comprised of 1× Ampligase Buffer (Fisher Scientific), 0.05 M KCl, 20% formamide, 0.1 μM Blocking Oligo, 0.2 μg/mL of BSA, 1 U/μl RiboLock (Thermo Fisher), and 0.2 μg/μl yeast tRNA (Thermo Fisher). Blocking solution was incubated with the sample for 30 minutes at room temperature and then washed 2×1 minutes with PBST.

The four padlock probes (Mouse-targeting, Type 1 and Type 2, Human-targeting, Type 1 and Type 2), have structures as illustrated in FIG. 45B, were hybridized to the sample, each at a final incubation concentration of 50 nM during padlock hybridization. Padlock Hybridization Solution consisted of: 1× Ampligase Buffer, 0.05M KCl, 20% formamide, 0.2 μg/μl BSA, and 0.2 μg/μl yeast tRNA. Cells were incubated for padlock hybridization at 55° C. for 15 minutes, followed by 45° C. for 120 minutes. Slides were then washed 3×5 minutes with Wash Buffer (10% formamide in 2× SSC), followed by 3×1 minute washes in PBST.

Padlock probes were ligated in Ligation Solution consisting of 1× T4 RNA ligase buffer, 10 nM ATP, 0.2 μg/μl BSA, 0.5 U/μL (FIG. 45D-F) or 0.05 U/μL (FIG. 45G-H) SplintR Ligase, and 1 U/μl RiboLock. Incubation time was 2 hours at room temperature, followed by 2×1 minute washes with PBST.

RCA was performed with 1× Phi29 Buffer, 5% glycerol, 0.2 μg/μl BSA, 0.25 nM dNTPs, 0.1 μM RCA initiator primer, and 0.5 U/μl Phi29 polymerase. Samples were incubated at 30° C. for 2 hours, then washed 5×1 minutes with PBST, 3×5 minutes with 65% formamide at 30° C., and 2×1 minute in PBST. Concatemers of repeating sequences illustrated in FIG. 45C were generated.

Cleave oligo 1 and probes detecting mouse (Cy3) and human (FAM) padlocks were hybridized to the sample in a solution of 1× SSC, 5% formamide, 60 nM each imaging probe, 0.1 μg/mL BSA, and 60 nM cleavage oligo. FIG. 45C is a schematic of the generated concatemers with associated cleaving oligonucleotides at restriction sites. This solution was incubated at 33° C. for 30 minutes, and washed at 33° C. with 2×5 minutes in 10% formamide in 2× SSC, 3×1 minute with 6× SSC.

Cells were imaged with an inverted Nikon Ti2-E microscope equipped with a Yokogawa CSU-W1 single disk spinning disk (50 μm pinhole size) using a 20× objective. Fluorescence was acquired from 488 nm and 560 nm through spinning disk confocal imaging, acquiring z-stack images through the depth of the cells. For display in the figure, z-stack images were maximum intensity projected and equally contrasted. FIGS. 45D and 45E are images of fluorescent-labeled probes in a HeLa/3T3 co-culture. Scale bar 100 μm. FIG. 45D shows FAM staining in cells morphologically representative of HeLa cells. FIG. 45E shows cy3 staining cells morphologically representative of 3T3 cells. This indicates concatemers are detected associated with intended targets.

Digestion of RCA Products and Polymerization

A coupled digestion/polymerization reaction mixture was prepared composed of 0.3 mM dNTP (each), 2× CutSmart Buffer (NEB), 2.5% Triton-X, 3 mM RNAseOUT (Thermo Fisher), 4 U/μl Maxima Reverse Transcriptase (Thermo Fisher), and 0.2 U/μl BtsI-v2 (NEB). No RT control received water in place of Maxima enzyme. "RT oligo added" control reaction received a 57 bp synthesized mimic of the predicted cleaved RT strand. Samples were incubated 50° C. 15 minutes, then 15 cycles of [60° C. 30 s, 50° C. 30 s, 8° C. 30 s, 15° C. 30 s, 25° C. 30 s, 30° C. 1 min, 37° C. 1 min, 42° C. 2 min], and 50° C. 15 minutes. After the final incubation step, the reaction mixture was collected and stored, and then a 6× SSC wash was performed, which was also collected and stored. Both samples were heat inactivated at 85° C. for 5 min. Following the 6× SSC wash, samples were washed 2×1 minute 60% formamide in 1×PBST (0.1% Tween), 2×1 minute in 1×PBST with 1M NaCl followed by 2×1 minute in PBST.

Second Digestion of RCA Products and Polymerization

Samples were hybridized as in the first round, but with 30 nM each of Cleave Oligo 2 and 3, and without the imager probe. Digestion/Polymerization reaction and cycling program were conducted as in the first round. In the second round, No RT control samples again received reaction mix without Maxima. "RT oligo added" control reaction was repeated as in the first round. Washes and handshake collection was conducted as for the first round.

Preparation of cDNA for NGS cDNA was a-tailed using a reaction mixture comprised of 1× ThermoPol reaction buffer (NEB), 1 mM dATP, and 2 U/mL of TdT enzyme (NEB). Cells were incubated in the reaction mixture for 45 minutes at 37° C., followed by 3 washes in PBST. Subsequently, cDNA was released by incubating the cells in an RNAseH displacement reaction consisting of 1× ThermoPol Buffer and 200 U/mL of RNAseH (NEB). Cells were incubated in displacement reaction for 45 minutes at 37° C., and the reaction was recovered from wells and heat inactivated at 75'C for 20 min, followed by purification with Ampure beads at a 1:1.8 sample:bead ratio, followed by elution in water.

Second strand synthesis was performed using an 'SSS oligo' consisting of 10 Ts on the 3' end, a 6N barcode, and a primer binding sequence for downstream PCR amplification. The second strand synthesis reaction comprised of 1× ThermoPol Buffer, 0.1 mM dNTP, 0.02 μM SSS oligo, 0.75 U/μL of BST polymerase large fragment (NEB), and ~⅓ of the recovered cDNA product (11 IL). Samples were incubated at 37° C. for 30 minutes, followed by a 20 minute inactivation at 80° C.

Second strand synthesis product was first amplified by PCR, with one side of the product containing a custom primer sequence for R1 of NGS, and the other side of the product containing the PCR amplification handle introduced at second strand synthesis. PCR reaction was performed with Q5 (NEB) manufacturer recommended PCR conditions. SYBR stain was included in the reaction to assess qPCR Ct values. Samples were run on a 4% agarose gel to assess size. Samples were then diluted 1:500 in water, with primers that attach P5 Illumina adapter and i5 indices to the custom primer side of the amplicon, and that attach R2-i7-P7 to the opposite side. Samples were pooled and gel purified to retain smear above ~200 bp. Samples were sequenced on the MiniSeq (Illumina) platform using standard manufacturer-recommended settings and custom R1 and i5 sequencing primers. In all qPCRs, samples were removed from the cycler at ~0.5 max Rn to prevent overamplification.

Preparation of Handshake Products for NGS

Recovered reaction and first wash solutions were purified with Ampure beads using a 1:1.8 sample to bead ratio. Products were amplified using Q5 PCR (standard manufacturer recommendations), with PCR primers that introduce a customer primer overhang for NGS. SYBR stain was included in the reaction to assess qPCR Ct values. Amplified products were then diluted 1:500 in water, and indexed using primers that attach P5 Illumina adapter and i5 indices to the custom primer side of the amplicon, and that attach R2-i7-P7 to the opposite side. Samples were sequenced on the MiniSeq (Illumina) platform using standard manufacturer-recommended settings and custom R1 and i5 sequencing primers. In all qPCRs, samples were removed from the cycler at ~0.5 max Rn to prevent overamplification.

Amplification of associated RT and Handshake Barcodes

To amplify both barcodes on the original padlock in association, RT reaction mixture was recovered from wells following the first cycle of digestion/polymerization and was purified 1:1.8 on Ampure beads. The resulting product was amplified in two reactions, which each had a distinct forward primer for amplifying Type 1 (Handshake) and Type 2 (RT) products. A schematic of the oligonucleotide, comprising handshake and RT primers, is shown in FIG. 45F with an expected size of 132 bp. PCR reaction was performed with Q5 (NEB) manufacturer recommended PCR conditions. SYBR stain was included in the reaction to enable samples to be removed from the cycler before reaching max Rn plateau. 2 ul of resulting samples were run on a 4% agarose gel to assess size and intensity against 75 ng of low MW DNA ladder (NEB). An image of the agarose gel is shown in FIG. 45G. PCR product using recovered digestion/polymerization reaction as template. Wells 1 and 2 were amplified 13 and 14 cycles, Control wells 5 and 6 were amplified 25 cycles. Bands in lanes 1 and 2 from type 1 and type 2 products, respectively, detect products of about 130 bp.

NGS Analysis of cDNA

For cDNA analysis, reads were parsed by finding the RT primer using pairwise alignment of the primer sequence to the read as well as finding polyA tails (minimum length of 10 bases) that are immediately 3' of the cDNA. Node Type ID was extracted as the 4 bases immediately 5 of the start of the RT primer sequence and the barcode as the 16 bases preceding the Node Type ID; reads without 20 bases 5' of the RT primer were discarded. Reads with >15 bp sequence between the RT priming sequence and polyA tail were mapped to a concatenation of the human and mouse genomes. Deduplication was performed using the combination of cDNA sequence, barcode, and Type ID. Among deduplicated reads with cDNA that mapped uniquely to either the human or mouse genome, the fraction of reads mapping to each species was calculated. The fraction of cDNA reads that map to Human or Mouse, for Human-targeting and Mouse-Targeting padlocks is shown in FIG. 45SH. The barplot shows approximately 30% of the human node reads mapping to human genes, with the balance mapping to mouse genes. Approximately 85-90% of the mouse nodes samples read to mouse genes. This disparity in reads to the respective genes may be due to mouse cells containing more cDNA than the human cells. In that case, the underlying distribution of mRNAs would be skewed significantly toward mouse transcripts. Another possibility is that the padlock targeting human Actb promiscuously binds to the mouse transcriptome, as the padlock mRNA binding sequences are quite similar. A further possibility is that the detection of mouse cDNA was higher than detection of human cDNA, for instance, due to accessibility in the different cell types.

NGS Analysis of Handshake Amplicons

For Handshake analysis, reads were parsed by finding the 5' PCR amplification sequence, 3' PCR amplification sequence, and the handshake sequence. Node Type 1 sequence was extracted as the 4 bp immediately 3' of the 5' PCR amplification sequence and node barcode 1 sequence was extracted as the 16 bp immediately 3' of the Node Type 1 sequence. Node Type 2 sequence was extracted as the reverse complement of the 4 bp immediately 5' of the 3' PCR amplification sequence and node barcode 2 was extracted as the reverse complement of the 16 bp immediately 3' of the Node Type 2 sequence. Reads that did not have exactly 20 bases between the 3' end of the 5' PCR amplification sequence and the 5' end of the handshake sequence or exactly 20 bases between the 3' end of the handshake sequence and the 5' end of the 3' PCR amplification sequence were discarded. For each Node Type 1, the node barcode 1 sequences were deduplicated and, similarly for each Node Type 2, the node barcode 2 sequences were deduplicated. Reads were deduplicated based on unique combinations of Node Type 1, Node Type 2, deduplicated node barcode 1, and deduplicated node barcode 2. NGS analysis of handshakes demonstrating amplicon structure and representation of four pair-wise handshakes (human-human, human-mouse, mouse-human, mouse-mouse) is shown in FIG. 45H. As expected in a co-cultured system of mouse and human cells that were targeted with mouse transcript-targeted (Types 1 and 2) node types and human transcript-targeted (Types 1 and 2) node types, a large majority of amplified handshakes have the expected structure and all four expected pairs of node-node handshakes are observed (Mouse Type 1 × Human Type 2, Mouse Type 1 × Mouse Type 2, Human Type 1 × Human Type 2, Human Type 1 × Mouse Type 2). As expected, these four pairs of node handshakes are observed in this experiment, since the node nucleic acids were free to diffuse within the well of co-cultured cells.

Example 15: Deconvolution of Simulated Node Data Sets

Computational simulations of node barcoding of targets were performed under 5 different conditions, and relative spatial positions of nodes were fit based on the simulated sequence record data. Nodes of different types are labeled as '[NodeType].[NodeID]', e.g. '0.13' would represent a node of type 0 with ID 13. An edge between nodes indicates at least one simulated record contained those two node ID's in it, with thicker lines indicating more records contained in that node pair.

Nodes and target 'molecules' at specified densities were randomly (uniformly) distributed in a 3D space of 20 (x) by 20 (y) by 2 (z) to simulate a tissue section volume. This could represent, for example, a section region of size 20 microns by 20 microns by 2 microns. Node types were also randomly (uniformly) selected and assigned for each node based on the total number of node types.

Barcoding was simulated by iterating through each target (e.g. in situ generated cDNA) and identifying the nearest nodes of each type. A record was stored as a list of nodes for each target to simulate concatenated target-node sequences. For example, if there were two node types, then each target record would contain two node ID's corresponding to the closest nodes of each of the two types. If there were 5 node types, then each target record would contain 5 node ID's corresponding to the closest nodes of each of the 5 types.

The node graph was constructed by iterating through each record and counting the number of times each pair of nodes appeared in a single record. An edge was constructed between nodes if there was at least one record containing that node pair, and weights were assigned to each to be equal to the number of times that node pair appeared together in the record list.

To re-construct the relative positions of nodes based on record simulation results, the Fruchterman-Reingold force-directed algorithm was used with edge weights corresponding to the node pair record counts.

Plots were generated showing actual or fitted node location in either 3D or 2D (X-Y), and nodes were colored based on node type. Nodes were annotated with node type and node ID ('[NodeType].[NodeID]'). and the line width of the edge corresponds to the count of records containing that node pair.

FIGS. 46A-46T are generated plots according to the following conditions:
Condition 1: 0.03 node density, 20 target density, 2 node types, 24 nodes with 40 edges recorded;
FIG. 46A: Actual 3D,
FIG. 46B: Actual 2D projection.
FIG. 46C: Fitted 3D,
FIG. 46D: Fitted 2D projection,
Condition 2: 0.2 node density, 10 target density, 2 node types, 160 nodes with 366 edges recorded;
FIG. 46E: Actual 3D,
FIG. 46F: Actual 2D projection.
FIG. 46G: Fitted 3D,
FIG. 46H: Fitted 2D projection,
Condition 3: 0.05 node density, 20 target density, 3 node types, 40 nodes with 127 edges recorded;
FIG. 46I: Actual 3D,
FIG. 46J: Actual 2D projection.
FIG. 46K: Fitted 3D,
FIG. 46L: Fitted 2D projection,
Condition 4: 0.1 node density, 30 target density, 2 node types, 80 nodes with 177 edges recorded;
FIG. 46M: Actual 3D,
FIG. 46N: Actual 2D projection.
FIG. 46O: Fitted 3D,
FIG. 46P: Fitted 2D projection,
Condition 5: 0.03 node density, 10 target density, 5 node types, 24 nodes with 129 edges recorded;
FIG. 46Q: Actual 3D,
FIG. 46R: Actual 2D projection.
FIG. 46S: Fitted 3D,
FIG. 46T: Fitted 2D projection.

The generated plots demonstrate the calculations are sufficiently robust to deconvolute association and location information from sequencing data across a range of parameters such as node density and node type.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of biological information generation, the method comprising:
providing node factories on a biological sample at node locations, wherein the node factories comprise one or more node nucleic acids, and wherein each node nucleic acid comprises:
a node barcode region;
one or more flanking node barcode hybridization regions;
a node nucleic acid restriction site; and
optionally, a node primer region;
amplifying the one or more node nucleic acids to generate concatemers of node nucleic acids, wherein the concatemers diffuse away from the node locations over time;
cleaving the concatemers into a plurality of node nucleic acids;

attaching two or more node nucleic acids generated by the node factories to generate multinode nucleic acids; and analyzing for a frequency of association of the two or more node nucleic acids, wherein the frequency of association provides information for spatial mapping of the biological sample.

2. The method of claim 1, wherein the node factories further comprise one or more factory target nucleic acids, wherein each factory target nucleic acid comprises:
   a target binding region;
   a target barcode region;
   one or more flanking target binding hybridization regions;
   a factory target nucleic acid restriction site; and
   optionally, a target primer region;
   wherein each factory target nucleic acid is contiguous to a node nucleic acid, and wherein the amplifying generates concatemers comprising repeats of node nucleic acids and factory target nucleic acids and the cleaving generates a plurality of node nucleic acids and factory target nucleic acids; and
   wherein the method further comprises:
      attaching the factory target nucleic acid to a target sequence; and
      measuring a frequency of association of the factory target nucleic acid and the target sequence, wherein the frequency of association provides information for spatial mapping of the biological sample.

3. The method of claim 1, wherein the amplifying comprises rolling circle amplification (RCA), strand-displacement amplification (SDA), Nicking Enzyme Amplification Reaction (NEAR), exponential amplification reaction (EXPAR), enzymatic oligonucleotide synthesis via internal inosine modification and exonuclease V, nick translation, Loop-Mediated Isothermal Amplification (LAMP), Helicase-Dependent Amplification (HDA), Multiple Displacement Amplification (MDA), Ligase Chain Reaction (LCR), Recombinase Polymerase Amplification (RPA), Ramification amplification method (RAM), Nucleic Acid Sequence-Based Amplification (NASBA), signal amplification by exchange reaction (SABER), or primer exchange reaction (PER).

4. The method of claim 1, wherein each node factory comprises a padlock probe comprising the node nucleic acid and the node nucleic acid restriction site, the method further comprising:
   hybridizing the padlock probe to a nucleic acid splint, wherein the nucleic acid splint comprises regions complementary to regions at 3' and 5' ends of the padlock probe;
   applying a ligase to the sample, wherein the ligase joins the 3' and 5' ends of the padlock probe;
   applying a rolling circle polymerase to the ligated padlock probe; and
   generating a concatemer comprising node nucleic acids and node nucleic acid restriction sites by RCA.

5. The method of claim 4, wherein the nucleic acid splint comprises at least part of an mRNA sequence in the biological sample.

6. The method of claim 4, wherein the nucleic acid splint is conjugated to a surface, a protein, a small molecule, a nucleic acid, a lipid or any combination thereof.

7. The method of claim 6, wherein the protein comprises a receptor, a ligand, an antibody, or any functional fragment thereof.

8. The method of claim 6, wherein the biological sample further comprises a feature, wherein the feature in the biological sample comprises a cell structure, a receptor, a scaffold, a matrix, a nucleic acid, a tissue, or an organelle.

9. The method of claim 4, further comprising depositing a restriction enzyme or nickase on the sample, wherein the restriction enzyme or nickase recognizes the node nucleic acid restriction site, thereby cleaving the concatemer to provide a plurality of node nucleic acids.

10. The method of claim 4, further comprising depositing a restriction enzyme or nickase on the sample, wherein the concatemer forms a hairpin comprising the node nucleic acid restriction site.

11. The method of claim 10, wherein the restriction enzyme makes a double-stranded cut at the node nucleic acid restriction site.

12. The method of claim 10, wherein the nickase makes a single stranded cut at the node nucleic acid restriction site.

13. The method of claim 4, further comprising:
   depositing an oligonucleotide on the sample, wherein the oligonucleotide hybridizes with a region comprising the node nucleic acid restriction site, forming a double-stranded restriction region,
   depositing a double-strand-specific restriction enzyme on the sample, wherein the restriction enzyme recognizes the node nucleic acid restriction site, thereby cleaving the concatemer to provide a plurality of node nucleic acids.

14. The method of claim 1, wherein the plurality of node nucleic acids are generated individually.

15. The method of claim 2, wherein the generated concatemer comprises alternating node nucleic acids, node nucleic acid restriction sites, factory target nucleic acids, and factory target nucleic acid restriction sites.

16. The method of claim 15, further comprising depositing a restriction enzyme or nickase on the sample, wherein the restriction enzyme or nickase recognizes the node nucleic acid restriction site and the factory target nucleic acid restriction site.

17. The method of claim 15, further comprising depositing a first restriction enzyme on the sample, wherein the first restriction enzyme recognizes the factory target nucleic acid restriction site and does not recognize the node nucleic acid restriction site, thereby generating a plurality nucleic acids each comprising the node nucleic acid and the factory target nucleic acid.

18. The method of claim 17, further comprising depositing a second restriction enzyme on the sample after the depositing the first restriction enzyme, wherein the second restriction enzyme recognizes the node nucleic acid restriction site, thereby generating separate pluralities of node nucleic acids and factory target nucleic acids.

19. The method of claim 2, wherein the one or more flanking node barcode hybridization regions or the one or more flanking target binding hybridization regions flank the node barcode region or the target binding region.

20. The method of claim 1, wherein the providing comprises an affinity reaction, conjugation, incorporation into a hydrogel, crosslinking, or photo-crosslinking.

21. The method of claim 20, wherein the node nucleic acids are conjugated to an antibody, antibody fragment, protein, nanobody, small molecule, nucleic acid therapeutic, lipid, nanoparticle, lipid nanoparticle or other affinity reagent.

22. The method of claim 1, wherein the attaching comprises hybridization, extension, ligation, splinted ligation, cross-junction synthesis, ligation and cross-interstrand crosslink (ICL) synthesis, cross ICL and nick synthesis, pairwise copying, or any combination thereof.

23. The method of claim 1, wherein the spatial mapping comprises sequencing the concatemer.

24. The method of claim 23, wherein the sequencing comprises chain termination sequencing, nanopore sequencing, sequencing by ligation, combinatorial probe anchor synthesis, sequencing by synthesis, pyrosequencing, ion semiconductor, or single-molecule real-time sequencing.

25. The method of claim 1, wherein the node barcodes comprise one or more fluorophore labels.

26. The method of claim 25, wherein the spatial mapping comprises imaging the concatemer.

27. The method of claim 26, wherein the one or more fluorophore labels are attached to the node barcodes by synthesis or hybridization.

28. The method of claim 1, wherein the node locations comprise a pattern, are preselected, are at random locations throughout the biological sample, or are at specific targets in the biological sample.

29. The method of claim 1, wherein the biological sample comprises cells in a synthetic matrix, a population of cells, a tissue sample, or a protein.

30. The method of claim 1, further comprising imaging the biological sample.

31. The method of claim 1, wherein the node barcode region is from about 3 to about 30 nucleotides.

32. The method of claim 1, wherein the node nucleic acid is from about 20 to about 50, from about 50 to about 100, from about 100 to about 200, from about 200 to about 500, from about 500 to about 1000, or more than 1000 nucleotides.

33. The method of claim 1, wherein the diffused node nucleic acids comprise a gradient of decreasing concentration with increased distance from the node location.

34. The method of claim 1, wherein the distribution area of diffused node nucleic acids from different node locations do not overlap.

35. The method of claim 1, wherein the distribution area of node nucleic acids from different node locations overlap.

36. The method of claim 35, wherein the node nucleic acids from two or more node locations combine by hybridization, extension, ligation, splinted ligation, cross-junction synthesis, ligation and cross-interstrand crosslink (ICL) synthesis, cross ICL and nick synthesis, pairwise copying, or any combination thereof.

37. The method of claim 1, wherein the node nucleic acids are double-stranded, single-stranded, comprise a hairpin structure, or any combination thereof.

38. The method of claim 1 further comprising controlling a diffusion factor, wherein a diffusion factor comprises a viscosity, a time, a temperature, a presence of crowding agents, a pH, an electric field, physical features, or any combination thereof.

39. The method of claim 38, wherein the viscosity is greater than 1 cP.

40. The method of claim 39, wherein the biological sample medium comprises a viscosity from about 1 to about 10 cP, from about 10 to about 20 cP, from about 20 to about 30 cP, from about 30 to about 40 cP, from about 40 to about 50 cP, from about 50 to about 60 cP, from about 60 to about 70 cP, from about 70 to about 80 cP, from about 80 to about 90 cP, from about 100 to about 150 cP, from about 150 to about 300 cP, from about 300 to about 500 cP, from about 500 to about 1000 cP, from about 1000 to about 2000 cP, from about 2000 to about 3000 cP.

* * * * *